US007314924B2

(12) United States Patent
Maine et al.

(10) Patent No.: US 7,314,924 B2

(45) Date of Patent: Jan. 1, 2008

(54) POLYNUCLEOTIDE ENCODING A GENETICALLY ENGINEERED P30 ANTIGEN

(75) Inventors: Gregory T. Maine, Gurnee, IL (US); Chandu B. Patel, Libertyville, IL (US); Sanford R. Ginsburg, Palatine, IL (US); Timothy R. Bliese, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 62 days.

(21) Appl. No.: 11/316,532

(22) Filed: Dec. 21, 2005

(65) Prior Publication Data

US 2006/0105451 A1 May 18, 2006

Related U.S. Application Data

(62) Division of application No. 10/263,153, filed on Oct. 2, 2002, now Pat. No. 7,094,879.

(51) Int. Cl.
*C12N 15/74* (2006.01)
*C07H 21/04* (2006.01)

(52) U.S. Cl. ..................................... 536/23.7; 536/23.1

(58) Field of Classification Search ..................... None
See application file for complete search history.

(56) References Cited

U.S. PATENT DOCUMENTS 6,329,157 B1 12/2001 Maine et al.
6,372,443 B1 4/2002 Jacobs et al.

FOREIGN PATENT DOCUMENTS

WO WO96/02654 2/1996
WO 99/61906 12/1999
WO WO99/66043 12/1999

OTHER PUBLICATIONS

He, et al., Nature Structural Biology, "Structure of the immunodominant surface antigen from the Toxoplasma gondii SRS superfamily." 9(8), 606-611, (2002).
Huskinson, et al., Journal of Clinical Microbiology, "Toxoplasma antigens recognized by human immunoglobulin a antibodies", 28(12), 2632-2636 (1990).
Kim, et al., Infection and Immunity, American Society for Microbiology, "Conformationally appropriate expression of the Toxoplasma antigen SAG1 (p30) in CHO cells" 62(1) 203-209 (1994).
Nam, et al., Korean Journal of Parasitology, "Analysis of antigenic domain of GST fused Major Surface protein (p30) fragments of Toxoplasma gondii", 34(2), 135-141 (1996).
Remington, J.S., et al., *Infectious Diseases of the Fetus and New-born Infant, Fourth Edition*, "Toxoplasmosis", J.S. Remington and J.O. Klein, Eds., pp. 140-267, Saunders, Philadelphia (1995).
Sabin, A.B. et al., *Science*, "Dyes as Microchemical Indicators of a New Immunity Phenomenon Affecting a Protozoon Parasiste (Toxoplasma)", vol. 108, pp. 660-663 (1948).
Jacobs, L., et al., *J. Parasitol*, "A Hemagglutination Test for Toxoplasmosis", vol. 43, pp. 308-314 (1957).
Walton, B.C. et al., *Am. J. Trop. Med. Hyg.* , "Comparison of the Indirect Fluorescent Antibody Test and Methylene Blue Dye Test for Detection of Antibodies to Toxoplasma Gondii", vol. 15, pp. 149-152 (1966).
Naot, Y. et al., *J. Infect. Dis.* , Án Enzyme-Linked Immunosorbent Assay for Detection of IgM Antibodies to Toxoplasma Gondii: Use for Diagnosis of Acute Acquired Toxoplasmosis, 142, pp. 757-766 (1980).
Prince, et al., *Mol. Biochem. Parasito*, "Cloining Expression, and cDNA Sequence of Surface Antigen P22 from Toxoplasma Gondii", vol. 43, pp. 97-106 (1990).
Cesbron-Delauw, et al., *Proc. Nat. Acad. Sci.* , "Molecular characterization of a 23-Kilodalton Major Antigen Secreted by Toxoplasma Gondii", vol. 86, pp. 7537-7541 (1989).
Johnson, et al., *Gene*, "Cloning of Toxoplasma Gondii Gene Fragments Encoding Diagnostic Antigens", vol. 99, pp. 127-132 (1991).
Prince, et al., *Mol. Biochem. Parasiotol*, "Cloning of cDNAs Encloding a 28 Kilodalton Antigen of Toxoplasma Gondii", vol. 34, pp. 3-13 (1989).
Bonhomme, et al., *J. Histochem. Cytochem*, "Quantitative Immunolocalization of a P29 Protein (GRA7), a New Antigen of Toxoplasma Gondii", vol. 46, pp. 1411-1421 (1998).
Burg, et al., *J. Immunol.*, "Molecular Analysis of the Gen Encoding the major Surave Antigen of Toxoplasma Gondii", vol. 141, pp. 3584-3591 (1998).
Mevelec, et al., *Mol. Biochem. Parasitol.*, "Molecular Cloning of GRA4, a Toxoplasma Gondii Dense Granule Protein, Recongnized by Mucosal IgA Antibodies", vol. 56, pp. 227-238 (1992).
Saavedra, et al., *J. Immunol.* , "Human T Cell Clone Identifies A Potentially Protective 54-kDa Protein Antigen of Toxoplasma Gondii Cloned and Expressed in *Excherichia coli*", vol. 147, pp. 1975-1982 (1991).
Safford, et al., *J. Clin. Pathol.* , "Automated Microparticle Enzyme Immunoassays for IgG and IgM Antibodies to Toxoplasma Gondii", 44:238-242 (1991).
Kapust and Waugh, *Protein Science , "Escherichia coli* Maltose-Binding Protein is Uncommonly Effective at Promoting the Solubility of Polypeptides To Which It Is Fused", 8, 1668-1674 (1991).
Robinson, et al., *J. Clin. Microbiol.*, "Analysis of the Humoral Response to the Flagellin Protein of Borrelia Burgdorferi: Cloning of Regions Capable of Differentiating Lyme Disease from Syphilis", 31:629-635 (1993).
Velge-Roussel, et al., *Molec. Biochem. Parasitol*, "Epitopic Analysis of the Toxoplasma Gondii Major Surface Antigen SAG1", 66:31-38 (1994).

(Continued)

*Primary Examiner*—Robert A. Zeman
(74) *Attorney, Agent, or Firm*—Audrey Bartnicki; Cheryl L. Becker

(57) ABSTRACT

The present invention relates to a genetically engineered P30 antigen and a combination or mixture of antigens (e.g., the genetically engineered P30 antigen and P35) that may be used in the detection of IgM and/or IgG antibodies to *Toxoplasma gondii*. Furthermore, the present invention also relates to methods of using this genetically engineered P30 antigen and combination of antigens, antibodies raised against this genetically engineered P30 antigen and combination of antigens, as well as kits and vaccines containing the genetically engineered P30 antigen and antigens present in the combination.

2 Claims, 84 Drawing Sheets

OTHER PUBLICATIONS

Desomonts, G. and Remington, J.S., *J. Clin. Microbiol*., "Direct Agglutination Test for Diagnosis of Toxoplasma Infection: Method for Increasing Sensitivity and Specificity", 11 :562-568 (1980).

Pouletty, et al. *J. Immunol. Methods*, "An Anti-human u Chain Monoclonal Antibody: Use for Detection of IgM Antibodies to Toxoplasma Gondii by Reverse Immunosorbent Assay", 76:289-298 (1985).

Zweig, HM, *Clin. Chem*. , "Receiver-Operating Characteristic (ROC) Plots: A Fundamental Evaluation Tool in Clinical Medicine", 39:561-577 (1993).

New England Biolabs, Inc. 1998/99 Catalog, pp. 136-137.

Gerhold, et al., *BioEssays*, vol. 18, No. 12, pp. 973-981 (1996).

Wells, et al, *Journal of Leukocyte Biology*, vol. 61, No. 5, pp. 545-550 (1997).

Russell, et al., *Journal of Molecular Biology*, vol. 244, pp. 332-350 (1994).

pMBP-c2X-ToxoP30(52-336aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG. 2 pMBP-c2X-ToxoP30(52-336aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.2A pMBP-c2X-ToxoP30(52-336aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACG GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu PheAlaGly AlaAlaGly
3421 AAGCATCAC TGTACCGTG AAACTGGAG TTTGCCGGG GCTGCAGGG
     SerAlaLys SerAlaAla GlyThrAla SerHisVal SerIlePhe
3466 TCAGCAAAA TCGGCTGCG GGAACAGCC AGTCACGTT TCCATTTTT
     AlaMetVal IleGlyLeu IleGlySer IleAlaAla CysValAla
3511 GCCATGGTG ATCGGACTT ATTGGCTCT ATCGCAGCT TGTGTCGCG
3556 TGAAAGCTT GGCACTGGC CGTCGTTTT ACAACGTCG TGACTGGGA
3601 AAACCCTGG CGTTACCCA ACTTAATCG CCTTGCAGC ACATCCCCC
3646 TTTCGCCAG CTGGCGTAA TAGCGAAGA GGCCCGCAC CGATCGCCC
3691 TTCCCAACA GTTGCGCAG CCTGAATGG CGAATGGCA GCTTGGCTG
3736 TTTTGGCGG ATGAGATAA GATTTTCAG CCTGATACA GATTAAATC
3781 AGAACGCAG AAGCGGTCT GATAAAACA GAATTTGCC TGGCGGCAG
3826 TAGCGCGGT GGTCCCACC TGACCCCAT GCCGAACTC AGAAGTGAA
3871 ACGCCGTAG CGCCGATGG TAGTGTGGG GTCTCCCCA TGCGAGAGT
3916 AGGGAACTG CCAGGCATC AAATAAAAC GAAAGGCTC AGTCGAAAG
3961 ACTGGGCCT TTCGTTTTA TCTGTTGTT TGTCGGTGA ACGCTCTCC
4006 TGAGTAGGA CAAATCCGC CGGGAGCGG ATTTGAACG TTGCGAAGC
4051 AACGGCCCG GAGGGTGGC GGGCAGGAC GCCCGCCAT AAACTGCCA
4096 GGCATCAAA TTAAGCAGA AGGCCATCC TGACGGATG GCCTTTTTG
```

FIG. 2B pMBP-c2X-ToxoP30(52-336aa)

| | | | | | |
|---|---|---|---|---|---|
| 4141 | CGTTTCTAC | AAACTCTTT | TTGTTTATT | TTTCTAAAT | ACATTCAAA |
| 4186 | TATGTATCC | GCTCATGAG | ACAATAACC | CTGATAAAT | GCTTCAATA |
| 4231 | ATATTGAAA | AAGGAAGAG | TATGAGTAT | TCAACATTT | CCGTGTCGC |
| 4276 | CCTTATTCC | CTTTTTTGC | GGCATTTTG | CCTTCCTGT | TTTTGCTCA |
| 4321 | CCCAGAAAC | GCTGGTGAA | AGTAAAAGA | TGCTGAAGA | TCAGTTGGG |
| 4366 | TGCACGAGT | GGGTTACAT | CGAACTGGA | TCTCAACAG | CGGTAAGAT |
| 4411 | CCTTGAGAG | TTTTCGCCC | CGAAGAACG | TTCTCCAAT | GATGAGCAC |
| 4456 | TTTTAAAGT | TCTGCTATG | TGGCGCGGT | ATTATCCCG | TGTTGACGC |
| 4501 | CGGGCAAGA | GCAACTCGG | TCGCCGCAT | ACACTATTC | TCAGAATGA |
| 4546 | CTTGGTTGA | GTACTCACC | AGTCACAGA | AAAGCATCT | TACGGATGG |
| 4591 | CATGACAGT | AAGAGAATT | ATGCAGTGC | TGCCATAAC | CATGAGTGA |
| 4636 | TAACACTGC | GGCCAACTT | ACTTCTGAC | AACGATCGG | AGGACCGAA |
| 4681 | GGAGCTAAC | CGCTTTTTT | GCACAACAT | GGGGGATCA | TGTAACTCG |
| 4726 | CCTTGATCG | TTGGGAACC | GGAGCTGAA | TGAAGCCAT | ACCAAACGA |
| 4771 | CGAGCGTGA | CACCACGAT | GCCTGTAGC | AATGGCAAC | AACGTTGCG |
| 4816 | CAAACTATT | AACTGGCGA | ACTACTTAC | TCTAGCTTC | CCGGCAACA |
| 4861 | ATTAATAGA | CTGGATGGA | GGCGGATAA | AGTTGCAGG | ACCACTTCT |
| 4906 | GCGCTCGGC | CCTTCCGGC | TGGCTGGTT | TATTGCTGA | TAAATCTGG |
| 4951 | AGCCGGTGA | GCGTGGGTC | TCGCGGTAT | CATTGCAGC | ACTGGGGCC |
| 4996 | AGATGGTAA | GCCCTCCCG | TATCGTAGT | TATCTACAC | GACGGGGAG |
| 5041 | TCAGGCAAC | TATGGATGA | ACGAAATAG | ACAGATCGC | TGAGATAGG |
| 5086 | TGCCTCACT | GATTAAGCA | TTGGTAACT | GTCAGACCA | AGTTTACTC |
| 5131 | ATATATACT | TTAGATTGA | TTTACCCCG | GTTGATAAT | CAGAAAAGC |
| 5176 | CCCAAAAAC | AGGAAGATT | GTATAAGCA | AATATTTAA | ATTGTAAAC |
| 5221 | GTTAATATT | TTGTTAAAA | TTCGCGTTA | AATTTTTGT | TAAATCAGC |
| 5266 | TCATTTTTT | AACCAATAG | GCCGAAATC | GGCAAAATC | CCTTATAAA |
| 5311 | TCAAAAGAA | TAGACCGAG | ATAGGGTTG | AGTGTTGTT | CCAGTTTGG |
| 5356 | AACAAGAGT | CCACTATTA | AAGAACGTG | GACTCCAAC | GTCAAAGGG |
| 5401 | CGAAAAACC | GTCTATCAG | GGCGATGGC | CCACTACGT | GAACCATCA |
| 5446 | CCCAAATCA | AGTTTTTTG | GGGTCGAGG | TGCCGTAAA | GCACTAAAT |
| 5491 | CGGAACCCT | AAAGGGAGC | CCCCGATTT | AGAGCTTGA | CGGGGAAAG |
| 5536 | CCGGCGAAC | GTGGCGAGA | AAGGAAGGG | AAGAAAGCG | AAAGGAGCG |
| 5581 | GGCGCTAGG | GCGCTGGCA | AGTGTAGCG | GTCACGCTG | CGCGTAACC |
| 5626 | ACCACACCC | GCCGCGCTT | AATGCGCCG | CTACAGGGC | GCGTAAAAG |
| 5671 | GATCTAGGT | GAAGATCCT | TTTTGATAA | TCTCATGAC | CAAAATCCC |
| 5716 | TTAACGTGA | GTTTTCGTT | CCACTGAGC | GTCAGACCC | CGTAGAAAA |
| 5761 | GATCAAAGG | ATCTTCTTG | AGATCCTTT | TTTTCTGCG | CGTAATCTG |
| 5806 | CTGCTTGCA | AACAAAAAA | ACCACCGCT | ACCAGCGGT | GGTTTGTTT |
| 5851 | GCCGGATCA | AGAGCTACC | AACTCTTTT | TCCGAAGGT | AACTGGCTT |
| 5896 | CAGCAGAGC | GCAGATACC | AAATACTGT | CCTTCTAGT | GTAGCCGTA |
| 5941 | GTTAGGCCA | CCACTTCAA | GAACTCTGT | AGCACCGCC | TACATACCT |
| 5986 | CGCTCTGCT | AATCCTGTT | ACCAGTGGC | TGCTGCCAG | TGGCGATAA |
| 6031 | GTCGTGTCT | TACCGGGTT | GGACTCAAG | ACGATAGTT | ACCGGATAA |
| 6076 | GGCGCAGCG | GTCGGGCTG | AACGGGGGG | TTCGTGCAC | ACAGCCCAG |
| 6121 | CTTGGAGCG | AACGACCTA | CACCGAACT | GAGATACCT | ACAGCGTGA |
| 6166 | GCTATGAGA | AAGCGCCAC | GCTTCCCGA | AGGGAGAAA | GGCGGACAG |

FIG.2C pMBP-c2X-ToxoP30(52-336aa)

6211 GTATCCGGT AAGCGGCAG GGTCGGAAC AGGAGAGCG CACGAGGGA
6256 GCTTCCAGG GGGAAACGC CTGGTATCT TTATAGTCC TGTCGGGTT
6301 TCGCCACCT CTGACTTGA GCGTCGATT TTTGTGATG CTCGTCAGG
6346 GGGGCGGAG CCTATGGAA AAACGCCAG CAACGCGGC CTTTTTACG
6391 GTTCCTGGC CTTTTGCTG GCCTTTTGC TCACATGTT CTTTCCTGC
6436 GTTATCCCC TGATTCTGT GGATAACCG TATTACCGC CTTTGAGTG
6481 AGCTGATAC CGCTCGCCG CAGCCGAAC GACCGAGCG CAGCGAGTC
6526 AGTGAGCGA GGAAGCGGA AGAGCGCCT GATGCGGTA TTTTCTCCT
6571 TACGCATCT GTGCGGTAT TTCACACCG CATATATGG TGCACTCTC
6616 AGTACAATC TGCTCTGAT GCCGCATAG TTAAGCCAG TATACACTC
6661 CGCTATCGC TACGTGACT GGGTCATGG CTGCGCCCC GACACCCGC
6706 CAACACCCG CTGACGCGC CCTGACGGG CTTGTCTGC TCCCGGCAT
6751 CCGCTTACA GACAAGCTG TGACCGTCT CCGGGAGCT GCATGTGTC
6796 AGAGGTTTT CACCGTCAT CACCGAAAC GCGCGAGGC AGCTGCGGT
6841 AAAGCTCAT CAGCGTGGT CGTGCAGCG ATTCACAGA TGTCTGCCT
6886 GTTCATCCG CGTCCAGCT CGTTGAGTT TCTCCAGAA GCGTTAATG
6931 TCTGGCTTC TGATAAAGC GGGCCATGT TAAGGGCGG TTTTTTCCT
6976 GTTTGGTCA CTGATGCCT CCGTGTAAG GGGGATTTC TGTTCATGG
7021 GGGTAATGA TACCGATGA AACGAGAGA GGATGCTCA CGATACGGG
7066 TTACTGATG ATGAACATG CCCGGTTAC TGGAACGTT GTGAGGGTA
7111 AACAACTGG CGGTATGGA TGCGGCGGG ACCAGAGAA AAATCACTC
7156 AGGGTCAAT GCCAGCGCT TCGTTAATA CAGATGTAG GTGTTCCAC
7201 AGGGTAGCC AGCAGCATC CTGCGATGC AGATCCGGA ACATAATGG
7246 TGCAGGGCG CTGACTTCC GCGTTTCCA GACTTTACG AAACACGGA
7291 AACCGAAGA CCATTCATG TTGTTGCTC AGGTCGCAG ACGTTTTGC
7336 AGCAGCAGT CGCTTCACG TTCGCTCGC GTATCGGTG ATTCATTCT
7381 GCTAACCAG TAAGGCAAC CCCGCCAGC CTAGCCGGG TCCTCAACG
7426 ACAGGAGCA CGATCATGC GCACCCGTG GCCAGGACC CAACGCTGC
7471 CCGAAATT

FIG.2D

ToxoP30(52-336aa)

```
    LeuValAla AsnGlnVal ValThrCys ProAspLys LysSerThr
  1 CTTGTTGCC AATCAAGTT GTCACCTGC CCAGATAAA AAATCGACA
    AlaAlaVal IleLeuThr ProThrGlu AsnHisPhe ThrLeuLys
 46 GCCGCGGTC ATTCTCACA CCGACGGAG AACCACTTC ACTCTCAAG
    CysProLys ThrAlaLeu ThrGluPro ProThrLeu AlaTyrSer
 91 TGCCCTAAA ACAGCGCTC ACAGAGCCT CCCACTCTT GCGTACTCA
    ProAsnArg GlnIleCys ProAlaGly ThrThrSer SerCysThr
136 CCCAACAGG CAAATCTGC CCAGCGGGT ACTACAAGT AGCTGTACA
    SerLysAla ValThrLeu SerSerLeu IleProGlu AlaGluAsp
181 TCAAAGGCT GTAACATTG AGCTCCTTG ATTCCTGAA GCAGAAGAT
    SerTrpTrp ThrGlyAsp SerAlaSer LeuAspThr AlaGlyIle
226 AGCTGGTGG ACGGGGGAT TCTGCTAGT CTCGACACG GCAGGCATC
    LysLeuThr ValProIle GluLysPhe ProValThr ThrGlnThr
271 AAACTCACG GTTCCAATC GAGAAGTTC CCCGTGACA ACGCAGACG
    PheValVal GlyCysIle LysGlyAsp AspAlaGln SerCysMet
316 TTTGTGGTC GGTTGCATC AAGGGAGAC GACGCACAG AGTTGTATG
    ValThrVal ThrValGln AlaArgAla SerSerVal ValAsnAsn
361 GTCACAGTG ACAGTACAA GCCAGAGCC TCATCGGTC GTCAATAAT
    ValAlaArg CysSerTyr GlyAlaAsp SerThrLeu GlyProVal
406 GTCGCAAGG TGCTCCTAC GGTGCAGAC AGCACTCTT GGTCCTGTC
    LysLeuSer AlaGluGly ProThrThr MetThrLeu ValCysGly
451 AAGTTGTCT GCGGAAGGA CCCACTACA ATGACCCTC GTGTGCGGG
    LysAspGly ValLysVal ProGlnAsp AsnAsnGln TyrCysSer
496 AAAGATGGA GTCAAAGTT CCTCAAGAC AACAATCAG TACTGTTCC
    GlyThrThr LeuThrGly CysAsnGlu LysSerPhe LysAspIle
541 GGGACGACG CTGACTGGT TGCAACGAG AAATCGTTC AAAGATATT
    LeuProLys LeuThrGlu AsnProTrp GlnGlyAsn AlaSerSer
586 TTGCCAAAA TTAACTGAG AACCCGTGG CAGGGTAAC GCTTCGAGT
    AspLysGly AlaThrLeu ThrIleLys LysGluAla PheProAla
631 GATAAGGGT GCCACGCTA ACGATCAAG AAGGAAGCA TTTCCAGCC
    GluSerLys SerValIle IleGlyCys ThrGlyGly SerProGlu
676 GAGTCAAAA AGCGTCATT ATTGGATGC ACAGGGGGA TCGCCTGAG
    LysHisHis CysThrVal LysLeuGlu PheAlaGly AlaAlaGly
721 AAGCATCAC TGTACCGTG AAACTGGAG TTTGCCGGG GCTGCAGGG
    SerAlaLys SerAlaAla GlyThrAla SerHisVal SerIlePhe
766 TCAGCAAAA TCGGCTGCG GGAACAGCC AGTCACGTT TCCATTTTT
    AlaMetVal IleGlyLeu IleGlySer IleAlaAla CysValAla
811 GCCATGGTG ATCGGACTT ATTGGCTCT ATCGCAGCT TGTGTCGCG
```

FIG.3 pMBP-p2X-ToxoP30(52-336aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleLys ThrGlyAla ArgIleLeu AlaLeuSer AlaLeuThr
1531 AAAATAAAA ACAGGTGCA CGCATCCTC GCATTATCC GCATTAACG
     ThrMetMet PheSerAla SerAlaLeu AlaLysIle GluGluGly
1576 ACGATGATG TTTTCCGCC TCGGCTCTC GCCAAAATC GAAGAAGGT
     LysLeuVal IleTrpIle AsnGlyAsp LysGlyTyr AsnGlyLeu
1621 AAACTGGTA ATCTGGATT AACGGCGAT AAAGGCTAT AACGGTCTC
     AlaGluVal GlyLysLys PheGluLys AspThrGly IleLysVal
1666 GCTGAAGTC GGTAAGAAA TTCGAGAAA GATACCGGA ATTAAAGTC
     ThrValGlu HisProAsp LysLeuGlu GluLysPhe ProGlnVal
1711 ACCGTTGAG CATCCGGAT AAACTGGAA GAGAAATTC CCACAGGTT
     AlaAlaThr GlyAspGly ProAspIle IlePheTrp AlaHisAsp
```

FIG.5 pMBP-p2X-ToxoP30(52-336aa)

```
1756 GCGGCAACT GGCGATGGC CCTGACATT ATCTTCTGG GCACACGAC
     ArgPheGly GlyTyrAla GlnSerGly LeuLeuAla GluIleThr
1801 CGCTTTGGT GGCTACGCT CAATCTGGC CTGTTGGCT GAAATCACC
     ProAspLys AlaPheGln AspLysLeu TyrProPhe ThrTrpAsp
1846 CCGGACAAA GCGTTCCAG GACAAGCTG TATCCGTTT ACCTGGGAT
     AlaValArg TyrAsnGly LysLeuIle AlaTyrPro IleAlaVal
1891 GCCGTACGT TACAACGGC AAGCTGATT GCTTACCCG ATCGCTGTT
     GluAlaLeu SerLeuIle TyrAsnLys AspLeuLeu ProAsnPro
1936 GAAGCGTTA TCGCTGATT TATAACAAA GATCTGCTG CCGAACCCG
     ProLysThr TrpGluGlu IleProAla LeuAspLys GluLeuLys
1981 CCAAAAACC TGGGAAGAG ATCCCGGCG CTGGATAAA GAACTGAAA
     AlaLysGly LysSerAla LeuMetPhe AsnLeuGln GluProTyr
2026 GCGAAAGGT AAGAGCGCG CTGATGTTC AACCTGCAA GAACCGTAC
     PheThrTrp ProLeuIle AlaAlaAsp GlyGlyTyr AlaPheLys
2071 TTCACCTGG CCGCTGATT GCTGCTGAC GGGGGTTAT GCGTTCAAG
     TyrGluAsn GlyLysTyr AspIleLys AspValGly ValAspAsn
2116 TATGAAAAC GGCAAGTAC GACATTAAA GACGTGGGC GTGGATAAC
     AlaGlyAla LysAlaGly LeuThrPhe LeuValAsp LeuIleLys
2161 GCTGGCGCG AAAGCGGGT CTGACCTTC CTGGTTGAC CTGATTAAA
     AsnLysHis MetAsnAla AspThrAsp TyrSerIle AlaGluAla
2206 AACAAACAC ATGAATGCA GACACCGAT TACTCCATC GCAGAAGCT
     AlaPheAsn LysGlyGlu ThrAlaMet ThrIleAsn GlyProTrp
2251 GCCTTTAAT AAAGGCGAA ACAGCGATG ACCATCAAC GGCCCGTGG
     AlaTrpSer AsnIleAsp ThrSerLys ValAsnTyr GlyValThr
2296 GCATGGTCC AACATCGAC ACCAGCAAA GTGAATTAT GGTGTAACG
     ValLeuPro ThrPheLys GlyGlnPro SerLysPro PheValGly
2341 GTACTGCCG ACCTTCAAG GGTCAACCA TCCAAACCG TTCGTTGGC
     ValLeuSer AlaGlyIle AsnAlaAla SerProAsn LysGluLeu
2386 GTGCTGAGC GCAGGTATT AACGCCGCC AGTCCGAAC AAAGAGCTG
     AlaLysGlu PheLeuGlu AsnTyrLeu LeuThrAsp GluGlyLeu
2431 GCAAAAGAG TTCCTCGAA AACTATCTG CTGACTGAT GAAGGTCTG
     GluAlaVal AsnLysAsp LysProLeu GlyAlaVal AlaLeuLys
2476 GAAGCGGTT AATAAAGAC AAACCGCTG GGTGCCGTA GCGCTGAAG
     SerTyrGlu GluGluLeu AlaLysAsp ProArgIle AlaAlaThr
2521 TCTTACGAG GAAGAGTTG GCGAAAGAT CCACGTATT GCCGCCACT
     MetGluAsn AlaGlnLys GlyGluIle MetProAsn IleProGln
2566 ATGGAAAAC GCCCAGAAA GGTGAAATC ATGCCGAAC ATCCCGCAG
     MetSerAla PheTrpTyr AlaValArg ThrAlaVal IleAsnAla
2611 ATGTCCGCT TTCTGGTAT GCCGTGCGT ACTGCGGTG ATCAACGCC
     AlaSerGly ArgGlnThr ValAspGlu AlaLeuLys AspAlaGln
2656 GCCAGCGGT CGTCAGACT GTCGATGAA GCCCTGAAA GACGCGCAG
     ThrAsnSer SerSerAsn AsnAsnAsn AsnAsnAsn AsnAsnAsn
2701 ACTAATTCG AGCTCGAAC AACAACAAC AATAACAAT AACAACAAC
     LeuGlyIle GluGlyArg IleSerGlu PheLeuVal AlaAsnGln
2746 CTCGGGATC GAGGGAAGG ATTTCAGAA TTCCTTGTT GCCAATCAA
     ValValThr CysProAsp LysLysSer ThrAlaAla ValIleLeu
```

FIG.5A pMBP-p2X-ToxoP30(52-336aa)

```
2791  GTTGTCACC TGCCCAGAT AAAAAATCG ACAGCCGCG GTCATTCTC
      ThrProThr GluAsnHis PheThrLeu LysCysPro LysThrAla
2836  ACACCGACG GAGAACCAC TTCACTCTC AAGTGCCCT AAAACAGCG
      LeuThrGlu ProProThr LeuAlaTyr SerProAsn ArgGlnIle
2881  CTCACAGAG CCTCCCACT CTTGCGTAC TCACCCAAC AGGCAAATC
      CysProAla GlyThrThr SerSerCys ThrSerLys AlaValThr
2926  TGCCCAGCG GGTACTACA AGTAGCTGT ACATCAAAG GCTGTAACA
      LeuSerSer LeuIlePro GluAlaGlu AspSerTrp TrpThrGly
2971  TTGAGCTCC TTGATTCCT GAAGCAGAA GATAGCTGG TGGACGGGG
      AspSerAla SerLeuAsp ThrAlaGly IleLysLeu ThrValPro
3016  GATTCTGCT AGTCTCGAC ACGGCAGGC ATCAAACTC ACAGTTCCA
      IleGluLys PheProVal ThrThrGln ThrPheVal ValGlyCys
3061  ATCGAGAAG TTCCCCGTG ACAACGCAG ACGTTTGTG GTCGGTTGC
      IleLysGly AspAspAla GlnSerCys MetValThr ValThrVal
3106  ATCAAGGGA GACGACGCA CAGAGTTGT ATGGTCACA GTGACAGTA
      GlnAlaArg AlaSerSer ValValAsn AsnValAla ArgCysSer
3151  CAAGCCAGA GCCTCATCG GTCGTCAAT AATGTCGCA AGGTGCTCC
      TyrGlyAla AspSerThr LeuGlyPro ValLysLeu SerAlaGlu
3196  TACGGTGCA GACAGCACT CTTGGTCCT GTCAAGTTG TCTGCGGAA
      GlyProThr ThrMetThr LeuValCys GlyLysAsp GlyValLys
3241  GGACCCACT ACAATGACC CTCGTGTGC GGGAAAGAT GGAGTCAAA
      ValProGln AspAsnAsn GlnTyrCys SerGlyThr ThrLeuThr
3286  GTTCCTCAA GACAACAAT CAGTACTGT TCCGGGACG ACGCTGACT
      GlyCysAsn GluLysSer PheLysAsp IleLeuPro LysLeuThr
3331  GGTTGCAAC GAGAAATCG TTCAAAGAT ATTTTGCCA AAATTAACT
      GluAsnPro TrpGlnGly AsnAlaSer SerAspLys GlyAlaThr
3376  GAGAACCCG TGGCAGGGT AACGCTTCG AGTGATAAG GGTGCCACG
      LeuThrIle LysLysGlu AlaPhePro AlaGluSer LysSerVal
3421  CTAACGATC AAGAAGGAA GCATTTCCA GCCGAGTCA AAAAGCGTC
      IleIleGly CysThrGly GlySerPro GluLysHis HisCysThr
3466  ATTATTGGA TGCACAGGG GGATCGCCT GAGAAGCAT CACTGTACC
      ValLysLeu GluPheAla GlyAlaAla GlySerAla LysSerAla
3511  GTGAAACTG GAGTTTGCC GGGGCTGCA GGGTCAGCA AAATCGGCT
      AlaGlyThr AlaSerHis ValSerIle PheAlaMet ValIleGly
3556  GCGGGAACA GCCAGTCAC GTTTCCATT TTTGCCATG GTGATCGGA
      LeuIleGly SerIleAla AlaCysVal Ala
3601  CTTATTGGC TCTATCGCA GCTTGTGTC GCGTGAAAG CTTGGCACT
3646  GGCCGTCGT TTTACAACG TCGTGACTG GGAAAACCC TGGCGTTAC
3691  CCAACTTAA TCGCCTTGC AGCACATCC CCCTTTCGC CAGCTGGCG
3736  TAATAGCGA AGAGGCCCG CACCGATCG CCCTTCCCA ACAGTTGCG
3781  CAGCCTGAA TGGCGAATG GCAGCTTGG CTGTTTTGG CGGATGAGA
3826  TAAGATTTT CAGCCTGAT ACAGATTAA ATCAGAACG CAGAAGCGG
3871  TCTGATAAA ACAGAATTT GCCTGGCGG CAGTAGCGC GGTGGTCCC
3916  ACCTGACCC CATGCCGAA CTCAGAAGT GAAACGCCG TAGCGCCGA
3961  TGGTAGTGT GGGGTCTCC CCATGCGAG AGTAGGGAA CTGCCAGGC
4006  ATCAAATAA AACGAAAGG CTCAGTCGA AAGACTGGG CCTTTCGTT
```

FIG.5B pMBP-p2X-ToxoP30(52-336aa)

4051 TTATCTGTT GTTTGTCGG TGAACGCTC TCCTGAGTA GGACAAATC
4096 CGCCGGGAG CGGATTTGA ACGTTGCGA AGCAACGGC CCGGAGGGT
4141 GGCGGGCAG GACGCCCGC CATAAACTG CCAGGCATC AAATTAAGC
4186 AGAAGGCCA TCCTGACGG ATGGCCTTT TTGCGTTTC TACAAACTC
4231 TTTTTGTTT ATTTTTCTA AATACATTC AAATATGTA TCCGCTCAT
4276 GAGACAATA ACCCTGATA AATGCTTCA ATAATATTG AAAAAGGAA
4321 GAGTATGAG TATTCAACA TTTCCGTGT CGCCCTTAT TCCCTTTTT
4366 TGCGGCATT TTGCCTTCC TGTTTTTGC TCACCCAGA AACGCTGGT
4411 GAAAGTAAA AGATGCTGA AGATCAGTT GGGTGCACG AGTGGGTTA
4456 CATCGAACT GGATCTCAA CAGCGGTAA GATCCTTGA GAGTTTTCG
4501 CCCCGAAGA ACGTTCTCC AATGATGAG CACTTTTAA AGTTCTGCT
4546 ATGTGGCGC GGTATTATC CCGTGTTGA CGCCGGGCA AGAGCAACT
4591 CGGTCGCCG CATACACTA TTCTCAGAA TGACTTGGT TGAGTACTC
4636 ACCAGTCAC AGAAAAGCA TCTTACGGA TGGCATGAC AGTAAGAGA
4681 ATTATGCAG TGCTGCCAT AACCATGAG TGATAACAC TGCGGCCAA
4726 CTTACTTCT GACAACGAT CGGAGGACC GAAGGAGCT AACCGCTTT
4771 TTTGCACAA CATGGGGGA TCATGTAAC TCGCCTTGA TCGTTGGGA
4816 ACCGGAGCT GAATGAAGC CATACCAAA CGACGAGCG TGACACCAC
4861 GATGCCTGT AGCAATGGC AACAACGTT GCGCAAACT ATTAACTGG
4906 CGAACTACT TACTCTAGC TTCCCGGCA ACAATTAAT AGACTGGAT
4951 GGAGGCGGA TAAAGTTGC AGGACCACT TCTGCGCTC GGCCCTTCC
4996 GGCTGGCTG GTTTATTGC TGATAAATC TGGAGCCGG TGAGCGTGG
5041 GTCTCGCGG TATCATTGC AGCACTGGG GCCAGATGG TAAGCCCTC
5086 CCGTATCGT AGTTATCTA CACGACGGG GAGTCAGGC AACTATGGA
5131 TGAACGAAA TAGACAGAT CGCTGAGAT AGGTGCCTC ACTGATTAA
5176 GCATTGGTA ACTGTCAGA CCAAGTTTA CTCATATAT ACTTTAGAT
5221 TGATTTACC CCGGTTGAT AATCAGAAA AGCCCCAAA AACAGGAAG
5266 ATTGTATAA GCAAATATT TAAATTGTA AACGTTAAT ATTTTGTTA
5311 AAATTCGCG TTAAATTTT TGTTAAATC AGCTCATTT TTTAACCAA
5356 TAGGCCGAA ATCGGCAAA ATCCCTTAT AAATCAAAA GAATAGACC
5401 GAGATAGGG TTGAGTGTT GTTCCAGTT TGGAACAAG AGTCCACTA
5446 TTAAAGAAC GTGGACTCC AACGTCAAA GGGCGAAAA ACCGTCTAT
5491 CAGGGCGAT GGCCCACTA CGTGAACCA TCACCCAAA TCAAGTTTT
5536 TTGGGGTCG AGGTGCCGT AAAGCACTA AATCGGAAC CCTAAAGGG
5581 AGCCCCCGA TTTAGAGCT TGACGGGGA AAGCCGGCG AACGTGGCG
5626 AGAAAGGAA GGGAAGAAA GCGAAAGGA GCGGGCGCT AGGGCGCTG
5671 GCAAGTGTA GCGGTCACG CTGCGCGTA ACCACCACA CCCGCCGCG
5716 CTTAATGCG CCGCTACAG GGCGCGTAA AAGGATCTA GGTGAAGAT
5761 CCTTTTTGA TAATCTCAT GACCAAAAT CCCTTAACG TGAGTTTTC
5806 GTTCCACTG AGCGTCAGA CCCCGTAGA AAAGATCAA AGGATCTTC
5851 TTGAGATCC TTTTTTTCT GCGCGTAAT CTGCTGCTT GCAAACAAA
5896 AAAACCACC GCTACCAGC GGTGGTTTG TTTGCCGGA TCAAGAGCT
5941 ACCAACTCT TTTTCCGAA GGTAACTGG CTTCAGCAG AGCGCAGAT
5986 ACCAAATAC TGTCCTTCT AGTGTAGCC GTAGTTAGG CCACCACTT
6031 CAAGAACTC TGTAGCACC GCCTACATA CCTCGCTCT GCTAATCCT
6076 GTTACCAGT GGCTGCTGC CAGTGGCGA TAAGTCGTG TCTTACCGG

FIG.5C pMBP-p2X-ToxoP30(52-336aa)

6121 GTTGGACTC AAGACGATA GTTACCGGA TAAGGCGCA GCGGTCGGG
6166 CTGAACGGG GGGTTCGTG CACACAGCC CAGCTTGGA GCGAACGAC
6211 CTACACCGA ACTGAGATA CCTACAGCG TGAGCTATG AGAAAGCGC
6256 CACGCTTCC CGAAGGGAG AAAGGCGGA CAGGTATCC GGTAAGCGG
6301 CAGGGTCGG AACAGGAGA GCGCACGAG GGAGCTTCC AGGGGGAAA
6346 CGCCTGGTA TCTTTATAG TCCTGTCGG GTTTCGCCA CCTCTGACT
6391 TGAGCGTCG ATTTTTGTG ATGCTCGTC AGGGGGGCG GAGCCTATG
6436 GAAAAACGC CAGCAACGC GGCCTTTTT ACGGTTCCT GGCCTTTTG
6481 CTGGCCTTT TGCTCACAT GTTCTTTCC TGCGTTATC CCCTGATTC
6526 TGTGGATAA CCGTATTAC CGCCTTTGA GTGAGCTGA TACCGCTCG
6571 CCGCAGCCG AACGACCGA GCGCAGCGA GTCAGTGAG CGAGGAAGC
6616 GGAAGAGCG CCTGATGCG GTATTTTCT CCTTACGCA TCTGTGCGG
6661 TATTTCACA CCGCATATA TGGTGCACT CTCAGTACA ATCTGCTCT
6706 GATGCCGCA TAGTTAAGC CAGTATACA CTCCGCTAT CGCTACGTG
6751 ACTGGGTCA TGGCTGCGC CCCGACACC CGCCAACAC CCGCTGACG
6796 CGCCCTGAC GGGCTTGTC TGCTCCCGG CATCCGCTT ACAGACAAG
6841 CTGTGACCG TCTCCGGGA GCTGCATGT GTCAGAGGT TTTCACCGT
6886 CATCACCGA AACGCGCGA GGCAGCTGC GGTAAAGCT CATCAGCGT
6931 GGTCGTGCA GCGATTCAC AGATGTCTG CCTGTTCAT CCGCGTCCA
6976 GCTCGTTGA GTTTCTCCA GAAGCGTTA ATGTCTGGC TTCTGATAA
7021 AGCGGGCCA TGTTAAGGG CGGTTTTTT CCTGTTTGG TCACTGATG
7066 CCTCCGTGT AAGGGGGAT TTCTGTTCA TGGGGGTAA TGATACCGA
7111 TGAAACGAG AGAGGATGC TCACGATAC GGGTTACTG ATGATGAAC
7156 ATGCCCGGT TACTGGAAC GTTGTGAGG GTAAACAAC TGGCGGTAT
7201 GGATGCGGC GGGACCAGA GAAAAATCA CTCAGGGTC AATGCCAGC
7246 GCTTCGTTA ATACAGATG TAGGTGTTC CACAGGGTA GCCAGCAGC
7291 ATCCTGCGA TGCAGATCC GGAACATAA TGGTGCAGG GCGCTGACT
7336 TCCGCGTTT CCAGACTTT ACGAAACAC GGAAACCGA AGACCATTC
7381 ATGTTGTTG CTCAGGTCG CAGACGTTT TGCAGCAGC AGTCGCTTC
7426 ACGTTCGCT CGCGTATCG GTGATTCAT TCTGCTAAC CAGTAAGGC
7471 AACCCCGCC AGCCTAGCC GGGTCCTCA ACGACAGGA GCACGATCA
7516 TGCGCACCC GTGGCCAGG ACCCAACGC TGCCCGAAA TT

FIG.5D pMBP-c2X-ToxoP30del1C(52-324aa)

```
   1  CCGACACCA TCGAATGGT GCAAAACCT TTCGCGGTA TGGCATGAT
  46  AGCGCCCGG AAGAGAGTC AATTCAGGG TGGTGAATG TGAAACCAG
  91  TAACGTTAT ACGATGTCG CAGAGTATG CCGGTGTCT CTTATCAGA
 136  CCGTTTCCC GCGTGGTGA ACCAGGCCA GCCACGTTT CTGCGAAAA
 181  CGCGGGAAA AAGTGGAAG CGGCGATGG CGGAGCTGA ATTACATTC
 226  CCAACCGCG TGGCACAAC AACTGGCGG GCAAACAGT CGTTGCTGA
 271  TTGGCGTTG CCACCTCCA GTCTGGCCC TGCACGCGC CGTCGCAAA
 316  TTGTCGCGG CGATTAAAT CTCGCGCCG ATCAACTGG GTGCCAGCG
 361  TGGTGGTGT CGATGGTAG AACGAAGCG GCGTCGAAG CCTGTAAAG
 406  CGGCGGTGC ACAATCTTC TCGCGCAAC GCGTCAGTG GGCTGATCA
 451  TTAACTATC CGCTGGATG ACCAGGATG CCATTGCTG TGGAAGCTG
 496  CCTGCACTA ATGTTCCGG CGTTATTTC TTGATGTCT CTGACCAGA
 541  CACCCATCA ACAGTATTA TTTTCTCCC ATGAAGACG GTACGCGAC
 586  TGGGCGTGG AGCATCTGG TCGCATTGG GTCACCAGC AAATCGCGC
 631  TGTTAGCGG GCCCATTAA GTTCTGTCT CGGCGCGTC TGCGTCTGG
 676  CTGGCTGGC ATAAATATC TCACTCGCA ATCAAATTC AGCCGATAG
 721  CGGAACGGG AAGGCGACT GGAGTGCCA TGTCCGGTT TTCAACAAA
 766  CCATGCAAA TGCTGAATG AGGGCATCG TTCCCACTG CGATGCTGG
 811  TTGCCAACG ATCAGATGG CGCTGGGCG CAATGCGCG CCATTACCG
 856  AGTCCGGGC TGCGCGTTG GTGCGGATA TCTCGGTAG TGGGATACG
 901  ACGATACCG AAGACAGCT CATGTTATA TCCCGCCGT TAACCACCA
 946  TCAAACAGG ATTTTCGCC TGCTGGGGC AAACCAGCG TGGACCGCT
 991  TGCTGCAAC TCTCTCAGG GCCAGGCGG TGAAGGGCA ATCAGCTGT
1036  TGCCCGTCT CACTGGTGA AAAGAAAAA CCACCCTGG CGCCCAATA
1081  CGCAAACCG CCTCTCCCC GCGCGTTGG CCGATTCAT TAATGCAGC
1126  TGGCACGAC AGGTTTCCC GACTGGAAA GCGGGCAGT GAGCGCAAC
1171  GCAATTAAT GTAAGTTAG CTCACTCAT TAGGCACAA TTCTCATGT
1216  TTGACAGCT TATCATCGA CTGCACGGT GCACCAATG CTTCTGGCG
1261  TCAGGCAGC CATCGGAAG CTGTGGTAT GGCTGTGCA GGTCGTAAA
1306  TCACTGCAT AATTCGTGT CGCTCAAGG CGCACTCCC GTTCTGGAT
1351  AATGTTTTT TGCGCCGAC ATCATAACG GTTCTGGCA AATATTCTG
1396  AAATGAGCT GTTGACAAT TAATCATCG GCTCGTATA ATGTGTGGA
1441  ATTGTGAGC GGATAACAA TTTCACACA GGAAACAGC CAGTCCGTT
                                                  Met
1486  TAGGTGTTT TCACGAGCA CTTCACCAA CAAGGACCA TAGCATATG
      LysIleGlu GluGlyLys LeuValIle TrpIleAsn GlyAspLys
1531  AAAATCGAA GAAGGTAAA CTGGTAATC TGGATTAAC GGCGATAAA
      GlyTyrAsn GlyLeuAla GluValGly LysLysPhe GluLysAsp
1576  GGCTATAAC GGTCTCGCT GAAGTCGGT AAGAAATTC GAGAAAGAT
      ThrGlyIle LysValThr ValGluHis ProAspLys LeuGluGlu
1621  ACCGGAATT AAAGTCACC GTTGAGCAT CCGGATAAA CTGGAAGAG
      LysPhePro GlnValAla AlaThrGly AspGlyPro AspIleIle
1666  AAATTCCCA CAGGTTGCG GCAACTGGC GATGGCCCT GACATTATC
      PheTrpAla HisAspArg PheGlyGly TyrAlaGln SerGlyLeu
1711  TTCTGGGCA CACGACCGC TTTGGTGGC TACGCTCAA TCTGGCCTG
      LeuAlaGlu IleThrPro AspLysAla PheGlnAsp LysLeuTyr
```

FIG.8 pMBP-c2X-ToxoP30del1C(52-324aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.8A pMBP-c2X-ToxoP30del1C(52-324aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu PheAlaGly AlaAlaGly
3421 AAGCATCAC TGTACCGTG AAACTGGAG TTTGCCGGG GCTGCAGGG
     SerAlaLys SerAlaAla GlyThrAla SerHisVal SerIlePhe
3466 TCAGCAAAA TCGGCTGCG GGAACAGCC AGTCACGTT TCCATTTTT
     AlaMetVal
3511 GCCATGGTG TGAAAGCTT GGCACTGGC CGTCGTTTT ACAACGTCG
3556 TGACTGGGA AAACCCTGG CGTTACCCA ACTTAATCG CCTTGCAGC
3601 ACATCCCCC TTTCGCCAG CTGGCGTAA TAGCGAAGA GGCCCGCAC
3646 CGATCGCCC TTCCCAACA GTTGCGCAG CCTGAATGG CGAATGGCA
3691 GCTTGGCTG TTTTGGCGG ATGAGATAA GATTTTCAG CCTGATACA
3736 GATTAAATC AGAACGCAG AAGCGGTCT GATAAAACA GAATTTGCC
3781 TGGCGGCAG TAGCGCGGT GGTCCCACC TGACCCCAT GCCGAACTC
3826 AGAAGTGAA ACGCCGTAG CGCCGATGG TAGTGTGGG GTCTCCCCA
3871 TGCGAGAGT AGGGAACTG CCAGGCATC AAATAAAAC GAAAGGCTC
3916 AGTCGAAAG ACTGGGCCT TTCGTTTTA TCTGTTGTT TGTCGGTGA
3961 ACGCTCTCC TGAGTAGGA CAAATCCGC CGGGAGCGG ATTTGAACG
4006 TTGCGAAGC AACGGCCCG GAGGGTGGC GGGCAGGAC GCCCGCCAT
4051 AAACTGCCA GGCATCAAA TTAAGCAGA AGGCCATCC TGACGGATG
4096 GCCTTTTTG CGTTTCTAC AAACTCTTT TTGTTTATT TTTCTAAAT
```

FIG.8B pMBP-c2X-ToxoP30del1C(52-324aa)

```
4141 ACATTCAAA TATGTATCC GCTCATGAG ACAATAACC CTGATAAAT
4186 GCTTCAATA ATATTGAAA AAGGAAGAG TATGAGTAT TCAACATTT
4231 CCGTGTCGC CCTTATTCC CTTTTTTGC GGCATTTTG CCTTCCTGT
4276 TTTTGCTCA CCCAGAAAC GCTGGTGAA AGTAAAAGA TGCTGAAGA
4321 TCAGTTGGG TGCACGAGT GGGTTACAT CGAACTGGA TCTCAACAG
4366 CGGTAAGAT CCTTGAGAG TTTTCGCCC CGAAGAACG TTCTCCAAT
4411 GATGAGCAC TTTTAAAGT TCTGCTATG TGGCGCGGT ATTATCCCG
4456 TGTTGACGC CGGGCAAGA GCAACTCGG TCGCCGCAT ACACTATTC
4501 TCAGAATGA CTTGGTTGA GTACTCACC AGTCACAGA AAAGCATCT
4546 TACGGATGG CATGACAGT AAGAGAATT ATGCAGTGC TGCCATAAC
4591 CATGAGTGA TAACACTGC GGCCAACTT ACTTCTGAC AACGATCGG
4636 AGGACCGAA GGAGCTAAC CGCTTTTTT GCACAACAT GGGGGATCA
4681 TGTAACTCG CCTTGATCG TTGGGAACC GGAGCTGAA TGAAGCCAT
4726 ACCAAACGA CGAGCGTGA CACCACGAT GCCTGTAGC AATGGCAAC
4771 AACGTTGCG CAAACTATT AACTGGCGA ACTACTTAC TCTAGCTTC
4816 CCGGCAACA ATTAATAGA CTGGATGGA GGCGGATAA AGTTGCAGG
4861 ACCACTTCT GCGCTCGGC CCTTCCGGC TGGCTGGTT TATTGCTGA
4906 TAAATCTGG AGCCGGTGA GCGTGGGTC TCGCGGTAT CATTGCAGC
4951 ACTGGGGCC AGATGGTAA GCCCTCCCG TATCGTAGT TATCTACAC
4996 GACGGGGAG TCAGGCAAC TATGGATGA ACGAAATAG ACAGATCGC
5041 TGAGATAGG TGCCTCACT GATTAAGCA TTGGTAACT GTCAGACCA
5086 AGTTTACTC ATATATACT TTAGATTGA TTTACCCCG GTTGATAAT
5131 CAGAAAAGC CCCAAAAAC AGGAAGATT GTATAAGCA AATATTTAA
5176 ATTGTAAAC GTTAATATT TTGTTAAAA TTCGCGTTA AATTTTTGT
5221 TAAATCAGC TCATTTTTT AACCAATAG GCCGAAATC GGCAAAATC
5266 CCTTATAAA TCAAAAGAA TAGACCGAG ATAGGGTTG AGTGTTGTT
5311 CCAGTTTGG AACAAGAGT CCACTATTA AAGAACGTG GACTCCAAC
5356 GTCAAAGGG CGAAAAACC GTCTATCAG GGCGATGGC CCACTACGT
5401 GAACCATCA CCCAAATCA AGTTTTTTG GGGTCGAGG TGCCGTAAA
5446 GCACTAAAT CGGAACCCT AAAGGGAGC CCCCGATTT AGAGCTTGA
5491 CGGGGAAAG CCGGCGAAC GTGGCGAGA AAGGAAGGG AAGAAAGCG
5536 AAAGGAGCG GGCGCTAGG GCGCTGGCA AGTGTAGCG GTCACGCTG
5581 CGCGTAACC ACCACACCC GCCGCGCTT AATGCGCCG CTACAGGGC
5626 GCGTAAAAG GATCTAGGT GAAGATCCT TTTTGATAA TCTCATGAC
5671 CAAAATCCC TTAACGTGA GTTTTCGTT CCACTGAGC GTCAGACCC
5716 CGTAGAAAA GATCAAAGG ATCTTCTTG AGATCCTTT TTTTCTGCG
5761 CGTAATCTG CTGCTTGCA AACAAAAAA ACCACCGCT ACCAGCGGT
5806 GGTTTGTTT GCCGGATCA AGAGCTACC AACTCTTTT TCCGAAGGT
5851 AACTGGCTT CAGCAGAGC GCAGATACC AAATACTGT CCTTCTAGT
5896 GTAGCCGTA GTTAGGCCA CCACTTCAA GAACTCTGT AGCACCGCC
5941 TACATACCT CGCTCTGCT AATCCTGTT ACCAGTGGC TGCTGCCAG
5986 TGGCGATAA GTCGTGTCT TACCGGGTT GGACTCAAG ACGATAGTT
6031 ACCGGATAA GGCGCAGCG GTCGGGCTG AACGGGGGG TTCGTGCAC
6076 ACAGCCCAG CTTGGAGCG AACGACCTA CACCGAACT GAGATACCT
6121 ACAGCGTGA GCTATGAGA AAGCGCCAC GCTTCCCGA AGGGAGAAA
6166 GGCGGACAG GTATCCGGT AAGCGGCAG GGTCGGAAC AGGAGAGCG
```

FIG.8C pMBP-c2X-ToxoP30del1C(52-324aa)

```
6211  CACGAGGGA GCTTCCAGG GGGAAACGC CTGGTATCT TTATAGTCC
6256  TGTCGGGTT TCGCCACCT CTGACTTGA GCGTCGATT TTTGTGATG
6301  CTCGTCAGG GGGGCGGAG CCTATGGAA AAACGCCAG CAACGCGGC
6346  CTTTTTACG GTTCCTGGC CTTTTGCTG GCCTTTTGC TCACATGTT
6391  CTTTCCTGC GTTATCCCC TGATTCTGT GGATAACCG TATTACCGC
6436  CTTTGAGTG AGCTGATAC CGCTCGCCG CAGCCGAAC GACCGAGCG
6481  CAGCGAGTC AGTGAGCGA GGAAGCGGA AGAGCGCCT GATGCGGTA
6526  TTTTCTCCT TACGCATCT GTGCGGTAT TTCACACCG CATATATGG
6571  TGCACTCTC AGTACAATC TGCTCTGAT GCCGCATAG TTAAGCCAG
6616  TATACACTC CGCTATCGC TACGTGACT GGGTCATGG CTGCGCCCC
6661  GACACCCGC CAACACCCG CTGACGCGC CCTGACGGG CTTGTCTGC
6706  TCCCGGCAT CCGCTTACA GACAAGCTG TGACCGTCT CCGGGAGCT
6751  GCATGTGTC AGAGGTTTT CACCGTCAT CACCGAAAC GCGCGAGGC
6796  AGCTGCGGT AAAGCTCAT CAGCGTGGT CGTGCAGCG ATTCACAGA
6841  TGTCTGCCT GTTCATCCG CGTCCAGCT CGTTGAGTT TCTCCAGAA
6886  GCGTTAATG TCTGGCTTC TGATAAAGC GGGCCATGT TAAGGGCGG
6931  TTTTTTCCT GTTTGGTCA CTGATGCCT CCGTGTAAG GGGGATTTC
6976  TGTTCATGG GGGTAATGA TACCGATGA AACGAGAGA GGATGCTCA
7021  CGATACGGG TTACTGATG ATGAACATG CCCGGTTAC TGGAACGTT
7066  GTGAGGGTA AACAACTGG CGGTATGGA TGCGGCGGG ACCAGAGAA
7111  AAATCACTC AGGGTCAAT GCCAGCGCT TCGTTAATA CAGATGTAG
7156  GTGTTCCAC AGGGTAGCC AGCAGCATC CTGCGATGC AGATCCGGA
7201  ACATAATGG TGCAGGGCG CTGACTTCC GCGTTTCCA GACTTTACG
7246  AAACACGGA AACCGAAGA CCATTCATG TTGTTGCTC AGGTCGCAG
7291  ACGTTTTGC AGCAGCAGT CGCTTCACG TTCGCTCGC GTATCGGTG
7336  ATTCATTCT GCTAACCAG TAAGGCAAC CCCGCCAGC CTAGCCGGG
7381  TCCTCAACG ACAGGAGCA CGATCATGC GCACCCGTG GCCAGGACC
7426  CAACGCTGC CCGAAATT
```

FIG.8D

ToxoP30del1C(52-324aa)

| | | | | | |
|---|---|---|---|---|---|
| | LeuValAla | AsnGlnVal | ValThrCys | ProAspLys | LysSerThr |
| 1 | CTTGTTGCC | AATCAAGTT | GTCACCTGC | CCAGATAAA | AAATCGACA |
| | AlaAlaVal | IleLeuThr | ProThrGlu | AsnHisPhe | ThrLeuLys |
| 46 | GCCGCGGTC | ATTCTCACA | CCGACGGAG | AACCACTTC | ACTCTCAAG |
| | CysProLys | ThrAlaLeu | ThrGluPro | ProThrLeu | AlaTyrSer |
| 91 | TGCCCTAAA | ACAGCGCTC | ACAGAGCCT | CCCACTCTT | GCGTACTCA |
| | ProAsnArg | GlnIleCys | ProAlaGly | ThrThrSer | SerCysThr |
| 136 | CCCAACAGG | CAAATCTGC | CCAGCGGGT | ACTACAAGT | AGCTGTACA |
| | SerLysAla | ValThrLeu | SerSerLeu | IleProGlu | AlaGluAsp |
| 181 | TCAAAGGCT | GTAACATTG | AGCTCCTTG | ATTCCTGAA | GCAGAAGAT |
| | SerTrpTrp | ThrGlyAsp | SerAlaSer | LeuAspThr | AlaGlyIle |
| 226 | AGCTGGTGG | ACGGGGGAT | TCTGCTAGT | CTCGACACG | GCAGGCATC |
| | LysLeuThr | ValProIle | GluLysPhe | ProValThr | ThrGlnThr |
| 271 | AAACTCACA | GTTCCAATC | GAGAAGTTC | CCCGTGACA | ACGCAGACG |
| | PheValVal | GlyCysIle | LysGlyAsp | AspAlaGln | SerCysMet |
| 316 | TTTGTGGTC | GGTTGCATC | AAGGGAGAC | GACGCACAG | AGTTGTATG |
| | ValThrVal | ThrValGln | AlaArgAla | SerSerVal | ValAsnAsn |
| 361 | GTCACAGTG | ACAGTACAA | GCCAGAGCC | TCATCGGTC | GTCAATAAT |
| | ValAlaArg | CysSerTyr | GlyAlaAsp | SerThrLeu | GlyProVal |
| 406 | GTCGCAAGG | TGCTCCTAC | GGTGCAGAC | AGCACTCTT | GGTCCTGTC |
| | LysLeuSer | AlaGluGly | ProThrThr | MetThrLeu | ValCysGly |
| 451 | AAGTTGTCT | GCGGAAGGA | CCCACTACA | ATGACCCTC | GTGTGCGGG |
| | LysAspGly | ValLysVal | ProGlnAsp | AsnAsnGln | TyrCysSer |
| 496 | AAAGATGGA | GTCAAAGTT | CCTCAAGAC | AACAATCAG | TACTGTTCC |
| | GlyThrThr | LeuThrGly | CysAsnGlu | LysSerPhe | LysAspIle |
| 541 | GGGACGACG | CTGACTGGT | TGCAACGAG | AAATCGTTC | AAAGATATT |
| | LeuProLys | LeuThrGlu | AsnProTrp | GlnGlyAsn | AlaSerSer |
| 586 | TTGCCAAAA | TTAACTGAG | AACCCGTGG | CAGGGTAAC | GCTTCGAGT |
| | AspLysGly | AlaThrLeu | ThrIleLys | LysGluAla | PheProAla |
| 631 | GATAAGGGT | GCCACGCTA | ACGATCAAG | AAGGAAGCA | TTTCCAGCC |
| | GluSerLys | SerValIle | IleGlyCys | ThrGlyGly | SerProGlu |
| 676 | GAGTCAAAA | AGCGTCATT | ATTGGATGC | ACAGGGGGA | TCGCCTGAG |
| | LysHisHis | CysThrVal | LysLeuGlu | PheAlaGly | AlaAlaGly |
| 721 | AAGCATCAC | TGTACCGTG | AAACTGGAG | TTTGCCGGG | GCTGCAGGG |
| | SerAlaLys | SerAlaAla | GlyThrAla | SerHisVal | SerIlePhe |
| 766 | TCAGCAAAA | TCGGCTGCG | GGAACAGCC | AGTCACGTT | TCCATTTTT |
| | AlaMetVal | | | | |
| 811 | GCCATGGTG | | | | |

FIG. 9 pMBP-c2X-ToxoP30del2(52-311aa)

1 CCGACACCA TCGAATGGT GCAAAACCT TTCGCGGTA TGGCATGAT
46 AGCGCCCGG AAGAGAGTC AATTCAGGG TGGTGAATG TGAAACCAG
91 TAACGTTAT ACGATGTCG CAGAGTATG CCGGTGTCT CTTATCAGA
136 CCGTTTCCC GCGTGGTGA ACCAGGCCA GCCACGTTT CTGCGAAAA
181 CGCGGGAAA AAGTGGAAG CGGCGATGG CGGAGCTGA ATTACATTC
226 CCAACCGCG TGGCACAAC AACTGGCGG GCAAACAGT CGTTGCTGA
271 TTGGCGTTG CCACCTCCA GTCTGGCCC TGCACGCGC CGTCGCAAA
316 TTGTCGCGG CGATTAAAT CTCGCGCCG ATCAACTGG GTGCCAGCG
361 TGGTGGTGT CGATGGTAG AACGAAGCG GCGTCGAAG CCTGTAAAG
406 CGGCGGTGC ACAATCTTC TCGCGCAAC GCGTCAGTG GGCTGATCA
451 TTAACTATC CGCTGGATG ACCAGGATG CCATTGCTG TGGAAGCTG
496 CCTGCACTA ATGTTCCGG CGTTATTTC TTGATGTCT CTGACCAGA
541 CACCCATCA ACAGTATTA TTTTCTCCC ATGAAGACG GTACGCGAC
586 TGGGCGTGG AGCATCTGG TCGCATTGG GTCACCAGC AAATCGCGC
631 TGTTAGCGG GCCCATTAA GTTCTGTCT CGGCGCGTC TGCGTCTGG
676 CTGGCTGGC ATAAATATC TCACTCGCA ATCAAATTC AGCCGATAG
721 CGGAACGGG AAGGCGACT GGAGTGCCA TGTCCGGTT TTCAACAAA
766 CCATGCAAA TGCTGAATG AGGGCATCG TTCCCACTG CGATGCTGG
811 TTGCCAACG ATCAGATGG CGCTGGGCG CAATGCGCG CCATTACCG
856 AGTCCGGGC TGCGCGTTG GTGCGGATA TCTCGGTAG TGGGATACG
901 ACGATACCG AAGACAGCT CATGTTATA TCCCGCCGT TAACCACCA
946 TCAAACAGG ATTTTCGCC TGCTGGGGC AAACCAGCG TGGACCGCT
991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
Met
1486 TAGGTGTTT TCACGAGCA CTTCACCAA CAAGGACCA TAGCATATG
LysIleGlu GluGlyLys LeuValIle TrpIleAsn GlyAspLys
1531 AAAATCGAA GAAGGTAAA CTGGTAATC TGGATTAAC GGCGATAAA
GlyTyrAsn GlyLeuAla GluValGly LysLysPhe GluLysAsp
1576 GGCTATAAC GGTCTCGCT GAAGTCGGT AAGAAATTC GAGAAAGAT
ThrGlyIle LysValThr ValGluHis ProAspLys LeuGluGlu
1621 ACCGGAATT AAAGTCACC GTTGAGCAT CCGGATAAA CTGGAAGAG
LysPhePro GlnValAla AlaThrGly AspGlyPro AspIleIle
1666 AAATTCCCA CAGGTTGCG GCAACTGGC GATGGCCCT GACATTATC
PheTrpAla HisAspArg PheGlyGly TyrAlaGln SerGlyLeu
1711 TTCTGGGCA CACGACCGC TTTGGTGGC TACGCTCAA TCTGGCCTG
LeuAlaGlu IleThrPro AspLysAla PheGlnAsp LysLeuTyr

FIG. 11 pMBP-c2X-ToxoP30del2(52-311aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.11A pMBP-c2X-ToxoP30del2(52-311aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu PheAlaGly AlaAlaGly
3421 AAGCATCAC TGTACCGTG AAACTGGAG TTTGCCGGG GCTGCAGGG
     SerAlaLys SerAla
3466 TCAGCAAAA TCGGCTTGA AAGCTTGGC ACTGGCCGT CGTTTTACA
3511 ACGTCGTGA CTGGGAAAA CCCTGGCGT TACCCAACT TAATCGCCT
3556 TGCAGCACA TCCCCCTTT CGCCAGCTG GCGTAATAG CGAAGAGGC
3601 CCGCACCGA TCGCCCTTC CCAACAGTT GCGCAGCCT GAATGGCGA
3646 ATGGCAGCT TGGCTGTTT TGGCGGATG AGATAAGAT TTTCAGCCT
3691 GATACAGAT TAAATCAGA ACGCAGAAG CGGTCTGAT AAAACAGAA
3736 TTTGCCTGG CGGCAGTAG CGCGGTGGT CCCACCTGA CCCCATGCC
3781 GAACTCAGA AGTGAAACG CCGTAGCGC CGATGGTAG TGTGGGGTC
3826 TCCCCATGC GAGAGTAGG GAACTGCCA GGCATCAAA TAAAACGAA
3871 AGGCTCAGT CGAAAGACT GGGCCTTTC GTTTTATCT GTTGTTTGT
3916 CGGTGAACG CTCTCCTGA GTAGGACAA ATCCGCCGG GAGCGGATT
3961 TGAACGTTG CGAAGCAAC GGCCCGGAG GGTGGCGGG CAGGACGCC
4006 CGCCATAAA CTGCCAGGC ATCAAATTA AGCAGAAGG CCATCCTGA
4051 CGGATGGCC TTTTTGCGT TTCTACAAA CTCTTTTTG TTTATTTTT
4096 CTAAATACA TTCAAATAT GTATCCGCT CATGAGACA ATAACCCTG
4141 ATAAATGCT TCAATAATA TTGAAAAAG GAAGAGTAT GAGTATTCA
```

FIG.11B pMBP-c2X-ToxoP30del2(52-311aa)

| | | | | | |
|---|---|---|---|---|---|
| 4186 | ACATTTCCG | TGTCGCCCT | TATTCCCTT | TTTTGCGGC | ATTTTGCCT |
| 4231 | TCCTGTTTT | TGCTCACCC | AGAAACGCT | GGTGAAAGT | AAAAGATGC |
| 4276 | TGAAGATCA | GTTGGGTGC | ACGAGTGGG | TTACATCGA | ACTGGATCT |
| 4321 | CAACAGCGG | TAAGATCCT | TGAGAGTTT | TCGCCCCGA | AGAACGTTC |
| 4366 | TCCAATGAT | GAGCACTTT | TAAAGTTCT | GCTATGTGG | CGCGGTATT |
| 4411 | ATCCCGTGT | TGACGCCGG | GCAAGAGCA | ACTCGGTCG | CCGCATACA |
| 4456 | CTATTCTCA | GAATGACTT | GGTTGAGTA | CTCACCAGT | CACAGAAAA |
| 4501 | GCATCTTAC | GGATGGCAT | GACAGTAAG | AGAATTATG | CAGTGCTGC |
| 4546 | CATAACCAT | GAGTGATAA | CACTGCGGC | CAACTTACT | TCTGACAAC |
| 4591 | GATCGGAGG | ACCGAAGGA | GCTAACCGC | TTTTTTGCA | CAACATGGG |
| 4636 | GGATCATGT | AACTCGCCT | TGATCGTTG | GGAACCGGA | GCTGAATGA |
| 4681 | AGCCATACC | AAACGACGA | GCGTGACAC | CACGATGCC | TGTAGCAAT |
| 4726 | GGCAACAAC | GTTGCGCAA | ACTATTAAC | TGGCGAACT | ACTTACTCT |
| 4771 | AGCTTCCCG | GCAACAATT | AATAGACTG | GATGGAGGC | GGATAAAGT |
| 4816 | TGCAGGACC | ACTTCTGCG | CTCGGCCCT | TCCGGCTGG | CTGGTTTAT |
| 4861 | TGCTGATAA | ATCTGGAGC | CGGTGAGCG | TGGGTCTCG | CGGTATCAT |
| 4906 | TGCAGCACT | GGGGCCAGA | TGGTAAGCC | CTCCCGTAT | CGTAGTTAT |
| 4951 | CTACACGAC | GGGGAGTCA | GGCAACTAT | GGATGAACG | AAATAGACA |
| 4996 | GATCGCTGA | GATAGGTGC | CTCACTGAT | TAAGCATTG | GTAACTGTC |
| 5041 | AGACCAAGT | TTACTCATA | TATACTTTA | GATTGATTT | ACCCCGGTT |
| 5086 | GATAATCAG | AAAAGCCCC | AAAAACAGG | AAGATTGTA | TAAGCAAAT |
| 5131 | ATTTAAATT | GTAAACGTT | AATATTTTG | TTAAAATTC | GCGTTAAAT |
| 5176 | TTTTGTTAA | ATCAGCTCA | TTTTTTAAC | CAATAGGCC | GAAATCGGC |
| 5221 | AAAATCCCT | TATAAATCA | AAAGAATAG | ACCGAGATA | GGGTTGAGT |
| 5266 | GTTGTTCCA | GTTTGGAAC | AAGAGTCCA | CTATTAAAG | AACGTGGAC |
| 5311 | TCCAACGTC | AAAGGGCGA | AAAACCGTC | TATCAGGGC | GATGGCCCA |
| 5356 | CTACGTGAA | CCATCACCC | AAATCAAGT | TTTTTGGGG | TCGAGGTGC |
| 5401 | CGTAAAGCA | CTAAATCGG | AACCCTAAA | GGGAGCCCC | CGATTTAGA |
| 5446 | GCTTGACGG | GGAAAGCCG | GCGAACGTG | GCGAGAAAG | GAAGGGAAG |
| 5491 | AAAGCGAAA | GGAGCGGGC | GCTAGGGCG | CTGGCAAGT | GTAGCGGTC |
| 5536 | ACGCTGCGC | GTAACCACC | ACACCCGCC | GCGCTTAAT | GCGCCGCTA |
| 5581 | CAGGGCGCG | TAAAAGGAT | CTAGGTGAA | GATCCTTTT | TGATAATCT |
| 5626 | CATGACCAA | AATCCCTTA | ACGTGAGTT | TTCGTTCCA | CTGAGCGTC |
| 5671 | AGACCCCGT | AGAAAAGAT | CAAAGGATC | TTCTTGAGA | TCCTTTTTT |
| 5716 | TCTGCGCGT | AATCTGCTG | CTTGCAAAC | AAAAAAACC | ACCGCTACC |
| 5761 | AGCGGTGGT | TTGTTTGCC | GGATCAAGA | GCTACCAAC | TCTTTTTCC |
| 5806 | GAAGGTAAC | TGGCTTCAG | CAGAGCGCA | GATACCAAA | TACTGTCCT |
| 5851 | TCTAGTGTA | GCCGTAGTT | AGGCCACCA | CTTCAAGAA | CTCTGTAGC |
| 5896 | ACCGCCTAC | ATACCTCGC | TCTGCTAAT | CCTGTTACC | AGTGGCTGC |
| 5941 | TGCCAGTGG | CGATAAGTC | GTGTCTTAC | CGGGTTGGA | CTCAAGACG |
| 5986 | ATAGTTACC | GGATAAGGC | GCAGCGGTC | GGGCTGAAC | GGGGGGTTC |
| 6031 | GTGCACACA | GCCCAGCTT | GGAGCGAAC | GACCTACAC | CGAACTGAG |
| 6076 | ATACCTACA | GCGTGAGCT | ATGAGAAAG | CGCCACGCT | TCCCGAAGG |
| 6121 | GAGAAAGGC | GGACAGGTA | TCCGGTAAG | CGGCAGGGT | CGGAACAGG |
| 6166 | AGAGCGCAC | GAGGGAGCT | TCCAGGGGG | AAACGCCTG | GTATCTTTA |
| 6211 | TAGTCCTGT | CGGGTTTCG | CCACCTCTG | ACTTGAGCG | TCGATTTTT |

FIG. 11C pMBP-c2X-ToxoP30del2(52-311aa)

```
6256 GTGATGCTC GTCAGGGGG GCGGAGCCT ATGGAAAAA CGCCAGCAA
6301 CGCGGCCTT TTTACGGTT CCTGGCCTT TTGCTGGCC TTTTGCTCA
6346 CATGTTCTT TCCTGCGTT ATCCCCTGA TTCTGTGGA TAACCGTAT
6391 TACCGCCTT TGAGTGAGC TGATACCGC TCGCCGCAG CCGAACGAC
6436 CGAGCGCAG CGAGTCAGT GAGCGAGGA AGCGGAAGA GCGCCTGAT
6481 GCGGTATTT TCTCCTTAC GCATCTGTG CGGTATTTC ACACCGCAT
6526 ATATGGTGC ACTCTCAGT ACAATCTGC TCTGATGCC GCATAGTTA
6571 AGCCAGTAT ACACTCCGC TATCGCTAC GTGACTGGG TCATGGCTG
6616 CGCCCCGAC ACCCGCCAA CACCCGCTG ACGCGCCCT GACGGGCTT
6661 GTCTGCTCC CGGCATCCG CTTACAGAC AAGCTGTGA CCGTCTCCG
6706 GGAGCTGCA TGTGTCAGA GGTTTTCAC CGTCATCAC CGAAACGCG
6751 CGAGGCAGC TGCGGTAAA GCTCATCAG CGTGGTCGT GCAGCGATT
6796 CACAGATGT CTGCCTGTT CATCCGCGT CCAGCTCGT TGAGTTTCT
6841 CCAGAAGCG TTAATGTCT GGCTTCTGA TAAAGCGGG CCATGTTAA
6886 GGGCGGTTT TTTCCTGTT TGGTCACTG ATGCCTCCG TGTAAGGGG
6931 GATTTCTGT TCATGGGGG TAATGATAC CGATGAAAC GAGAGAGGA
6976 TGCTCACGA TACGGGTTA CTGATGATG AACATGCCC GGTTACTGG
7021 AACGTTGTG AGGGTAAAC AACTGGCGG TATGGATGC GGCGGGACC
7066 AGAGAAAAA TCACTCAGG GTCAATGCC AGCGCTTCG TTAATACAG
7111 ATGTAGGTG TTCCACAGG GTAGCCAGC AGCATCCTG CGATGCAGA
7156 TCCGGAACA TAATGGTGC AGGGCGCTG ACTTCCGCG TTTCCAGAC
7201 TTTACGAAA CACGGAAAC CGAAGACCA TTCATGTTG TTGCTCAGG
7246 TCGCAGACG TTTTGCAGC AGCAGTCGC TTCACGTTC GCTCGCGTA
7291 TCGGTGATT CATTCTGCT AACCAGTAA GGCAACCCC GCCAGCCTA
7336 GCCGGGTCC TCAACGACA GGAGCACGA TCATGCGCA CCCGTGGCC
7381 AGGACCCAA CGCTGCCCG AAATT
```

FIG. 11D

ToxoP30del2(52-311aa)

```
    LeuValAla AsnGlnVal ValThrCys ProAspLys LysSerThr
1   CTTGTTGCC AATCAAGTT GTCACCTGC CCAGATAAA AAATCGACA
    AlaAlaVal IleLeuThr ProThrGlu AsnHisPhe ThrLeuLys
46  GCCGCGGTC ATTCTCACA CCGACGGAG AACCACTTC ACTCTCAAG
    CysProLys ThrAlaLeu ThrGluPro ProThrLeu AlaTyrSer
91  TGCCCTAAA ACAGCGCTC ACAGAGCCT CCCACTCTT GCGTACTCA
    ProAsnArg GlnIleCys ProAlaGly ThrThrSer SerCysThr
136 CCCAACAGG CAAATCTGC CCAGCGGGT ACTACAAGT AGCTGTACA
    SerLysAla ValThrLeu SerSerLeu IleProGlu AlaGluAsp
181 TCAAAGGCT GTAACATTG AGCTCCTTG ATTCCTGAA GCAGAAGAT
    SerTrpTrp ThrGlyAsp SerAlaSer LeuAspThr AlaGlyIle
226 AGCTGGTGG ACGGGGGAT TCTGCTAGT CTCGACACG GCAGGCATC
    LysLeuThr ValProIle GluLysPhe ProValThr ThrGlnThr
271 AAACTCACA GTTCCAATC GAGAAGTTC CCCGTGACA ACGCAGACG
    PheValVal GlyCysIle LysGlyAsp AspAlaGln SerCysMet
316 TTTGTGGTC GGTTGCATC AAGGGAGAC GACGCACAG AGTTGTATG
    ValThrVal ThrValGln AlaArgAla SerSerVal ValAsnAsn
361 GTCACAGTG ACAGTACAA GCCAGAGCC TCATCGGTC GTCAATAAT
    ValAlaArg CysSerTyr GlyAlaAsp SerThrLeu GlyProVal
406 GTCGCAAGG TGCTCCTAC GGTGCAGAC AGCACTCTT GGTCCTGTC
    LysLeuSer AlaGluGly ProThrThr MetThrLeu ValCysGly
451 AAGTTGTCT GCGGAAGGA CCCACTACA ATGACCCTC GTGTGCGGG
    LysAspGly ValLysVal ProGlnAsp AsnAsnGln TyrCysSer
496 AAAGATGGA GTCAAAGTT CCTCAAGAC AACAATCAG TACTGTTCC
    GlyThrThr LeuThrGly CysAsnGlu LysSerPhe LysAspIle
541 GGGACGACG CTGACTGGT TGCAACGAG AAATCGTTC AAAGATATT
    LeuProLys LeuThrGlu AsnProTrp GlnGlyAsn AlaSerSer
586 TTGCCAAAA TTAACTGAG AACCCGTGG CAGGGTAAC GCTTCGAGT
    AspLysGly AlaThrLeu ThrIleLys LysGluAla PheProAla
631 GATAAGGGT GCCACGCTA ACGATCAAG AAGGAAGCA TTTCCAGCC
    GluSerLys SerValIle IleGlyCys ThrGlyGly SerProGlu
676 GAGTCAAAA AGCGTCATT ATTGGATGC ACAGGGGGA TCGCCTGAG
    LysHisHis CysThrVal LysLeuGlu PheAlaGly AlaAlaGly
721 AAGCATCAC TGTACCGTG AAACTGGAG TTTGCCGGG GCTGCAGGG
    SerAlaLys SerAla
766 TCAGCAAAA TCGGCT
```

FIG.12 pMBP-c2X-ToxoP30del3C(52-300aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.15 pMBP-c2X-ToxoP30del3C(52-300aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG. 15A pMBP-c2X-ToxoP30del3C(52-300aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGluGly ProThrThr MetThrLeu ValCysGly
3151  AAGTTGTCT GCGGAAGGA CCCACTACA ATGACCCTC GTGTGCGGG
      LysAspGly ValLysVal ProGlnAsp AsnAsnGln TyrCysSer
3196  AAAGATGGA GTCAAAGTT CCTCAAGAC AACAATCAG TACTGTTCC
      GlyThrThr LeuThrGly CysAsnGlu LysSerPhe LysAspIle
3241  GGGACGACG CTGACTGGT TGCAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGlyCys ThrGlyGly SerProGlu
3376  GAGTCAAAA AGCGTCATT ATTGGATGC ACAGGGGGA TCGCCTGAG
      LysHisHis CysThrVal LysLeuGlu
3421  AAGCATCAC TGTACCGTG AAACTGGAG TGAAAGCTT GGCACTGGC
3466  CGTCGTTTT ACAACGTCG TGACTGGGA AAACCCTGG CGTTACCCA
3511  ACTTAATCG CCTTGCAGC ACATCCCCC TTTCGCCAG CTGGCGTAA
3556  TAGCGAAGA GGCCCGCAC CGATCGCCC TTCCCAACA GTTGCGCAG
3601  CCTGAATGG CGAATGGCA GCTTGGCTG TTTTGGCGG ATGAGATAA
3646  GATTTTCAG CCTGATACA GATTAAATC AGAACGCAG AAGCGGTCT
3691  GATAAAACA GAATTTGCC TGGCGGCAG TAGCGCGGT GGTCCCACC
3736  TGACCCCAT GCCGAACTC AGAAGTGAA ACGCCGTAG CGCCGATGG
3781  TAGTGTGGG GTCTCCCCA TGCGAGAGT AGGGAACTG CCAGGCATC
3826  AAATAAAAC GAAAGGCTC AGTCGAAAG ACTGGGCCT TTCGTTTTA
3871  TCTGTTGTT TGTCGGTGA ACGCTCTCC TGAGTAGGA CAAATCCGC
3916  CGGGAGCGG ATTTGAACG TTGCGAAGC AACGGCCCG GAGGGTGGC
3961  GGGCAGGAC GCCCGCCAT AAACTGCCA GGCATCAAA TTAAGCAGA
4006  AGGCCATCC TGACGGATG GCCTTTTTG CGTTTCTAC AAACTCTTT
4051  TTGTTTATT TTTCTAAAT ACATTCAAA TATGTATCC GCTCATGAG
4096  ACAATAACC CTGATAAAT GCTTCAATA ATATTGAAA AAGGAAGAG
4141  TATGAGTAT TCAACATTT CCGTGTCGC CCTTATTCC CTTTTTTGC
4186  GGCATTTTG CCTTCCTGT TTTTGCTCA CCCAGAAAC GCTGGTGAA
```

FIG. 15B pMBP-c2X-ToxoP30del3C(52-300aa)

| | | | | | |
|---|---|---|---|---|---|
| 4231 | AGTAAAAGA | TGCTGAAGA | TCAGTTGGG | TGCACGAGT | GGGTTACAT |
| 4276 | CGAACTGGA | TCTCAACAG | CGGTAAGAT | CCTTGAGAG | TTTTCGCCC |
| 4321 | CGAAGAACG | TTCTCCAAT | GATGAGCAC | TTTTAAAGT | TCTGCTATG |
| 4366 | TGGCGCGGT | ATTATCCCG | TGTTGACGC | CGGGCAAGA | GCAACTCGG |
| 4411 | TCGCCGCAT | ACACTATTC | TCAGAATGA | CTTGGTTGA | GTACTCACC |
| 4456 | AGTCACAGA | AAAGCATCT | TACGGATGG | CATGACAGT | AAGAGAATT |
| 4501 | ATGCAGTGC | TGCCATAAC | CATGAGTGA | TAACACTGC | GGCCAACTT |
| 4546 | ACTTCTGAC | AACGATCGG | AGGACCGAA | GGAGCTAAC | CGCTTTTTT |
| 4591 | GCACAACAT | GGGGGATCA | TGTAACTCG | CCTTGATCG | TTGGGAACC |
| 4636 | GGAGCTGAA | TGAAGCCAT | ACCAAACGA | CGAGCGTGA | CACCACGAT |
| 4681 | GCCTGTAGC | AATGGCAAC | AACGTTGCG | CAAACTATT | AACTGGCGA |
| 4726 | ACTACTTAC | TCTAGCTTC | CCGGCAACA | ATTAATAGA | CTGGATGGA |
| 4771 | GGCGGATAA | AGTTGCAGG | ACCACTTCT | GCGCTCGGC | CCTTCCGGC |
| 4816 | TGGCTGGTT | TATTGCTGA | TAAATCTGG | AGCCGGTGA | GCGTGGGTC |
| 4861 | TCGCGGTAT | CATTGCAGC | ACTGGGGCC | AGATGGTAA | GCCCTCCCG |
| 4906 | TATCGTAGT | TATCTACAC | GACGGGGAG | TCAGGCAAC | TATGGATGA |
| 4951 | ACGAAATAG | ACAGATCGC | TGAGATAGG | TGCCTCACT | GATTAAGCA |
| 4996 | TTGGTAACT | GTCAGACCA | AGTTTACTC | ATATATACT | TTAGATTGA |
| 5041 | TTTACCCCG | GTTGATAAT | CAGAAAAGC | CCCAAAAAC | AGGAAGATT |
| 5086 | GTATAAGCA | AATATTTAA | ATTGTAAAC | GTTAATATT | TTGTTAAAA |
| 5131 | TTCGCGTTA | AATTTTTGT | TAAATCAGC | TCATTTTTT | AACCAATAG |
| 5176 | GCCGAAATC | GGCAAAATC | CCTTATAAA | TCAAAAGAA | TAGACCGAG |
| 5221 | ATAGGGTTG | AGTGTTGTT | CCAGTTTGG | AACAAGAGT | CCACTATTA |
| 5266 | AAGAACGTG | GACTCCAAC | GTCAAAGGG | CGAAAAACC | GTCTATCAG |
| 5311 | GGCGATGGC | CCACTACGT | GAACCATCA | CCCAAATCA | AGTTTTTTG |
| 5356 | GGGTCGAGG | TGCCGTAAA | GCACTAAAT | CGGAACCCT | AAAGGGAGC |
| 5401 | CCCCGATTT | AGAGCTTGA | CGGGGAAAG | CCGGCGAAC | GTGGCGAGA |
| 5446 | AAGGAAGGG | AAGAAAGCG | AAAGGAGCG | GGCGCTAGG | GCGCTGGCA |
| 5491 | AGTGTAGCG | GTCACGCTG | CGCGTAACC | ACCACACCC | GCCGCGCTT |
| 5536 | AATGCGCCG | CTACAGGGC | GCGTAAAAG | GATCTAGGT | GAAGATCCT |
| 5581 | TTTTGATAA | TCTCATGAC | CAAAATCCC | TTAACGTGA | GTTTTCGTT |
| 5626 | CCACTGAGC | GTCAGACCC | CGTAGAAAA | GATCAAAGG | ATCTTCTTG |
| 5671 | AGATCCTTT | TTTTCTGCG | CGTAATCTG | CTGCTTGCA | AACAAAAAA |
| 5716 | ACCACCGCT | ACCAGCGGT | GGTTTGTTT | GCCGGATCA | AGAGCTACC |
| 5761 | AACTCTTTT | TCCGAAGGT | AACTGGCTT | CAGCAGAGC | GCAGATACC |
| 5806 | AAATACTGT | CCTTCTAGT | GTAGCCGTA | GTTAGGCCA | CCACTTCAA |
| 5851 | GAACTCTGT | AGCACCGCC | TACATACCT | CGCTCTGCT | AATCCTGTT |
| 5896 | ACCAGTGGC | TGCTGCCAG | TGGCGATAA | GTCGTGTCT | TACCGGGTT |
| 5941 | GGACTCAAG | ACGATAGTT | ACCGGATAA | GGCGCAGCG | GTCGGGCTG |
| 5986 | AACGGGGGG | TTCGTGCAC | ACAGCCCAG | CTTGGAGCG | AACGACCTA |
| 6031 | CACCGAACT | GAGATACCT | ACAGCGTGA | GCTATGAGA | AAGCGCCAC |
| 6076 | GCTTCCCGA | AGGGAGAAA | GGCGGACAG | GTATCCGGT | AAGCGGCAG |
| 6121 | GGTCGGAAC | AGGAGAGCG | CACGAGGGA | GCTTCCAGG | GGGAAACGC |
| 6166 | CTGGTATCT | TTATAGTCC | TGTCGGGTT | TCGCCACCT | CTGACTTGA |
| 6211 | GCGTCGATT | TTTGTGATG | CTCGTCAGG | GGGGCGGAG | CCTATGGAA |
| 6256 | AAACGCCAG | CAACGCGGC | CTTTTTACG | GTTCCTGGC | CTTTTGCTG |

FIG. 15C pMBP-c2X-ToxoP30del3C(52-300aa)

| | | | | | |
|---|---|---|---|---|---|
| 6301 | GCCTTTTGC | TCACATGTT | CTTTCCTGC | GTTATCCCC | TGATTCTGT |
| 6346 | GGATAACCG | TATTACCGC | CTTTGAGTG | AGCTGATAC | CGCTCGCCG |
| 6391 | CAGCCGAAC | GACCGAGCG | CAGCGAGTC | AGTGAGCGA | GGAAGCGGA |
| 6436 | AGAGCGCCT | GATGCGGTA | TTTTCTCCT | TACGCATCT | GTGCGGTAT |
| 6481 | TTCACACCG | CATATATGG | TGCACTCTC | AGTACAATC | TGCTCTGAT |
| 6526 | GCCGCATAG | TTAAGCCAG | TATACACTC | CGCTATCGC | TACGTGACT |
| 6571 | GGGTCATGG | CTGCGCCCC | GACACCCGC | CAACACCCG | CTGACGCGC |
| 6616 | CCTGACGGG | CTTGTCTGC | TCCCGGCAT | CCGCTTACA | GACAAGCTG |
| 6661 | TGACCGTCT | CCGGGAGCT | GCATGTGTC | AGAGGTTTT | CACCGTCAT |
| 6706 | CACCGAAAC | GCGCGAGGC | AGCTGCGGT | AAAGCTCAT | CAGCGTGGT |
| 6751 | CGTGCAGCG | ATTCACAGA | TGTCTGCCT | GTTCATCCG | CGTCCAGCT |
| 6796 | CGTTGAGTT | TCTCCAGAA | GCGTTAATG | TCTGGCTTC | TGATAAAGC |
| 6841 | GGGCCATGT | TAAGGGCGG | TTTTTTCCT | GTTTGGTCA | CTGATGCCT |
| 6886 | CCGTGTAAG | GGGGATTTC | TGTTCATGG | GGGTAATGA | TACCGATGA |
| 6931 | AACGAGAGA | GGATGCTCA | CGATACGGG | TTACTGATG | ATGAACATG |
| 6976 | CCCGGTTAC | TGGAACGTT | GTGAGGGTA | AACAACTGG | CGGTATGGA |
| 7021 | TGCGGCGGG | ACCAGAGAA | AAATCACTC | AGGGTCAAT | GCCAGCGCT |
| 7066 | TCGTTAATA | CAGATGTAG | GTGTTCCAC | AGGGTAGCC | AGCAGCATC |
| 7111 | CTGCGATGC | AGATCCGGA | ACATAATGG | TGCAGGGCG | CTGACTTCC |
| 7156 | GCGTTTCCA | GACTTTACG | AAACACGGA | AACCGAAGA | CCATTCATG |
| 7201 | TTGTTGCTC | AGGTCGCAG | ACGTTTTGC | AGCAGCAGT | CGCTTCACG |
| 7246 | TTCGCTCGC | GTATCGGTG | ATTCATTCT | GCTAACCAG | TAAGGCAAC |
| 7291 | CCCGCCAGC | CTAGCCGGG | TCCTCAACG | ACAGGAGCA | CGATCATGC |
| 7336 | GCACCCGTG | GCCAGGACC | CAACGCTGC | CCGAAATT | |

FIG.15D

ToxoP30del3C(52-300aa)

```
    LeuValAla AsnGlnVal ValThrCys ProAspLys LysSerThr
  1 CTTGTTGCC AATCAAGTT GTCACCTGC CCAGATAAA AAATCGACA
    AlaAlaVal IleLeuThr ProThrGlu AsnHisPhe ThrLeuLys
 46 GCCGCGGTC ATTCTCACA CCGACGGAG AACCACTTC ACTCTCAAG
    CysProLys ThrAlaLeu ThrGluPro ProThrLeu AlaTyrSer
 91 TGCCCTAAA ACAGCGCTC ACAGAGCCT CCCACTCTT GCGTACTCA
    ProAsnArg GlnIleCys ProAlaGly ThrThrSer SerCysThr
136 CCCAACAGG CAAATCTGC CCAGCGGGT ACTACAAGT AGCTGTACA
    SerLysAla ValThrLeu SerSerLeu IleProGlu AlaGluAsp
181 TCAAAGGCT GTAACATTG AGCTCCTTG ATTCCTGAA GCAGAAGAT
    SerTrpTrp ThrGlyAsp SerAlaSer LeuAspThr AlaGlyIle
226 AGCTGGTGG ACGGGGGAT TCTGCTAGT CTCGACACG GCAGGCATC
    LysLeuThr ValProIle GluLysPhe ProValThr ThrGlnThr
271 AAACTCACA GTTCCAATC GAGAAGTTC CCCGTGACA ACGCAGACG
    PheValVal GlyCysIle LysGlyAsp AspAlaGln SerCysMet
316 TTTGTGGTC GGTTGCATC AAGGGAGAC GACGCACAG AGTTGTATG
    ValThrVal ThrValGln AlaArgAla SerSerVal ValAsnAsn
361 GTCACAGTG ACAGTACAA GCCAGAGCC TCATCGGTC GTCAATAAT
    ValAlaArg CysSerTyr GlyAlaAsp SerThrLeu GlyProVal
406 GTCGCAAGG TGCTCCTAC GGTGCAGAC AGCACTCTT GGTCCTGTC
    LysLeuSer AlaGluGly ProThrThr MetThrLeu ValCysGly
451 AAGTTGTCT GCGGAAGGA CCCACTACA ATGACCCTC GTGTGCGGG
    LysAspGly ValLysVal ProGlnAsp AsnAsnGln TyrCysSer
496 AAAGATGGA GTCAAAGTT CCTCAAGAC AACAATCAG TACTGTTCC
    GlyThrThr LeuThrGly CysAsnGlu LysSerPhe LysAspIle
541 GGGACGACG CTGACTGGT TGCAACGAG AAATCGTTC AAAGATATT
    LeuProLys LeuThrGlu AsnProTrp GlnGlyAsn AlaSerSer
586 TTGCCAAAA TTAACTGAG AACCCGTGG CAGGGTAAC GCTTCGAGT
    AspLysGly AlaThrLeu ThrIleLys LysGluAla PheProAla
631 GATAAGGGT GCCACGCTA ACGATCAAG AAGGAAGCA TTTCCAGCC
    GluSerLys SerValIle IleGlyCys ThrGlyGly SerProGlu
676 GAGTCAAAA AGCGTCATT ATTGGATGC ACAGGGGGA TCGCCTGAG
    LysHisHis CysThrVal LysLeuGlu
721 AAGCATCAC TGTACCGTG AAACTGGAG
```

FIG.16 pMBP-c2X-ToxoP30del4C(52-294aa)

1 CCGACACCA TCGAATGGT GCAAAACCT TTCGCGGTA TGGCATGAT
46 AGCGCCCGG AAGAGAGTC AATTCAGGG TGGTGAATG TGAAACCAG
91 TAACGTTAT ACGATGTCG CAGAGTATG CCGGTGTCT CTTATCAGA
136 CCGTTTCCC GCGTGGTGA ACCAGGCCA GCCACGTTT CTGCGAAAA
181 CGCGGGAAA AAGTGGAAG CGGCGATGG CGGAGCTGA ATTACATTC
226 CCAACCGCG TGGCACAAC AACTGGCGG GCAAACAGT CGTTGCTGA
271 TTGGCGTTG CCACCTCCA GTCTGGCCC TGCACGCGC CGTCGCAAA
316 TTGTCGCGG CGATTAAAT CTCGCGCCG ATCAACTGG GTGCCAGCG
361 TGGTGGTGT CGATGGTAG AACGAAGCG GCGTCGAAG CCTGTAAAG
406 CGGCGGTGC ACAATCTTC TCGCGCAAC GCGTCAGTG GGCTGATCA
451 TTAACTATC CGCTGGATG ACCAGGATG CCATTGCTG TGGAAGCTG
496 CCTGCACTA ATGTTCCGG CGTTATTTC TTGATGTCT CTGACCAGA
541 CACCCATCA ACAGTATTA TTTTCTCCC ATGAAGACG GTACGCGAC
586 TGGGCGTGG AGCATCTGG TCGCATTGG GTCACCAGC AAATCGCGC
631 TGTTAGCGG GCCCATTAA GTTCTGTCT CGGCGCGTC TGCGTCTGG
676 CTGGCTGGC ATAAATATC TCACTCGCA ATCAAATTC AGCCGATAG
721 CGGAACGGG AAGGCGACT GGAGTGCCA TGTCCGGTT TTCAACAAA
766 CCATGCAAA TGCTGAATG AGGGCATCG TTCCCACTG CGATGCTGG
811 TTGCCAACG ATCAGATGG CGCTGGGCG CAATGCGCG CCATTACCG
856 AGTCCGGGC TGCGCGTTG GTGCGGATA TCTCGGTAG TGGGATACG
901 ACGATACCG AAGACAGCT CATGTTATA TCCCGCCGT TAACCACCA
946 TCAAACAGG ATTTTCGCC TGCTGGGGC AAACCAGCG TGGACCGCT
991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
Met
1486 TAGGTGTTT TCACGAGCA CTTCACCAA CAAGGACCA TAGCATATG
LysIleGlu GluGlyLys LeuValIle TrpIleAsn GlyAspLys
1531 AAAATCGAA GAAGGTAAA CTGGTAATC TGGATTAAC GGCGATAAA
GlyTyrAsn GlyLeuAla GluValGly LysLysPhe GluLysAsp
1576 GGCTATAAC GGTCTCGCT GAAGTCGGT AAGAAATTC GAGAAAGAT
ThrGlyIle LysValThr ValGluHis ProAspLys LeuGluGlu
1621 ACCGGAATT AAAGTCACC GTTGAGCAT CCGGATAAA CTGGAAGAG
LysPhePro GlnValAla AlaThrGly AspGlyPro AspIleIle
1666 AAATTCCCA CAGGTTGCG GCAACTGGC GATGGCCCT GACATTATC
PheTrpAla HisAspArg PheGlyGly TyrAlaGln SerGlyLeu
1711 TTCTGGGCA CACGACCGC TTTGGTGGC TACGCTCAA TCTGGCCTG
LeuAlaGlu IleThrPro AspLysAla PheGlnAsp LysLeuTyr

FIG.19 pMBP-c2X-ToxoP30del4C(52-294aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.19A pMBP-c2X-ToxoP30del4C(52-294aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis
3421 AAGCATCAC TGAAAGCTT GGCACTGGC CGTCGTTTT ACAACGTCG
3466 TGACTGGGA AAACCCTGG CGTTACCCA ACTTAATCG CCTTGCAGC
3511 ACATCCCCC TTTCGCCAG CTGGCGTAA TAGCGAAGA GGCCCGCAC
3556 CGATCGCCC TTCCCAACA GTTGCGCAG CCTGAATGG CGAATGGCA
3601 GCTTGGCTG TTTTGGCGG ATGAGATAA GATTTTCAG CCTGATACA
3646 GATTAAATC AGAACGCAG AAGCGGTCT GATAAAACA GAATTTGCC
3691 TGGCGGCAG TAGCGCGGT GGTCCCACC TGACCCCAT GCCGAACTC
3736 AGAAGTGAA ACGCCGTAG CGCCGATGG TAGTGTGGG GTCTCCCCA
3781 TGCGAGAGT AGGGAACTG CCAGGCATC AAATAAAAC GAAAGGCTC
3826 AGTCGAAAG ACTGGGCCT TTCGTTTTA TCTGTTGTT TGTCGGTGA
3871 ACGCTCTCC TGAGTAGGA CAAATCCGC CGGGAGCGG ATTTGAACG
3916 TTGCGAAGC AACGGCCCG GAGGGTGGC GGGCAGGAC GCCCGCCAT
3961 AAACTGCCA GGCATCAAA TTAAGCAGA AGGCCATCC TGACGGATG
4006 GCCTTTTTG CGTTTCTAC AAACTCTTT TTGTTTATT TTTCTAAAT
4051 ACATTCAAA TATGTATCC GCTCATGAG ACAATAACC CTGATAAAT
4096 GCTTCAATA ATATTGAAA AAGGAAGAG TATGAGTAT TCAACATTT
4141 CCGTGTCGC CCTTATTCC CTTTTTTGC GGCATTTTG CCTTCCTGT
4186 TTTTGCTCA CCCAGAAAC GCTGGTGAA AGTAAAAGA TGCTGAAGA
```

FIG.19B pMBP-c2X-ToxoP30del4C(52-294aa)

```
4231  TCAGTTGGG TGCACGAGT GGGTTACAT CGAACTGGA TCTCAACAG
4276  CGGTAAGAT CCTTGAGAG TTTTCGCCC CGAAGAACG TTCTCCAAT
4321  GATGAGCAC TTTTAAAGT TCTGCTATG TGGCGCGGT ATTATCCCG
4366  TGTTGACGC CGGGCAAGA GCAACTCGG TCGCCGCAT ACACTATTC
4411  TCAGAATGA CTTGGTTGA GTACTCACC AGTCACAGA AAAGCATCT
4456  TACGGATGG CATGACAGT AAGAGAATT ATGCAGTGC TGCCATAAC
4501  CATGAGTGA TAACACTGC GGCCAACTT ACTTCTGAC AACGATCGG
4546  AGGACCGAA GGAGCTAAC CGCTTTTTT GCACAACAT GGGGGATCA
4591  TGTAACTCG CCTTGATCG TTGGGAACC GGAGCTGAA TGAAGCCAT
4636  ACCAAACGA CGAGCGTGA CACCACGAT GCCTGTAGC AATGGCAAC
4681  AACGTTGCG CAAACTATT AACTGGCGA ACTACTTAC TCTAGCTTC
4726  CCGGCAACA ATTAATAGA CTGGATGGA GGCGGATAA AGTTGCAGG
4771  ACCACTTCT GCGCTCGGC CCTTCCGGC TGGCTGGTT TATTGCTGA
4816  TAAATCTGG AGCCGGTGA GCGTGGGTC TCGCGGTAT CATTGCAGC
4861  ACTGGGGCC AGATGGTAA GCCCTCCCG TATCGTAGT TATCTACAC
4906  GACGGGGAG TCAGGCAAC TATGGATGA ACGAAATAG ACAGATCGC
4951  TGAGATAGG TGCCTCACT GATTAAGCA TTGGTAACT GTCAGACCA
4996  AGTTTACTC ATATATACT TTAGATTGA TTTACCCCG GTTGATAAT
5041  CAGAAAAGC CCCAAAAAC AGGAAGATT GTATAAGCA AATATTTAA
5086  ATTGTAAAC GTTAATATT TTGTTAAAA TTCGCGTTA AATTTTTGT
5131  TAAATCAGC TCATTTTTT AACCAATAG GCCGAAATC GGCAAAATC
5176  CCTTATAAA TCAAAAGAA TAGACCGAG ATAGGGTTG AGTGTTGTT
5221  CCAGTTTGG AACAAGAGT CCACTATTA AAGAACGTG GACTCCAAC
5266  GTCAAAGGG CGAAAAACC GTCTATCAG GGCGATGGC CCACTACGT
5311  GAACCATCA CCCAAATCA AGTTTTTTG GGGTCGAGG TGCCGTAAA
5356  GCACTAAAT CGGAACCCT AAAGGGAGC CCCCGATTT AGAGCTTGA
5401  CGGGGAAAG CCGGCGAAC GTGGCGAGA AAGGAAGGG AAGAAAGCG
5446  AAAGGAGCG GGCGCTAGG GCGCTGGCA AGTGTAGCG GTCACGCTG
5491  CGCGTAACC ACCACACCC GCCGCGCTT AATGCGCCG CTACAGGGC
5536  GCGTAAAAG GATCTAGGT GAAGATCCT TTTTGATAA TCTCATGAC
5581  CAAAATCCC TTAACGTGA GTTTTCGTT CCACTGAGC GTCAGACCC
5626  CGTAGAAAA GATCAAAGG ATCTTCTTG AGATCCTTT TTTTCTGCG
5671  CGTAATCTG CTGCTTGCA AACAAAAAA ACCACCGCT ACCAGCGGT
5716  GGTTTGTTT GCCGGATCA AGAGCTACC AACTCTTTT TCCGAAGGT
5761  AACTGGCTT CAGCAGAGC GCAGATACC AAATACTGT CCTTCTAGT
5806  GTAGCCGTA GTTAGGCCA CCACTTCAA GAACTCTGT AGCACCGCC
5851  TACATACCT CGCTCTGCT AATCCTGTT ACCAGTGGC TGCTGCCAG
5896  TGGCGATAA GTCGTGTCT TACCGGGTT GGACTCAAG ACGATAGTT
5941  ACCGGATAA GGCGCAGCG GTCGGGCTG AACGGGGGG TTCGTGCAC
5986  ACAGCCCAG CTTGGAGCG AACGACCTA CACCGAACT GAGATACCT
6031  ACAGCGTGA GCTATGAGA AAGCGCCAC GCTTCCCGA AGGGAGAAA
6076  GGCGGACAG GTATCCGGT AAGCGGCAG GGTCGGAAC AGGAGAGCG
6121  CACGAGGGA GCTTCCAGG GGGAAACGC CTGGTATCT TTATAGTCC
6166  TGTCGGGTT TCGCCACCT CTGACTTGA GCGTCGATT TTTGTGATG
6211  CTCGTCAGG GGGGCGGAG CCTATGGAA AAACGCCAG CAACGCGGC
6256  CTTTTTACG GTTCCTGGC CTTTTGCTG GCCTTTTGC TCACATGTT
```

FIG.19C pMBP-c2X-ToxoP30del4C(52-294aa)

```
6301  CTTTCCTGC GTTATCCCC TGATTCTGT GGATAACCG TATTACCGC
6346  CTTTGAGTG AGCTGATAC CGCTCGCCG CAGCCGAAC GACCGAGCG
6391  CAGCGAGTC AGTGAGCGA GGAAGCGGA AGAGCGCCT GATGCGGTA
6436  TTTTCTCCT TACGCATCT GTGCGGTAT TTCACACCG CATATATGG
6481  TGCACTCTC AGTACAATC TGCTCTGAT GCCGCATAG TTAAGCCAG
6526  TATACACTC CGCTATCGC TACGTGACT GGGTCATGG CTGCGCCCC
6571  GACACCCGC CAACACCCG CTGACGCGC CCTGACGGG CTTGTCTGC
6616  TCCCGGCAT CCGCTTACA GACAAGCTG TGACCGTCT CCGGGAGCT
6661  GCATGTGTC AGAGGTTTT CACCGTCAT CACCGAAAC GCGCGAGGC
6706  AGCTGCGGT AAAGCTCAT CAGCGTGGT CGTGCAGCG ATTCACAGA
6751  TGTCTGCCT GTTCATCCG CGTCCAGCT CGTTGAGTT TCTCCAGAA
6796  GCGTTAATG TCTGGCTTC TGATAAAGC GGGCCATGT TAAGGGCGG
6841  TTTTTTCCT GTTTGGTCA CTGATGCCT CCGTGTAAG GGGGATTTC
6886  TGTTCATGG GGGTAATGA TACCGATGA AACGAGAGA GGATGCTCA
6931  CGATACGGG TTACTGATG ATGAACATG CCCGGTTAC TGGAACGTT
6976  GTGAGGGTA AACAACTGG CGGTATGGA TGCGGCGGG ACCAGAGAA
7021  AAATCACTC AGGGTCAAT GCCAGCGCT TCGTTAATA CAGATGTAG
7066  GTGTTCCAC AGGGTAGCC AGCAGCATC CTGCGATGC AGATCCGGA
7111  ACATAATGG TGCAGGGCG CTGACTTCC GCGTTTCCA GACTTTACG
7156  AAACACGGA AACCGAAGA CCATTCATG TTGTTGCTC AGGTCGCAG
7201  ACGTTTTGC AGCAGCAGT CGCTTCACG TTCGCTCGC GTATCGGTG
7246  ATTCATTCT GCTAACCAG TAAGGCAAC CCCGCCAGC CTAGCCGGG
7291  TCCTCAACG ACAGGAGCA CGATCATGC GCACCCGTG GCCAGGACC
7336  CAACGCTGC CCGAAATT
```

FIG.19D

ToxoP30del4C(52-294aa)

```
     LeuValAla AsnGlnVal ValThrCys ProAspLys LysSerThr
  1  CTTGTTGCC AATCAAGTT GTCACCTGC CCAGATAAA AAATCGACA
     AlaAlaVal IleLeuThr ProThrGlu AsnHisPhe ThrLeuLys
 46  GCCGCGGTC ATTCTCACA CCGACGGAG AACCACTTC ACTCTCAAG
     CysProLys ThrAlaLeu ThrGluPro ProThrLeu AlaTyrSer
 91  TGCCCTAAA ACAGCGCTC ACAGAGCCT CCCACTCTT GCGTACTCA
     ProAsnArg GlnIleCys ProAlaGly ThrThrSer SerCysThr
136  CCCAACAGG CAAATCTGC CCAGCGGGT ACTACAAGT AGCTGTACA
     SerLysAla ValThrLeu SerSerLeu IleProGlu AlaGluAsp
181  TCAAAGGCT GTAACATTG AGCTCCTTG ATTCCTGAA GCAGAAGAT
     SerTrpTrp ThrGlyAsp SerAlaSer LeuAspThr AlaGlyIle
226  AGCTGGTGG ACGGGGGAT TCTGCTAGT CTCGACACG GCAGGCATC
     LysLeuThr ValProIle GluLysPhe ProValThr ThrGlnThr
271  AAACTCACA GTTCCAATC GAGAAGTTC CCCGTGACA ACGCAGACG
     PheValVal GlyCysIle LysGlyAsp AspAlaGln SerCysMet
316  TTTGTGGTC GGTTGCATC AAGGGAGAC GACGCACAG AGTTGTATG
     ValThrVal ThrValGln AlaArgAla SerSerVal ValAsnAsn
361  GTCACAGTG ACAGTACAA GCCAGAGCC TCATCGGTC GTCAATAAT
     ValAlaArg CysSerTyr GlyAlaAsp SerThrLeu GlyProVal
406  GTCGCAAGG TGCTCCTAC GGTGCAGAC AGCACTCTT GGTCCTGTC
     LysLeuSer AlaGluGly ProThrThr MetThrLeu ValCysGly
451  AAGTTGTCT GCGGAAGGA CCCACTACA ATGACCCTC GTGTGCGGG
     LysAspGly ValLysVal ProGlnAsp AsnAsnGln TyrCysSer
496  AAAGATGGA GTCAAAGTT CCTCAAGAC AACAATCAG TACTGTTCC
     GlyThrThr LeuThrGly CysAsnGlu LysSerPhe LysAspIle
541  GGGACGACG CTGACTGGT TGCAACGAG AAATCGTTC AAAGATATT
     LeuProLys LeuThrGlu AsnProTrp GlnGlyAsn AlaSerSer
586  TTGCCAAAA TTAACTGAG AACCCGTGG CAGGGTAAC GCTTCGAGT
     AspLysGly AlaThrLeu ThrIleLys LysGluAla PheProAla
631  GATAAGGGT GCCACGCTA ACGATCAAG AAGGAAGCA TTTCCAGCC
     GluSerLys SerValIle IleGlyCys ThrGlyGly SerProGlu
676  GAGTCAAAA AGCGTCATT ATTGGATGC ACAGGGGGA TCGCCTGAG
     LysHisHis
721  AAGCATCAC
```

FIG. 20 pMBP-c2X-ToxoP30del4del8(83-294aa)

1 CCGACACCA TCGAATGGT GCAAAACCT TTCGCGGTA TGGCATGAT
46 AGCGCCCGG AAGAGAGTC AATTCAGGG TGGTGAATG TGAAACCAG
91 TAACGTTAT ACGATGTCG CAGAGTATG CCGGTGTCT CTTATCAGA
136 CCGTTTCCC GCGTGGTGA ACCAGGCCA GCCACGTTT CTGCGAAAA
181 CGCGGGAAA AAGTGGAAG CGGCGATGG CGGAGCTGA ATTACATTC
226 CCAACCGCG TGGCACAAC AACTGGCGG GCAAACAGT CGTTGCTGA
271 TTGGCGTTG CCACCTCCA GTCTGGCCC TGCACGCGC CGTCGCAAA
316 TTGTCGCGG CGATTAAAT CTCGCGCCG ATCAACTGG GTGCCAGCG
361 TGGTGGTGT CGATGGTAG AACGAAGCG GCGTCGAAG CCTGTAAAG
406 CGGCGGTGC ACAATCTTC TCGCGCAAC GCGTCAGTG GGCTGATCA
451 TTAACTATC CGCTGGATG ACCAGGATG CCATTGCTG TGGAAGCTG
496 CCTGCACTA ATGTTCCGG CGTTATTTC TTGATGTCT CTGACCAGA
541 CACCCATCA ACAGTATTA TTTTCTCCC ATGAAGACG GTACGCGAC
586 TGGGCGTGG AGCATCTGG TCGCATTGG GTCACCAGC AAATCGCGC
631 TGTTAGCGG GCCCATTAA GTTCTGTCT CGGCGCGTC TGCGTCTGG
676 CTGGCTGGC ATAAATATC TCACTCGCA ATCAAATTC AGCCGATAG
721 CGGAACGGG AAGGCGACT GGAGTGCCA TGTCCGGTT TTCAACAAA
766 CCATGCAAA TGCTGAATG AGGGCATCG TTCCCACTG CGATGCTGG
811 TTGCCAACG ATCAGATGG CGCTGGGCG CAATGCGCG CCATTACCG
856 AGTCCGGGC TGCGCGTTG GTGCGGATA TCTCGGTAG TGGGATACG
901 ACGATACCG AAGACAGCT CATGTTATA TCCCGCCGT TAACCACCA
946 TCAAACAGG ATTTTCGCC TGCTGGGGC AAACCAGCG TGGACCGCT
991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
Met
1486 TAGGTGTTT TCACGAGCA CTTCACCAA CAAGGACCA TAGCATATG
LysIleGlu GluGlyLys LeuValIle TrpIleAsn GlyAspLys
1531 AAAATCGAA GAAGGTAAA CTGGTAATC TGGATTAAC GGCGATAAA
GlyTyrAsn GlyLeuAla GluValGly LysLysPhe GluLysAsp
1576 GGCTATAAC GGTCTCGCT GAAGTCGGT AAGAAATTC GAGAAAGAT
ThrGlyIle LysValThr ValGluHis ProAspLys LeuGluGlu
1621 ACCGGAATT AAAGTCACC GTTGAGCAT CCGGATAAA CTGGAAGAG
LysPhePro GlnValAla AlaThrGly AspGlyPro AspIleIle
1666 AAATTCCCA CAGGTTGCG GCAACTGGC GATGGCCCT GACATTATC
PheTrpAla HisAspArg PheGlyGly TyrAlaGln SerGlyLeu
1711 TTCTGGGCA CACGACCGC TTTGGTGGC TACGCTCAA TCTGGCCTG
LeuAlaGlu IleThrPro AspLysAla PheGlnAsp LysLeuTyr

FIG.22 pMBP-c2X-ToxoP30del4del8(83-294aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     ProLysThr AlaLeuThr GluProPro ThrLeuAla TyrSerPro
2701 CCTAAAACA GCGCTCACA GAGCCTCCC ACTCTTGCG TACTCACCC
     AsnArgGln IleCysPro AlaGlyThr ThrSerSer CysThrSer
2746 AACAGGCAA ATCTGCCCA GCGGGTACT ACAAGTAGC TGTACATCA
     LysAlaVal ThrLeuSer SerLeuIle ProGluAla GluAspSer
```

FIG.22A pMBP-c2X-ToxoP30del4del8(83-294aa)

2791 AAGGCTGTA ACATTGAGC TCCTTGATT CCTGAAGCA GAAGATAGC
TrpTrpThr GlyAspSer AlaSerLeu AspThrAla GlyIleLys
2836 TGGTGGACG GGGGATTCT GCTAGTCTC GACACGGCA GGCATCAAA
LeuThrVal ProIleGlu LysPhePro ValThrThr GlnThrPhe
2881 CTCACAGTT CCAATCGAG AAGTTCCCC GTGACAACG CAGACGTTT
ValValGly CysIleLys GlyAspAsp AlaGlnSer CysMetVal
2926 GTGGTCGGT TGCATCAAG GGAGACGAC GCACAGAGT TGTATGGTC
ThrValThr ValGlnAla ArgAlaSer SerValVal AsnAsnVal
2971 ACAGTGACA GTACAAGCC AGAGCCTCA TCGGTCGTC AATAATGTC
AlaArgCys SerTyrGly AlaAspSer ThrLeuGly ProValLys
3016 GCAAGGTGC TCCTACGGT GCAGACAGC ACTCTTGGT CCTGTCAAG
LeuSerAla GluGlyPro ThrThrMet ThrLeuVal CysGlyLys
3061 TTGTCTGCG GAAGGACCC ACTACAATG ACCCTCGTG TGCGGGAAA
AspGlyVal LysValPro GlnAspAsn AsnGlnTyr CysSerGly
3106 GATGGAGTC AAAGTTCCT CAAGACAAC AATCAGTAC TGTTCCGGG
ThrThrLeu ThrGlyCys AsnGluLys SerPheLys AspIleLeu
3151 ACGACGCTG ACTGGTTGC AACGAGAAA TCGTTCAAA GATATTTTG
ProLysLeu ThrGluAsn ProTrpGln GlyAsnAla SerSerAsp
3196 CCAAAATTA ACTGAGAAC CCGTGGCAG GGTAACGCT TCGAGTGAT
LysGlyAla ThrLeuThr IleLysLys GluAlaPhe ProAlaGlu
3241 AAGGGTGCC ACGCTAACG ATCAAGAAG GAAGCATTT CCAGCCGAG
SerLysSer ValIleIle GlyCysThr GlyGlySer ProGluLys
3286 TCAAAAAGC GTCATTATT GGATGCACA GGGGGATCG CCTGAGAAG
HisHis
3331 CATCACTGA AAGCTTGGC ACTGGCCGT CGTTTTACA ACGTCGTGA
3376 CTGGGAAAA CCCTGGCGT TACCCAACT TAATCGCCT TGCAGCACA
3421 TCCCCCTTT CGCCAGCTG GCGTAATAG CGAAGAGGC CCGCACCGA
3466 TCGCCCTTC CCAACAGTT GCGCAGCCT GAATGGCGA ATGGCAGCT
3511 TGGCTGTTT TGGCGGATG AGATAAGAT TTTCAGCCT GATACAGAT
3556 TAAATCAGA ACGCAGAAG CGGTCTGAT AAAACAGAA TTTGCCTGG
3601 CGGCAGTAG CGCGGTGGT CCCACCTGA CCCCATGCC GAACTCAGA
3646 AGTGAAACG CCGTAGCGC CGATGGTAG TGTGGGGTC TCCCCATGC
3691 GAGAGTAGG GAACTGCCA GGCATCAAA TAAAACGAA AGGCTCAGT
3736 CGAAAGACT GGGCCTTTC GTTTTATCT GTTGTTTGT CGGTGAACG
3781 CTCTCCTGA GTAGGACAA ATCCGCCGG GAGCGGATT TGAACGTTG
3826 CGAAGCAAC GGCCCGGAG GGTGGCGGG CAGGACGCC CGCCATAAA
3871 CTGCCAGGC ATCAAATTA AGCAGAAGG CCATCCTGA CGGATGGCC
3916 TTTTTGCGT TTCTACAAA CTCTTTTTG TTTATTTTT CTAAATACA
3961 TTCAAATAT GTATCCGCT CATGAGACA ATAACCCTG ATAAATGCT
4006 TCAATAATA TTGAAAAAG GAAGAGTAT GAGTATTCA ACATTTCCG
4051 TGTCGCCCT TATTCCCTT TTTTGCGGC ATTTTGCCT TCCTGTTTT
4096 TGCTCACCC AGAAACGCT GGTGAAAGT AAAAGATGC TGAAGATCA
4141 GTTGGGTGC ACGAGTGGG TTACATCGA ACTGGATCT CAACAGCGG
4186 TAAGATCCT TGAGAGTTT TCGCCCCGA AGAACGTTC TCCAATGAT
4231 GAGCACTTT TAAAGTTCT GCTATGTGG CGCGGTATT ATCCCGTGT
4276 TGACGCCGG GCAAGAGCA ACTCGGTCG CCGCATACA CTATTCTCA

FIG.22B pMBP-c2X-ToxoP30del4del8(83-294aa)

| | | | | | |
|---|---|---|---|---|---|
| 4321 | GAATGACTT | GGTTGAGTA | CTCACCAGT | CACAGAAAA | GCATCTTAC |
| 4366 | GGATGGCAT | GACAGTAAG | AGAATTATG | CAGTGCTGC | CATAACCAT |
| 4411 | GAGTGATAA | CACTGCGGC | CAACTTACT | TCTGACAAC | GATCGGAGG |
| 4456 | ACCGAAGGA | GCTAACCGC | TTTTTTGCA | CAACATGGG | GGATCATGT |
| 4501 | AACTCGCCT | TGATCGTTG | GGAACCGGA | GCTGAATGA | AGCCATACC |
| 4546 | AAACGACGA | GCGTGACAC | CACGATGCC | TGTAGCAAT | GGCAACAAC |
| 4591 | GTTGCGCAA | ACTATTAAC | TGGCGAACT | ACTTACTCT | AGCTTCCCG |
| 4636 | GCAACAATT | AATAGACTG | GATGGAGGC | GGATAAAGT | TGCAGGACC |
| 4681 | ACTTCTGCG | CTCGGCCCT | TCCGGCTGG | CTGGTTTAT | TGCTGATAA |
| 4726 | ATCTGGAGC | CGGTGAGCG | TGGGTCTCG | CGGTATCAT | TGCAGCACT |
| 4771 | GGGGCCAGA | TGGTAAGCC | CTCCCGTAT | CGTAGTTAT | CTACACGAC |
| 4816 | GGGGAGTCA | GGCAACTAT | GGATGAACG | AAATAGACA | GATCGCTGA |
| 4861 | GATAGGTGC | CTCACTGAT | TAAGCATTG | GTAACTGTC | AGACCAAGT |
| 4906 | TTACTCATA | TATACTTTA | GATTGATTT | ACCCCGGTT | GATAATCAG |
| 4951 | AAAAGCCCC | AAAAACAGG | AAGATTGTA | TAAGCAAAT | ATTTAAATT |
| 4996 | GTAAACGTT | AATATTTTG | TTAAAATTC | GCGTTAAAT | TTTTGTTAA |
| 5041 | ATCAGCTCA | TTTTTTAAC | CAATAGGCC | GAAATCGGC | AAAATCCCT |
| 5086 | TATAAATCA | AAAGAATAG | ACCGAGATA | GGGTTGAGT | GTTGTTCCA |
| 5131 | GTTTGGAAC | AAGAGTCCA | CTATTAAAG | AACGTGGAC | TCCAACGTC |
| 5176 | AAAGGGCGA | AAAACCGTC | TATCAGGGC | GATGGCCCA | CTACGTGAA |
| 5221 | CCATCACCC | AAATCAAGT | TTTTTGGGG | TCGAGGTGC | CGTAAAGCA |
| 5266 | CTAAATCGG | AACCCTAAA | GGGAGCCCC | CGATTTAGA | GCTTGACGG |
| 5311 | GGAAAGCCG | GCGAACGTG | GCGAGAAAG | GAAGGGAAG | AAAGCGAAA |
| 5356 | GGAGCGGGC | GCTAGGGCG | CTGGCAAGT | GTAGCGGTC | ACGCTGCGC |
| 5401 | GTAACCACC | ACACCCGCC | GCGCTTAAT | GCGCCGCTA | CAGGGCGCG |
| 5446 | TAAAAGGAT | CTAGGTGAA | GATCCTTTT | TGATAATCT | CATGACCAA |
| 5491 | AATCCCTTA | ACGTGAGTT | TTCGTTCCA | CTGAGCGTC | AGACCCCGT |
| 5536 | AGAAAAGAT | CAAAGGATC | TTCTTGAGA | TCCTTTTTT | TCTGCGCGT |
| 5581 | AATCTGCTG | CTTGCAAAC | AAAAAAACC | ACCGCTACC | AGCGGTGGT |
| 5626 | TTGTTTGCC | GGATCAAGA | GCTACCAAC | TCTTTTTCC | GAAGGTAAC |
| 5671 | TGGCTTCAG | CAGAGCGCA | GATACCAAA | TACTGTCCT | TCTAGTGTA |
| 5716 | GCCGTAGTT | AGGCCACCA | CTTCAAGAA | CTCTGTAGC | ACCGCCTAC |
| 5761 | ATACCTCGC | TCTGCTAAT | CCTGTTACC | AGTGGCTGC | TGCCAGTGG |
| 5806 | CGATAAGTC | GTGTCTTAC | CGGGTTGGA | CTCAAGACG | ATAGTTACC |
| 5851 | GGATAAGGC | GCAGCGGTC | GGGCTGAAC | GGGGGGTTC | GTGCACACA |
| 5896 | GCCCAGCTT | GGAGCGAAC | GACCTACAC | CGAACTGAG | ATACCTACA |
| 5941 | GCGTGAGCT | ATGAGAAAG | CGCCACGCT | TCCCGAAGG | GAGAAAGGC |
| 5986 | GGACAGGTA | TCCGGTAAG | CGGCAGGGT | CGGAACAGG | AGAGCGCAC |
| 6031 | GAGGGAGCT | TCCAGGGGG | AAACGCCTG | GTATCTTTA | TAGTCCTGT |
| 6076 | CGGGTTTCG | CCACCTCTG | ACTTGAGCG | TCGATTTTT | GTGATGCTC |
| 6121 | GTCAGGGGG | GCGGAGCCT | ATGGAAAAA | CGCCAGCAA | CGCGGCCTT |
| 6166 | TTTACGGTT | CCTGGCCTT | TTGCTGGCC | TTTTGCTCA | CATGTTCTT |
| 6211 | TCCTGCGTT | ATCCCCTGA | TTCTGTGGA | TAACCGTAT | TACCGCCTT |
| 6256 | TGAGTGAGC | TGATACCGC | TCGCCGCAG | CCGAACGAC | CGAGCGCAG |
| 6301 | CGAGTCAGT | GAGCGAGGA | AGCGGAAGA | GCGCCTGAT | GCGGTATTT |
| 6346 | TCTCCTTAC | GCATCTGTG | CGGTATTTC | ACACCGCAT | ATATGGTGC |

FIG.22C pMBP-c2X-ToxoP30del4del8(83-294aa)

```
6391  ACTCTCAGT ACAATCTGC TCTGATGCC GCATAGTTA AGCCAGTAT
6436  ACACTCCGC TATCGCTAC GTGACTGGG TCATGGCTG CGCCCCGAC
6481  ACCCGCCAA CACCCGCTG ACGCGCCCT GACGGGCTT GTCTGCTCC
6526  CGGCATCCG CTTACAGAC AAGCTGTGA CCGTCTCCG GGAGCTGCA
6571  TGTGTCAGA GGTTTTCAC CGTCATCAC CGAAACGCG CGAGGCAGC
6616  TGCGGTAAA GCTCATCAG CGTGGTCGT GCAGCGATT CACAGATGT
6661  CTGCCTGTT CATCCGCGT CCAGCTCGT TGAGTTTCT CCAGAAGCG
6706  TTAATGTCT GGCTTCTGA TAAAGCGGG CCATGTTAA GGGCGGTTT
6751  TTTCCTGTT TGGTCACTG ATGCCTCCG TGTAAGGGG GATTTCTGT
6796  TCATGGGGG TAATGATAC CGATGAAAC GAGAGAGGA TGCTCACGA
6841  TACGGGTTA CTGATGATG AACATGCCC GGTTACTGG AACGTTGTG
6886  AGGGTAAAC AACTGGCGG TATGGATGC GGCGGGACC AGAGAAAAA
6931  TCACTCAGG GTCAATGCC AGCGCTTCG TTAATACAG ATGTAGGTG
6976  TTCCACAGG GTAGCCAGC AGCATCCTG CGATGCAGA TCCGGAACA
7021  TAATGGTGC AGGGCGCTG ACTTCCGCG TTTCCAGAC TTTACGAAA
7066  CACGGAAAC CGAAGACCA TTCATGTTG TTGCTCAGG TCGCAGACG
7111  TTTTGCAGC AGCAGTCGC TTCACGTTC GCTCGCGTA TCGGTGATT
7156  CATTCTGCT AACCAGTAA GGCAACCCC GCCAGCCTA GCCGGGTCC
7201  TCAACGACA GGAGCACGA TCATGCGCA CCCGTGGCC AGGACCCAA
7246  CGCTGCCCG AAATT
```

FIG.22D

ToxoP30del4del8(83-294aa)

```
    ProLysThr AlaLeuThr GluProPro ThrLeuAla TyrSerPro
  1 CCTAAAACA GCGCTCACA GAGCCTCCC ACTCTTGCG TACTCACCC
    AsnArgGln IleCysPro AlaGlyThr ThrSerSer CysThrSer
 46 AACAGGCAA ATCTGCCCA GCGGGTACT ACAAGTAGC TGTACATCA
    LysAlaVal ThrLeuSer SerLeuIle ProGluAla GluAspSer
 91 AAGGCTGTA ACATTGAGC TCCTTGATT CCTGAAGCA GAAGATAGC
    TrpTrpThr GlyAspSer AlaSerLeu AspThrAla GlyIleLys
136 TGGTGGACG GGGGATTCT GCTAGTCTC GACACGGCA GGCATCAAA
    LeuThrVal ProIleGlu LysPhePro ValThrThr GlnThrPhe
181 CTCACAGTT CCAATCGAG AAGTTCCCC GTGACAACG CAGACGTTT
    ValValGly CysIleLys GlyAspAsp AlaGlnSer CysMetVal
226 GTGGTCGGT TGCATCAAG GGAGACGAC GCACAGAGT TGTATGGTC
    ThrValThr ValGlnAla ArgAlaSer SerValVal AsnAsnVal
271 ACAGTGACA GTACAAGCC AGAGCCTCA TCGGTCGTC AATAATGTC
    AlaArgCys SerTyrGly AlaAspSer ThrLeuGly ProValLys
316 GCAAGGTGC TCCTACGGT GCAGACAGC ACTCTTGGT CCTGTCAAG
    LeuSerAla GluGlyPro ThrThrMet ThrLeuVal CysGlyLys
361 TTGTCTGCG GAAGGACCC ACTACAATG ACCCTCGTG TGCGGGAAA
    AspGlyVal LysValPro GlnAspAsn AsnGlnTyr CysSerGly
406 GATGGAGTC AAAGTTCCT CAAGACAAC AATCAGTAC TGTTCCGGG
    ThrThrLeu ThrGlyCys AsnGluLys SerPheLys AspIleLeu
451 ACGACGCTG ACTGGTTGC AACGAGAAA TCGTTCAAA GATATTTTG
    ProLysLeu ThrGluAsn ProTrpGln GlyAsnAla SerSerAsp
496 CCAAAATTA ACTGAGAAC CCGTGGCAG GGTAACGCT TCGAGTGAT
    LysGlyAla ThrLeuThr IleLysLys GluAlaPhe ProAlaGlu
541 AAGGGTGCC ACGCTAACG ATCAAGAAG GAAGCATTT CCAGCCGAG
    SerLysSer ValIleIle GlyCysThr GlyGlySer ProGluLys
586 TCAAAAAGC GTCATTATT GGATGCACA GGGGGATCG CCTGAGAAG
    HisHis
631 CATCAC
```

FIG.23 pMBP-c2X-ToxoP30del10(52-284aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                  Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.25 pMBP-c2X-ToxoP30del10(52-284aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.25A pMBP-c2X-ToxoP30del10(52-284aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGlyGly ProThrThr MetThrLeu ValCysGly
3151  AAGTTGTCT GCGGGAGGA CCCACTACA ATGACCCTC GTGTGCGGG
      LysAspGly ValLysVal ProGlnAsp AsnAsnGln TyrCysSer
3196  AAAGATGGA GTCAAAGTT CCTCAAGAC AACAATCAG TACTGTTCC
      GlyThrThr LeuThrGly CysAsnGlu LysSerPhe LysAspIle
3241  GGGACGACG CTGACTGGT TGCAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGly
3376  GAGTCAAAA AGCGTCATT ATTGGATGA AAGCTTGGC ACTGGCCGT
3421  CGTTTTACA ACGTCGTGA CTGGGAAAA CCCTGGCGT TACCCAACT
3466  TAATCGCCT TGCAGCACA TCCCCCTTT CGCCAGCTG GCGTAATAG
3511  CGAAGAGGC CCGCACCGA TCGCCCTTC CCAACAGTT GCGCAGCCT
3556  GAATGGCGA ATGGCAGCT TGGCTGTTT TGGCGGATG AGATAAGAT
3601  TTTCAGCCT GATACAGAT TAAATCAGA ACGCAGAAG CGGTCTGAT
3646  AAAACAGAA TTTGCCTGG CGGCAGTAG CGCGGTGGT CCCACCTGA
3691  CCCCATGCC GAACTCAGA AGTGAAACG CCGTAGCGC CGATGGTAG
3736  TGTGGGGTC TCCCCATGC GAGAGTAGG GAACTGCCA GGCATCAAA
3781  TAAAACGAA AGGCTCAGT CGAAAGACT GGGCCTTTC GTTTTATCT
3826  GTTGTTTGT CGGTGAACG CTCTCCTGA GTAGGACAA ATCCGCCGG
3871  GAGCGGATT TGAACGTTG CGAAGCAAC GGCCCGGAG GGTGGCGGG
3916  CAGGACGCC CGCCATAAA CTGCCAGGC ATCAAATTA AGCAGAAGG
3961  CCATCCTGA CGGATGGCC TTTTTGCGT TTCTACAAA CTCTTTTTG
4006  TTTATTTTT CTAAATACA TTCAAATAT GTATCCGCT CATGAGACA
4051  ATAACCCTG ATAAATGCT TCAATAATA TTGAAAAAG GAAGAGTAT
4096  GAGTATTCA ACATTTCCG TGTCGCCCT TATTCCCTT TTTTGCGGC
4141  ATTTTGCCT TCCTGTTTT TGCTCACCC AGAAACGCT GGTGAAAGT
4186  AAAAGATGC TGAAGATCA GTTGGGTGC ACGAGTGGG TTACATCGA
4231  ACTGGATCT CAACAGCGG TAAGATCCT TGAGAGTTT TCGCCCCGA
```

FIG.25B pMBP-c2X-ToxoP30del10(52-284aa)

```
4276  AGAACGTTC  TCCAATGAT  GAGCACTTT  TAAAGTTCT  GCTATGTGG
4321  CGCGGTATT  ATCCCGTGT  TGACGCCGG  GCAAGAGCA  ACTCGGTCG
4366  CCGCATACA  CTATTCTCA  GAATGACTT  GGTTGAGTA  CTCACCAGT
4411  CACAGAAAA  GCATCTTAC  GGATGGCAT  GACAGTAAG  AGAATTATG
4456  CAGTGCTGC  CATAACCAT  GAGTGATAA  CACTGCGGC  CAACTTACT
4501  TCTGACAAC  GATCGGAGG  ACCGAAGGA  GCTAACCGC  TTTTTTGCA
4546  CAACATGGG  GGATCATGT  AACTCGCCT  TGATCGTTG  GGAACCGGA
4591  GCTGAATGA  AGCCATACC  AAACGACGA  GCGTGACAC  CACGATGCC
4636  TGTAGCAAT  GGCAACAAC  GTTGCGCAA  ACTATTAAC  TGGCGAACT
4681  ACTTACTCT  AGCTTCCCG  GCAACAATT  AATAGACTG  GATGGAGGC
4726  GGATAAAGT  TGCAGGACC  ACTTCTGCG  CTCGGCCCT  TCCGGCTGG
4771  CTGGTTTAT  TGCTGATAA  ATCTGGAGC  CGGTGAGCG  TGGGTCTCG
4816  CGGTATCAT  TGCAGCACT  GGGGCCAGA  TGGTAAGCC  CTCCCGTAT
4861  CGTAGTTAT  CTACACGAC  GGGGAGTCA  GGCAACTAT  GGATGAACG
4906  AAATAGACA  GATCGCTGA  GATAGGTGC  CTCACTGAT  TAAGCATTG
4951  GTAACTGTC  AGACCAAGT  TTACTCATA  TATACTTTA  GATTGATTT
4996  ACCCCGGTT  GATAATCAG  AAAAGCCCC  AAAAACAGG  AAGATTGTA
5041  TAAGCAAAT  ATTTAAATT  GTAAACGTT  AATATTTTG  TTAAAATTC
5086  GCGTTAAAT  TTTTGTTAA  ATCAGCTCA  TTTTTTAAC  CAATAGGCC
5131  GAAATCGGC  AAAATCCCT  TATAAATCA  AAAGAATAG  ACCGAGATA
5176  GGGTTGAGT  GTTGTTCCA  GTTTGGAAC  AAGAGTCCA  CTATTAAAG
5221  AACGTGGAC  TCCAACGTC  AAAGGGCGA  AAAACCGTC  TATCAGGGC
5266  GATGGCCCA  CTACGTGAA  CCATCACCC  AAATCAAGT  TTTTTGGGG
5311  TCGAGGTGC  CGTAAAGCA  CTAAATCGG  AACCCTAAA  GGGAGCCCC
5356  CGATTTAGA  GCTTGACGG  GGAAAGCCG  GCGAACGTG  GCGAGAAAG
5401  GAAGGGAAG  AAAGCGAAA  GGAGCGGGC  GCTAGGGCG  CTGGCAAGT
5446  GTAGCGGTC  ACGCTGCGC  GTAACCACC  ACACCCGCC  GCGCTTAAT
5491  GCGCCGCTA  CAGGGCGCG  TAAAAGGAT  CTAGGTGAA  GATCCTTTT
5536  TGATAATCT  CATGACCAA  AATCCCTTA  ACGTGAGTT  TTCGTTCCA
5581  CTGAGCGTC  AGACCCCGT  AGAAAAGAT  CAAAGGATC  TTCTTGAGA
5626  TCCTTTTTT  TCTGCGCGT  AATCTGCTG  CTTGCAAAC  AAAAAAACC
5671  ACCGCTACC  AGCGGTGGT  TTGTTTGCC  GGATCAAGA  GCTACCAAC
5716  TCTTTTTCC  GAAGGTAAC  TGGCTTCAG  CAGAGCGCA  GATACCAAA
5761  TACTGTCCT  TCTAGTGTA  GCCGTAGTT  AGGCCACCA  CTTCAAGAA
5806  CTCTGTAGC  ACCGCCTAC  ATACCTCGC  TCTGCTAAT  CCTGTTACC
5851  AGTGGCTGC  TGCCAGTGG  CGATAAGTC  GTGTCTTAC  CGGGTTGGA
5896  CTCAAGACG  ATAGTTACC  GGATAAGGC  GCAGCGGTC  GGGCTGAAC
5941  GGGGGGTTC  GTGCACACA  GCCCAGCTT  GGAGCGAAC  GACCTACAC
5986  CGAACTGAG  ATACCTACA  GCGTGAGCT  ATGAGAAAG  CGCCACGCT
6031  TCCCGAAGG  GAGAAAGGC  GGACAGGTA  TCCGGTAAG  CGGCAGGGT
6076  CGGAACAGG  AGAGCGCAC  GAGGGAGCT  TCCAGGGGG  AAACGCCTG
6121  GTATCTTTA  TAGTCCTGT  CGGGTTTCG  CCACCTCTG  ACTTGAGCG
6166  TCGATTTTT  GTGATGCTC  GTCAGGGGG  GCGGAGCCT  ATGGAAAAA
6211  CGCCAGCAA  CGCGGCCTT  TTTACGGTT  CCTGGCCTT  TTGCTGGCC
6256  TTTTGCTCA  CATGTTCTT  TCCTGCGTT  ATCCCCTGA  TTCTGTGGA
6301  TAACCGTAT  TACCGCCTT  TGAGTGAGC  TGATACCGC  TCGCCGCAG
```

FIG.25C pMBP-c2X-ToxoP30del10(52-284aa)

```
6346  CCGAACGAC CGAGCGCAG CGAGTCAGT GAGCGAGGA AGCGGAAGA
6391  GCGCCTGAT GCGGTATTT TCTCCTTAC GCATCTGTG CGGTATTTC
6436  ACACCGCAT ATATGGTGC ACTCTCAGT ACAATCTGC TCTGATGCC
6481  GCATAGTTA AGCCAGTAT ACACTCCGC TATCGCTAC GTGACTGGG
6526  TCATGGCTG CGCCCCGAC ACCCGCCAA CACCCGCTG ACGCGCCCT
6571  GACGGGCTT GTCTGCTCC CGGCATCCG CTTACAGAC AAGCTGTGA
6616  CCGTCTCCG GGAGCTGCA TGTGTCAGA GGTTTTCAC CGTCATCAC
6661  CGAAACGCG CGAGGCAGC TGCGGTAAA GCTCATCAG CGTGGTCGT
6706  GCAGCGATT CACAGATGT CTGCCTGTT CATCCGCGT CCAGCTCGT
6751  TGAGTTTCT CCAGAAGCG TTAATGTCT GGCTTCTGA TAAAGCGGG
6796  CCATGTTAA GGGCGGTTT TTTCCTGTT TGGTCACTG ATGCCTCCG
6841  TGTAAGGGG GATTTCTGT TCATGGGGG TAATGATAC CGATGAAAC
6886  GAGAGAGGA TGCTCACGA TACGGGTTA CTGATGATG AACATGCCC
6931  GGTTACTGG AACGTTGTG AGGGTAAAC AACTGGCGG TATGGATGC
6976  GGCGGGACC AGAGAAAAA TCACTCAGG GTCAATGCC AGCGCTTCG
7021  TTAATACAG ATGTAGGTG TTCCACAGG GTAGCCAGC AGCATCCTG
7066  CGATGCAGA TCCGGAACA TAATGGTGC AGGGCGCTG ACTTCCGCG
7111  TTTCCAGAC TTTACGAAA CACGGAAAC CGAAGACCA TTCATGTTG
7156  TTGCTCAGG TCGCAGACG TTTTGCAGC AGCAGTCGC TTCACGTTC
7201  GCTCGCGTA TCGGTGATT CATTCTGCT AACCAGTAA GGCAACCCC
7246  GCCAGCCTA GCCGGGTCC TCAACGACA GGAGCACGA TCATGCGCA
7291  CCCGTGGCC AGGACCCAA CGCTGCCCG AAATT
```

FIG.25D

ToxoP30del10(52-284aa)

| | | | | | |
|---|---|---|---|---|---|
| | LeuValAla | AsnGlnVal | ValThrCys | ProAspLys | LysSerThr |
| 1 | CTTGTTGCC | AATCAAGTT | GTCACCTGC | CCAGATAAA | AAATCGACA |
| | AlaAlaVal | IleLeuThr | ProThrGlu | AsnHisPhe | ThrLeuLys |
| 46 | GCCGCGGTC | ATTCTCACA | CCGACGGAG | AACCACTTC | ACTCTCAAG |
| | CysProLys | ThrAlaLeu | ThrGluPro | ProThrLeu | AlaTyrSer |
| 91 | TGCCCTAAA | ACAGCGCTC | ACAGAGCCT | CCCACTCTT | GCGTACTCA |
| | ProAsnArg | GlnIleCys | ProAlaGly | ThrThrSer | SerCysThr |
| 136 | CCCAACAGG | CAAATCTGC | CCAGCGGGT | ACTACAAGT | AGCTGTACA |
| | SerLysAla | ValThrLeu | SerSerLeu | IleProGlu | AlaGluAsp |
| 181 | TCAAAGGCT | GTAACATTG | AGCTCCTTG | ATTCCTGAA | GCAGAAGAT |
| | SerTrpTrp | ThrGlyAsp | SerAlaSer | LeuAspThr | AlaGlyIle |
| 226 | AGCTGGTGG | ACGGGGGAT | TCTGCTAGT | CTCGACACG | GCAGGCATC |
| | LysLeuThr | ValProIle | GluLysPhe | ProValThr | ThrGlnThr |
| 271 | AAACTCACA | GTTCCAATC | GAGAAGTTC | CCCGTGACA | ACGCAGACG |
| | PheValVal | GlyCysIle | LysGlyAsp | AspAlaGln | SerCysMet |
| 316 | TTTGTGGTC | GGTTGCATC | AAGGGAGAC | GACGCACAG | AGTTGTATG |
| | ValThrVal | ThrValGln | AlaArgAla | SerSerVal | ValAsnAsn |
| 361 | GTCACAGTG | ACAGTACAA | GCCAGAGCC | TCATCGGTC | GTCAATAAT |
| | ValAlaArg | CysSerTyr | GlyAlaAsp | SerThrLeu | GlyProVal |
| 406 | GTCGCAAGG | TGCTCCTAC | GGTGCAGAC | AGCACTCTT | GGTCCTGTC |
| | LysLeuSer | AlaGlyGly | ProThrThr | MetThrLeu | ValCysGly |
| 451 | AAGTTGTCT | GCGGGAGGA | CCCACTACA | ATGACCCTC | GTGTGCGGG |
| | LysAspGly | ValLysVal | ProGlnAsp | AsnAsnGln | TyrCysSer |
| 496 | AAAGATGGA | GTCAAAGTT | CCTCAAGAC | AACAATCAG | TACTGTTCC |
| | GlyThrThr | LeuThrGly | CysAsnGlu | LysSerPhe | LysAspIle |
| 541 | GGGACGACG | CTGACTGGT | TGCAACGAG | AAATCGTTC | AAAGATATT |
| | LeuProLys | LeuThrGlu | AsnProTrp | GlnGlyAsn | AlaSerSer |
| 586 | TTGCCAAAA | TTAACTGAG | AACCCGTGG | CAGGGTAAC | GCTTCGAGT |
| | AspLysGly | AlaThrLeu | ThrIleLys | LysGluAla | PheProAla |
| 631 | GATAAGGGT | GCCACGCTA | ACGATCAAG | AAGGAAGCA | TTTCCAGCC |
| | GluSerLys | SerValIle | IleGly | | |
| 676 | GAGTCAAAA | AGCGTCATT | ATTGGA | | |

FIG.26 pMBP-c2X-ToxoP30del11(52-214aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.28 pMBP-c2X-ToxoP30del11(52-214aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.28A pMBP-c2X-ToxoP30del11(52-214aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu Val
3151 AAGTTGTCT GCGGAAGGA CCCACTACA ATGACCCTC GTGTGAAAG
3196 CTTGGCACT GGCCGTCGT TTTACAACG TCGTGACTG GGAAAACCC
3241 TGGCGTTAC CCAACTTAA TCGCCTTGC AGCACATCC CCCTTTCGC
3286 CAGCTGGCG TAATAGCGA AGAGGCCCG CACCGATCG CCCTTCCCA
3331 ACAGTTGCG CAGCCTGAA TGGCGAATG GCAGCTTGG CTGTTTTGG
3376 CGGATGAGA TAAGATTTT CAGCCTGAT ACAGATTAA ATCAGAACG
3421 CAGAAGCGG TCTGATAAA ACAGAATTT GCCTGGCGG CAGTAGCGC
3466 GGTGGTCCC ACCTGACCC CATGCCGAA CTCAGAAGT GAAACGCCG
3511 TAGCGCCGA TGGTAGTGT GGGGTCTCC CCATGCGAG AGTAGGGAA
3556 CTGCCAGGC ATCAAATAA AACGAAAGG CTCAGTCGA AAGACTGGG
3601 CCTTTCGTT TTATCTGTT GTTTGTCGG TGAACGCTC TCCTGAGTA
3646 GGACAAATC CGCCGGGAG CGGATTTGA ACGTTGCGA AGCAACGGC
3691 CCGGAGGGT GGCGGGCAG GACGCCCGC CATAAACTG CCAGGCATC
3736 AAATTAAGC AGAAGGCCA TCCTGACGG ATGGCCTTT TTGCGTTTC
3781 TACAAACTC TTTTTGTTT ATTTTTCTA AATACATTC AAATATGTA
3826 TCCGCTCAT GAGACAATA ACCCTGATA AATGCTTCA ATAATATTG
3871 AAAAAGGAA GAGTATGAG TATTCAACA TTTCCGTGT CGCCCTTAT
3916 TCCCTTTTT TGCGGCATT TTGCCTTCC TGTTTTTGC TCACCCAGA
3961 AACGCTGGT GAAAGTAAA AGATGCTGA AGATCAGTT GGGTGCACG
4006 AGTGGGTTA CATCGAACT GGATCTCAA CAGCGGTAA GATCCTTGA
4051 GAGTTTTCG CCCCGAAGA ACGTTCTCC AATGATGAG CACTTTTAA
4096 AGTTCTGCT ATGTGGCGC GGTATTATC CCGTGTTGA CGCCGGGCA
4141 AGAGCAACT CGGTCGCCG CATACACTA TTCTCAGAA TGACTTGGT
4186 TGAGTACTC ACCAGTCAC AGAAAAGCA TCTTACGGA TGGCATGAC
4231 AGTAAGAGA ATTATGCAG TGCTGCCAT AACCATGAG TGATAACAC
4276 TGCGGCCAA CTTACTTCT GACAACGAT CGGAGGACC GAAGGAGCT
4321 AACCGCTTT TTTGCACAA CATGGGGGA TCATGTAAC TCGCCTTGA
4366 TCGTTGGGA ACCGGAGCT GAATGAAGC CATACCAAA CGACGAGCG
4411 TGACACCAC GATGCCTGT AGCAATGGC AACAACGTT GCGCAAACT
4456 ATTAACTGG CGAACTACT TACTCTAGC TTCCCGGCA ACAATTAAT
```

FIG.28B pMBP-c2X-ToxoP30del11(52-214aa)

4501 AGACTGGAT GGAGGCGGA TAAAGTTGC AGGACCACT TCTGCGCTC
4546 GGCCCTTCC GGCTGGCTG GTTTATTGC TGATAAATC TGGAGCCGG
4591 TGAGCGTGG GTCTCGCGG TATCATTGC AGCACTGGG GCCAGATGG
4636 TAAGCCCTC CCGTATCGT AGTTATCTA CACGACGGG GAGTCAGGC
4681 AACTATGGA TGAACGAAA TAGACAGAT CGCTGAGAT AGGTGCCTC
4726 ACTGATTAA GCATTGGTA ACTGTCAGA CCAAGTTTA CTCATATAT
4771 ACTTTAGAT TGATTTACC CCGGTTGAT AATCAGAAA AGCCCCAAA
4816 AACAGGAAG ATTGTATAA GCAAATATT TAAATTGTA AACGTTAAT
4861 ATTTTGTTA AAATTCGCG TTAAATTTT TGTTAAATC AGCTCATTT
4906 TTTAACCAA TAGGCCGAA ATCGGCAAA ATCCCTTAT AAATCAAAA
4951 GAATAGACC GAGATAGGG TTGAGTGTT GTTCCAGTT TGGAACAAG
4996 AGTCCACTA TTAAAGAAC GTGGACTCC AACGTCAAA GGGCGAAAA
5041 ACCGTCTAT CAGGGCGAT GGCCCACTA CGTGAACCA TCACCCAAA
5086 TCAAGTTTT TTGGGGTCG AGGTGCCGT AAAGCACTA AATCGGAAC
5131 CCTAAAGGG AGCCCCCGA TTTAGAGCT TGACGGGGA AAGCCGGCG
5176 AACGTGGCG AGAAAGGAA GGGAAGAAA GCGAAAGGA GCGGGCGCT
5221 AGGGCGCTG GCAAGTGTA GCGGTCACG CTGCGCGTA ACCACCACA
5266 CCCGCCGCG CTTAATGCG CCGCTACAG GGCGCGTAA AAGGATCTA
5311 GGTGAAGAT CCTTTTTGA TAATCTCAT GACCAAAAT CCCTTAACG
5356 TGAGTTTTC GTTCCACTG AGCGTCAGA CCCCGTAGA AAAGATCAA
5401 AGGATCTTC TTGAGATCC TTTTTTTCT GCGCGTAAT CTGCTGCTT
5446 GCAAACAAA AAAACCACC GCTACCAGC GGTGGTTTG TTTGCCGGA
5491 TCAAGAGCT ACCAACTCT TTTTCCGAA GGTAACTGG CTTCAGCAG
5536 AGCGCAGAT ACCAAATAC TGTCCTTCT AGTGTAGCC GTAGTTAGG
5581 CCACCACTT CAAGAACTC TGTAGCACC GCCTACATA CCTCGCTCT
5626 GCTAATCCT GTTACCAGT GGCTGCTGC CAGTGGCGA TAAGTCGTG
5671 TCTTACCGG GTTGGACTC AAGACGATA GTTACCGGA TAAGGCGCA
5716 GCGGTCGGG CTGAACGGG GGGTTCGTG CACACAGCC CAGCTTGGA
5761 GCGAACGAC CTACACCGA ACTGAGATA CCTACAGCG TGAGCTATG
5806 AGAAAGCGC CACGCTTCC CGAAGGGAG AAAGGCGGA CAGGTATCC
5851 GGTAAGCGG CAGGGTCGG AACAGGAGA GCGCACGAG GGAGCTTCC
5896 AGGGGGAAA CGCCTGGTA TCTTTATAG TCCTGTCGG GTTTCGCCA
5941 CCTCTGACT TGAGCGTCG ATTTTTGTG ATGCTCGTC AGGGGGGCG
5986 GAGCCTATG GAAAAACGC CAGCAACGC GGCCTTTTT ACGGTTCCT
6031 GGCCTTTTG CTGGCCTTT TGCTCACAT GTTCTTTCC TGCGTTATC
6076 CCCTGATTC TGTGGATAA CCGTATTAC CGCCTTTGA GTGAGCTGA
6121 TACCGCTCG CCGCAGCCG AACGACCGA GCGCAGCGA GTCAGTGAG
6166 CGAGGAAGC GGAAGAGCG CCTGATGCG GTATTTTCT CCTTACGCA
6211 TCTGTGCGG TATTTCACA CCGCATATA TGGTGCACT CTCAGTACA
6256 ATCTGCTCT GATGCCGCA TAGTTAAGC CAGTATACA CTCCGCTAT
6301 CGCTACGTG ACTGGGTCA TGGCTGCGC CCCGACACC CGCCAACAC
6346 CCGCTGACG CGCCCTGAC GGGCTTGTC TGCTCCCGG CATCCGCTT
6391 ACAGACAAG CTGTGACCG TCTCCGGGA GCTGCATGT GTCAGAGGT
6436 TTTCACCGT CATCACCGA AACGCGCGA GGCAGCTGC GGTAAAGCT
6481 CATCAGCGT GGTCGTGCA GCGATTCAC AGATGTCTG CCTGTTCAT
6526 CCGCGTCCA GCTCGTTGA GTTTCTCCA GAAGCGTTA ATGTCTGGC

FIG.28C pMBP-c2X-ToxoP30del11(52-214aa)

```
6571  TTCTGATAA AGCGGGCCA TGTTAAGGG CGGTTTTTT CCTGTTTGG
6616  TCACTGATG CCTCCGTGT AAGGGGGAT TTCTGTTCA TGGGGGTAA
6661  TGATACCGA TGAAACGAG AGAGGATGC TCACGATAC GGGTTACTG
6706  ATGATGAAC ATGCCCGGT TACTGGAAC GTTGTGAGG GTAAACAAC
6751  TGGCGGTAT GGATGCGGC GGGACCAGA GAAAAATCA CTCAGGGTC
6796  AATGCCAGC GCTTCGTTA ATACAGATG TAGGTGTTC CACAGGGTA
6841  GCCAGCAGC ATCCTGCGA TGCAGATCC GGAACATAA TGGTGCAGG
6886  GCGCTGACT TCCGCGTTT CCAGACTTT ACGAAACAC GGAAACCGA
6931  AGACCATTC ATGTTGTTG CTCAGGTCG CAGACGTTT TGCAGCAGC
6976  AGTCGCTTC ACGTTCGCT CGCGTATCG GTGATTCAT TCTGCTAAC
7021  CAGTAAGGC AACCCCGCC AGCCTAGCC GGGTCCTCA ACGACAGGA
7066  GCACGATCA TGCGCACCC GTGGCCAGG ACCCAACGC TGCCCGAAA
7111  TT
```

FIG.28D

ToxoP30del11(52-214aa)

| | | | | | |
|---|---|---|---|---|---|
| | LeuValAla | AsnGlnVal | ValThrCys | ProAspLys | LysSerThr |
| 1 | CTTGTTGCC | AATCAAGTT | GTCACCTGC | CCAGATAAA | AAATCGACA |
| | AlaAlaVal | IleLeuThr | ProThrGlu | AsnHisPhe | ThrLeuLys |
| 46 | GCCGCGGTC | ATTCTCACA | CCGACGGAG | AACCACTTC | ACTCTCAAG |
| | CysProLys | ThrAlaLeu | ThrGluPro | ProThrLeu | AlaTyrSer |
| 91 | TGCCCTAAA | ACAGCGCTC | ACAGAGCCT | CCCACTCTT | GCGTACTCA |
| | ProAsnArg | GlnIleCys | ProAlaGly | ThrThrSer | SerCysThr |
| 136 | CCCAACAGG | CAAATCTGC | CCAGCGGGT | ACTACAAGT | AGCTGTACA |
| | SerLysAla | ValThrLeu | SerSerLeu | IleProGlu | AlaGluAsp |
| 181 | TCAAAGGCT | GTAACATTG | AGCTCCTTG | ATTCCTGAA | GCAGAAGAT |
| | SerTrpTrp | ThrGlyAsp | SerAlaSer | LeuAspThr | AlaGlyIle |
| 226 | AGCTGGTGG | ACGGGGGAT | TCTGCTAGT | CTCGACACG | GCAGGCATC |
| | LysLeuThr | ValProIle | GluLysPhe | ProValThr | ThrGlnThr |
| 271 | AAACTCACA | GTTCCAATC | GAGAAGTTC | CCCGTGACA | ACGCAGACG |
| | PheValVal | GlyCysIle | LysGlyAsp | AspAlaGln | SerCysMet |
| 316 | TTTGTGGTC | GGTTGCATC | AAGGGAGAC | GACGCACAG | AGTTGTATG |
| | ValThrVal | ThrValGln | AlaArgAla | SerSerVal | ValAsnAsn |
| 361 | GTCACAGTG | ACAGTACAA | GCCAGAGCC | TCATCGGTC | GTCAATAAT |
| | ValAlaArg | CysSerTyr | GlyAlaAsp | SerThrLeu | GlyProVal |
| 406 | GTCGCAAGG | TGCTCCTAC | GGTGCAGAC | AGCACTCTT | GGTCCTGTC |
| | LysLeuSer | AlaGluGly | ProThrThr | MetThrLeu | Val |
| 451 | AAGTTGTCT | GCGGAAGGA | CCCACTACA | ATGACCCTC | GTG |

FIG.29 pMBP-c2X-ToxoP30MIX1

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                  Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.31 pMBP-c2X-ToxoP30MIX1

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.31A pMBP-c2X-ToxoP30MIX1

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsp AsnAsnGln TyrAlaSer
3196 AAAGATGGA GTCAAAGTT CCTCAAGAC AATAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TTCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG GCCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AAGGAAGAG
4141 TATGAGTAT TCAACATTT CCGTGTCGC CCTTATTCC CTTTTTTGC
4186 GGCATTTTG CCTTCCTGT TTTTGCTCA CCCAGAAAC GCTGGTGAA
```

FIG.31B pMBP-c2X-ToxoP30MIX1

4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTGAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GGCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA AACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG GTCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGGCGGAG CCTATGGAA
6256 AAACGCCAG CAACGCGGC CTTTTTACG GTTCCTGGC CTTTTGCTG

FIG.31C pMBP-c2X-ToxoP30MIX1

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIG.31D

ToxoP30MIX1

```
    LeuValAla AsnGlnVal ValThrCys ProAspLys LysSerThr
1   CTTGTTGCC AATCAAGTT GTCACCTGC CCAGATAAA AAATCGACA
    AlaAlaVal IleLeuThr ProThrGlu AsnHisPhe ThrLeuLys
46  GCCGCGGTC ATTCTCACA CCGACGGAG AACCACTTC ACTCTCAAG
    CysProLys ThrAlaLeu ThrGluPro ProThrLeu AlaTyrSer
91  TGCCCTAAA ACAGCGCTC ACAGAGCCT CCCACTCTT GCGTACTCA
    ProAsnArg GlnIleCys ProAlaGly ThrThrSer SerCysThr
136 CCCAACAGG CAAATCTGC CCAGCGGGT ACTACAAGT AGCTGTACA
    SerLysAla ValThrLeu SerSerLeu IleProGlu AlaGluAsp
181 TCAAAGGCT GTAACATTG AGCTCCTTG ATTCCTGAA GCAGAAGAT
    SerTrpTrp ThrGlyAsp SerAlaSer LeuAspThr AlaGlyIle
226 AGCTGGTGG ACGGGGGAT TCTGCTAGT CTCGACACG GCAGGCATC
    LysLeuThr ValProIle GluLysPhe ProValThr ThrGlnThr
271 AAACTCACA GTTCCAATC GAGAAGTTC CCCGTGACA ACGCAGACG
    PheValVal GlyCysIle LysGlyAsp AspAlaGln SerCysMet
316 TTTGTGGTC GGTTGCATC AAGGGAGAC GACGCACAG AGTTGTATG
    ValThrVal ThrValGln AlaArgAla SerSerVal ValAsnAsn
361 GTCACGGTG ACAGTACAA GCCAGAGCC TCATCGGTC GTCAATAAT
    ValAlaArg CysSerTyr GlyAlaAsp SerThrLeu GlyProVal
406 GTCGCAAGG TGCTCCTAC GGTGCAGAC AGCACTCTT GGTCCTGTC
    LysLeuSer AlaGluGly ProThrThr MetThrLeu ValAlaGly
451 AAGTTGTCT GCGGAAGGA CCCACTACA ATGACCCTC GTGGCTGGG
    LysAspGly ValLysVal ProGlnAsp AsnAsnGln TyrAlaSer
496 AAAGATGGA GTCAAAGTT CCTCAAGAC AATAATCAG TACGCTTCC
    GlyThrThr LeuThrGly AlaAsnGlu LysSerPhe LysAspIle
541 GGGACGACG CTGACTGGT GCTAACGAG AAATCGTTC AAAGATATT
    LeuProLys LeuThrGlu AsnProTrp GlnGlyAsn AlaSerSer
586 TTGCCAAAA TTAACTGAG AACCCGTGG CAGGGTAAC GCTTCGAGT
    AspLysGly AlaThrLeu ThrIleLys LysGluAla PheProAla
631 GATAAGGGT GCCACGCTA ACGATCAAG AAGGAAGCA TTTCCAGCC
    GluSerLys SerValIle IleGlyAla ThrGlyGly SerProGlu
676 GAGTCAAAA AGCGTCATT ATTGGAGCT ACAGGGGGA TCGCCTGAG
    LysHisHis AlaThrVal LysLeuGlu
721 AAGCATCAC GCTACCGTG AAACTGGAG
```

FIG.32 pMBP-c2X-ToxoP30MIX3

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                  Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.33 pMBP-c2X-ToxoP30MIX3

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.33A pMBP-c2X-ToxoP30MIX3

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg AlaSerTyr GlyAlaAsp SerThrLeu GlyProVal
3106 GTCGCAAGG GCTTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsp AsnAsnGln TyrAlaSer
3196 AAAGATGGA GTCAAAGTT CCTCAAGAC AACAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TTCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG GCCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AAGGAAGAG
4141 TATGAGTAT TCAACATTT CCGTGTCGC CCTTATTCC CTTTTTTGC
4186 GGCATTTTG CCTTCCTGT TTTTGCTCA CCCAGAAAC GCTGGTGAA
```

FIG.33B pMBP-c2X-ToxoP30MIX3

```
4231  AGTAAAAGA TGCTGAAGA TCAGTTGGG TGCACGAGT GGGTTACAT
4276  CGAACTGGA TCTCAACAG CGGTAAGAT CCTTGAGAG TTTTCGCCC
4321  CGAAGAACG TTCTCCAAT GATGAGCAC TTTTAAAGT TCTGCTATG
4366  TGGCGCGGT ATTATCCCG TGTTGACGC CGGGCAAGA GCAACTCGG
4411  TCGCCGCAT ACACTATTC TCAGAATGA CTTGGTTGA GTACTCACC
4456  AGTCACAGA AAAGCATCT TACGGATGG CATGACAGT AAGAGAATT
4501  ATGCAGTGC TGCCATAAC CATGAGTGA TAACACTGC GGCCAACTT
4546  ACTTCTGAC AACGATCGG AGGACCGAA GGAGCTAAC CGCTTTTTT
4591  GCACAACAT GGGGGATCA TGTAACTCG CCTTGATCG TTGGGAACC
4636  GGAGCTGAA TGAAGCCAT ACCAAACGA CGAGCGTGA CACCACGAT
4681  GCCTGTAGC AATGGCAAC AACGTTGCG CAAACTATT AACTGGCGA
4726  ACTACTTAC TCTAGCTTC CCGGCAACA ATTAATAGA CTGGATGGA
4771  GGCGGATAA AGTTGCAGG ACCACTTCT GCGCTCGGC CCTTCCGGC
4816  TGGCTGGTT TATTGCTGA TAAATCTGG AGCCGGTGA GCGTGGGTC
4861  TCGCGGTAT CATTGCAGC ACTGGGGCC AGATGGTAA GCCCTCCCG
4906  TATCGTAGT TATCTACAC GACGGGGAG TCAGGCAAC TATGGATGA
4951  ACGAAATAG ACAGATCGC TGAGATAGG TGCCTCACT GATTAAGCA
4996  TTGGTAACT GTCAGACCA AGTTTACTC ATATATACT TTAGATTGA
5041  TTTACCCCG GTTGATAAT CAGAAAAGC CCCAAAAAC AGGAAGATT
5086  GTATAAGCA AATATTTAA ATTGTAAAC GTTAATATT TTGTTAAAA
5131  TTCGCGTTA AATTTTTGT TAAATCAGC TCATTTTTT AACCAATAG
5176  GCCGAAATC GGCAAAATC CCTTATAAA TCAAAAGAA TAGACCGAG
5221  ATAGGGTTG AGTGTTGTT CCAGTTTGG AACAAGAGT CCACTATTA
5266  AAGAACGTG GACTCCAAC GTCAAAGGG CGAAAAACC GTCTATCAG
5311  GGCGATGGC CCACTACGT GAACCATCA CCCAAATCA AGTTTTTTG
5356  GGGTCGAGG TGCCGTAAA GCACTAAAT CGGAACCCT AAAGGGAGC
5401  CCCCGATTT AGAGCTTGA CGGGGAAAG CCGGCGAAC GTGGCGAGA
5446  AAGGAAGGG AAGAAAGCG AAAGGAGCG GGCGCTAGG GCGCTGGCA
5491  AGTGTAGCG GTCACGCTG CGCGTAACC ACCACACCC GCCGCGCTT
5536  AATGCGCCG CTACAGGGC GCGTAAAAG GATCTAGGT GAAGATCCT
5581  TTTTGATAA TCTCATGAC CAAAATCCC TTAACGTGA GTTTTCGTT
5626  CCACTGAGC GTCAGACCC CGTAGAAAA GATCAAAGG ATCTTCTTG
5671  AGATCCTTT TTTTCTGCG CGTAATCTG CTGCTTGCA AACAAAAAA
5716  ACCACCGCT ACCAGCGGT GGTTTGTTT GCCGGATCA AGAGCTACC
5761  AACTCTTTT TCCGAAGGT AACTGGCTT CAGCAGAGC GCAGATACC
5806  AAATACTGT CCTTCTAGT GTAGCCGTA GTTAGGCCA CCACTTCAA
5851  GAACTCTGT AGCACCGCC TACATACCT CGCTCTGCT AATCCTGTT
5896  ACCAGTGGC TGCTGCCAG TGGCGATAA GTCGTGTCT TACCGGGTT
5941  GGACTCAAG ACGATAGTT ACCGGATAA GGCGCAGCG GTCGGGCTG
5986  AACGGGGGG TTCGTGCAC ACAGCCCAG CTTGGAGCG AACGACCTA
6031  CACCGAACT GAGATACCT ACAGCGTGA GCTATGAGA AAGCGCCAC
6076  GCTTCCCGA AGGGAGAAA GGCGGACAG GTATCCGGT AAGCGGCAG
6121  GGTCGGAAC AGGAGAGCG CACGAGGGA GCTTCCAGG GGGAAACGC
6166  CTGGTATCT TTATAGTCC TGTCGGGTT TCGCCACCT CTGACTTGA
6211  GCGTCGATT TTTGTGATG CTCGTCAGG GGGGCGGAG CCTATGGAA
6256  AAACGCCAG CAACGCGGC CTTTTTACG GTTCCTGGC CTTTTGCTG
```

FIG.33C pMBP-c2X-ToxoP30MIX3

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIG.33D

ToxoP30MIX3

| | | | | | |
|---|---|---|---|---|---|
| | LeuValAla | AsnGlnVal | ValThrCys | ProAspLys | LysSerThr |
| 1 | CTTGTTGCC | AATCAAGTT | GTCACCTGC | CCAGATAAA | AAATCGACA |
| | AlaAlaVal | IleLeuThr | ProThrGlu | AsnHisPhe | ThrLeuLys |
| 46 | GCCGCGGTC | ATTCTCACA | CCGACGGAG | AACCACTTC | ACTCTCAAG |
| | CysProLys | ThrAlaLeu | ThrGluPro | ProThrLeu | AlaTyrSer |
| 91 | TGCCCTAAA | ACAGCGCTC | ACAGAGCCT | CCCACTCTT | GCGTACTCA |
| | ProAsnArg | GlnIleCys | ProAlaGly | ThrThrSer | SerCysThr |
| 136 | CCCAACAGG | CAAATCTGC | CCAGCGGGT | ACTACAAGT | AGCTGTACA |
| | SerLysAla | ValThrLeu | SerSerLeu | IleProGlu | AlaGluAsp |
| 181 | TCAAAGGCT | GTAACATTG | AGCTCCTTG | ATTCCTGAA | GCAGAAGAT |
| | SerTrpTrp | ThrGlyAsp | SerAlaSer | LeuAspThr | AlaGlyIle |
| 226 | AGCTGGTGG | ACGGGGGAT | TCTGCTAGT | CTCGACACG | GCAGGCATC |
| | LysLeuThr | ValProIle | GluLysPhe | ProValThr | ThrGlnThr |
| 271 | AAACTCACA | GTTCCAATC | GAGAAGTTC | CCCGTGACA | ACGCAGACG |
| | PheValVal | GlyCysIle | LysGlyAsp | AspAlaGln | SerCysMet |
| 316 | TTTGTGGTC | GGTTGCATC | AAGGGAGAC | GACGCACAG | AGTTGTATG |
| | ValThrVal | ThrValGln | AlaArgAla | SerSerVal | ValAsnAsn |
| 361 | GTCACGGTG | ACAGTACAA | GCCAGAGCC | TCATCGGTC | GTCAATAAT |
| | ValAlaArg | AlaSerTyr | GlyAlaAsp | SerThrLeu | GlyProVal |
| 406 | GTCGCAAGG | GCTTCCTAC | GGTGCAGAC | AGCACTCTT | GGTCCTGTC |
| | LysLeuSer | AlaGluGly | ProThrThr | MetThrLeu | ValAlaGly |
| 451 | AAGTTGTCT | GCGGAAGGA | CCCACTACA | ATGACCCTC | GTGGCTGGG |
| | LysAspGly | ValLysVal | ProGlnAsp | AsnAsnGln | TyrAlaSer |
| 496 | AAAGATGGA | GTCAAAGTT | CCTCAAGAC | AACAATCAG | TACGCTTCC |
| | GlyThrThr | LeuThrGly | AlaAsnGlu | LysSerPhe | LysAspIle |
| 541 | GGGACGACG | CTGACTGGT | GCTAACGAG | AAATCGTTC | AAAGATATT |
| | LeuProLys | LeuThrGlu | AsnProTrp | GlnGlyAsn | AlaSerSer |
| 586 | TTGCCAAAA | TTAACTGAG | AACCCGTGG | CAGGGTAAC | GCTTCGAGT |
| | AspLysGly | AlaThrLeu | ThrIleLys | LysGluAla | PheProAla |
| 631 | GATAAGGGT | GCCACGCTA | ACGATCAAG | AAGGAAGCA | TTTCCAGCC |
| | GluSerLys | SerValIle | IleGlyAla | ThrGlyGly | SerProGlu |
| 676 | GAGTCAAAA | AGCGTCATT | ATTGGAGCT | ACAGGGGGA | TCGCCTGAG |
| | LysHisHis | AlaThrVal | LysLeuGlu | | |
| 721 | AAGCATCAC | GCTACCGTG | AAACTGGAG | | |

FIG.34 pMBP-c2X-ToxoP30MIX5

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.35 pMBP-c2X-ToxoP30MIX5

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     AlaProLys ThrAlaLeu ThrGluPro ProThrLeu AlaTyrSer
```

FIG.35A pMBP-c2X-ToxoP30MIX5

```
2791  GCTCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACGGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGluGly ProThrThr MetThrLeu ValAlaGly
3151  AAGTTGTCT GCGGAAGGA CCCACTACA ATGACCCTC GTGGCTGGG
      LysAspGly ValLysVal ProGlnAsp AsnAsnGln TyrAlaSer
3196  AAAGATGGA GTCAAAGTT CCTCAAGAC AACAATCAG TACGCTTCC
      GlyThrThr LeuThrGly AlaAsnGlu LysSerPhe LysAspIle
3241  GGGACGACG CTGACTGGT GCTAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGlyAla ThrGlyGly SerProGlu
3376  GAGTCAAAA AGCGTCATT ATTGGAGCT ACAGGGGGA TCGCCTGAG
      LysHisHis AlaThrVal LysLeuGlu
3421  AAGCATCAC GCTACCGTG AAACTGGAG TGAAAGCTT GGCACTGGC
3466  CGTCGTTTT ACAACGTCG TGACTGGGA AAACCCTGG CGTTACCCA
3511  ACTTAATCG CCTTGCAGC ACATCCCCC TTTCGCCAG CTGGCGTAA
3556  TAGCGAAGA GGCCCGCAC CGATCGCCC TTCCCAACA GTTGCGCAG
3601  CCTGAATGG CGAATGGCA GCTTGGCTG TTTTGGCGG ATGAGATAA
3646  GATTTTCAG CCTGATACA GATTAAATC AGAACGCAG AAGCGGTCT
3691  GATAAAACA GAATTTGCC TGGCGGCAG TAGCGCGGT GGTCCCACC
3736  TGACCCCAT GCCGAACTC AGAAGTGAA ACGCCGTAG CGCCGATGG
3781  TAGTGTGGG GTCTCCCCA TGCGAGAGT AGGGAACTG CCAGGCATC
3826  AAATAAAAC GAAAGGCTC AGTCGAAAG ACTGGGCCT TTCGTTTTA
3871  TCTGTTGTT TGTCGGTGA ACGCTCTCC TGAGTAGGA CAAATCCGC
3916  CGGGAGCGG ATTTGAACG TTGCGAAGC AACGGCCCG GAGGGTGGC
3961  GGGCAGGAC GCCCGCCAT AAACTGCCA GGCATCAAA TTAAGCAGA
4006  AGGCCATCC TGACGGATG GCCTTTTTG CGTTTCTAC AAACTCTTT
4051  TTGTTTATT TTTCTAAAT ACATTCAAA TATGTATCC GCTCATGAG
4096  ACAATAACC CTGATAAAT GCTTCAATA ATATTGAAA AAGGAAGAG
4141  TATGAGTAT TCAACATTT CCGTGTCGC CCTTATTCC CTTTTTTGC
4186  GGCATTTTG CCTTCCTGT TTTTGCTCA CCCAGAAAC GCTGGTGAA
```

FIG.35B pMBP-c2X-ToxoP30MIX5

| | | | | | |
|---|---|---|---|---|---|
| 4231 | AGTAAAAGA | TGCTGAAGA | TCAGTTGGG | TGCACGAGT | GGGTTACAT |
| 4276 | CGAACTGGA | TCTCAACAG | CGGTAAGAT | CCTTGAGAG | TTTTCGCCC |
| 4321 | CGAAGAACG | TTCTCCAAT | GATGAGCAC | TTTTAAAGT | TCTGCTATG |
| 4366 | TGGCGCGGT | ATTATCCCG | TGTTGACGC | CGGGCAAGA | GCAACTCGG |
| 4411 | TCGCCGCAT | ACACTATTC | TCAGAATGA | CTTGGTTGA | GTACTCACC |
| 4456 | AGTCACAGA | AAAGCATCT | TACGGATGG | CATGACAGT | AAGAGAATT |
| 4501 | ATGCAGTGC | TGCCATAAC | CATGAGTGA | TAACACTGC | GGCCAACTT |
| 4546 | ACTTCTGAC | AACGATCGG | AGGACCGAA | GGAGCTAAC | CGCTTTTTT |
| 4591 | GCACAACAT | GGGGGATCA | TGTAACTCG | CCTTGATCG | TTGGGAACC |
| 4636 | GGAGCTGAA | TGAAGCCAT | ACCAAACGA | CGAGCGTGA | CACCACGAT |
| 4681 | GCCTGTAGC | AATGGCAAC | AACGTTGCG | CAAACTATT | AACTGGCGA |
| 4726 | ACTACTTAC | TCTAGCTTC | CCGGCAACA | ATTAATAGA | CTGGATGGA |
| 4771 | GGCGGATAA | AGTTGCAGG | ACCACTTCT | GCGCTCGGC | CCTTCCGGC |
| 4816 | TGGCTGGTT | TATTGCTGA | TAAATCTGG | AGCCGGTGA | GCGTGGGTC |
| 4861 | TCGCGGTAT | CATTGCAGC | ACTGGGGCC | AGATGGTAA | GCCCTCCCG |
| 4906 | TATCGTAGT | TATCTACAC | GACGGGGAG | TCAGGCAAC | TATGGATGA |
| 4951 | ACGAAATAG | ACAGATCGC | TGAGATAGG | TGCCTCACT | GATTAAGCA |
| 4996 | TTGGTAACT | GTCAGACCA | AGTTTACTC | ATATATACT | TTAGATTGA |
| 5041 | TTTACCCCG | GTTGATAAT | CAGAAAAGC | CCCAAAAAC | AGGAAGATT |
| 5086 | GTATAAGCA | AATATTTAA | ATTGTAAAC | GTTAATATT | TTGTTAAAA |
| 5131 | TTCGCGTTA | AATTTTTGT | TAAATCAGC | TCATTTTTT | AACCAATAG |
| 5176 | GCCGAAATC | GGCAAAATC | CCTTATAAA | TCAAAAGAA | TAGACCGAG |
| 5221 | ATAGGGTTG | AGTGTTGTT | CCAGTTTGG | AACAAGAGT | CCACTATTA |
| 5266 | AAGAACGTG | GACTCCAAC | GTCAAAGGG | CGAAAAACC | GTCTATCAG |
| 5311 | GGCGATGGC | CCACTACGT | GAACCATCA | CCCAAATCA | AGTTTTTTG |
| 5356 | GGGTCGAGG | TGCCGTAAA | GCACTAAAT | CGGAACCCT | AAAGGGAGC |
| 5401 | CCCCGATTT | AGAGCTTGA | CGGGGAAAG | CCGGCGAAC | GTGGCGAGA |
| 5446 | AAGGAAGGG | AAGAAAGCG | AAAGGAGCG | GGCGCTAGG | GCGCTGGCA |
| 5491 | AGTGTAGCG | GTCACGCTG | CGCGTAACC | ACCACACCC | GCCGCGCTT |
| 5536 | AATGCGCCG | CTACAGGGC | GCGTAAAAG | GATCTAGGT | GAAGATCCT |
| 5581 | TTTTGATAA | TCTCATGAC | CAAAATCCC | TTAACGTGA | GTTTTCGTT |
| 5626 | CCACTGAGC | GTCAGACCC | CGTAGAAAA | GATCAAAGG | ATCTTCTTG |
| 5671 | AGATCCTTT | TTTTCTGCG | CGTAATCTG | CTGCTTGCA | AACAAAAAA |
| 5716 | ACCACCGCT | ACCAGCGGT | GGTTTGTTT | GCCGGATCA | AGAGCTACC |
| 5761 | AACTCTTTT | TCCGAAGGT | AACTGGCTT | CAGCAGAGC | GCAGATACC |
| 5806 | AAATACTGT | CCTTCTAGT | GTAGCCGTA | GTTAGGCCA | CCACTTCAA |
| 5851 | GAACTCTGT | AGCACCGCC | TACATACCT | CGCTCTGCT | AATCCTGTT |
| 5896 | ACCAGTGGC | TGCTGCCAG | TGGCGATAA | GTCGTGTCT | TACCGGGTT |
| 5941 | GGACTCAAG | ACGATAGTT | ACCGGATAA | GGCGCAGCG | GTCGGGCTG |
| 5986 | AACGGGGGG | TTCGTGCAC | ACAGCCCAG | CTTGGAGCG | AACGACCTA |
| 6031 | CACCGAACT | GAGATACCT | ACAGCGTGA | GCTATGAGA | AAGCGCCAC |
| 6076 | GCTTCCCGA | AGGGAGAAA | GGCGGACAG | GTATCCGGT | AAGCGGCAG |
| 6121 | GGTCGGAAC | AGGAGAGCG | CACGAGGGA | GCTTCCAGG | GGGAAACGC |
| 6166 | CTGGTATCT | TTATAGTCC | TGTCGGGTT | TCGCCACCT | CTGACTTGA |
| 6211 | GCGTCGATT | TTTGTGATG | CTCGTCAGG | GGGGCGGAG | CCTATGGAA |
| 6256 | AAACGCCAG | CAACGCGGC | CTTTTTACG | GTTCCTGGC | CTTTTGCTG |

FIG.35C pMBP-c2X-ToxoP30MIX5

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIG.35D

ToxoP30MIX5

| | | | | | |
|---|---|---|---|---|---|
| | LeuValAla | AsnGlnVal | ValThrCys | ProAspLys | LysSerThr |
| 1 | CTTGTTGCC | AATCAAGTT | GTCACCTGC | CCAGATAAA | AAATCGACA |
| | AlaAlaVal | IleLeuThr | ProThrGlu | AsnHisPhe | ThrLeuLys |
| 46 | GCCGCGGTC | ATTCTCACA | CCGACGGAG | AACCACTTC | ACTCTCAAG |
| | AlaProLys | ThrAlaLeu | ThrGluPro | ProThrLeu | AlaTyrSer |
| 91 | GCTCCTAAA | ACAGCGCTC | ACAGAGCCT | CCCACTCTT | GCGTACTCA |
| | ProAsnArg | GlnIleCys | ProAlaGly | ThrThrSer | SerCysThr |
| 136 | CCCAACAGG | CAAATCTGC | CCAGCGGGT | ACTACAAGT | AGCTGTACA |
| | SerLysAla | ValThrLeu | SerSerLeu | IleProGlu | AlaGluAsp |
| 181 | TCAAAGGCT | GTAACATTG | AGCTCCTTG | ATTCCTGAA | GCAGAAGAT |
| | SerTrpTrp | ThrGlyAsp | SerAlaSer | LeuAspThr | AlaGlyIle |
| 226 | AGCTGGTGG | ACGGGGGAT | TCTGCTAGT | CTCGACACG | GCAGGCATC |
| | LysLeuThr | ValProIle | GluLysPhe | ProValThr | ThrGlnThr |
| 271 | AAACTCACA | GTTCCAATC | GAGAAGTTC | CCCGTGACA | ACGCAGACG |
| | PheValVal | GlyCysIle | LysGlyAsp | AspAlaGln | SerCysMet |
| 316 | TTTGTGGTC | GGTTGCATC | AAGGGAGAC | GACGCACAG | AGTTGTATG |
| | ValThrVal | ThrValGln | AlaArgAla | SerSerVal | ValAsnAsn |
| 361 | GTCACGGTG | ACAGTACAA | GCCAGAGCC | TCATCGGTC | GTCAATAAT |
| | ValAlaArg | CysSerTyr | GlyAlaAsp | SerThrLeu | GlyProVal |
| 406 | GTCGCAAGG | TGCTCCTAC | GGTGCAGAC | AGCACTCTT | GGTCCTGTC |
| | LysLeuSer | AlaGluGly | ProThrThr | MetThrLeu | ValAlaGly |
| 451 | AAGTTGTCT | GCGGAAGGA | CCCACTACA | ATGACCCTC | GTGGCTGGG |
| | LysAspGly | ValLysVal | ProGlnAsp | AsnAsnGln | TyrAlaSer |
| 496 | AAAGATGGA | GTCAAAGTT | CCTCAAGAC | AACAATCAG | TACGCTTCC |
| | GlyThrThr | LeuThrGly | AlaAsnGlu | LysSerPhe | LysAspIle |
| 541 | GGGACGACG | CTGACTGGT | GCTAACGAG | AAATCGTTC | AAAGATATT |
| | LeuProLys | LeuThrGlu | AsnProTrp | GlnGlyAsn | AlaSerSer |
| 586 | TTGCCAAAA | TTAACTGAG | AACCCGTGG | CAGGGTAAC | GCTTCGAGT |
| | AspLysGly | AlaThrLeu | ThrIleLys | LysGluAla | PheProAla |
| 631 | GATAAGGGT | GCCACGCTA | ACGATCAAG | AAGGAAGCA | TTTCCAGCC |
| | GluSerLys | SerValIle | IleGlyAla | ThrGlyGly | SerProGlu |
| 676 | GAGTCAAAA | AGCGTCATT | ATTGGAGCT | ACAGGGGGA | TCGCCTGAG |
| | LysHisHis | AlaThrVal | LysLeuGlu | | |
| 721 | AAGCATCAC | GCTACCGTG | AAACTGGAG | | |

FIG.36

POLYNUCLEOTIDE ENCODING A GENETICALLY ENGINEERED P30 ANTIGEN

The present application is a divisional of U.S. patent application Ser. No. 10/263,153, now U.S. Pat. No. 7,094, 879, filed on Oct. 2, 2002, hereby incorporated in its entirety by reference.

BACKGROUND OF THE INVENTION

1. Technical Field

The present invention relates to a genetically engineered P30 antigen as well as a combination or mixture of antigens which may be used in the detection of IgM and/or IgG antibodies to *Toxoplasma gondii*. Furthermore, the present invention also relates to methods of using this genetically engineered P30 antigen and combination of antigens, antibodies raised against this genetically engineered P30 antigen and combination of antigens, as well as kits and vaccines containing the genetically engineered P30 antigen and antigens present in the combination.

2. Background Information

*Toxoplasma gondii* is an obligate intracellular parasite which is classified among the Coccidia. This parasite has relatively broad host range infecting both mammals and birds. The organism is ubiquitous in nature and exists in three forms: tachyzoite, cyst, and oocyst (Remington, J. S., McLeod, R., Desmonds, G., Infectious Diseases of the Fetus and Newborn Infant (J. S. Remington and J. O. Klein, Eds.), pp. 140-267, Saunders, Philadelphia (1995)). Tachyzoites, found during acute infection, are the invasive form capable of invading all nucleated mammalian cells. After the acute stage of infection, tissue cysts called bradyzoites are formed within host cells and persist within the host organism for the life of the host. Cysts are important in transmission of infection, especially in humans, as the ingestion of raw or undercooked meat can result in the ingestion of bradyzoites which can infect the individual resulting in an acute infection. Oocysts represent a stage of sexual reproduction which occurs only in the intestinal lining of the cat family from which they are excreted in the feces.

A *T. gondii* infection acquired through contaminated meat or cat feces in a healthy adult is often asymptomatic. In pregnant women and immunosuppressed patients, the clinical outcome can be very serious. An acute infection with *T. gondii* acquired during pregnancy, especially during the first trimester, can result in intrauterine transmission to the unborn fetus resulting in severe fetal and neonatal complications, including mental retardation and fetal death. Recrudescence of a previous *T. gondii* infection or an acute infection in an immunosuppressed individual can be pathogenic. Toxoplasmic encephalitis is a major cause of morbidity and mortality in AIDS patients. *Toxoplasma* infection has also been shown to be a significant cause of chorioretinitis in children and adults.

Diagnosis of infection with *T. gondii* may be established by the isolation of *T. gondii* from blood or body fluids, demonstration of the presence of the organism in the placenta or tissues of the fetus, demonstration of the presence of antigen by detection of specific nucleic acid sequences (e.g., DNA probes), or detection of *T. gondii* specific immunoglobulins synthesized by the host in response to infection using serologic tests.

The detection of *T. gondii* specific antibodies and determination of antibody titer are important tools used in the diagnosis of toxoplasmosis. The most widely used serologic tests for the diagnosis of toxoplasmosis are the Sabin-Feldman dye test (Sabin, A. B. and Feldman, H. A. (1948) Science 108, 660-663), the indirect hemagglutination (IHA) test (Jacobs, L. and Lunde, M. (1957) J. Parasitol. 43, 308-314), the IFA test (Walton, B. C. et al. (1966) Am. J. Trop. Med. Hyg. 15, 149-152), the agglutination test (Fondation Mérieux, Sérologie de I'Infection Toxoplasmique en Particulier à Son Début: Méthodes et Interprétation des Résultants, Lyon, 182 pp. (1975)) and the ELISA (Naot, Y. and Remington, J. S. (1980) J. Infect. Dis. 142, 757-766). The ELISA test is one the easiest tests to perform, and many automated serologic tests for the detection of *Toxoplasma* specific IgM and IgG are commercially available.

The current tests for the detection of IgM and IgG antibodies in infected individuals can vary widely in their ability to detect serum antibody. Hence, there is significant inter-assay variation seen among the commercially available kits. The differences observed between the different commercial kits are caused primarily by the preparation of the antigen used for the serologic test. Most kits use either whole or sonicated tachyzoites grown in tissue culture or in mice which contain a high proportion of extra-parasitic material, for example, mammalian cells, tissue culture components, etc. Due to the lack of a purified, standardized antigen or standard method for preparing the tachyzoite antigen, it is not surprising that inter-assay variability exists resulting in different assays having different performance characteristics in terms of assay sensitivity and specificity.

Given the limitations of serologic tests employing the tachyzoite antigen, as described above, as well as the persistent problems regarding determination of onset of infection, purified recombinant antigens obtained by molecular biology are an attractive alternative in that they can be purified and standardized. In the literature, a number of Toxo genes have been cloned and expressed in a suitable host to produce immunoreactive, recombinant Toxo antigens. For example, the Toxo P22 (SAG2), P24 (GRA1), P25, P28 (GRA2), P29 (GRA7), P30 (SAG1), P35, P41 (GRA4), P54 (ROP2), P66 (ROP1), and the Toxo P68 antigens have been described (Prince et al. (1990) Mol. Biochem. Parasitol 43, 97-106; Cesbron-Delauw et al. (1989) Proc. Nat. Acad. Sci. 86, 7537-7541; Johnson et al. (1991) Gene 99, 127-132; Prince et al. (1989) Mol. Biochem. Parasitol. 34, 3-13; Bonhomme et al. (1998) J. Histochem. Cytochem. 46, 1411-1421; Burg et al. (1988) J. Immunol. 141, 3584-3591; Knapp et al. (1989) EPA 431541A2; Mevelec et al. (1992) Mol. Biochem. Parasitol. 56, 227-238; Saavedra et al. (1991) J. Immunol. 147, 1975-1982); EPA 751 147).

It is plausible that no single Toxo antigen can replace the tachyzoite in an initial screening immunoassay for the detection of Toxo-specific immunoglobulins. This may be due to several reasons. First, the antibodies produced during infection vary with the stage of infection, i.e., the antibodies produced by an infected individual vary over time reacting with different epitopes. Secondly, the epitopes present in a recombinant antigen may be different or less reactive than native antigen prepared from the tachyzoite depending on the host used for expression and the purification scheme employed. Thirdly, different recombinant antigens may be needed to detect the different classes of immunoglobulins produced in response to an infection, e.g., IgM, IgG, IgA and IgE.

In order to overcome the limitations of the tachyzoite antigen in terms of assay specificity and sensitivity, a search was done for Toxo antigens which could be used in combination in order to configure new assays for the detection of Toxo-specific immunoglobulins. Maine et al. (in U.S. Pat.

No. 6,329,157 B1) disclose recombinant Toxo antigen cocktails for the detection of Toxo-specific IgG and IgM. It was determined that the above mentioned Toxo antigen cocktails could be improved and enhanced by expression of Toxo P30 in *E. coli* as a soluble protein with genetically engineered modifications. This genetically engineered P30 antigen and improved antigen cocktail will be described in further detail below.

SUMMARY OF THE INVENTION

The present invention includes a genetically engineered *Toxoplasma gondii* P30 antigen as well as a composition comprising both *Toxoplasma gondii* genetically engineered P30 antigen and P35 antigen. This genetically engineered antigen and composition may be used as diagnostic reagents, and the genetically engineered antigen and the antigens within this composition may be produced either recombinantly or synthetically.

In particular, the present invention includes an isolated nucleotide sequence or fragment thereof comprising or complementary to a nucleotide sequence having at least 70% nucleotide sequence identity to a nucleotide sequence selected from the group consisting of SEQ ID NO:22, SEQ ID NO:27 and SEQ ID NO:63. The present invention also includes an isolated nucleotide sequence or fragment thereof encoding a polypeptide, wherein the polypeptide has at least 70% amino acid sequence identity to an amino acid sequence selected from the group consisting of SEQ ID NO:23, SEQ ID NO:28 and SEQ ID NO:64. The present invention also includes a purified polypeptide encoded by any of the nucleotide sequences presented above.

Additionally, the present invention includes a purified polypeptide or fragment thereof having at least 70% amino acid sequence identity to an amino acid sequence selected from the group consisting of SEQ ID NO:23, SEQ ID NO:28 and SEQ ID NO:64. Also, the present invention includes a purified polypeptide or fragment thereof comprising an amino acid sequence having 1-6 additional amino acids at the C-terminus of SEQ ID NO:28. The invention also includes a purified polypeptide or fragment thereof comprising an amino acid sequence as in SEQ ID NO:23 in which any one or more of the five C-terminal amino acids have been changed from cysteine to alanine. Further, the present invention also includes a polyclonal or monoclonal antibody directed against these purified polypeptides.

The present invention also includes a composition comprising a polypeptide, wherein the polypeptide comprises an amino acid sequence selected from the group consisting of SEQ ID NO:23, SEQ ID NO:28 and SEQ ID NO:64. This composition may be used as a diagnostic reagent, and the polypeptide of the composition may be produced by recombinant or synthetic means.

Additionally, the present invention includes a method for detecting the presence of IgM antibodies to *Toxoplasma gondii* in a test sample comprising the steps of: a) contacting the test sample suspected of containing the IgM antibodies with a composition comprising a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64; and b) detecting the presence of polypeptide/IgM antibody complexes, wherein presence of the complexes indicates presence of the IgM antibodies in the test sample.

Furthermore, the present invention also includes a method for detecting the presence of IgM antibodies to *Toxoplasma gondii* in a test sample comprising the steps of: a) contacting the test sample suspected of containing the IgM antibodies with a composition comprising a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64, for a time and under conditions sufficient for the formation of IgM antibody/antigen complexes; b) adding a conjugate to the resulting IgM antibody/antigen complexes for a time and under conditions sufficient to allow said conjugate to bind to the bound antibody, wherein the conjugate comprises an antibody attached to a signal-generating compound capable of generating a detectable signal; and c) detecting presence of IgM antibodies which may be present in the test sample by detecting presence of a signal generated by the signal-generating compound.

Moreover, the present invention encompasses a method for detecting the presence of IgG antibodies to *Toxoplasma gondii* in a test sample comprising the steps of: a) contacting the test sample suspected of containing the IgG antibodies with a composition comprising: 1) a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64 and 2) P35; and b) detecting presence of antigen/IgG antibody complexes, presence of the complexes indicating presence of said IgG antibodies in the test sample.

The invention also encompasses a method for detecting the presence of IgG antibodies to *Toxoplasma gondii* in a test sample comprising the steps of: a) contacting the test sample suspected of containing the IgG antibodies with a composition comprising: 1) a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64 and 2) P35, for a time and under conditions sufficient for formation of IgG antibody/antigen complexes; b) adding a conjugate to resulting IgG antibody/antigen complexes for a time and under conditions sufficient to allow the conjugate to bind to bound antibody, wherein the conjugate comprises an antibody attached to a signal-generating compound capable of generating a detectable signal; and c) detecting IgG antibodies which may be present in the test sample by detecting presence of a signal generated by said signal-generating compound.

Furthermore, the present invention includes a method for detecting the presence of IgM antibodies to *Toxoplasma gondii* in a test sample comprising the steps of: a) contacting the test sample suspected of containing the IgM antibodies with anti-antibody specific for the IgM antibodies for a time and under conditions sufficient to allow for formation of anti-antibody/IgM antibody complexes; b) adding a conjugate to resulting anti-antibody/IgM antibody complexes for a time and under conditions sufficient to allow the conjugate to bind to bound antibody, wherein the conjugate comprises a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, attached to a signal generating compound capable of generating a detectable signal; and c) detecting IgM antibodies which may be present in the test sample by detecting presence of a signal generated by the signal-generating compound.

Further, the present invention includes a method for detecting the presence of IgG antibodies to *Toxoplasma gondii* in a test sample comprising the steps of: a) contacting the test sample suspected of containing the IgG antibodies with anti-antibody specific for the IgG antibodies for a time and under conditions sufficient to allow for formation of anti-antibody/IgG antibody complexes; b) adding a conjugate to resulting anti-antibody/IgG antibody complexes for a time and under conditions sufficient to allow the conjugate to bind to bound antibody, wherein the conjugate comprises: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal; and c) detecting IgG antibodies which may be present in the test sample by detecting the presence of a signal generated by each of the signal-generating compounds.

The present invention also encompasses a vaccine comprising: a) at least one polypeptide selected from the group consisting of: 1) a polypeptide, wherein the polypeptide comprises amino acid sequence having at least 70% amino acid sequence identity to an amino acid sequence selected from the group consisting of SEQ ID NO:23, SEQ ID NO:28 and SEQ ID NO:64 and 2) P35, and b) a pharmaceutically acceptable adjuvant.

Also, the invention includes a kit for determining the presence of IgM antibodies to *Toxoplasma gondii* in a test sample comprising a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; and a conjugate comprising an antibody attached to a signal-generating compound capable of generating a detectable signal.

Also, the present invention includes a kit for determining the presence of IgG antibodies to *Toxoplasma gondii* in a test sample comprising: a composition comprising 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64 and 2) P35; and a conjugate comprising an antibody attached to a signal-generating compound capable of generating a detectable signal.

Additionally, the present invention encompasses a kit for determining the presence of IgM antibodies to *Toxoplasma gondii* in a test sample comprising:

a) an anti-antibody specific for IgM antibody; and b) a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64.

Furthermore, the present invention includes a kit for determining the presence of IgM antibodies to *Toxoplasma gondii* in a test sample comprising:

a) an anti-antibody specific for IgM antibody;

b) a conjugate comprising: 1) a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, attached to 2) a signal-generating compound capable of generating a detectable signal.

Also, the invention includes a kit for determining the presence of IgG antibodies to *Toxoplasma gondii* in a test sample comprising:

a) an anti-antibody specific for IgG antibody; and b) a composition comprising: 1) a polypeptide, wherein said polypeptide comprises an amino acid sequence having at least 70% amino acid sequence identity to an amino acid sequence selected from the group consisting of SEQ ID NO:23, SEQ ID NO:28 and SEQ ID NO:64 and 2) P35.

Another kit of the present invention includes a kit for determining the presence of IgG antibodies to *Toxoplasma gondii* in a test sample comprising:

a) an anti-antibody specific for IgG antibody;

b) a conjugate comprising: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal.

Further, the present invention includes a method for detecting the presence of IgM antibodies to *Toxoplasma gondii* in a test sample comprising the steps of: (a) contacting said test sample suspected of containing IgM antibodies with anti-antibody specific for the IgM antibodies for a time and under conditions sufficient to allow for formation of anti-antibody IgM complexes; (b) adding antigen to resulting anti-antibody/IgM complexes for a time and under conditions sufficient to allow the antigen to bind to bound IgM antibody, the antigen comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; and (c) adding a conjugate to resulting anti-antibody/IgM/antigen complexes, the conjugate comprising a composition comprising monoclonal or polyclonal antibody attached to a signal-generating compound capable of generating a detectable signal; and (d) detecting IgM antibodies which may be present in the test sample by detecting a signal generated by the signal-generating compound.

Additionally, the invention includes a method for detecting the presence of IgG antibodies to *Toxoplasma gondii* in a test sample comprising the steps of: (a) contacting the test sample suspected of containing IgG antibodies with anti-antibody specific for the IgG antibodies for a time and under conditions sufficient to allow for formation of anti-antibody IgG complexes; (b) adding antigen to resulting anti-antibody/IgG complexes for a time and under conditions sufficient to allow the antigen to bind to bound IgG antibody, the antigen comprising a mixture of 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35; (c) adding a conjugate to resulting anti-antibody/IgG/antigen complexes, the conjugate comprising a composition comprising a monoclonal or polyclonal antibody attached to a signal-generating compound capable of generating a detectable signal; and (d) detecting IgG antibodies which may be present in the test sample by detecting a signal generated by the signal-generating compound.

The present invention also includes a method for detecting the presence of IgM and IgG antibodies to *Toxoplasma gondii* in a test sample comprising the steps of: a) contacting the test sample suspected of containing said IgM and IgG antibodies with a composition comprising 1) a polypeptide, wherein said polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, for a time and under conditions sufficient for the formation of IgM and IgG antibody/antigen complexes; b) adding a conjugate to the resulting IgM antibody/antigen complexes and IgG antibody/antigen complexes for a time and under conditions sufficient to allow the conjugate to bind to the bound IgM and IgG antibody, wherein the conjugate comprises an antibody attached to a signal-generating compound capable of generating a detectable signal; and c) detecting the presence of IgM and IgG antibodies which may be present in said test sample by detecting a signal generated by the signal-generating compound.

The invention also encompasses a method for detecting the presence of IgM and IgG antibodies to *Toxoplasma gondii* in a test sample comprising the steps of: a) contacting the test sample suspected of containing the IgM and IgG antibodies with anti-antibody specific for the IgM antibodies and the IgG antibodies for a time and under conditions sufficient to allow for formation of anti-antibody/IgM antibody complexes and anti-antibody/IgG antibody complexes; b) adding a conjugate to resulting anti-antibody/IgM antibody complexes and resulting anti-antibody/IgG antibody complexes for a time and under conditions sufficient to allow the conjugate to bind to bound antibody, wherein the conjugate comprises a composition comprising: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal; and c) detecting IgM and IgG antibodies which may be present in the test sample by detecting a signal generated by the signal-generating compound.

Moreover, the present invention also encompasses a method for detecting the presence of IgM and IgG antibodies to *Toxoplasma gondii* in a test sample comprising the steps of: (a) contacting the test sample suspected of containing IgM and IgG antibodies with anti-antibody specific for the IgM antibodies and with anti-antibody specific for the IgG antibodies for a time and under conditions sufficient to allow for formation of anti-antibody/IgM complexes and anti-antibody/IgG complexes; (b) adding antigen to resulting anti-antibody/IgM complexes and resulting anti-antibody/IgG complexes for a time and under conditions sufficient to allow said antigen to bind to bound IgM and IgG antibody, the antigen comprising a mixture of: 1) a polypeptide, wherein said polypeptide comprises an amino acid sequence selected from the group consisting of SEQ ID NO:23, SEQ ID NO:28 and SEQ ID NO:64 and 2) P35; and (c) adding a conjugate to resulting anti-antibody/IgM/antigen complexes and anti-antibody/IgG/antigen complexes, the conjugate comprising a composition comprising monoclonal or polyclonal antibody attached to a signal-generating compound capable of generating a detectable signal; and (d) detecting IgM and IgG antibodies which may be present in the test sample by detecting a signal generated by the signal-generating compound.

The present invention also includes a method of producing monoclonal antibodies comprising the steps of injecting a non-human mammal with a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; fusing spleen cells of the non-human mammal with myeloma cells in order to generate hybridomas; and culturing the hybridomas for a time and under conditions sufficient for the hybridomas to produce the monoclonal antibodies.

Moreover, the present invention encompasses the plasmid pMBP-c2X-ToxoP30del3C(52-300aa), the plasmid pMBP-c2X-ToxoP30del4C(52-294aa), as well as the plasmid pMBP-c2X-ToxoP30MIX1.

The invention also includes an isolated nucleotide sequence comprising or complementary to the nucleotide sequence of SEQ ID NO:20 as well as a purified polypeptide comprising the amino acid sequence of SEQ ID NO:21.

Furthermore, the present invention includes an isolated nucleotide sequence comprising or complementary to the nucleotide sequence of SEQ ID NO:25 as well as a purified polypeptide comprising the amino acid sequence of SEQ ID NO:26.

Additionally, the invention includes an isolated nucleotide sequence comprising or complementary to the nucleotide sequence of SEQ ID NO:61 as well as a purified polypeptide comprising the amino acid sequence of SEQ ID NO:62.

The present invention also includes portions or fragments of ToxoP30del3C(52-300aa), ToxoP30del4C(52-294aa), or ToxoP30MIX1, which have the same antigenic properties as the region of ToxoP30del3C(52-300aa) which consists of amino acids 1-249, as the region of ToxoP30del4C(52-294aa) which consists of amino acids 1-243, and the region of ToxoP30MIX1 which consists of amino acids 1-249, respectively.

All U.S. patents and publications referred to herein are hereby incorporated in their entirety by reference.

BRIEF DESCRIPTION OF THE DRAWINGS

FIG. 2 represents the DNA sequence [SEQ ID NO:3] of nucleotides 1-7478 encoding the amino acid sequence [SEQ ID NO:4] of the MBP-ToxoP30(52-336aa) fusion protein of plasmid pMBP-c2X-ToxoP30(52-336aa).

FIG. 3 represents the DNA sequence [SEQ ID NO:5] of nucleotides 1-855 of the ToxoP30(52-336aa) gene and the corresponding encoded amino acid sequence [SEQ ID NO:6] of the ToxoP30(52-336aa) protein.

FIG. 5 represents the DNA sequence [SEQ ID NO:7] of nucleotides 1-7553 and the corresponding encoded amino acid sequence [SEQ ID NO:8] of the MBP-ToxoP30(52-336aa) fusion protein of plasmid pMBP-p2X-ToxoP30(52-336aa).

FIG. 8 represents the DNA sequence [SEQ ID NO:10] of nucleotides 1-7442 and the corresponding encoded amino acid sequence [SEQ ID NO:11] of the MBP-ToxoP30del1C (52-324aa) fusion protein of plasmid pMBP-c2X-ToxoP30del1C(52-324aa).

FIG. 9 represents the DNA sequence [SEQ ID NO:12] of nucleotides 1-819 of the ToxoP30del1C(52-324) gene and the corresponding encoded amino acid sequence [SEQ ID NO:13] of the ToxoP30del1C(52-324aa) protein.

FIG. 11 represents the DNA sequence [SEQ ID NO:15] of nucleotides 1-7403 and the corresponding encoded amino acid sequence [SEQ ID NO:16] of the MBP-ToxoP30del2 (52-311aa) fusion protein of plasmid pMBP-c2X-ToxoP30del2(52-311aa).

FIG. 12 represents the DNA sequence [SEQ ID NO:17] of nucleotides 1-780 of the ToxoP30del2(52-311aa) gene and the corresponding encoded amino acid sequence [SEQ ID NO:18] of the ToxoP30del2(52-311aa) protein.

FIG. 15 represents the DNA sequence [SEQ ID NO:20] of nucleotides 1-7370 and the corresponding encoded amino acid sequence [SEQ ID NO:21] of the MBP-ToxoP30del3C (52-300aa) fusion protein of plasmid pMBP-c2X-ToxoP30del3C(52-300aa).

FIG. 16 represents the DNA sequence [SEQ ID NO:22] of nucleotides 1-747 of the ToxoP30del3(52-300aa) and the corresponding encoded amino acid sequence [SEQ ID NO:23] of the ToxoP30del3C(52-300aa) protein.

FIG. 19 represents the DNA sequence [SEQ ID NO:25] of nucleotides 1-7352 and the corresponding encoded amino acid sequence [SEQ ID NO:26] of the MBP-ToxoP30del4C (52-294aa) fusion protein of plasmid pMBP-c2X-ToxoP30del4C(52-294aa).

FIG. 20 represents the DNA sequence [SEQ ID NO:27] of nucleotides 1-729 of the ToxoP30del4C(52-294aa) gene and the corresponding encoded amino acid sequence [SEQ ID NO:28] of the ToxoP30del4C(52-294aa) protein.

FIG. 22 represents the DNA sequence [SEQ ID NO:30] of nucleotides 1-7259 and the corresponding encoded amino acid sequence [SEQ ID NO:31] of the MBP-ToxoP30del4del8(83-294aa) fusion protein of plasmid pMBP-c2X-ToxoP30del4del8(83-294aa).

FIG. 23 represents the DNA sequence [SEQ ID NO:32] of nucleotides 1-636 of the ToxoP30del4del8(83-294aa) gene and the corresponding amino acid sequence [SEQ ID NO:33] of the ToxoP30del4del8(83-294aa) protein.

FIG. 25 represents the DNA sequence [SEQ ID NO:35] of nucleotides 1-7322 and the corresponding encoded amino acid sequence [SEQ ID NO:36] of the MBP-ToxoP30del10 (52-284aa) fusion protein of plasmid pMBP-c2X-ToxoP30del10(52-284aa).

FIG. 26 represents the DNA sequence [SEQ ID NO:37] of nucleotides 1-699 of the ToxoP30del10(52-284aa) gene and the corresponding encoded amino acid sequence [SEQ ID NO:38] of the ToxoP30del10(52-284aa) protein.

FIG. 28 represents the DNA sequence [SEQ ID NO:40] of nucleotides 1-7112 and the corresponding encoded amino acid sequence [SEQ ID NO:41] of the MBP-ToxoP30del11 (52-214aa) fusion protein of plasmid pMBP-c2X-ToxoP30del11(52-214aa).

FIG. 29 represents the DNA sequence [SEQ ID NO:42] of nucleotides 1-489 of the ToxoP30del11(52-214aa) gene and the corresponding encoded amino acid sequence [SEQ ID NO:43] of the ToxoP30del11(52-214aa) protein.

FIG. 31 represents the DNA sequence [SEQ ID NO:61] of nucleotides 1-7370 and the corresponding encoded amino acid sequence [SEQ ID NO:62] of the MBP-ToxoP30MIX1 fusion protein of plasmid pMBP-c2X-ToxoP30MIX1.

FIG. 32 represents the DNA sequence [SEQ ID NO:63] of nucleotides 1-747 of the ToxoP30MIX1 gene and the corresponding encoded amino acid sequence [SEQ ID NO:64] of the ToxoP30MIX1 protein.

FIG. 33 represents the DNA sequence [SEQ ID NO:66] of nucleotides 1-7370 and the corresponding encoded amino acid sequence [SEQ ID NO:67] of the MBP-ToxoP30MIX3 fusion protein of plasmid pMBP-c2X-ToxoP30MIX3.

FIG. 34 represents the DNA sequence [SEQ ID NO:68] of nucleotides 1-747 of the ToxoP30MIX3 gene and the corresponding amino acid sequence [SEQ ID NO:69] of the ToxoP30MIX3 protein.

FIG. 35 represents the DNA sequence [SEQ ID NO:71] of nucleotides 1-7370 and the corresponding encoded amino acid sequence [SEQ ID NO:72] of the MBP-ToxoP30MIX5 fusion protein of plasmid pMBP-c2X-ToxoP30MIX5.

FIG. 36 represents the DNA sequence [SEQ ID NO:73] of nucleotides 1-747 of the ToxoP30MIX5 gene and the corresponding encoded amino acid sequence [SEQ ID NO:74] of the ToxoP30MIX5 protein.

DETAILED DESCRIPTION OF THE INVENTION

Figure 1:
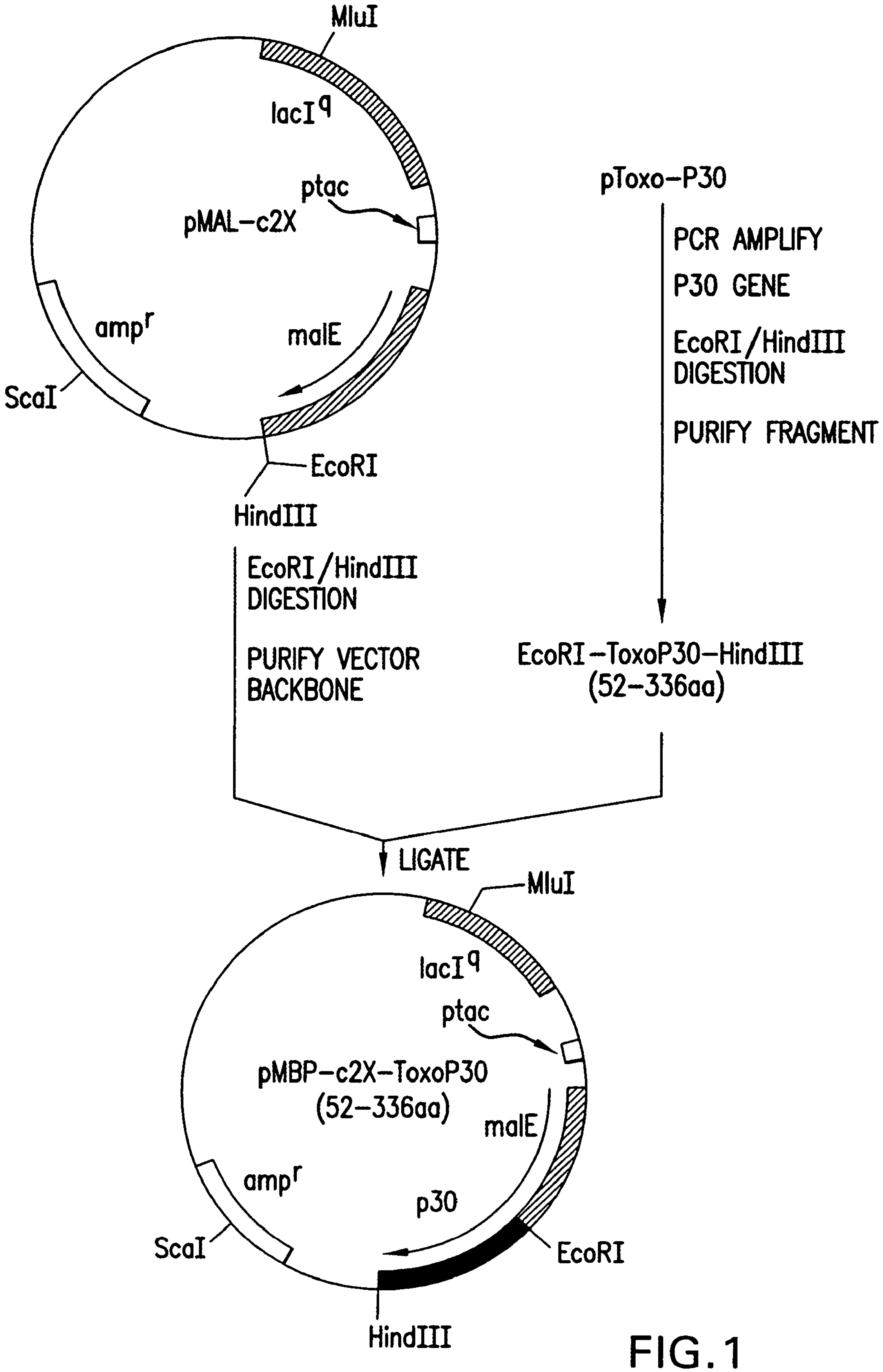
FIG. 1 is a schematic of the construction of plasmid pMBP-c2X-ToxoP30(52-336aa). (The amino acid range in parentheses, noted here and throughout the application, refers to the amino acid sequence (e.g., present in the plasmid, protein, etc.) which has been derived from the native P30 antigen.)

The difficulties of known assays for the detection of IgG and IgM antibodies to *T. gondii* have been described, in detail, above. Thus, there was a need to discover immunoassays that could accurately detect the presence of such antibodies in positive serum or plasma, thereby eliminating the problem of false negative or false positive tests. The present invention provides such needed immunoassays and, in particular, an antigen and combinations of antigens which accurately detect the presence of IgG and/or IgM antibodies in human sera.

In particular, the present invention includes genetically engineered versions of the P30 antigen referred to herein as “ToxoP30del3C(52-300aa)” and “ToxoP30del4C(52-294aa)”, which contain small and precise deletions at the C-terminus of each protein that maximize the anti-Toxo IgG and IgM immunoreactivity of the P30 antigen in an immunoassay. The present invention also includes a genetically engineered version of the P30 antigen referred to herein as “ToxoP30MIX1”, which contains the same deletion at the C-terminus as ToxoP30del3C(52-300aa) as well as five C-terminal cysteine residues changed to alanine. The invention also includes a polypeptide comprising the amino acid sequence of ToxoP30del3C(52-300aa) in which any one or more of the last five cysteines at the C-terminus have been changed to alanine.

The nucleotide sequence of the gene encoding the ToxoP30del3C antigen is shown in FIG. 16 and is represented by SEQ ID NO:22. The amino acid sequence of this antigen is also shown in FIG. 16 and is represented by SEQ ID NO:23. The nucleotide sequence of the gene encoding the ToxoP30del4C antigen is shown in FIG. 20 and is represented by SEQ ID NO:27. The amino acid sequence of this antigen is also shown in FIG. 20 and is represented by SEQ ID NO: 28. The nucleotide sequence of the gene encoding the ToxoP30MIX1 antigen is shown in FIG. 32 and is represented by SEQ ID NO:63. The amino acid sequence of this antigen is also shown in FIG. 32 and is represented by SEQ ID NO:64.

It should be noted that the present invention also encompasses nucleotide sequences comprising or complementary to a nucleotide sequence having at least about 70% nucleotide sequence identity, preferably at least about 80% nucleotide sequence identity, and more preferably at least about 90% nucleotide sequence identity to the nucleotide sequence of SEQ ID NO:22, SEQ ID NO:27 or SEQ ID NO:63. (All integers within the ranges noted above (i.e., between 70 and 100) are also considered to fall within the scope of the present invention.) The sequence having the above-described percent identity or complementary sequences may be derived from species or sources other than from which the isolated, original sequences were derived.

Also, it should be noted that the present invention encompasses a polypeptide sequence comprising an amino acid sequence having at least about 70% amino acid sequence identity, preferably at least about 80% amino acid sequence identity, and more preferably at least about 90% amino acid sequence identity to the amino acid sequence of SEQ ID NO:23, SEQ ID NO:28 or SEQ ID NO:64. (All integers within the ranges noted above (i.e, between 70 and 100) are also considered to fall within the scope of the present invention.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which is hybridizable, under moderately stringent conditions, to a nucleic acid having a nucleotide sequence comprising or complementary to the nucleotide sequences described above. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferably at least about 25 nucleotides identical or complementary to a region of the specified nucleotide sequence. (See U.S. Pat. No. 6,183,952 B1.) In contrast, a "fragment" of a specified polypeptide refers to an amino acid sequence which comprises at least about 5 amino acids, more preferably at least about 10 amino acids, and even more preferably at least 15 amino acids derived from the specified polypeptide.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. A fragment or subfragment that is functionally equivalent to the original polypeptide sequence from which it is derived refers to a sequence which has the same properties (e.g., binding, antigenic, etc.) as the original polypeptide.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al., European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

Furthermore, the present invention also includes a polyclonal or monoclonal antibody raised against ToxoP30del3C, ToxoP30del4C, or ToxoP30MIX1. Such an antibody may be used, for example, in an immunoassay, a vaccine, a kit, or for research purposes.

As noted above, the present invention also encompasses a composition or mixture comprising the following two antigens: genetically engineered P30 and P35. This combination or mixture of antigens may be utilized for the detection of IgG in IgG-positive sera or plasma (i.e., as a diagnostic reagent). Furthermore, the antigens may be produced either recombinantly or synthetically. Additionally, the present invention also includes a composition comprising antibodies raised against these antigens.

Further, as noted above, present invention also includes the genetically engineered P30 antigen. This antigen may be used for the detection of IgM in IgM-positive sera or plasma (i.e., as a diagnostic reagent), and the antigen may be produced either recombinantly or synthetically. Furthermore, the present invention also includes antibodies raised against this antigen.

If, in fact, one wishes to measure both the titer of IgM and IgG in a serum or plasma sample, then a composition or mixture of antigens such as genetically engineered P30 and P35 may be utilized in an immunoassay. Such a combination of antigens is also included within the scope of the present invention.

The present invention also includes methods of detecting IgM and/or IgG using the combinations of antigens described above. More specifically, there are two basic types of assays, competitive and non-competitive (e.g., immunometric and sandwich). In both assays, antibody or antigen reagents are covalently or non-covalently attached to the solid phase. Linking agents for covalent attachment are known and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product (see also U.S. Pat. No. 6,395,472 B1). Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

In particular, two illustrative examples of an immunometric antibody-capture based immunoassay are the IMx Toxo IgM and Toxo IgG antibody assays manufactured by Abbott Laboratories (Abbott Park, Ill.). Both assays are automated Microparticle Enzyme Immunoassays (MEIA) which measure antibodies to *Toxoplasma gondii* (*T. gondii*) in human serum or plasma (Safford et al. (1991) J. Clin. Pathol. 44:238-242). One assay qualitatively measures IgM antibodies, indicative of recent exposure or acute infection, and the other assay quantitatively measures IgG, indicative of chronic or past infection. These assays use microparticles coated with *T. gondii* antigens as the solid phase. In particular, specimen is added to the coated microparticles to allow antibodies specific for *T. gondii* to bind. Subsequently, an alkaline phosphatase conjugated anti-human IgM (or anti-human IgG) is added that specifically binds to IgM (or IgG) class antibodies complexed to the *T. gondii* antigens. Following addition of a suitable substrate (e.g., 4-methyumbelliferyl phosphate), the rate of enzyme-catalyzed turnover is monitored based upon fluorescence.

The mixture of genetically engineered P30 and P35 may be used in the IgG Abbott immunoassay, and the genetically engineered P30 antigen alone may be utilized in the IgM Abbott immunoassay. Additionally, a mixture of genetically engineered P30 and P35 may be utilized in either assay, if desired. Furthermore, it must be noted that other non-Abbott assays or platforms may also be utilized, with each antigen or combination of antigens for purposes of the present invention.

Thus, the present invention includes a method of detecting IgM antibodies in a test sample comprising the steps of: (a) contacting the test sample suspected of containing the IgM antibodies with genetically engineered P30; (b) detecting the presence of IgM antibodies present in the test sample. More specifically, the present invention includes a method of detecting IgM antibodies in a test sample comprising the steps of: (a) contacting the test sample suspected of containing the IgM antibodies with genetically engineered P30 for a time and under conditions sufficient to allow the formation of IgM antibody/antigen complexes; (b) adding a conjugate to the resulting IgM antibody/antigen complexes for a time and under conditions sufficient to allow the conjugate to bind to the bound antibody, the conjugate comprising an antibody (directed against the IgM) attached to a signal generating compound capable of generating a detectable signal; (c) detecting the presence of the IgM antibody which may be present in the test sample by detecting the signal generated by the signal generating compound. A control or calibrator may also be used which binds to this antigen. Furthermore, the method may also comprise the use of P35 in addition to genetically engineered P30.

Additionally, the present invention further includes a method for detecting the presence of IgM which may be present in a test sample. This method comprises the steps of: (a) contacting the test sample suspected of containing IgM antibodies with anti-antibody specific for the IgM, for a time and under conditions sufficient to allow for formation of anti-antibody/IgM complexes and (b) detecting the presence of IgM which may be present in the test sample. (Such anti-antibodies are commercially available and may be created, for example, by immunizing a mammal with purified mu-chain of the antibody.)

More specifically, this method may comprise the steps of: (a) contacting the test sample suspected of containing the IgM antibodies with anti-antibody specific for the IgM, under time and conditions sufficient to allow the formation of anti-antibody/IgM complexes; (b) adding a conjugate to the resulting anti-antibody/IgM complexes for a time and under conditions sufficient to allow the conjugate to bind to the bound antibody, the conjugate comprising genetically engineered P30 attached to a signal generating compound capable of generating a detectable signal; and (c) detecting the presence of the IgM antibodies which may be present in the test sample by detecting the signal generated by the signal generating compound. A control or calibrator may be used which comprises antibody to the anti-antibody. Furthermore, the conjugate may also comprise P35, if desired.

In each of the above assays, IgG may be detected by substituting the genetically engineered P30 with a genetically engineered P30 and P35 mixture. Also, anti-antibody specific for IgG will be used. Additionally, if one wishes to detect both IgM and IgG antibodies, genetically engineered P30 and P35 may be utilized in the immunoassay.

The present invention also encompasses a third method for detecting the presence of IgM in a test sample. This method comprises the steps of: (a) contacting the test sample suspected of containing IgM antibodies with anti-antibody specific for the IgM, under time and conditions sufficient to allow the formation of anti-antibody IgM complexes; (b) adding antigen to the resulting anti-antibody/IgM complexes for a time and under conditions sufficient to allow the antigen to bind to the bound IgM antibody, the antigen comprising the genetically engineered P30; and (c) adding a conjugate to the resulting anti-antibody/IgM/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the IgM antibodies which may be present in the test sample by detecting the signal generated by the signal generating compound. Again, a control or calibrator may be used which comprises antibody to the anti-antibody. The antigen mixture may further comprise P35, if desired.

In this method, IgG may be detected by substituting the genetically engineered P30 antigen with a genetically engineered P30 and P35 mixture, and utilizing anti-antibody specific for IgG. However, if one wishes to detect both IgM and IgG antibodies, genetically engineered P30 and P35 may be utilized in the immunoassay.

It should also be noted that all of the above methods may be used to detect IgA antibodies (with an alpha-specific conjugate) and/or IgE antibodies (with an epsilon-specific conjugate) should such detection be desired.

Additionally, the present invention also includes a vaccine comprising a mixture of genetically engineered P30 and P35 antigens and a pharmaceutically acceptable adjuvant. Such a vaccine may be administered if one desires to raise IgG antibodies in a mammal. The present invention also includes a vaccine comprising the genetically engineered P30 antigen and a pharmaceutically acceptable adjuvant (e.g., Freund's adjuvant or Phosphate Buffered Saline). Such a vaccine may be administered if one desires to raise IgM antibodies in a mammal. Additionally, the present invention also includes a vaccine comprising a mixture of genetically engineered P30 and P35 antigens as well as a pharmaceutically acceptable adjuvant. This vaccine should be administered if one desires to raise both IgM and IgG antibodies in a mammal.

Kits are also included within the scope of the present invention. More specifically, the present invention includes kits for determining the presence of IgG and/or IgM. In particular, a kit for determining the presence of IgM in a test sample comprises a) genetically engineered P30; and b) a conjugate comprising an antibody (directed against IgM) attached to a signal-generating compound capable of generating a detectable signal. The kit may also contain a control or calibrator which comprises a reagent which binds to genetically engineered P30.

Again, if one desires to detect IgG, rather than IgM, the kit will comprise a mixture of genetically engineered P30 and P35, rather than genetically engineered P30, as well as an antibody directed against IgG. If one wishes to detect both IgM and IgG, the kit will comprise genetically engineered P30 and P35.

The present invention also includes another type of kit for detecting IgM and/or IgG in a test sample. If utilized for detecting the presence of IgM, the kit may comprise a) an anti-antibody specific for IgM, and b) genetically engineered P30. A control or calibrator comprising a reagent which binds to genetically engineered P30 may also be included. More specifically, the kit may comprise a) an anti-antibody specific for IgM, and b) a conjugate comprising genetically engineered P30, the conjugate being attached to a signal-generating compound capable of generating a detectable signal. Again, the kit may also comprise a control or calibrator comprising a reagent which binds to genetically engineered P30.

Additionally, if one desires to detect IgG, rather than IgM, the kit will comprise a mixture of genetically engineered P30 and P35, rather than genetically engineered P30 alone, as well as anti-antibody specific for IgG. If one wishes to detect both IgM and IgG, the kit may comprise genetically engineered P30 and P35.

The present invention may be illustrated by the use of the following non-limiting examples:

EXAMPLE 1

General Methodology

Materials and Sources

Restriction enzymes, T4 DNA ligase, and the pMAL™ Protein Fusion and Purification System were purchased from New England Biolabs, Inc. (Beverly, Mass.).

DNA and protein molecular weight standards, plasmid mini-prep kit, ethidium bromide, and pre-cast polyacrylamide gels, were purchased from BioRad Laboratories (Richmond, Calif.).

Maltose was purchased from Sigma Chemical Co. (St. Louis, Mo.).

QIAquick PCR Purification Kit and QIAquick Gel Extraction Kit were purchased from Qiagen, Inc. (Valencia, Calif.).

Synthetic oligonucleotides were purchased from Sigma Genosys (The Woodlands, Tex.).

EPICURIAN *Coli*™ XL-1 BLUE (recA1 endA1 gyrA96 thi-1 hsdR17 supE44 relA1 lac [F' proAB lacI$^q$ ZDM15 Tn10 (Tet$^r$)]) supercompetent *E. coli* cells were obtained from Stratagene Cloning Systems, Inc. (La Jolla, Calif.).

A GeneAmp™ reagent kit (gene amplification kit) and AmpliTaq™ DNA Polymerase (gene amplification kit) were purchased from Perkin-Elmer Cetus (Norwalk, Conn.).

SeaKem GTG agarose was purchased from BioWhittaker Molecular Applications (Rockland, Me.).

Bacto-Tryptone, Bacto-Yeast Extract, Bacto-Agar ampicillin, buffers, isopropyl-β-D-thiogalactoside (IPTG), bovine serum albumin (BSA), Sephacryl S-300, fetal calf serum (Toxo antibody free), sucrose, sodium azide, urea, EDTA, Triton X-100, 1-ethyl-3-(3-dimethylaminopropyl) carbodiimide (EDAC), 2-(N-moropholino)ethanesulfonic acid (MES), inorganic salts, sodium dodecyl sulfate (SDS), Tween 20, glycerol, 4-methylumbelliferyl phosphate (MUP), tris-(hydroxymethyl)aminomethane (Tris), AxSYM Toxo IgG and IgM assay reagents, calibrators, and controls, sulfate-derivatized microparticles, non-fat dry milk, Nipasept, A56620, Brij-35, mouse serum, mannitol, AXSYM instrument, reagents, and commodities were purchased from Abbott Manufacturing, Inc. (Abbott Park, Ill.).

Media, Buffers and General Reagents

"Superbroth II" contained 11.25 g/L tryptone, 22.5 g/L yeast extract, 11.4 g/L potassium phosphate dibasic, 1.7 g/L potassium phosphate monobasic, 10 ml/L glycerol, adjusted pH to 7.2 with sodium hydroxide.

General Methods

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in the manipulation of DNA and transformation of DNA into *E. coli*, for polymerase chain reaction (PCR), and for purification of maltose binding protein (MBP) and MBP fusion proteins. Standard procedures were used for preparation of *E. coli* lysates containing CMP-KDO synthetase (CKS) (U.S. Pat. No. 6,329,157 B1), restriction analysis of DNA on agarose gels, purification of DNA fragments from agarose gels, and ligation of DNA fragments with T4 DNA ligase. (Maniatis et al., *Molecular Cloning: A Laboratory Manual*, $2^{nd}$ ed. (Cold Spring Harbor Laboratory Press, New York, 1989)). DNA sequence analysis was performed by Lark Technologies, Inc. (Houston, Tex.).

EXAMPLE 2

Construction of pMBP-ToxoP30 Expression Vectors

In order to improve the immunoreactivity of the Toxo antigen cocktails described in U.S. Pat. No. 6,329,157 B1 in an immunoassay, a suitable heterologous protein expression system was pursued that would permit the production of soluble Toxo P30 in *E. coli*. The *E. coli* maltose binding protein (MBP) fusion and purification system described in U.S. Pat. No. 5,643,758 has been found to be useful for the production and purification of soluble fusion proteins in *E. coli*. (In particular, the vectors described therein have sequences coding for the recognition site of a specific protease (e.g., Factor Xa, enterokinase or Genenase™) such that the protein of interest may be cleaved from MBP.) Fusion of proteins to MBP enhances their solubility in *E. coli* (Kapust and Waugh (1999) Protein Science 8, 1668-1674). Several different constructs were made taking into consideration the observation that native Toxo P30 is post-translationally cleaved prior to insertion into the tachyzoite membrane (Burg et al. (1988) J. Immunol. 141:3584-3591). The exact cleavage sites for Toxo P30 are unknown.

Plasmid pToxo-P30 described in U.S. Pat. No. 6,329,157 B1 was used as template DNA for a series of PCR reactions to generate DNA fragments containing different portions of the Toxo P30 gene. The pToxo-P30 plasmid DNA was prepared using standard methods. The pMAL-c2X (cytoplasmic expression vector) and pMAL-p2X (periplasmic expression vector) plasmids were purchased from New England Biolabs, Beverly Mass. and were digested with the restriction enzymes EcoRI and HindIII in preparation for subcloning the Toxo P30 gene fragments.

Step A: Construction of pMBP-c2X-ToxoP30(52-336aa)

The plasmid pMBP-c2X-ToxoP30(52-336aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 1). Plasmid pMAL-c2X was digested with EcoRI/HindIII and the vector backbone was purified with a Qiaquick PCR purification kit. A sense primer, starting at nucleotide 464 of the P30 gene containing an EcoRI site and an antisense primer containing a HindIII site, starting at nucleotide 1318 of the P30 gene (Burg et al. (1988) J. Immunol. 141:3584-3591) were synthesized as shown below:

Sense Primer
[SEQ ID NO:1]
5'-GGCGAATTCCTTGTTGCCAATCAAGTTGTCACC-3'
(EcoRI site is underlined)

Antisense Primer
[SEQ ID NO:2]
5'-CGCTGAAGCTTTCACGCGACACAAGCTGCGA-3'
(HindIII site is underlined)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 855 base pair DNA fragment containing Toxo P30 was purified with a Qiaquick PCR purification kit. The purified 855 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30(52-336aa) contained the Toxo P30 gene cloned at the EcoRI/HindIII sites of pMAL-c2X. The complete DNA sequence [SEQ ID NO:3] of plasmid pMBP-c2X-ToxoP30(52-336aa) is shown in FIG. 2 and the corresponding amino acid sequence [SEQ ID NO:4] of the MBP-ToxoP30(52-336aa) fusion protein is also shown in FIG. 2, wherein amino acid residues 392-676 of SEQ ID NO:4 correspond to amino acids 52-336 of the P30 antigen of *Toxoplasma gondii*. The DNA sequence [SEQ ID NO:5] of ToxoP30(52-336aa) is shown in FIG. 3, and the corresponding amino acid sequence [SEQ ID NO:6] of the ToxoP30(52-336aa) protein is also shown in FIG. 3, wherein amino acid residues 1-285 of SEQ ID NO:6 correspond to amino acids 52-336 of the P30 antigen of *Toxoplasma gondii*.

Step B: Construction of pMBP-p2X-ToxoP30(52-336aa)

Figure 4:
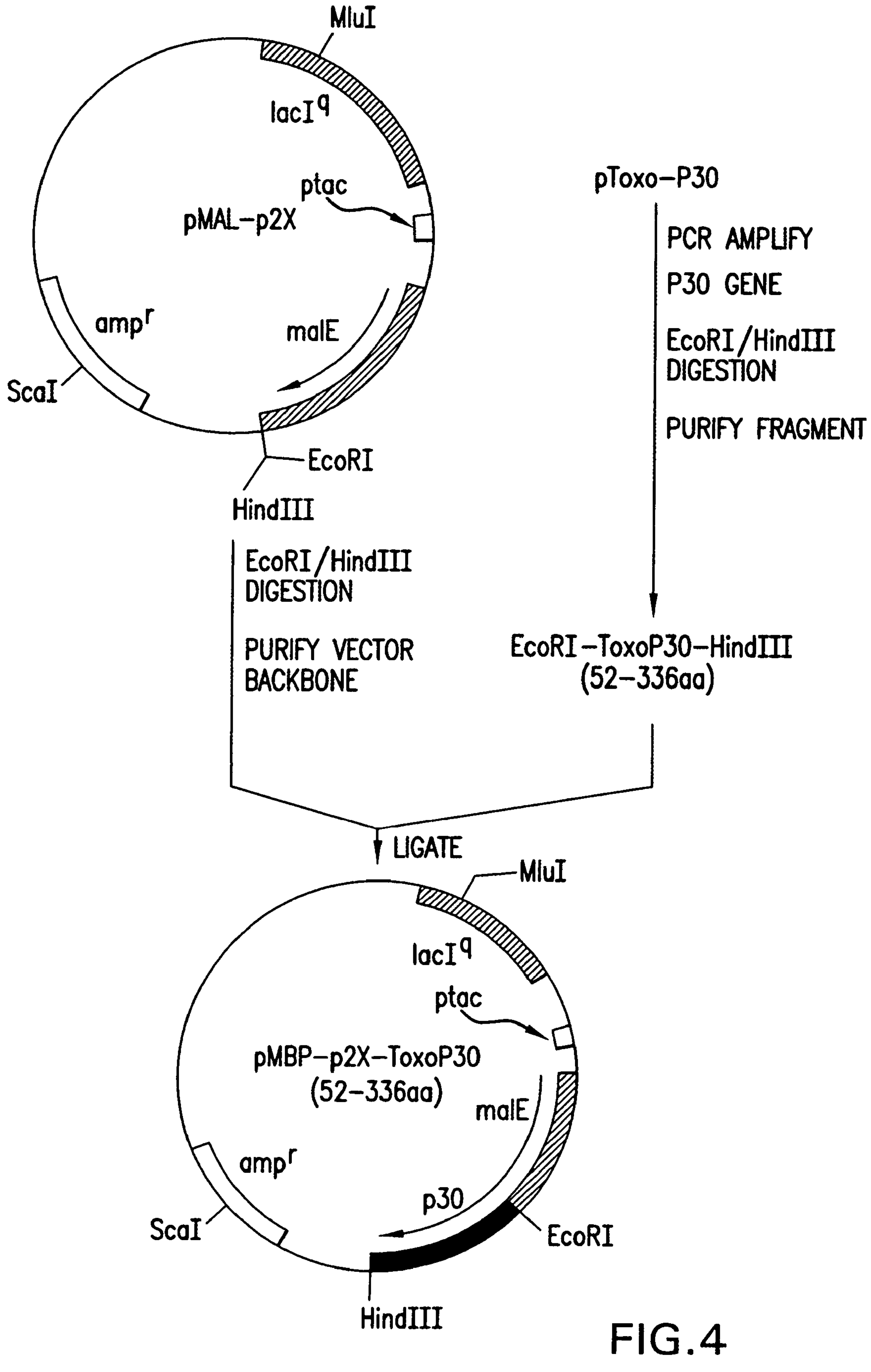
FIG. 4 is a schematic of the construction of plasmid pMBP-p2X-ToxoP30(52-336aa).

The plasmid pMBP-p2X-ToxoP30(52-336aa) was constructed by cloning a DNA fragment containing Toxo P30, obtained by PCR amplification of Toxo P30 DNA contained in plasmid pToxo-P30, into the EcoRI/HindIII sites of pMAL-p2X (FIG. 4). Plasmid pMAL-p2X was digested with EcoRI/HindIII, and the vector backbone was purified with a Qiaquick PCR purification kit. A sense primer, starting at nucleotide 464 of the P30 gene containing an EcoRI site, and an antisense primer containing a HindIII site, starting at nucleotide 1318 of the P30 gene (Burg et al. (1988) J. Immunol. 141:3584-3591) were synthesized as shown below:

Sense Primer
[SEQ ID NO:1]
5'-GGCGAATTCCTTGTTGCCAATCAAGTTGTCACC-3'
(EcoRI site is underlined.)

Antisense Primer
[SEQ ID NO:2]

-continued

```
5'-CGCTGAAGCTTTCACGCGACACAAGCTGCGA-3'
(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 855 base pair DNA fragment containing Toxo P30 was purified with a Qiaquick PCR purification kit. The purified 855 base pair fragment was ligated to pMAL-p2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-p2X-ToxoP30(52-336aa) contained the Toxo P30 gene cloned at the EcoRI/HindIII sites of pMAL-p2X. The complete DNA sequence [SEQ ID NO:7] of plasmid pMBP-p2X-ToxoP30(52-336aa) is shown in FIG. 5, and the corresponding amino acid sequence [SEQ ID NO:8] of the MBP-ToxoP30P(52-336aa) fusion protein is shown in FIG. 5, wherein amino acid residues 417-701 of SEQ ID NO:8 correspond to amino acids 52-336 of the P30 antigen of *Toxoplasma gondii.*

Step C: Construction of pMBP-c2X-ToxoP30del1C(52-324aa)

Figure 6:
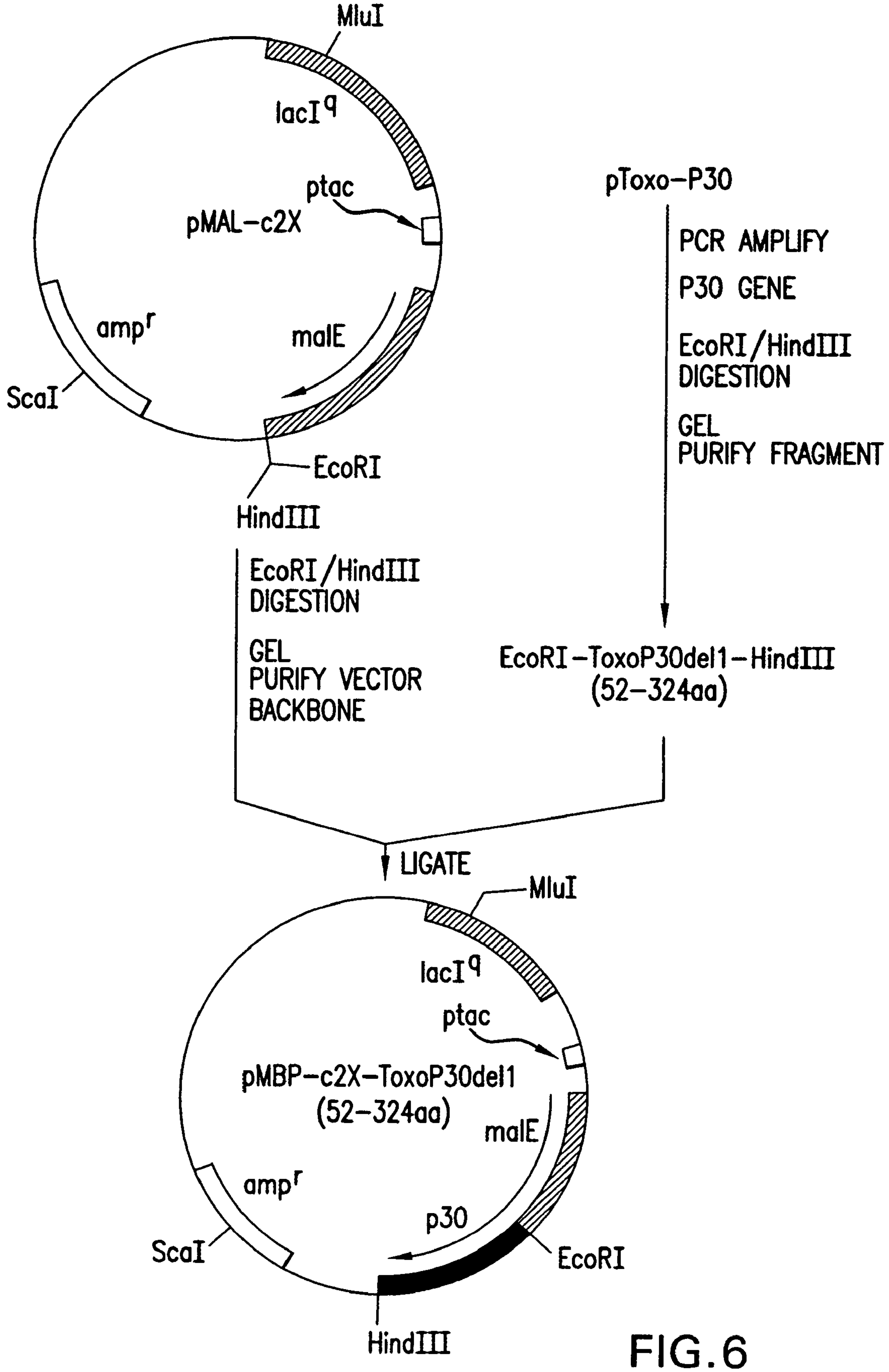
FIG. 6 is a schematic of the construction of plasmid pMBP-c2X-ToxoP30del1(52-324aa).

The plasmid pMBP-c2X-ToxoP30del1(52-324aa), an intermediate in the construction of plasmid pMBP-c2X-ToxoP30del1C, was constructed by cloning a DNA fragment containing Toxo P30, obtained by PCR amplification of Toxo P30 DNA contained in plasmid pToxo-P30, into the EcoRI/HindIII sites of pMAL-c2X (FIG. 6). Plasmid pMAL-c2X was digested with EcoRI/HindIII and the vector backbone was purified on an agarose gel. A sense primer, starting at nucleotide 464 of the P30 gene containing an EcoRI site and an antisense primer containing a HindIII site, starting at nucleotide 1282 of the P30 gene (Burg et al. (1988) J. Immunol. 141:3584-3591) were synthesized as shown below:

```
Sense Primer
                                        [SEQ ID NO:1]
5'-GGCGAATTCCTTGTTGCCAATCAAGTTGTCACC-3'
(EcoRI site is underlined.)

Antisense Primer
                                        [SEQ ID NO:9]
5'-CAGGTCAAGCTTTCACACCATGGCAAAAATGGAAACGTG-3'
(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 819 base pair DNA fragment containing Toxo P30del1 was purified on an agarose gel. The purified 819 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del1(52-324aa) contained the Toxo P30del1 gene cloned at the EcoRI/HindIII sites of pMAL-c2X.

Figure 7:
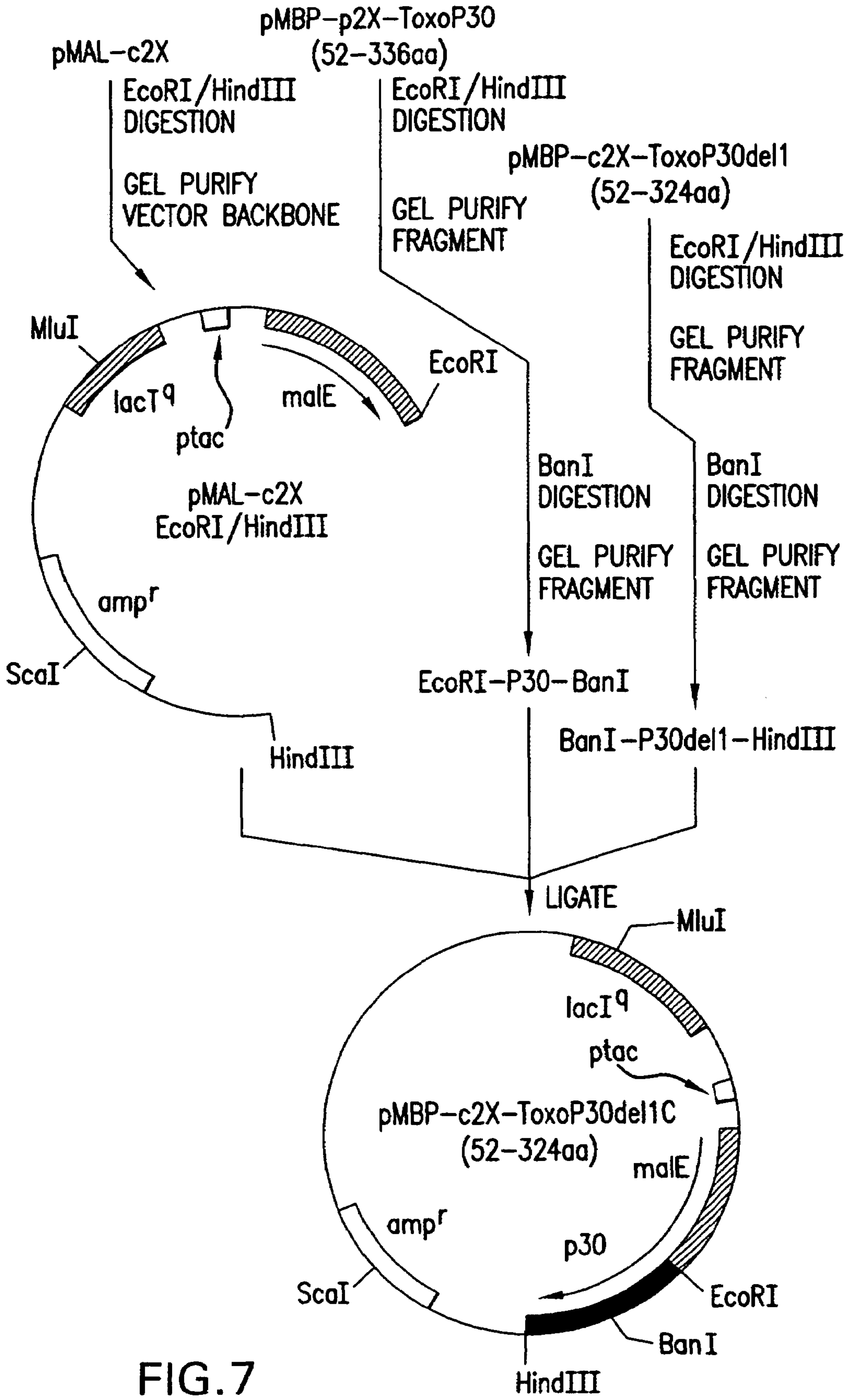
FIG. 7 is a schematic of the construction of plasmid pMBP-c2X-ToxoP30del1C(52-324aa).

Analysis of the DNA sequence of plasmid pMBP-c2X-ToxoP30del1(52-324aa) and analysis of the corresponding amino acid sequence revealed base changes in the P30 gene resulting in two amino acid changes from the published sequence (Burg et al. (1988) J. Immunol. 141:3584-3591). These mutations were located downstream of the synthetic EcoRI site (nucleotide 464) and upstream of a BanI site (nucleotide 1100) following the numbering convention of Burg et al., cited above. The mutations in plasmid pMBP-c2X-ToxoP30del1(52-324aa) were corrected as follows: Plasmid pMBP-c2X-ToxoP30del1C(52-324aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del1(52-324aa), containing the 3' portion of the Toxo P30del1 gene, into the EcoRI/HindIII sites of pMAL-c2X (FIG. 7). Plasmid pMAL-c2X was digested with EcoRI/HindIII, and the vector backbone was purified on an agarose gel. Plasmid DNAs pMBP-p2X-ToxoP30(52-336aa) and pMBP-c2X-ToxoP30del1(52-324aa) were prepared by general methods. Plasmids pMBP-p2X-ToxoP30(52-336aa) and pMBP-c2X-ToxoP30del1(52-324aa) were digested with EcoRI/HindIII and the 855 and 819 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 819 base pair EcoRI/HindIII fragment was digested with BanI and the 182 base pair BanI/HindIII fragment, containing the 3' portion of the Toxo P30del1 gene, was purified on an agarose gel. The purified 637 and 182 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del1C (52-324aa) contained the Toxo P30del1C gene cloned at the EcoRI/HindIII sites of pMAL-c2X. The complete DNA sequence [SEQ ID NO:10] of plasmid pMBP-c2X-ToxoP30del1C(52-324aa) is shown in FIG. 8 and the corresponding amino acid sequence [SEQ ID NO:11] of the MBP-ToxoP30del1C(52-324aa) fusion protein is also shown in FIG. 8, wherein amino acid residues 392-664 of SEQ ID NO:11 correspond to amino acids 52-324 of the P30 antigen of *Toxoplasma gondii*. The DNA sequence [SEQ ID NO:12] of ToxoP30del1C(52-324aa) is shown in FIG. 9 and the corresponding amino acid sequence [SEQ ID NO:13] of the ToxoP30del1C(52-324aa) protein is also shown in FIG. 9, wherein amino acid residues 1-273 of SEQ ID NO:13 correspond to amino acids 52-324 of the P30 antigen of *Toxoplasma gondii.*

Step D: Construction of pMBP-c2X-ToxoP30del2(52-311aa)

Figure 10:
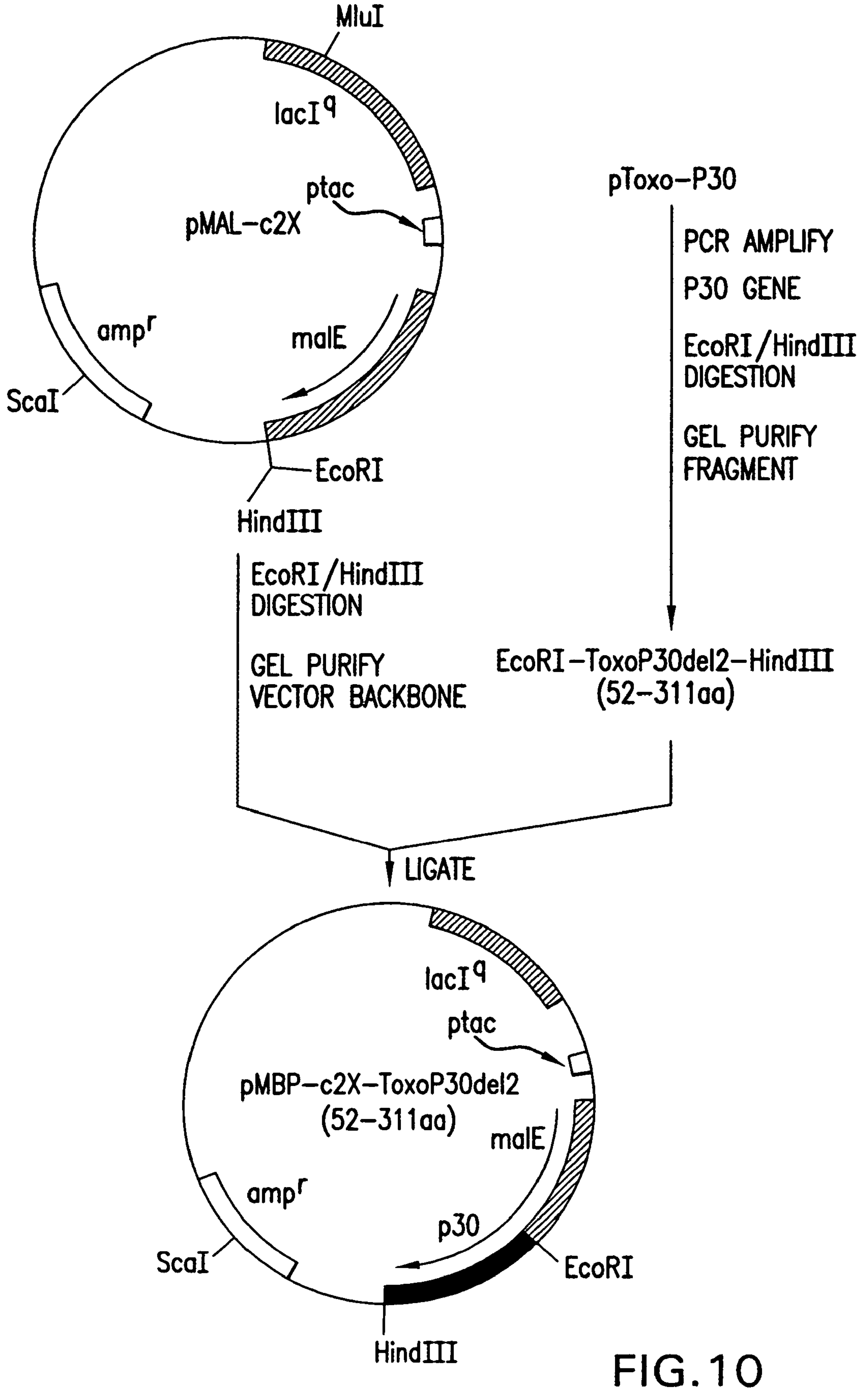
FIG. 10 is a schematic of the construction of plasmid pMBP-c2X-ToxoP30del2(52-311aa).

The plasmid pMBP-c2X-ToxoP30del2(52-311aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 10). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1243 of the P30 gene (Burg et al. (1988) J. Immunol. 141:3584-3591) were synthesized as shown below:

Sense Primer

[SEQ ID NO:1]

5'-GGCGAATTCCTTGTTGCCAATCAAGTTGTCACC-3'

(EcoRI site is underlined.)

Antisense Primer

[SEQ ID NO:14]

5'-CAGGTCAAGCTTTCAAGCCGATTTTGCTGACCCTGCAGCCC-3'

(HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 780 base pair DNA fragment containing Toxo P30del2 was purified on an agarose gel. The purified 780 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del2(52-311aa) contained the Toxo P30del2 gene cloned at the EcoRI/HindIII sites of pMAL-c2X. The complete DNA sequence [SEQ ID NO:15] of plasmid pMBP-c2X-ToxoP30del2(52-311aa) is shown in FIG. 11, and the corresponding amino acid sequence [SEQ ID NO:16] of the MBP-ToxoP30del2(52-311aa) fusion protein is also shown in FIG. 11, wherein amino acid residues 392-651 of SEQ ID NO:16 correspond to amino acids 52-311 of the P30 antigen of *Toxoplasma gondii*. The DNA sequence [SEQ ID NO:17] of ToxoP30del2(52-311aa) is shown in FIG. 12 and the corresponding amino acid sequence [SEQ ID NO:18] of the ToxoP30del2(52-311aa) protein is also shown in FIG. 12, wherein amino acid residues 1-260 of SEQ ID NO:18 correspond to amino acids 52-311 of the P30 antigen of *Toxoplasma gondii*.

Step E: Construction of pMBP-c2X-ToxoP30del3C(52-300aa)

Figure 13:
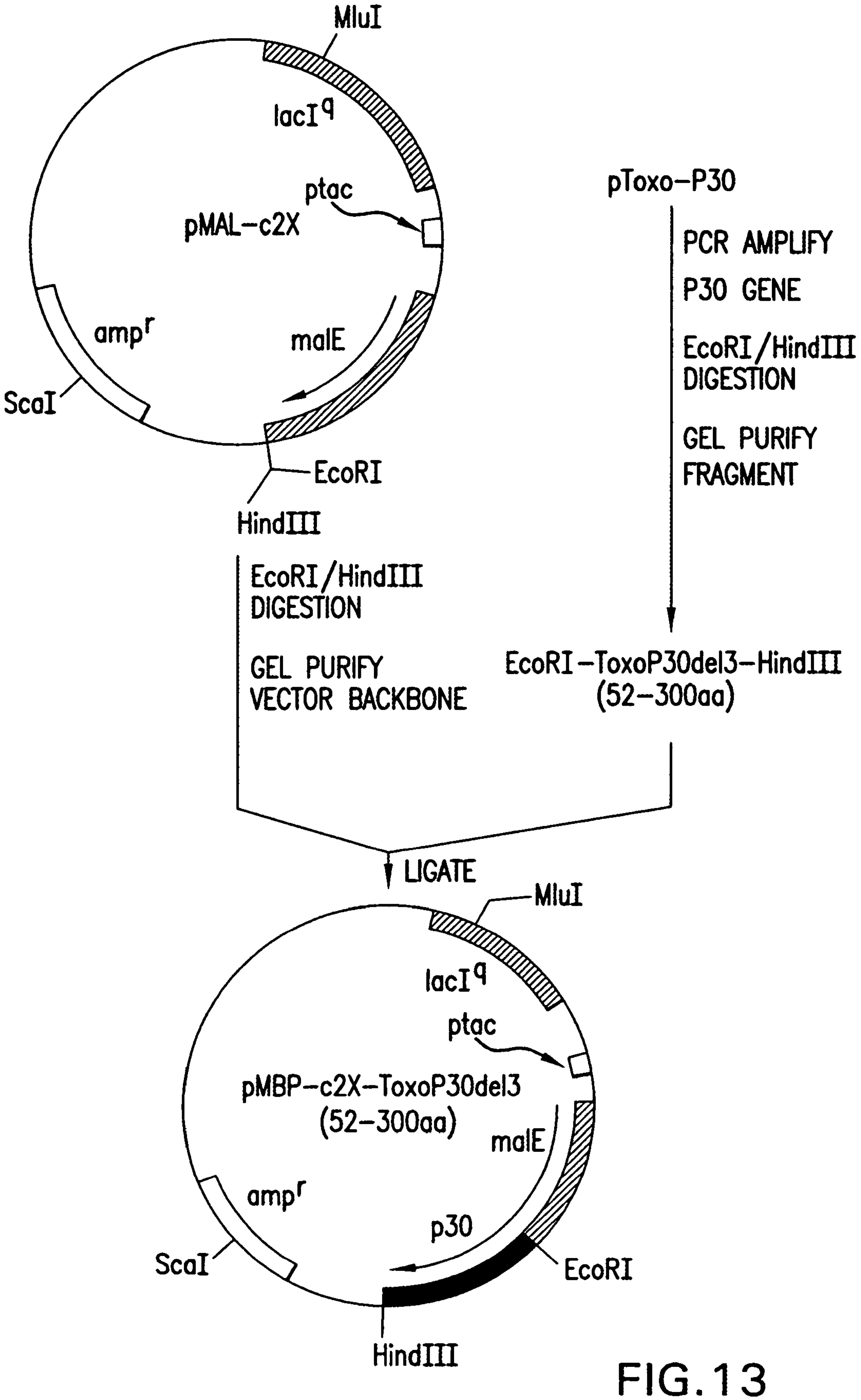
FIG. 13 is a schematic of the construction of plasmid pMBP-c2X-ToxoP30del3(52-300aa).

The plasmid pMBP-c2X-ToxoP30del3(52-300aa), an intermediate in the construction of plasmid pMBP-c2X-ToxoP30del3C(52-300aa), was constructed by cloning a DNA fragment containing Toxo P30, obtained by PCR amplification of Toxo P30 DNA contained in plasmid pToxo-P30, into the EcoRI/HindIII sites of pMAL-c2X (FIG. 13). Plasmid pMAL-c2X was digested with EcoRI/HindIII, and the vector backbone was purified on an agarose gel. A sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

Sense Primer

[SEQ ID NO:1]

5'-GGCGAATTCCTTGTTGCCAATCAAGTTGTCACC-3'

(EcoRI site is underlined.)

Antisense Primer

[SEQ ID NO:19]

5'-CAGGTCAAGCTTTCACTCCAGTTTCACGGTACAGTG-3'

(HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 747 base pair DNA fragment containing Toxo P30del3 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del3(52-300aa) contained the Toxo P30del3 gene cloned at the EcoRI/HindIII sites of pMAL-c2X.

Figure 14:
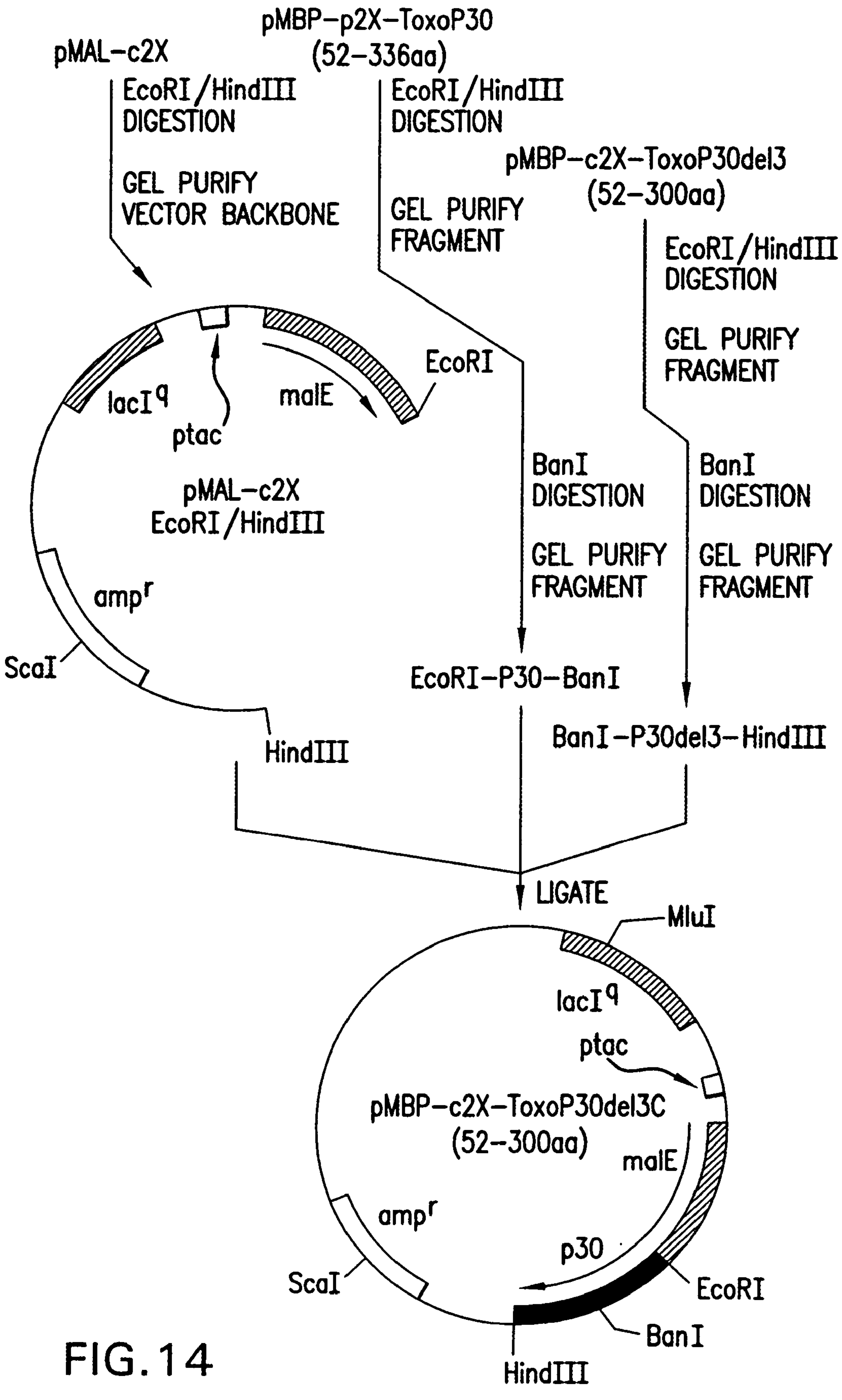
FIG. 14 is a schematic of the construction of plasmid pMBP-c2X-ToxoP30del3C(52-300aa).

Analysis of the DNA sequence of plasmid pMBP-c2X-ToxoP30del3(52-300aa) and analysis of the corresponding amino acid sequence revealed a single base change in the P30 gene that resulted in the substitution of an amino acid for a stop codon, leading to premature chain termination of the P30 protein. This mutation was located downstream of the synthetic EcoRI site (nucleotide 464) and upstream of a BanI site (nucleotide 1100) following the numbering convention of Burg et al. The mutation in plasmid pMBP-c2X-ToxoP30del3(52-300aa) was corrected as follows:

Plasmid pMBP-c2X-ToxoP30del3C(52-300aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del3(52-300aa), containing the 3' portion of the Toxo P30del3 gene, into the EcoRI/HindIII sites of pMAL-c2X (FIG. 14). Plasmid pMBP-c2X-ToxoP30del3C(52-300aa) was deposited with the ATCC 10801 University Boulevard, Manassas, Va. 20110-2209, under terms of the Budapest Treaty on Sep. 26, 2002, and was accorded Accession No. ATCC 4722.

Plasmid pMAL-c2X was digested with EcoRI/HindIII and the vector backbone was purified on an agarose gel. Plasmid DNAs pMBP-p2X-ToxoP30(52-336aa) and pMBP-c2X-ToxoP30del3(52-300aa) were prepared by general methods. Plasmids pMBP-p2X-ToxoP30(52-336aa) and pMBP-c2X-ToxoP30del3(52-300aa) were digested with EcoRI/HindIII and the 855 and 747 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 747 base pair EcoRI/HindIII fragment was digested with BanI and the 110 base pair BanI/HindIII fragment, containing the 3' portion of the Toxo P30del3 gene, was purified on an agarose gel. The purified 637 and 110 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del3C (52-300aa) contained the ToxoP30del3C gene cloned at the EcoRI/HindIII sites of pMAL-c2X. The complete DNA sequence [SEQ ID NO:20] of plasmid pMBP-c2X-ToxoP30del3C(52-300aa) is shown in FIG. 15 and the corresponding amino acid sequence [SEQ ID NO:21] of the MBP-ToxoP30del3C(52-300aa) fusion protein is also shown in FIG. 15, wherein amino acid residues 392-640 of SEQ ID NO:21 correspond to amino acids 52-300 of the P30 antigen of *Toxoplasma gondii*. The DNA sequence [SEQ ID NO:22] of ToxoP30del3C(52-300aa) is shown in FIG. 16 and the corresponding amino acid sequence [SEQ ID NO:23] of the ToxoP30del3C(52-300aa) protein is also shown in FIG. 16, wherein amino acid residues 1-249 of SEQ ID NO:23 correspond to amino acids 52-300 of the P30 antigen of *Toxoplasma gondii*.

Step F: Construction of pMBP-c2X-ToxoP30del4C(52-294aa)

Figure 17:
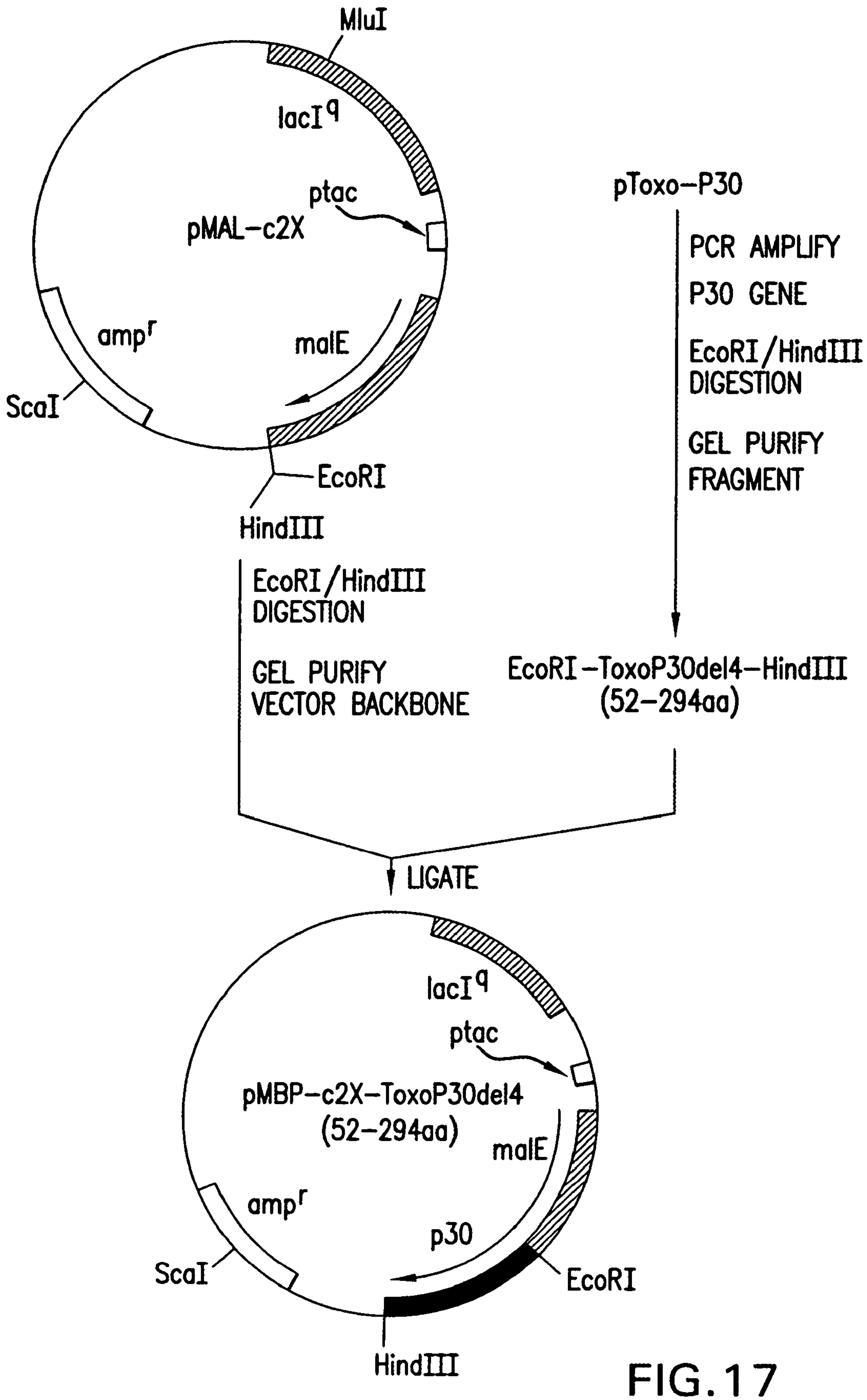
FIG. 17 is a schematic of the construction of plasmid pMBP-c2X-ToxoP30del4(52-294aa).

The plasmid pMBP-c2X-ToxoP30del4(52-294aa), an intermediate in the construction of plasmid pMBP-c2X-ToxoP30del4C(52-294aa), was constructed by cloning a DNA fragment containing Toxo P30, obtained by PCR amplification of Toxo P30 DNA contained in plasmid pToxo-P30, into the EcoRI/HindIII sites of pMAL-c2X (FIG. 17). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1192 of the P30 gene (Burg et al. (1988) J. Immunol. 141:3584-3591) were synthesized as shown below:

```
Sense Primer
                                        [SEQ ID NO:1]
5'-GGCGAATTCCTTGTTGCCAATCAAGTTGTCACC-3'
(EcoRI site is underlined)

Antisense Primer
                                        [SEQ ID NO:24]
5'-CAGGTCAAGCTTTCAGTGATGCTTCTCAGGCGATCCCC-3'
(HindIII site is underlined)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 729 base pair DNA fragment containing Toxo P30del4 was purified on an agarose gel. The purified 729 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4(52-294aa) contained the Toxo P30del4 gene cloned at the EcoRI/HindIII sites of pMAL-c2X.

Figure 18:
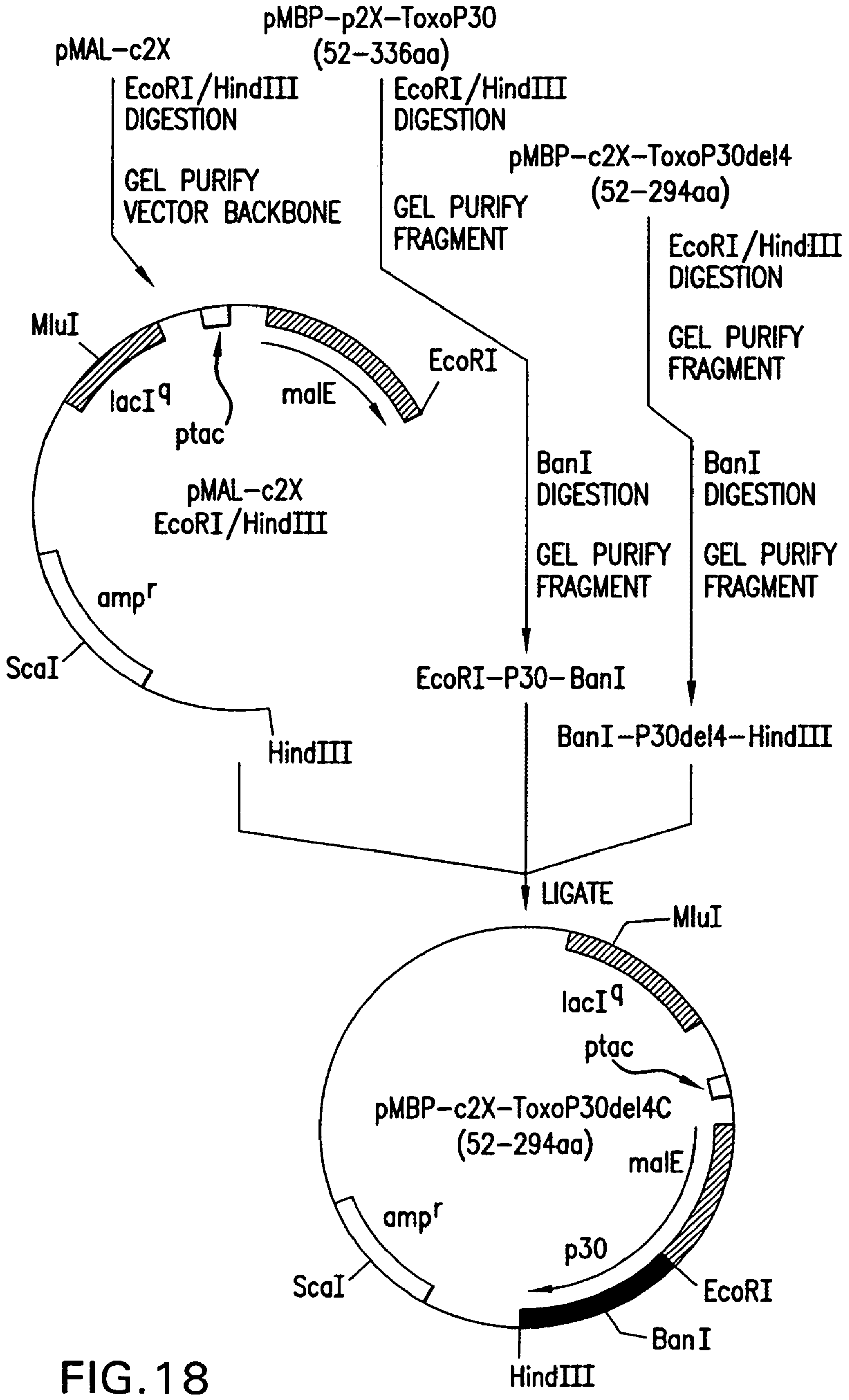
FIG. 18 is a schematic of the construction of plasmid pMBP-c2X-ToxoP30del4C(52-294aa).

Analysis of the DNA sequence of plasmid pMBP-c2X-ToxoP30del4(52-294aa) and analysis of the corresponding amino acid sequence revealed base changes in the P30 gene resulting in two amino acid changes from the published sequence (Burg et al. (1988) J. Immunol. 141:3584-3591). These mutations were located downstream of the synthetic EcoRI site (nucleotide 464) and upstream of a BanI site (nucleotide 1100) following the numbering convention of Burg et al. The mutations in plasmid pMBP-c2X-ToxoP30del4(52-294aa) were corrected as follows:

Plasmid pMBP-c2X-ToxoP30del4C(52-294aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del4(52-294aa), containing the 3' portion of the ToxoP30del4 gene, into the EcoRI/HindIII sites of pMAL-c2X (FIG. 18). Plasmid pMBP-c2X-ToxoP30del4C(52-294aa) was deposited with the ATCC 10801 University Boulevard, Manassas, Va. 20110-2209, under terms of the Budapest Treaty on Sep. 26, 2002, and was accorded Accession No. ATCC 4723.

Plasmid pMAL-c2X was digested with EcoRI/HindIII and the vector backbone was purified on an agarose gel. Plasmid DNAs pMBP-p2X-ToxoP30(52-336aa) and pMBP-c2X-ToxoP30del4(52-294aa) were prepared by general methods. Plasmids pMBP-p2X-ToxoP30(52-336aa) and pMBP-c2X-ToxoP30del4(52-294aa) were digested with EcoRI/HindIII and the 855 and 729 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 729 base pair EcoRI/HindIII fragment was digested with BanI and the 92 base pair BanI/HindIII fragment, containing the 3' portion of the Toxo P30del4 gene and purified on an agarose gel. The purified 637 and 92 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4C (52-294aa) contained the Toxo P30del4C gene cloned at the EcoRI/HindIII sites of pMAL-c2X. The complete DNA sequence [SEQ ID NO:25] of plasmid pMBP-c2X-ToxoP30del4C(52-294aa) is shown in FIG. 19 and the corresponding amino acid sequence [SEQ ID NO:26] of the MBP-ToxoP30del4C(52-294aa) fusion protein is also shown in FIG. 19, wherein amino acid residues 392-634 of SEQ ID NO:26 correspond to amino acids 52-294 of the P30 antigen of *Toxoplasma gondii*. The DNA sequence [SEQ ID NO:27] of ToxoP30del4C(52-294aa) is shown in FIG. 20 and the corresponding amino acid sequence [SEQ ID NO:28] of the ToxoP30del4C(52-294aa) protein is also shown in FIG. 20, wherein amino acid residues 1-243 of SEQ ID NO:28 correspond to amino acids 52-294 of the P30 antigen of *Toxoplasma gondii*.

Step G: Construction of pMBP-c2X-ToxoP30del4del8(83-294aa)

Figure 21:
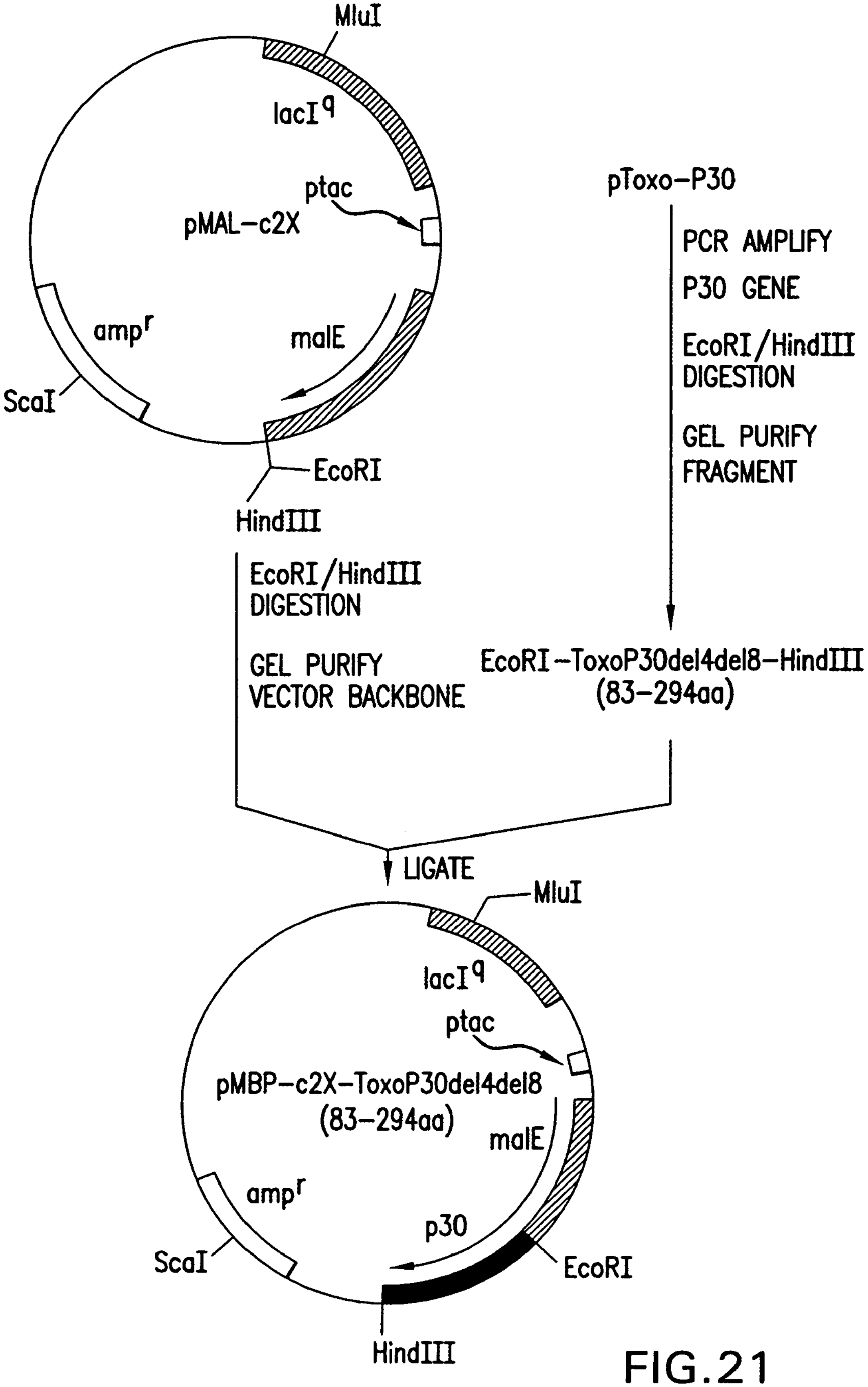
FIG. 21 is a schematic of the construction of plasmid pMBP-c2X-ToxoP30del4del8(83-294aa).

The plasmid pMBP-c2X-ToxoP30del4del8(83-294aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 21). Plasmid pMAL-c2X was digested with EcoRI/HindIII and the vector backbone was purified on an agarose gel. A sense primer, starting at nucleotide 557 of the P30 gene containing an EcoRI site, and an antisense primer containing a HindIII site, starting at nucleotide 1192 of the P30 gene (Burg et al. (1988) J. Immunol. 141:3584-3591) were synthesized as shown below:

```
Sense Primer
                                        [SEQ ID NO:29]
5'-GGCGAATTCCCTAAAACAGCGCTCACAGAG-3'
(EcoRI site is underlined.)

Antisense Primer
                                        [SEQ ID NO:24]
5'-CAGGTCAAGCTTTCAGTGATGCTTCTCAGGCGATCCCC-3'
(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 636 base pair DNA fragment containing Toxo P30del4del8 was purified on an agarose gel. The purified 636 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-

ToxoP30del4del8(83-294aa) contained the ToxoP30del4del8 gene cloned at the EcoRI/HindIII sites of pMAL-c2X. The complete DNA sequence [SEQ ID NO:30] of plasmid pMBP-c2X-ToxoP30del4del8(83-294aa) is shown in FIG. 22 and the corresponding amino acid sequence [SEQ ID NO:31] of the MBP-ToxoP30del4del8 (83-294aa) fusion protein is also shown in FIG. 22, wherein amino acid residues 392-603 of SEQ ID NO:31 correspond to amino acids 83-294 of the P30 antigen of *Toxoplasma gondii*. The DNA sequence [SEQ ID NO:32] of ToxoP30del4del8(83-294aa) is shown in FIG. 23 and the corresponding amino acid sequence [SEQ ID NO:33] of the ToxoP30del4del8(83-294aa) protein is also shown in FIG. 23, wherein amino acid residues 1-212 of SEQ ID NO:33 correspond to amino acids 83-294 of the P30 antigen of *Toxoplasma gondii*.

Step H: Construction of pMBP-c2X-ToxoP30del10(52-284aa)

Figure 24:
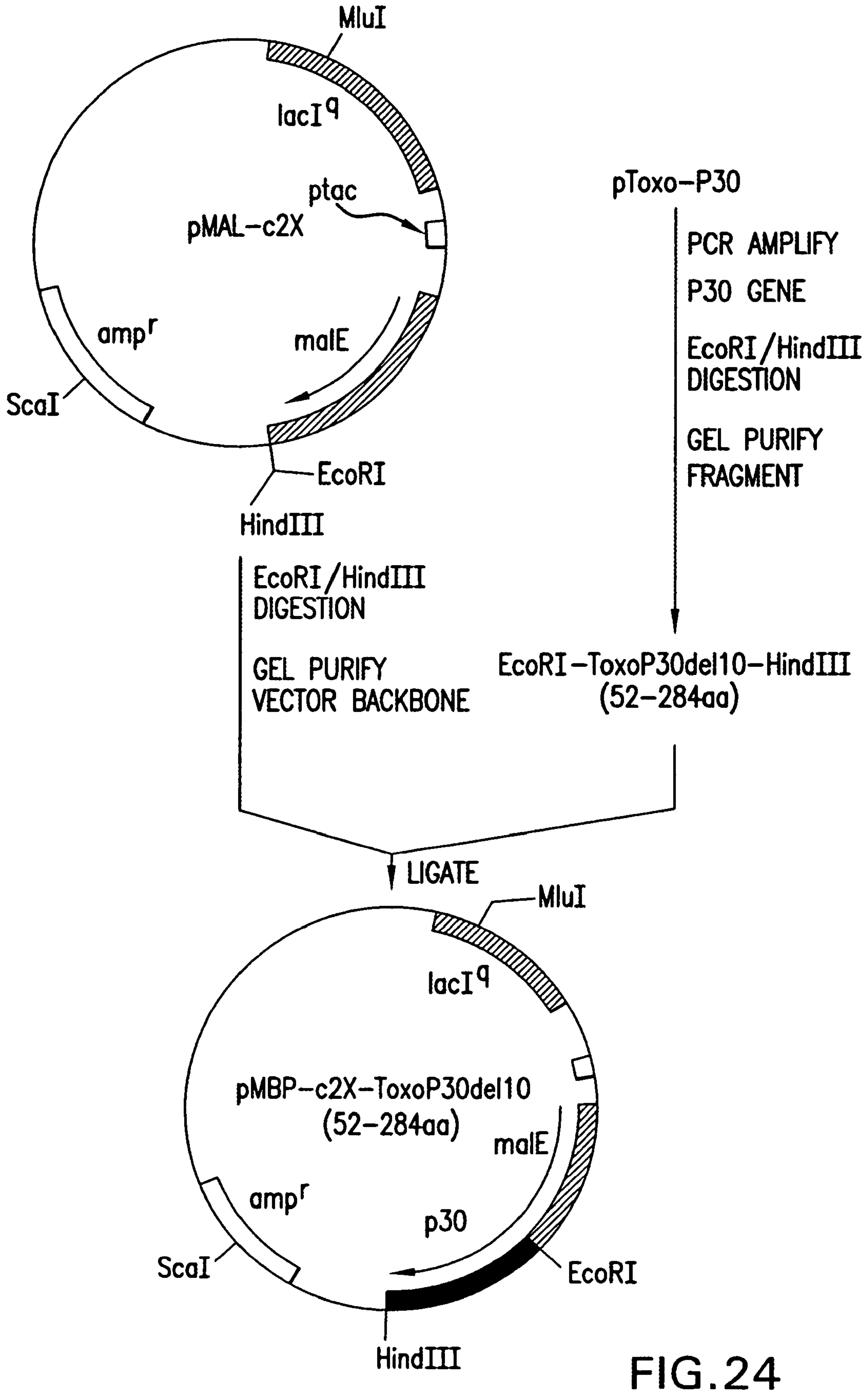
FIG. 24 is a schematic of the construction of plasmid pMBP-c2X-ToxoP30del10(52-284aa).

The plasmid pMBP-c2X-ToxoP30del10(52-284aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 24). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1162 of the P30 gene (Burg et al. (1988) J. Immunol. 141:3584-3591) were synthesized as shown below:

```
Sense Primer
                                          [SEQ ID NO:1]
5'-GGCGAATTCCTTGTTGCCAATCAAGTTGTCACC-3'
(EcoRI site is underlined.)

Antisense Primer
                                          [SEQ ID NO:34]
5'-CAGGTCAAGCTTTCATCCAATAATGACGCTTTTTGACTC-3'
(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 699 base pair DNA fragment containing Toxo P30del10 was purified on an agarose gel. The purified 699 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del10(52-284aa) contained the Toxo P30del10 gene cloned at the EcoRI/HindIII sites of pMAL-c2X. The complete DNA sequence [SEQ ID NO:35] of plasmid pMBP-c2X-ToxoP30del10(52-284aa) is shown in FIG. 25 and the corresponding amino acid sequence [SEQ ID NO:36] of the MBP-ToxoP30del10(52-284aa) fusion protein is also shown in FIG. 25, wherein amino acid residues 392-624 of SEQ ID NO:36 correspond to amino acids 52-284 of the P30 antigen of *Toxoplasma gondii*, with the exception that amino acid residue 546 of SEQ ID NO:36 is glycine instead of glutamic acid. The DNA sequence [SEQ ID NO:37] of ToxoP30del10 (52-284aa) is shown in FIG. 26 and the corresponding amino acid sequence [SEQ ID NO:38] of the ToxoP30del10(52-284aa) protein is also shown in FIG. 26, wherein amino acid residues 1-233 of SEQ ID NO:38 correspond to amino acids 52-284 of the P30 antigen of *Toxoplasma gondii*, with the exception that amino acid residue 155 of SEQ ID NO:38 is glycine instead of glutamic acid.

Step I: Construction of pMBP-c2X-ToxoP30del11(52-214aa)

Figure 27:
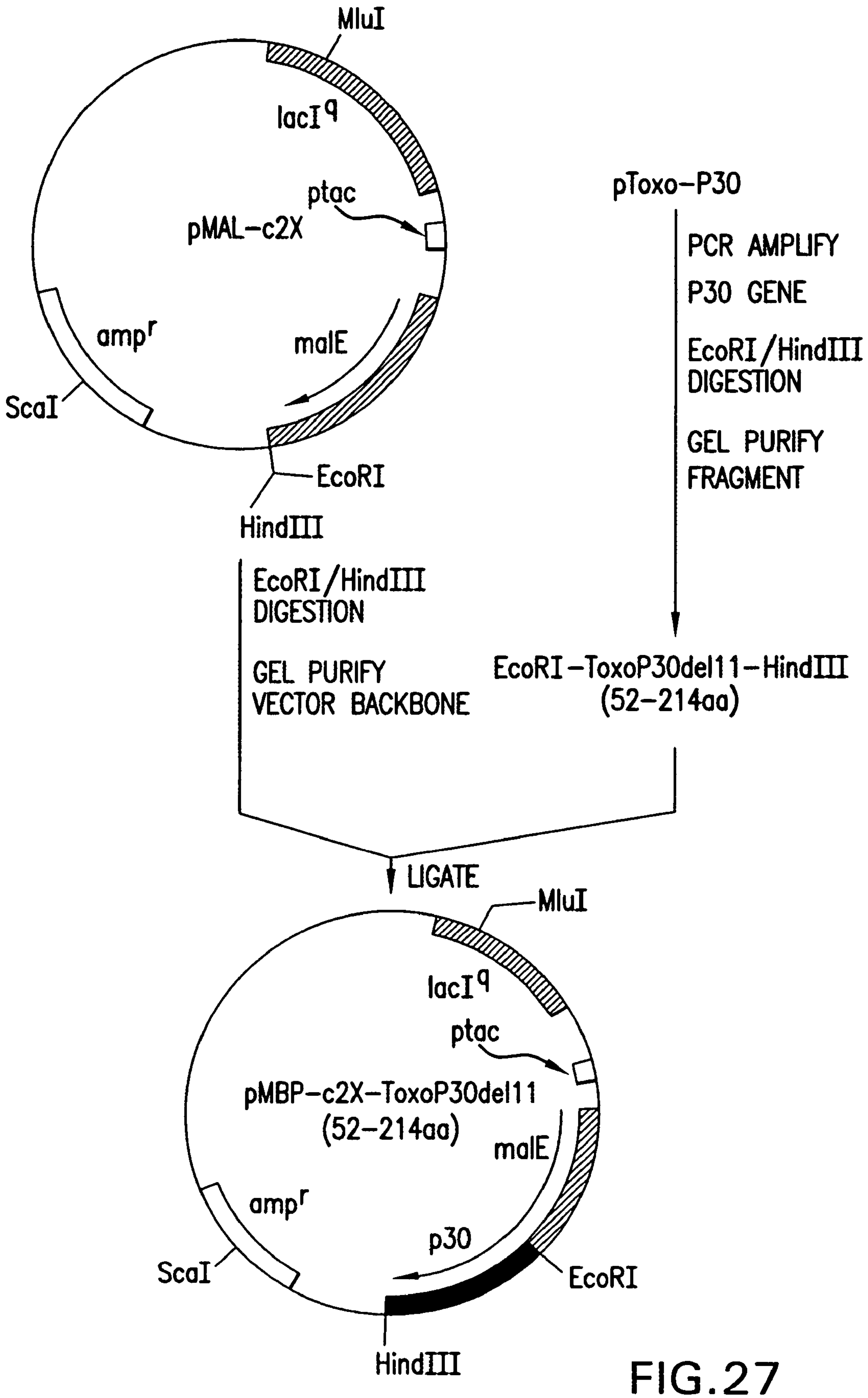
FIG. 27 is a schematic of the construction of plasmid pMBP-c2X-ToxoP30del11(52-214aa).

The plasmid pMBP-c2X-ToxoP30del11(52-214aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 27). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 952 of the P30 gene (Burg et al. (1988) J. Immunol. 141:3584-3591) were synthesized as shown below:

```
Sense Primer
                                          [SEQ ID NO:1]
5'-GGCGAATTCCTTGTTGCCAATCAAGTTGTCACC-3'
(EcoRI site is underlined.)

Antisense Primer
                                          [SEQ ID NO:39]
5'-CAGGTCAAGCTTTCACACGAGGGTCATTGTAGTGGG-3'
(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 489 base pair DNA fragment containing Toxo P30del11 was purified on an agarose gel. The purified 489 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del11(52-214aa) contained the Toxo P30del11 gene cloned at the EcoRI/HindIII sites of pMAL-c2X. The complete DNA sequence [SEQ ID NO:40] of plasmid pMBP-c2X-ToxoP30del11(52-214aa) is shown in FIG. 28 and the corresponding amino acid sequence [SEQ ID NO:41] of the MBP-ToxoP30del11(52-214aa) fusion protein is also shown in FIG. 28, wherein amino acid residues 392-554 of SEQ ID NO:41 correspond to amino acids 52-214 of the P30 antigen of *Toxoplasma gondii*. The DNA sequence [SEQ ID NO:42] of ToxoP30del11(52-214aa) is shown in FIG. 29 and the corresponding amino acid sequence [SEQ ID NO:43] of the ToxoP30del11(52-214aa) protein is also shown in FIG. 29, wherein amino acid residues 1-163 of SEQ ID NO:43 correspond to amino acids 52-214 of the P30 antigen of *Toxoplasma gondii*.

EXAMPLE 3

Expression of rpMBP-c2X-ToxoP30 Antigens in *E. coli*

Step A: Expression of Cloned Genes in *E. coli*

Bacterial clones pMBP-c2X-ToxoP30(52-336aa), pMBP-c2X-ToxoP30del1C(52-324aa), pMBP-c2X-ToxoP30del2 (52-311aa), pMBP-c2X-ToxoP30del3C(52-300aa), pMBP-c2X-ToxoP30del4C(52-294aa), pMBP-c2X-

ToxoP30del4del8(83-294aa), pMBP-c2X-ToxoP30del10 (52-284aa) and pMBP-c2X-ToxoP30del11(52-214aa) expressing the MBP fusion proteins rpMBP-c2X-ToxoP30 (52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) of Example 2 were grown in "SUPERBROTH II" media containing 100 μg/ml ampicillin to log phase, and the synthesis of the MBP-ToxoP30 fusion proteins was induced by the addition of IPTG as previously described (Robinson et al. (1993) J. Clin. Microbiol. 31:629-635). After 4 hours post-induction, the cells were harvested, and the cell pellets were stored at −80° C. until protein purification occurred.

Step B: Purification of MBP-ToxoP30 Fusion Proteins

Soluble fusion proteins rpMBP-c2X-ToxoP30(52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11 (52-214aa) were purified after lysis from cell paste following the New England Biolabs pMAL Protein Fusion and Purification instruction manual. Following lysis and centrifugation, the crude supernatants containing the fusion proteins were loaded onto an amylose affinity column. Following washing of the column, the fusion proteins were eluted from the column with maltose, appropriate column fractions were pooled and filtered through a 0.2μ filter, and then stored at 2-8° C. until coating onto microparticles.

EXAMPLE 4

Evaluation of rpMBP-c2X-ToxoP30 Antigens in an Automated Toxo IgG and IgM Immunoassay Step A: Coating of rpMBP-c2X-ToxoP30 Antigens onto Microparticles Prior to coating microparticles, the rpMBP-c2X-ToxoP30 (52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) antigens were diluted to a concentration of 1 mg/ml and incubated at 37° C. for 24 hours. Following the heat treatment step, the rpMBP-c2X-ToxoP30 antigens were coated separately onto sulfate-derivatized polystyrene microparticles (1-5% solids) in a vessel containing MES pH 6.2 buffer with EDAC for 30 minutes at room temperature, on an end over end rotator. The coated microparticles were then collected by centrifugation at 14,000×g for 10 minutes, and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1-0.3% solids and filled into plastic bottles.

Step B: Description of the AxSYM® Toxo IgG v2 Reagent Pack, Calibrators, Controls, Panel 6, and Assay Diskette The reagent pack for the automated AxSYM Toxo IgG v2 assay is designed for the detection of human anti-Toxo IgG and consists of the following components. Bottle number one contains microparticles coated with purified recombinant Toxo antigens (Example 4A) in a microparticle storage buffer. In order to prevent human anti-MBP or anti-CKS antibodies causing a false positive reaction in the assay, purified MBP or CKS can be added to the microparticle storage buffer. Bottle number two contains the preferred conjugate, a goat anti-human IgG alkaline phosphatase conjugate. This conjugate is titered to determine a working concentration of 0.1-5 μg/ml. The conjugate is diluted into a conjugate diluent containing Tris buffer, pH 7.4, sodium, calcium, magnesium, and zinc chloride, Nipasept, A56620, non-fat dry milk, Brij-35, mouse serum, and mannitol. Bottle number three contains the preferred assay diluent to minimize non-specific binding to the microparticles and assay matrix. This assay diluent consists of a Tris buffer, pH 7.5 containing sodium chloride, sodium EDTA, non-fat dry milk, Nipasept, A56620, and Tween 20. Bottle number four contains a phosphate buffer line diluent.

Six Assay Calibrators labeled A-F are derived from Toxo IgG positive plasma pools or human anti-Toxo IgG monoclonal antibodies and are required to calibrate the AxSYM® Toxo IgG v2 assay. These calibrators are matched to calibrators previously matched to the TOX-S WHO International Standard. The concentration range of these calibrators is 0-300 IU/ml. Positive and Negative controls are required to evaluate the assay calibration and establish assay validity. The Positive Control is prepared from Toxo IgG positive plasma pools or human anti-Toxo IgG monoclonal antibodies. The Negative Control is prepared from Toxo IgG negative plasma pools. Panel 6 is a pool of Toxo IgG and IgM positive plasma units derived from blood donors with an acute toxoplasmosis.

The assay diskette for the AxSYM® Toxo IgG v2 assay contains the assay protocol software necessary to run the automated immunoassay on the Abbott "AxSYM®" instrument (Abbott Laboratories, Abbott Park, Ill.). In addition to the AxSYM® Toxo IgG v2 Reagent Pack, assay Calibrators, and Controls described above, the following assay components located on the instrument are required to run the assay: Sample Cups, AxSYM® Line Diluent, MEIA buffer, Reaction Vessels, MUP, and Matrix Cells. The sequence of events for the automated assay are as follows: The pipetting probe in the kitting center delivers the patient sample and line diluent to the reaction vessel sample well; the pipetting probe then kits the appropriate volumes of assay diluent, line diluent, and conjugate required for the assay from the reagent pack into the designated reaction vessel wells; this probe then delivers the recombinant Toxo antigen coated microparticles from the reagent pack and an aliquot of the diluted sample to the designated reaction vessel well; the reaction vessel is then transferred to the process carousel; Toxo-specific antibodies bind to the Toxo recombinant antigen coated microparticles forming an antigen-antibody complex; assay diluent is added to the reaction mixture and matrix cell and then an aliquot of the reaction mixture is transferred to the glass fiber matrix in the auxiliary carousel; the microparticles bind irreversibly to the matrix; the matrix is washed with MEIA buffer and line diluent to remove unbound antibodies; goat anti-human IgG alkaline phosphate conjugate is added to the matrix and binds to the Toxo-specific IgG captured by the Toxo recombinant antigens; the matrix is then washed with MEIA buffer to remove any unbound enzyme-antibody conjugate; the enzyme substrate MUP is added to the matrix; the alkaline phosphatase enzyme present on the matrix attached to the goat anti-human IgG catalyzes the hydrolysis of the phosphoryl moiety from MUP, producing a highly fluorescent product which is measured by the AxSYM MEIA optical system; the signal intensity (rate counts) is proportional to the amount of Toxo-specific IgG antibodies present in the sample.

Step C: Description of the AxSYM Toxo® IgM v2 Reagent Pack, Index Calibrator, Controls, and Assay Diskette The reagent pack for the automated AxSYM Toxo IgM v2 assay is designed for the detection of human anti-Toxo IgM and consists of the following components. Bottle number one contains microparticles coated with purified recombinant Toxo antigens (Example 4A) in a microparticle storage buffer. In order to prevent human anti-MBP or anti-CKS antibodies causing a false positive reaction in the assay, purified MBP or CKS can be added to the microparticle storage buffer. Bottle number two contains the preferred conjugate, a goat anti-human IgM alkaline phosphatase conjugate. This conjugate is titered to determine a working concentration of 0.1-5 μg/ml. The conjugate is diluted into a conjugate diluent containing Tris buffer, pH 7.4, sodium, calcium, magnesium, and zinc chloride, Nipasept, A56620, non-fat dry milk, Brij-35, mouse serum, and mannitol. Bottle number three contains the preferred assay diluent to minimize non-specific binding to the microparticles and assay matrix. This assay diluent consists of a Tris buffer, pH 7.5 containing sodium chloride, sodium EDTA, non-fat dry milk, Nipasept, A56620, and Tween 20. Bottle number four contains either phosphate buffer line diluent or RF Neutralization Buffer.

The Index Calibrator is derived from Toxo IgM positive plasma pools or human anti-Toxo IgM monoclonal antibodies and is required to calibrate the AxSYM® Toxo IgM v2 assay. Positive and Negative controls are required to evaluate the assay calibration and establish assay validity. The Positive Control is prepared from Toxo IgM positive plasma pools or human anti-Toxo IgM monoclonal antibodies. The Negative Control is prepared from Toxo IgM negative plasma pools.

The assay diskette for the AxSYM® Toxo IgM v2 assay contains the assay protocol software necessary to run the automated immunoassay on the Abbott "AxSYM" instrument (Abbott Laboratories, Abbott Park, Ill.). In addition to the AxSYM® Toxo IgM v2 Reagent Pack, Index Calibrator, and Controls described above, the following assay components located on the instrument are required to run the assay: Sample Cups, AxSYM® Line Diluent, MEIA buffer, Reaction Vessels, MUP, and Matrix Cells. The sequence of events for the automated assay are as follows: The pipetting probe in the kitting center delivers the patient sample and line diluent to the reaction vessel sample well; the pipetting probe then kits the appropriate volumes of assay diluent, line diluent or RF Neutralization Buffer, and conjugate required for the assay from the reagent pack into the designated reaction vessel wells; this probe then delivers the recombinant Toxo antigen coated microparticles from the reagent pack and an aliquot of the diluted sample to the designated reaction vessel well; the reaction vessel is then transferred to the process carousel; Toxo-specific antibodies bind to the Toxo recombinant antigen coated microparticles forming an antigen-antibody complex; assay diluent is added to the reaction mixture and matrix cell and then an aliquot of the reaction mixture is transferred to the glass fiber matrix in the auxiliary carousel; the microparticles bind irreversibly to the matrix; the matrix is washed with MEIA buffer and line diluent or RF Neutralization Buffer to remove unbound antibodies; goat anti-human IgM alkaline phosphate conjugate is added to the matrix and binds to the Toxo-specific IgM captured by the Toxo recombinant antigens; the matrix is then washed with MEIA buffer to remove any unbound enzyme-antibody conjugate; the enzyme substrate MUP is added to the matrix; the alkaline phosphatase enzyme present on the matrix attached to the goat anti-human IgM catalyzes the hydrolysis of the phosphoryl moiety from MUP, producing a highly fluorescent product which is measured by the AxSYM® MEIA optical system; the signal intensity (rate counts) is proportional to the amount of Toxo-specific IgM antibodies present in the sample.

Step D: Evaluation of MBP fusion proteins rpMBP-c2X-ToxoP30(52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) in the AxSYM® Toxo IgG v2 and Toxo IgM v2 Immunoassays The AxSYM® Toxo IgG and IgM reagent packs were assembled as described in Examples 4B and 4C using the microparticles coated with the Toxo antigens described in Example 4A. The Toxo IgG A and F calibrators (Acal and Fcal) and Panel 6 (PNL6) were tested with the AxSYM Toxo IgG v2 reagent packs and the Toxo IgM Negative Control (NC), Index Calibrator (IC), and Panel 6 (PNL6) were tested with the AxSYM® Toxo IgM v2 reagent packs. The results are shown below in Tables 1 and 2.

TABLE 1

Evaluation of the rpMBP-c2X-ToxoP30 Antigens in the AxSYM ® Toxo IgG v2 Assay

| | Rate Counts | | | | |
|---|---|---|---|---|---|
| Antigen Coated | Acal | Fcal | Fcal/ Acal | PNL6 | PNL6/ Acal |
| rpMBP-c2X-ToxoP30 (52-336aa) | 40 | 3495 | 87 | 643 | 16 |
| rpMBP-c2X-ToxoP30 del1C(52-324aa) | 29 | 2599 | 90 | 544 | 19 |
| rpMBP-c2X-ToxoP30 del2(52-311aa) | 28 | 3191 | 114 | 1129 | 40 |
| rpMBP-c2X-ToxoP30 del3C(52-300aa) | 29 | 3199 | 110 | 1112 | 38 |
| rpMBP-c2X-ToxoP30 del4C(52-294aa) | 29 | 3352 | 116 | 1302 | 45 |
| rpMBP-c2X-ToxoP30 del10(52-284aa) | 40 | 4277 | 107 | 1285 | 32 |
| rpMBP-c2X-ToxoP30 del11(52-214aa) | 48 | 4076 | 85 | 1118 | 23 |
| rpMBP-c2X-ToxoP30 del4del8(83-294aa) | 34 | 59 | 1.7 | 37 | 1.1 |

TABLE 2

Evaluation of the rpMBP-c2X-ToxoP30 Antigens in the AxSYM ® Toxo IgM v2 Assay

| | Rate Counts | | | |
|---|---|---|---|---|
| Antigen Coated | NC | IC | PNL6 | PNL6/ NC |
| rpMBP-c2X-ToxoP30 (52-336aa) | 33 | 175 | 210 | 6.4 |
| rpMBP-c2X-ToxoP30del1C (52-324aa) | 48 | 189 | 250 | 5.2 |
| rpMBP-c2X-ToxoP30del2 (52-311aa) | 43 | 315 | 440 | 10.2 |
| rpMBP-c2X-ToxoP30del3C (52-300aa) | 49 | 187 | 459 | 9.4 |

TABLE 2-continued

| Evaluation of the rpMBP-c2X-ToxoP30 Antigens in the AxSYM ® Toxo IgM v2 Assay | | | | |
|---|---|---|---|---|
| | Rate Counts | | | |
| Antigen Coated | NC | IC | PNL6 | PNL6/NC |
| rpMBP-c2X-ToxoP30del4C (52-294aa) | 51 | 203 | 527 | 10.3 |
| rpMBP-c2X-ToxoP30del10 (52-284aa) | 39 | 158 | 370 | 9.5 |
| rpMBP-c2X-ToxoP30del11 (52-214aa) | 36 | 130 | 312 | 8.7 |
| rpMBP-c2X-ToxoP30del4 del8(83-294aa) | 38 | 75 | 38 | 1.0 |

As can be seen in both Tables 1 and 2, a surprising result was obtained. In particular, deletion of amino acids from the C-terminus of the ToxoP30 antigen resulted in improved Toxo-specific IgG and IgM immunoreactivity, as measured by increased rate counts for Panel 6 and improved rate count ratios for Fcal/Acal, Panel 6/Acal, and Panel 6/NC, up to a deletion of 42 amino acids (compare protein rpMBP-c2X-ToxoP30del4C(52-294aa) with protein rpMBP-c2X-ToxoP30(52-336aa) in Tables 1 and 2). The genetically engineered rpMBP-c2X-ToxoP30del4C(52-294aa) protein yielded maximal rate counts for Panel 6 and maximal rate count ratios in both assays. These results suggest that small deletions of the C-terminus of ToxoP30 reveal or make available new epitopes for binding of Toxo-specific IgG and IgM that are occluded in the full-length protein. Deletion of additional C-terminal amino acids (compare protein rpMBP-c2X-ToxoP30del10(52-284aa) and rpMBP-c2X-ToxoP30del11(52-214aa) with protein rpMBP-c2X-ToxoP30del4C(52-294aa) in Tables 1 and 2) resulted in reduced immunoreactivity, suggesting the loss of IgG and IgM epitopes with larger C-terminal deletions. In contrast, the introduction of a small 30 amino acid deletion in the N-terminus of the optimal protein rpMBP-c2X-ToxoP30del4C, which generated the protein rpMBP-c2X-ToxoP30del4del8(83-294aa), completely abolished Toxo-specific IgG and IgM immunoreactivity. These results also suggest that some of the cysteine residues present in the C-terminal portion of the ToxoP30 protein are dispensable for optimal Toxo IgG and IgM immunoreactivity. For example, the optimal protein rpMBP-c2X-ToxoP30del4C (52-294aa) contains 11 cysteine residues and the protein rpMBP-c2X-ToxoP30del11(52-214aa), which demonstrated good but not optimal immunoreactivity, contains 7 cysteine residues.

EXAMPLE 5

Construction of Toxo P30 Synthetic Genes Containing Mutations Which Change Cysteine Residues to Alanine Based on the results obtained from deletion analysis of the Toxo P30 gene in Example 4D, a new series of MBP-ToxoP30 fusion proteins was constructed. Since there are 12 cysteine residues present in the mature Toxo P30 protein (Burg et al. (1988) J. Immunol. 141:3584-3591; Velge-Roussel et al. (1994) Molec. Biochem. Parasitol. 66:31-38), there are mathematically $2^{12}$ or 4,096 different Toxo P30 proteins that can be constructed which contain various combinations of changing one or more of the twelve cysteine residues to alanine. It would certainly be impossible to try all 4,096 different cysteine to alanine combinations to further optimize the immunoreactivity of the Toxo P30 antigen. Hence, the results in Example 4D were used to narrow the number of different mutant Toxo P30 genes to build that have the potential for improved Toxo IgG and IgM immunoreactivity in an automated immunoassay. Mutant oligonucleotides were designed for the in vitro synthesis of three Toxo P30 genes that contain mutations which change various cysteine residues to alanine, and also introduce the same 3' deletion in the Toxo P30 gene present in ToxoP30del3C(52-300aa) (SEQ ID NO:22 and FIG. 16).

The synthesis of each Toxo P30 gene required the synthesis and assembly of 16 overlapping oligonucleotides. These oligonucleotides ranged from 67-72 bases in length with neighboring oligonucleotides overlapping by 20-23 residues. The P30 genes were assembled by recursive PCR followed by PCR amplification of the assembled genes (Withers-Martinez et al. (1999) Protein Engr. 12:1113-1120; Prytulla et al. (1996) FEBS Lett. 399:283-289; Kataoka et al. (1998) Biochem. Biophys. Res. Comm. 250:409-413) using a P30 sense primer containing an EcoRI site and an antisense primer containing a HindIII site. After PCR amplification, the P30 gene was digested with EcoRI and HindIII, purified on an agarose gel, and ligated to the pMAL-c2X vector backbone which had been digested by EcoRI and HindIII as shown schematically in FIG. 30.

Step A: Construction of pMBP-c2X-ToxoP30MIX1

Figure 30:
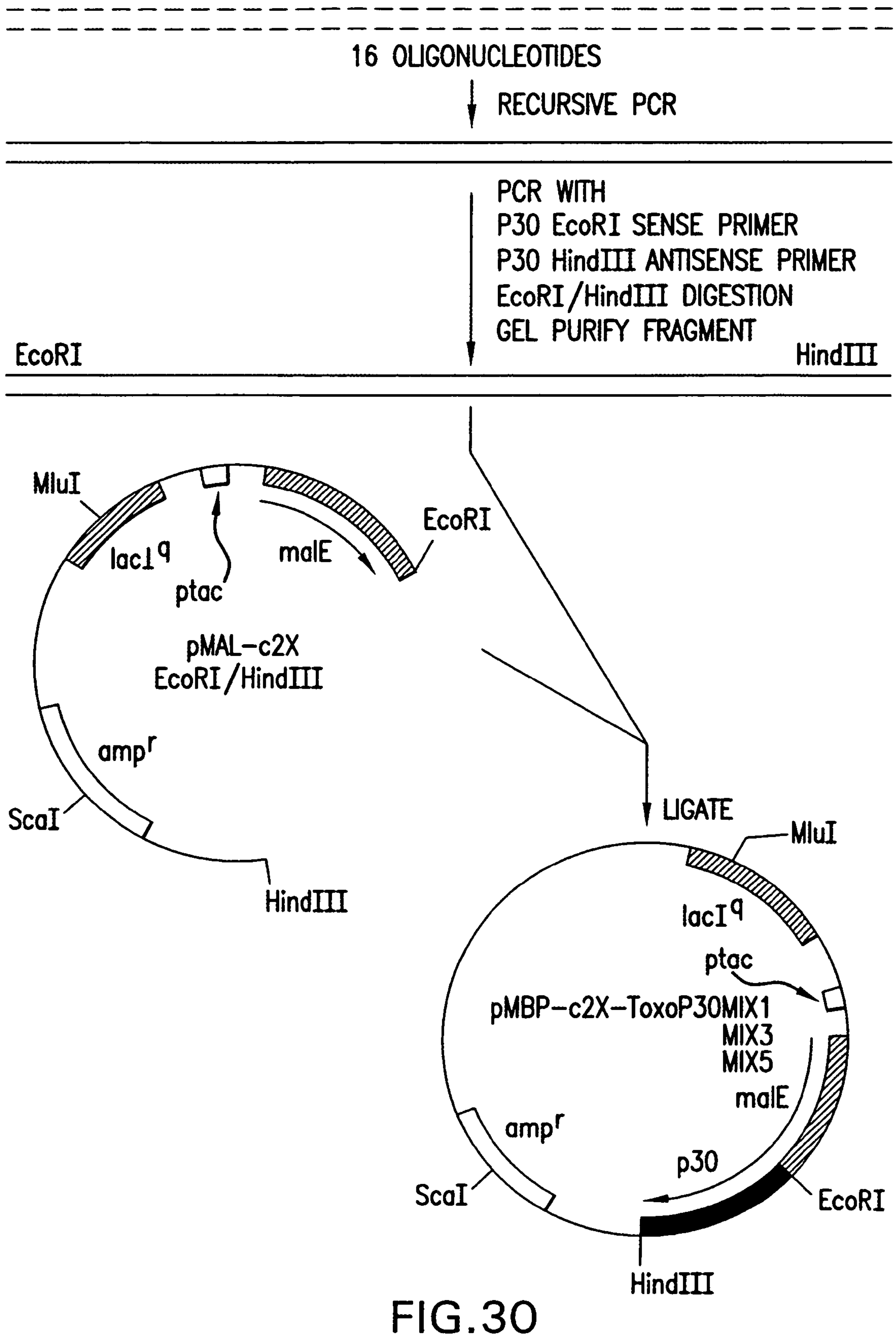
FIG. 30 is a schematic of the construction of plasmids pMBP-c2X-ToxoP30MIX1, pMBP-c2X-ToxoP30MIX3, and pMBP-c2X-ToxoP30MIX5.

The plasmid pMBP-c2X-ToxoP30MIX1 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX1 has been changed so that five of the twelve cysteine residues of Toxo P30 (cysteine nos. 8-12) have been changed to alanine. Plasmid pMAL-c2X was digested with EcoRI/HindIII and the vector backbone was purified on an agarose gel. The following oligonucleotides were synthesized for construction of the ToxoP30MIX1 gene:

```
P30.001
                                         [SEQ ID NO:44]
5'-CTTGTTGCCAATCAAGTTGTCACCTGCCCAGATAAAAAATCGACAGC
CGCGGTCATTCTCACACCGACGG-3'

P30.002
                                         [SEQ ID NO:45]
5'-GAGGCTCTGTGAGCGCTGTTTTAGGGCACTTGAGAGTGAAGTGGTTC
TCCGTCGGTGTGAGAATGACCG-3'

P30.003
                                         [SEQ ID NO:46]
5'-CCTAAAACAGCGCTCACAGAGCCTCCCACTCTTGCGTACTCACCCAA
CAGGCAAATCTGCCCAGCGG-3'

P30.004
                                         [SEQ ID NO:47]
5'-GGAATCAAGGAGCTCAATGTTACAGCCTTTGATGTACAGCTACTTGT
AGTACCCGCTGGGCAGATTTGCCTG-3'

P30.005
                                         [SEQ ID NO:48]
5'-GTAACATTGAGCTCCTTGATTCCTGAAGCAGAAGATAGCTGGTGGAC
GGGGGATTCTGCTAGTCTCGACACGG-3'

P30.006
                                         [SEQ ID NO:49]
5'-CTGCGTTGTCACGGGGAACTTCTCGATTGGAACTGTGAGTTTGATGC
CTGCCGTGTCGAGACTAGCAGAATC-3'
```

-continued

P30.007

[SEQ ID NO:50]

5'-GAAGTTCCCCGTGACAACGCAGACGTTTGTGGTCGGTTGCATCAAGG
GAGACGACGCACAGAGTTGTATG-3'

P30.008

[SEQ ID NO:51]

5'-GCGACATTATTGACGACCGATGAGGCTCTGGCTTGTACTGTCACCGT
GACCATACAACTCTGTGCGTCGTC-3'

P30.009

[SEQ ID NO:52]

5'-CATCGGTCGTCAATAATGTCGCAAGGTGCTCCTACGGTGCAGACAGC
ACTCTTGGTCCTGTCAAGTTGTC-3'

P30.010Ala8

[SEQ ID NO:53]

5'-GACTCCATCTTTCCCAGCCACGAGGGTCATTGTAGTGGGTCCTTCCG
CAGACAACTTGACAGGACCAAGAG-3'

P30.011Ala8Ala9

[SEQ ID NO:54]

5'-GTGGCTGGGAAAGATGGAGTCAAAGTTCCTCAAGACAACAATCAGTA
CGCTTCCGGGACGACGCTGACTGG-3'

P30.012Ala9Ala10

[SEQ ID NO:55]

5'-GTTCTCAGTTAATTTTGGCAAAATATCTTTGAACGATTTCTCGTTAG
CACCAGTCAGCGTCGTCCCGGAAG-3'

P30.013

[SEQ ID NO:56]

5'-GATATTTTGCCAAAATTAACTGAGAACCCGTGGCAGGGTAACGCTTC
GAGTGATAAGGGTGCCACGCTAAC-3'

P30.014

[SEQ ID NO:57]

5'-CCAATAATGACGCTTTTTGACTCGGCTGGAAATGCTTCCTTCTTGAT
CGTTAGCGTGGCACCCTTATCAC-3'

P30.015Ala11Ala12

[SEQ ID NO:58]

5'-GTCAAAAAGCGTCATTATTGGAGCTACAGGGGGATCGCCTGAGAAGC
ATCACGCTACCGTGAAACTGGAG-3'

P30.016Ala12

[SEQ ID NO:59]

5'-GACTGGCTGTTCCCGCAGCCGATTTTGCTGACCCTGCAGCCCCGGCA
AACTCCAGTTTCACGGTAGCGTG-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

Sense Primer

[SEQ ID NO:1]

5'-GGCGAATTCCTTGTTGCCAATCAAGTTGTCACC-3'
(EcoRI site is underlined.)

Antisense Primer

[SEQ ID NO:60]

5'-CAGGTCAAGCTTTCACTCCAGTTTCACGGTAGCGTG-3'
(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX1 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX1 contained the Toxo P30MIX1 gene cloned at the EcoRI/HindIII sites of pMAL-c2X. The complete DNA sequence [SEQ ID NO:61] of plasmid pMBP-c2X-ToxoP30MIX1 is shown in FIG. 31, and the corresponding amino acid sequence [SEQ ID NO:62] of the MBP-ToxoP30MIX1 fusion protein is also shown in FIG. 31, wherein cysteine amino acid residues located at 555, 570, 578, 625, 635 of SEQ ID NO:21 are now alanine amino acids located at 555, 570, 578, 625, 635 of SEQ ID NO:62. Plasmid pMBP-c2X-ToxoP30MIX1 was deposited with the ATCC 10801 University Boulevard, Manassas, Va. 20110-2209, under terms of the Budapest Treaty on Sep. 26, 2002, and was accorded Accession No. ATCC 4721. The DNA sequence [SEQ ID NO:63] of ToxoP30MIX1 is shown in FIG. 32, and the corresponding amino acid sequence [SEQ ID NO:64] of the ToxoP30MIX1 protein is also shown in FIG. 32, wherein cysteine amino acid residues located at 164, 179, 187, 234, 244 of SEQ ID NO:23 are now alanine amino acids located at 164, 179, 187, 234, 244 of SEQ ID NO:64.

Step B: Construction of pMBP-c2X-ToxoP30MIX3

The plasmid pMBP-c2X-ToxoP30MIX3 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX3 has been changed so that six of the twelve cysteine residues of Toxo P30 (cysteine nos. 7-12) have been changed to alanine. Plasmid pMAL-c2X was digested with EcoRI/HindIII, and the vector backbone was purified on an agarose gel. The following oligonucleotides were synthesized for construction of the ToxoP30MIX3 gene: P30.001 [SEQ ID NO:44]

P30.001

[SEQ ID NO:44]

5'-CTTGTTGCCAATCAAGTTGTCACCTGCCCAGATAAAAAATCGACAGC
CGCGGTCATTCTCACACCGACGG-3'

P30.002

[SEQ ID NO:45]

5'-GAGGCTCTGTGAGCGCTGTTTTAGGGCACTTGAGAGTGAAGTGGTTC
TCCGTCGGTGTGAGAATGACCG-3'

P30.003

[SEQ ID NO:46]

5'-CCTAAAACAGCGCTCACAGAGCCTCCCACTCTTGCGTACTCACCCAA
CAGGCAAATCTGCCCAGCGG-3'

P30.004

[SEQ ID NO:47]

5'-GGAATCAAGGAGCTCAATGTTACAGCCTTTGATGTACAGCTACTTGT
AGTACCCGCTGGGCAGATTTGCCTG-3'

P30.005

[SEQ ID NO:48]

5'-GTAACATTGAGCTCCTTGATTCCTGAAGCAGAAGATAGCTGGTGGAC
GGGGGATTCTGCTAGTCTCGACACGG-3'

-continued

P30.006

[SEQ ID NO:49]

5'-CTGCGTTGTCACGGGGAACTTCTCGATTGGAACTGTGAGTTTGATGC
CTGCCGTGTCGAGACTAGCAGAATC-3'

P30.007

[SEQ ID NO:50]

5'-GAAGTTCCCCGTGACAACGCAGACGTTTGTGGTCGGTTGCATCAAGG
GAGACGACGCACAGAGTTGTATG-3'

P30.008

[SEQ ID NO:51]

5'-GCGACATTATTGACGACCGATGAGGCTCTGGCTTGTACTGTCACCGT
GACCATACAACTCTGTGCGTCGTC-3'

P30.009Ala7

[SEQ ID NO:65]

5'-CATCGGTCGTCAATAATGTCGCAAGGGCTTCCTACGGTGCAGACAGC
ACTCTTGGTCCTGTCAAGTTGTC-3'

P30.010Ala8

[SEQ ID NO:53]

5'-GACTCCATCTTTCCCAGCCACGAGGGTCATTGTAGTGGGTCCTTCCG
CAGACAACTTGACAGGACCAAGAG-3'

P30.011Ala8Ala9

[SEQ ID NO:54]

5'-GTGGCTGGGAAAGATGGAGTCAAAGTTCCTCAAGACAACAATCAGTA
CGCTTCCGGGACGACGCTGACTGG-3'

P30.012Ala9Ala10

[SEQ ID NO:55]

5'-GTTCTCAGTTAATTTTGGCAAAATATCTTTGAACGATTTCTCGTTAG
CACCAGTCAGCGTCGTCCCGGAAG-3'

P30.013

[SEQ ID NO:56]

5'-GATATTTTGCCAAAATTAACTGAGAACCCGTGGCAGGGTAACGCTTC
GAGTGATAAGGGTGCCACGCTAAC-3'

P30.014

[SEQ ID NO:57]

5'-CCAATAATGACGCTTTTTGACTCGGCTGGAAATGCTTCCTTCTTGAT
CGTTAGCGTGGCACCCTTATCAC-3'

P30.015Ala11Ala12

[SEQ ID NO:58]

5'-GTCAAAAAGCGTCATTATTGGAGCTACAGGGGGATCGCCTGAGAAGC
ATCACGCTACCGTGAAACTGGAG-3'

P30.016Ala12

[SEQ ID NO:59]

5'-GACTGGCTGTTCCCGCAGCCGATTTTGCTGACCCTGCAGCCCCGGCA
AACTCCAGTTTCACGGTAGCGTG-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

Sense Primer

[SEQ ID NO:1]

5'-GGC<u>GAATTC</u>CTTGTTGCCAATCAAGTTGTCACC-3'
(EcoRI site is underlined.)

Antisense Primer

[SEQ ID NO:60]

5'-CAGGTC<u>AAGCTT</u>TCACTCCAGTTTCACGGTAGCGTG-3'
(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX3 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX3 contained the Toxo P30MIX3 gene cloned at the EcoRI/HindIII sites of pMAL-c2X. The complete DNA sequence [SEQ ID NO:66] of plasmid pMBP-c2X-ToxoP30MIX3 is shown in FIG. 33, and the corresponding amino acid sequence [SEQ ID NO:67] of the MBP-ToxoP30MIX3 fusion protein is also shown in FIG. 33, wherein cysteine amino acid residues located at 530, 555, 570, 578, 625, 635 of SEQ ID NO:21 are now alanine amino acids located at 530, 555, 570, 578, 625, 635 of SEQ ID NO:67. The DNA sequence [SEQ ID NO:68] of ToxoP30MIX3 is shown in FIG. 34, and the corresponding amino acid sequence [SEQ ID NO:69] of the ToxoP30MIX3 protein is also shown in FIG. 34, wherein cysteine amino acid residues located at 139, 164, 179, 187, 234, 244 of SEQ ID NO:23 are now alanine amino acids located at 139, 164, 179, 187, 234, 244 of SEQ ID NO:69.

Step C: Construction of pMBP-c2X-ToxoP30MIX5

The plasmid pMBP-c2X-ToxoP30MIX5 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX5 has been changed so that six of the twelve cysteine residues of Toxo P30 (cysteine nos. 2 and 8-12) have been changed to alanine. Plasmid pMAL-c2X was digested with EcoRI/HindIII and the vector backbone was purified on an agarose gel. The following oligonucleotides were synthesized for construction of the ToxoP30MIX5 gene:

P30.001

[SEQ ID NO:44]

5'-CTTGTTGCCAATCAAGTTGTCACCTGCCCAGATAAAAAATCGACAGC
CGCGGTCATTCTCACACCGACGG-3'

P30.002Ala2

[SEQ ID NO:70]

5'-GAGGCTCTGTGAGCGCTGTTTTAGGAGCCTTGAGAGTGAAGTGGTTC
TCCGTCGGTGTGAGAATGACCG-3'

P30.003

[SEQ ID NO:46]

5'-CCTAAAACAGCGCTCACAGAGCCTCCCACTCTTGCGTACTCACCCAA
CAGGCAAATCTGCCCAGCGG-3'

P30.004

[SEQ ID NO:47]

5'-GGAATCAAGGAGCTCAATGTTACAGCCTTTGATGTACAGCTACTTGT
AGTACCCGCTGGGCAGATTTGCCTG-3'

P30.005

[SEQ ID NO:48]

5'-GTAACATTGAGCTCCTTGATTCCTGAAGCAGAAGATAGCTGGTGGAC
GGGGGATTCTGCTAGTCTCGACACGG-3'

-continued

```
P30.006
                                          [SEQ ID NO:49]
5'-CTGCGTTGTCACGGGGAACTTCTCGATTGGAACTGTGAGTTTGATGC
CTGCCGTGTCGAGACTAGCAGAATC-3'

P30.007
                                          [SEQ ID NO:50]
5'-GAAGTTCCCCGTGACAACGCAGACGTTTGTGGTCGGTTGCATCAAGG
GAGACGACGCACAGAGTTGTATG-3'

P30.008
                                          [SEQ ID NO:51]
5'-GCGACATTATTGACGACCGATGAGGCTCTGGCTTGTACTGTCACCGT
GACCATACAACTCTGTGCGTCGTC-3'

P30.009
                                          [SEQ ID NO:52]
5'-CATCGGTCGTCAATAATGTCGCAAGGTGCTCCTACGGTGCAGACAGC
ACTCTTGGTCCTGTCAAGTTGTC-3'

P30.010Ala8
                                          [SEQ ID NO:53]
5'-GACTCCATCTTTCCCAGCCACGAGGGTCATTGTAGTGGGTCCTTCCG
CAGACAACTTGACAGGACCAAGAG-3'

P30.011Ala8Ala9
                                          [SEQ ID NO:54]
5'-GTGGCTGGGAAAGATGGAGTCAAAGTTCCTCAAGACAACAATCAGTA
CGCTTCCGGGACGACGCTGACTGG-3'

P30.012Ala9Ala10
                                          [SEQ ID NO:55]
5'-GTTCTCAGTTAATTTTGGCAAAATATCTTTGAACGATTTCTCGTTAG
CACCAGTCAGCGTCGTCCCGGAAG-3'

P30.013
                                          [SEQ ID NO:56]
5'-GATATTTTGCCAAAATTAACTGAGAACCCGTGGCAGGGTAACGCTTC
GAGTGATAAGGGTGCCACGCTAAC-3'

P30.014
                                          [SEQ ID NO:57]
5'-CCAATAATGACGCTTTTTGACTCGGCTGGAAATGCTTCCTTCTTGAT
CGTTAGCGTGGCACCCTTATCAC-3'

P30.015Ala11Ala12
                                          [SEQ ID NO:58]
5'-GTCAAAAAGCGTCATTATTGGAGCTACAGGGGGATCGCCTGAGAAGC
ATCACGCTACCGTGAAACTGGAG-3'

P30.016Ala12
                                          [SEQ ID NO:59]
5'-GACTGGCTGTTCCCGCAGCCGATTTTGCTGACCCTGCAGCCCCGGCA
AACTCCAGTTTCACGGTAGCGTG-3'
```

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

```
Sense Primer
                                          [SEQ ID NO:1]
5'-GGCGAATTCCTTGTTGCCAATCAAGTTGTCACC-3'
(EcoRI site is underlined.)

Antisense Primer
                                          [SEQ ID NO:60]
5'-CAGGTCAAGCTTTCACTCCAGTTTCACGGTAGCGTG-3'
(HindIII site is underlined.)
```

(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX5 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX5 contained the Toxo P30MIX5 gene cloned at the EcoRI/HindIII sites of pMAL-c2X. The complete DNA sequence [SEQ ID NO:71] of plasmid pMBP-c2X-ToxoP30MIX5 is shown in FIG. 35, and the corresponding amino acid sequence [SEQ ID NO:72] of the MBP-ToxoP30MIX5 fusion protein is also shown in FIG. 35, wherein cysteine amino acid residues-located at 422, 555, 570, 578, 625, 635 of SEQ ID NO:21 are now alanine amino acids located at 422, 555, 570, 578, 625, 635 of SEQ ID NO:72. The DNA sequence [SEQ ID NO:73] of ToxoP30MIX5 is shown in FIG. 36, and the corresponding amino acid sequence [SEQ ID NO:74] of the ToxoP30MIX5 protein is also shown in FIG. 36, wherein cysteine amino acid residues located at 31, 164, 179, 187, 234, 244 of SEQ ID NO:23 are now alanine amino acids located at 31, 164, 179, 187, 234, 244 of SEQ ID NO:74.

EXAMPLE 6

Expression of rpMBP-c2X-ToxoP30MIX Antigens in *E. coli*

Step A: Expression of Cloned Genes in *E. coli*

Bacterial clones pMBP-c2X-ToxoP30MIX1, pMBP-c2X-ToxoP30MIX3, and pMBP-c2X-ToxoP30MIX5 expressing the MBP fusion proteins rpMBP-c2X-ToxoP30MIX1, rpMBP-c2X-ToxoP30MIX3, and rpMBP-c2X-ToxoP30MIX5 of Example 5 were grown in "SUPER-BROTH II" media containing 100 μg/ml ampicillin to log phase, and the synthesis of the MBP-ToxoP30MIX fusion proteins was induced by the addition of IPTG as previously described (Robinson et al. (1993) J. Clin. Microbiol. 31:629-635). After 4 hours post-induction, the cells were harvested, and the cell pellets were stored at −80C until protein purification occurred.

Step B: Purification of MBP-ToxoP30MIX Fusion Proteins

Soluble fusion proteins rpMBP-c2X-ToxoP30MIX1, rpMBP-c2X-ToxoP30MIX3, and rpMBP-c2X-ToxoP30MIX5 were purified after lysis from cell paste following the New England Biolabs pMAL Protein Fusion and Purification instruction manual. Following lysis and centrifugation, the crude supernatants containing the fusion proteins were loaded onto an amylose affinity column. Following washing of the column, the fusion proteins were eluted from the column with maltose, appropriate column fractions were pooled and filtered through a 0.2% filter, and then stored at 2-8° C. until coating onto microparticles.

EXAMPLE 7

Evaluation of rpMBP-c2X-ToxoP30MIX Antigens in an Automated Toxo IgG and IgM Immunoassay Step A: Coating of rpMBP-c2X-ToxoP30MIX Antigens onto Microparticles Prior to coating microparticles, the rpMBP-c2X-ToxoP30MIX1, rpMBP-c2X-ToxoP30MIX3 and rpMBP-c2X-ToxoP30MIX5 antigens were diluted to a concentration of 1 mg/ml and incubated at 37° C. for 24 hours. Following the heat treatment step, the rpMBP-c2X-ToxoP30MIX antigens were coated separately onto sulfate-derivatized polystyrene microparticles (1-5% solids) in a vessel containing MES pH 6.2 buffer with EDAC for 30 minutes at room temperature, on an end over end rotator. The coated microparticles were then collected by centrifugation at 14,000×g for 10 minutes and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1-0.3% solids and filled into plastic bottles.

Step B: Evaluation of MBP fusion proteins rpMBP-c2X-ToxoP30MIX1, rpMBP-c2X-ToxoP30MIX3 and rpMBP-c2X-ToxoP30MIX5 in the AxSYM Toxo IgG v2 and Toxo IgM v2 Immunoassays The AxSYM® Toxo IgG and IgM reagent packs were assembled as described in Examples 4B and 4C using the microparticles coated with the Toxo antigens described in Example 7A. The Toxo IgG A and F calibrators (Acal and Fcal) and Panel 6 (PNL6) were tested with the AxSYM Toxo IgG v2 reagent packs and the Toxo IgM Negative Control (NC), Index Calibrator (IC), and Panel 6 (PNL6) were tested with the AxSYM Toxo IgM v2 reagent packs. The results are shown below in Tables 3 and 4.

TABLE 3

Evaluation of the rpMBP-c2X-ToxoP30MIX Antigens in the AxSYM Toxo IgG v2 Assay

| | Rate Counts | | | | |
|---|---|---|---|---|---|
| Antigen Coated | Acal | Fcal | Fcal/ Acal | PNL6 | PNL6/ Acal |
| rpMBP-c2X-ToxoP30 MIX1 (Ala8-12) | 34 | 3847 | 113 | 1445 | 43 |
| rpMBP-c2X-ToxoP30 MIX3 (Ala7-12) | 35 | 3704 | 106 | 1043 | 30 |
| rpMBP-c2X-ToxoP30 MIX5 (Ala2, Ala8-12) | 35 | 57 | 1.6 | 23 | 0.7 |

TABLE 4

Evaluation of the rpMBP-c2X-ToxoP30MIX Antigens in the AxSYM Toxo IgM v2 Assay

| | Rate Counts | | | |
|---|---|---|---|---|
| Antigen Coated | NC | IC | PNL6 | PNL6/ NC |
| rpMBP-c2X-ToxoP30 MIX1 (Ala8-12) | 37 | 149 | 459 | 12.4 |
| rpMBP-c2X-ToxoP30 MIX3 (Ala7-12) | 44 | 111 | 368 | 8.4 |

TABLE 4-continued

Evaluation of the rpMBP-c2X-ToxoP30MIX Antigens in the AxSYM Toxo IgM v2 Assay

| | Rate Counts | | | |
|---|---|---|---|---|
| Antigen Coated | NC | IC | PNL6 | PNL6/ NC |
| rpMBP-c2X-ToxoP30 MIX5 (Ala2, Ala8-12) | 31 | 49 | 27 | 0.9 |

As can be seen in Tables 3 and 4, the genetically engineered rpMBP-c2X-ToxoP30MIX1 antigen, which contained five C-terminal cysteine residues substituted with alanine, yielded the best Toxo IgG and IgM immunoreactivity as measured by the highest rate counts for Panel 6 and highest rate count ratios for Fcal/Acal, Panel 6/Acal, and Panel 6/NC. In addition, the rpMBP-c2X-ToxoP30MIX1 antigen yielded the highest rate counts for Panel6 and the highest Panel6/NC rate count ratio in the Toxo IgM v2 assay for any rpMBP-c2X-ToxoP30 antigen tested (see Tables 1 and 2). The rpMBP-c2X-ToxoP30MIX5 antigen, which contained five C-terminal cysteine residues substituted with alanine residues plus the substitution of cysteine no. 2 with alanine, was not immunoreactive in either assay. This result was consistent with the results obtained with the rpMBP-c2X-ToxoP30del4del8(83-294aa) antigen (see Tables 1 and 2), in which deletion of the first two cysteine residues of Toxo P30 resulted in complete loss of immunoreactivity. Thus, the surprising result was obtained that substitution of several cysteine residues in the C-terminal half of Toxo P30 with alanine results in superior Toxo IgG and IgM immunoreactivity of the antigen whereas substitution of a single cysteine with alanine in the N-terminal half of Toxo P30 completely abolishes immunoreactivity.

EXAMPLE 8

Purification and Coating of the rpToxoP35S Antigen

The rpToxoP35S antigen described in U.S. Pat. No. 6,329,157 B1 was expressed in *E. coli*, and cell paste was harvested as described in Example 6A. This antigen was then purified from cell paste and coated onto microparticles as described below.

Step A: Purification of the rpToxoP35S Antigen

The rpToxoP35S antigen was expressed in *E. coli* as an insoluble fusion protein. Following lysis of the cell paste, the inclusion bodies containing the rpToxoP35S antigen were washed with water, phosphate buffer, Triton X-100, and urea. The rpToxoP35S antigen was then solubilized in a SDS/DTT buffer and applied to a Sephacryl S-300 column. The appropriate column fractions were pooled, diluted to a concentration of 1 mg/ml and filtered through a 0.2μ filter, and then stored at −80° C. until coating.

Step B: Coating of the rpToxoP35S Antigen onto Microparticles

The rpToxoP35S antigen was thawed and brought into solution by mild warming followed by centrifugation to remove particulate matter. This antigen was then dialyzed against three changes of MES buffer, pH 6.2 at room temperature overnight and then coated onto sulfate-derivatized polystyrene microparticles (1-5% solids) in a vessel containing MES pH 6.2 buffer with EDAC for 30 minutes at room temperature, on an end over end rotator. The coated microparticles were then collected by centrifugation at 14,000×g for 10 minutes and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1-0.3% solids and filled into plastic bottles.

EXAMPLE 9

Development of Antigen Cocktails Employing the Genetically Engineered P30 Antigens After achieving a significant improvement in the Toxo IgG and IgM immunoreactivity of the P30 antigen through genetic engineering (Examples 4 and 7), a preliminary re-evaluation of microparticles coated with the Toxo antigens described in U.S. Pat. No. 6,329,157 B1 in the AxSYM® Toxo IgG v2 and IgM v2 assays was performed. Evaluation of these antigen coated microparticles in conjunction with microparticles coated with the P30 antigens rpMBP-c2X-ToxoP30del3C(52-300aa), rpMBP-c2X-ToxoP30del4C(52-294aa), and rpMBP-c2X-ToxoP30MIX1 suggested that a new combination of either the rpMBP-c2X-ToxoP30del3C(52-300aa), rpMBP-c2X-ToxoP30del4C(52-294aa), or rpMBP-c2X-ToxoP30MIX1 antigen with the rpToxoP35S antigen could improve the performance of the AxSYM® Toxo IgG v2 assay. In addition, the rpMBP-c2X-ToxoP30del3C(52-300aa), rpMBP-c2X-ToxoP30del4C(52-294aa), or rpMBP-c2X-ToxoP30MIX1 antigens alone could improve the performance of the AxSYM® Toxo IgM v2 assay. In order to demonstrate the diagnostic utility of the genetically engineered P30 antigens and the new genetically engineered P30/P35 antigen cocktail, human sera negative for Toxo antibodies and sera sourced from patients with an acute or chronic toxoplasmosis were tested in the AxSYM® Toxo IgG v2 and IgM v2 assays as described below.

Step A: Assembly of AxSYM® Toxo IgG v2 reagent packs

Purified Toxo antigens rpMBP-c2X-ToxoP30del3C(52-300aa), rpMBP-c2X-ToxoP30del4C(52-294aa), rpMBP-c2X-ToxoP30MIX1, and rpToxoP35S were coated unto microparticles as previously described in Examples 4A and 7A. The microparticles were then diluted to a final concentration 0.2% solids and the following three microparticle blends were made: 2:1 v/v blend of rpMBP-c2X-ToxoP30del3C(52-300aa):rpToxoP35S coated microparticles (labeled as P30del3/P35); 2:1 v/v blend of rpMBP-c2X-ToxoP30del4C(52-294aa):rpToxoP35S coated microparticles (labeled as P30del4/P35); and a 2:1 v/v blend of rpMBP-c2X-ToxoP30MIX1:rpToxoP35S coated microparticles (labeled as P30MIX1/P35). These three microparticle blends were filled into plastic bottles, assembled into individual AxSYM® Toxo IgG v2 reagent kits as described in Example 4B, and labeled as P30del3C/35, P30del4C/P35, and P30MIX1/P35.

Step B: Assembly of AxSYM® Toxo IgM v2 reagent packs

Purified Toxo antigens rpMBP-c2X-ToxoP30del3C(52-300aa), rpMBP-c2X-ToxoP30del4C(52-294aa), rpMBP-c2X-ToxoP30MIX1, and rpToxoP35S were coated onto microparticles as previously described in Examples 4A and 7A. The microparticles were then diluted to a final concentration of 0.2% solids and filled into plastic bottles. AxSYM® Toxo IgM v2 kits were assembled with each coated microparticle as described in Example 4C and labeled as P30del3C, P30del4C, and P30MIX1.

Step C: Human Sera for Testing

Three groups of human sera from a French population were tested in this evaluation: Group 1 (n=100) human sera negative for Toxo IgG and IgM antibodies by the Abbott IMx® Toxo IgG and IgM assays, respectively (Abbott Laboratories, Abbott Park, Ill.); Group 2 (n=56) human sera positive for Toxo IgG and negative for Toxo IgM antibodies by the Abbott IMx® Toxo IgG and IgM assays, respectively; Group 3 (n=52) human sera positive for Toxo IgG antibodies by a high sensitivity direct agglutination assay (HSDA) (Desmonts, G. and Remington, J. S. (1980) J. Clin. Microbiol. 11:562-568) and positive for Toxo IgM antibodies by an IgM immunocapture assay (IC-M) (Pouletty et al. (1985) J. Immunol. Methods 76:289-298). The assay calibrators and controls for the AxSYM® Toxo IgG v2 and Toxo IgM v2 assays were run as previously described in Examples 4B-D. The Abbott AxSYM® Toxo IgG and IgM assays (Abbott Laboratories Abbott Park, Ill.), which use the tachyzoite antigen for detection of Toxo-specific IgG and IgM, were included as reference assays during specimen testing.

Step D: Evaluation of the AxSYM® Toxo IgG v2 assays

All specimens in Groups 1-3 were tested by the AxSYM® Toxo IgG v2 assays (P30del3C/35, P30del4C/P35, and P30MIX1/P35) and by the AxSYM® Toxo IgG assay. The same assay cutoff of 3 IU/ml for the AxSYM Toxo IgG assay was employed for AxSYM® Toxo IgG v2 assays, with an equivocal zone from 2-3 IU/ml. The performance of the recombinant antigen based AxSYM® Toxo IgG v2 assays was compared to the tachyzoite antigen based AxSYM® Toxo IgG assay and is shown in Tables 5-7.

TABLE 5

Evaluation of the AxSYM ® Toxo IgG v2 P30del3C/P35 assay

| | | AxSYM® Toxo IgG | | | |
|---|---|---|---|---|---|
| | | POS | EQV | NEG | TOTAL |
| AxSYM® Toxo IgG v2 P30del3C/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9751

TABLE 6

Evaluation of the AxSYM ® Toxo IgG v2 P30del4C/P35 assay

| | | AxSYM® Toxo IgG | | | |
|---|---|---|---|---|---|
| | | POS | EQV | NEG | TOTAL |
| AxSYM® Toxo IgG v2 P30del4C/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9778

TABLE 7

Evaluation of the AxSYM ® Toxo IgG v2 P30MIX1/P35 assay

| | | AxSYM® Toxo IgG | | | |
|---|---|---|---|---|---|
| | | POS | EQV | NEG | TOTAL |
| AxSYM® Toxo IgG v2 P30MIX1/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9563

As can be seen from Tables 5-7, the AxSYM® Toxo IgG v2 assay using the combination of a genetically engineered antigen P30 antigen (P30del3C, P30del4C, or P30MIX1) with the P35 antigen is both a sensitive and specific assay for the detection of *Toxoplasma*-specific IgG as demonstrated by the overall high relative diagnostic sensitivity (100%), specificity (100%), and agreement (100%). All three AxSYM® Toxo IgG v2 assays were in excellent agreement quantitatively with the AxSYM® Toxo IgG assay, as measured by the correlation coefficients, all of which were 0.95 or greater. The Toxo recombinant antigen cocktail comprised of the genetically engineered Toxo P30 antigen (P30del3C, P30del4C, or P30MIX1) and the P35 antigen, in combination with the AxSYM® Toxo IgG v2 assay, is both necessary and sufficient to replace the tachyzoite for the detection of *Toxoplasma*-specific IgG antibody.

Furthermore, there are several advantages of the recombinant antigen cocktail over the tachyzoite antigen for use in detection of IgG antibodies. First, the antigens are purified, and the amount of each antigen loaded into the immunoassay can be accurately determined and standardized, e.g., protein concentration. This minimizes between lot differences commonly observed in kits manufactured with different tachyzoite antigen lots. Hence, different lots of kits manufactured with different antigen cocktail lots will be very consistent from lot to lot. Secondly, mouse or human monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Finally, kits manufactured with the antigen cocktail are more stable during storage over time, and the performance of the assay using these antigens remains consistent over the shelf life of the assay. Kits manufactured with the tachyzoite antigen are not as stable and their performance may vary over time.

Additionally, there are many advantages of using a cocktail over using a single antigen alone. For example, an immune response to infection varies by individual. Some individuals produce antibodies to P35 and not to P30 early in infection (acute toxoplasmosis), whereas some individuals produce antibodies to P30 and not to P35 later in infection (chronic toxoplasmosis). Thus, the antigen cocktail of the present invention will detect both groups of individuals.

Moreover, immune responses vary with time. For example, one individual may produce antibodies against P35 first and then later produce antibodies to only P30. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is known from previous Western Blot experiments with tachyzoite proteins that the immune response to *Toxoplasma* is directed against several antigens. Once again, the present antigen cocktail will allow for the detection of all antibodies produced in response to these antigens.

Step E: Evaluation of the AxSYM® Toxo IgM v2 assays

All specimens in Groups 1-3 were tested by the AxSYM® Toxo IgM v2 assays (P30del3C, P30del4C, and P30MIX1) and by the AxSYM® Toxo IgM assay. A receiver operator characteristic (ROC) was used to assist the determination of the preliminary cutoff for the AxSYM® Toxo IgM v2 assays (Index value≧0.6) (Zweig, HM (1993) Clin. Chem. 39:561-577). In addition, an equivocal zone of Index value 0.500-0.599 was introduced to account for assay imprecision. The performance of the recombinant antigen based AxSYM® Toxo IgM v2 assays was compared to the tachyzoite antigen based AxSYM® Toxo IgM assay and is shown in Tables 8-10.

TABLE 8

Evaluation of the AxSYM ® Toxo IgM v2 P30del3C assay

| | | AxSYM® Toxo IgM | | | |
|---|---|---|---|---|---|
| | | POS | EQV | NEG | TOTAL |
| AxSYM® Toxo IgM v2 P30del3C | POS | 33 | 2 | 7 | 42 |
| | EQV | 5 | 1 | 3 | 9 |
| | NEG | 0 | 2 | 155 | 157 |
| | TOTAL | 38 | 5 | 165 | 208 |

Sensitivity: 33/33 = 100%
Specificity: 155/162 = 95.7%
Agreement: 188/195 = 96.4%

TABLE 9

Evaluation of the AxSYM ® Toxo IgM v2 P30del4C assay

| | | AxSYM® Toxo IgM | | | |
|---|---|---|---|---|---|
| | | POS | EQV | NEG | TOTAL |
| AxSYM® Toxo IgM v2 P30del4C | POS | 34 | 2 | 9 | 45 |
| | EQV | 4 | 1 | 2 | 8 |
| | NEG | 0 | 2 | 154 | 155 |
| | TOTAL | 38 | 5 | 165 | 208 |

Sensitivity: 34/34 = 100%
Specificity: 154/163 = 94.5%
Agreement: 188/197 = 95.4%

TABLE 10

Evaluation of the AxSYM ® Toxo IgM v2 P30MIX1 assay

| | | AxSYM® Toxo IgM | | | |
|---|---|---|---|---|---|
| | | POS | EQV | NEG | TOTAL |
| AxSYM® Toxo IgM v2 P30MIX1 | POS | 35 | 2 | 8 | 45 |
| | EQV | 2 | 0 | 3 | 5 |
| | NEG | 1 | 3 | 154 | 158 |
| | TOTAL | 38 | 5 | 165 | 208 |

Sensitivity: 35/36 = 97.2%
Specificity: 154/162 = 95.1%
Agreement: 189/198 = 95.5%

As can be seen from Tables 8-10, the AxSYM® Toxo IgM v2 assay using the genetically engineered antigen P30 antigen (P30del3C, P30del4C, or P30MIX1) is both a sensitive and specific assay for the detection of *Toxoplasma*-specific IgG as demonstrated by the overall high relative diagnostic sensitivity (range=97.2%-100%), specificity (range 94.5%-95.7%), and agreement (range=95.4%-96.4%). The genetically engineered Toxo recombinant P30 antigen (P30del3C, P30del4C, or P30MIX1), in combination with the AxSYM® Toxo IgM v2 assay, is both necessary and sufficient to replace the tachyzoite for the detection of *Toxoplasma*-specific IgM antibody.

Furthermore, there are several advantages of the genetically engineered recombinant Toxo P30 antigen over the tachyzoite antigen for use in detection of IgM antibodies. First, the antigen is purified, and the amount of antigen loaded into the immunoassay can be accurately determined and standardized, e.g., protein concentration. This minimizes lot-to-to differences commonly observed in kits manufactured with different tachyzoite antigen lots. Hence, different lots of kits manufactured with different recombinant antigen lots will be very consistent from lot to lot. Secondly, mouse or human monoclonal antibodies to the recombinant Toxo antigen are used to monitor coating of the proteins to the solid phase. This further ensures that each lot produced is consistent. Third, the true clinical sensitivity of the assay using the purified antigens will be higher by virtue of the fact of the higher specific activity of the purified antigen. Finally, kits manufactured with the recombinant antigen are more stable during storage over time, and the performance of the assay using this antigen remains consistent over the shelf life of the assay. Kits manufactured with the tachyzoite antigen are not as stable and their performance may vary over time.

The invention claimed is:

1. An isolated polynucleotide comprising the nucleotide sequence of SEQ ID NO:63.

2. An isolated polynucleotide encoding a polypeptide comprising the amino acid sequence of SEQ ID NO:64.

* * * * *

UNITED STATES PATENT AND TRADEMARK OFFICE

CERTIFICATE OF CORRECTION

PATENT NO. : 7,314,924 B2
APPLICATION NO. : 11/316532
DATED : January 1, 2008
INVENTOR(S) : Maine et al.

It is certified that error appears in the above-identified patent and that said Letters Patent is hereby corrected as shown below:

Title Page, item (56), under "Other Publications", in Column 1, Line 5, delete "a antibodies"," and insert -- A antibodies", --.

Title Page, item (56), under "Other Publications", in Column 1, Line 18, delete "Parasiste" and insert -- Parasite --.

Title Page, item (56), under "Other Publications", in Column 2, Line 11, delete ""Cloining" and insert -- "Cloning --.

Title Page, item (56), under "Other Publications", in Column 2, Line 19, delete "Parasiotol," and insert -- Parasitol, --.

Title Page, item (56), under "Other Publications", in Column 2, Line 20, delete "Enclоding" and insert -- Encoding --.

Title Page, item (56), under "Other Publications", in Column 2, Line 25, delete "Gen" and insert -- Gene --.

Title Page, item (56), under "Other Publications", in Column 2, Line 29, delete "Recongnized" and insert -- Recognized --.

Title Page, item (56), under "Other Publications", in Column 2, Line 33, delete "Excherichia" and insert -- Escherichia --.

Signed and Sealed this

Twenty-ninth Day of June, 2010

David J. Kappos

*Director of the United States Patent and Trademark Office*

SEQUENCE LISTING

```
<160> NUMBER OF SEQ ID NOS: 74

<210> SEQ ID NO 1
<211> LENGTH: 33
<212> TYPE: DNA
<213> ORGANISM: Artificial Sequence
<220> FEATURE:
<223> OTHER INFORMATION: Sense Primer

<400> SEQUENCE: 1
```

-continued

```
ggcgaattcc ttgttgccaa tcaagttgtc acc                                33


<210> SEQ ID NO 2
<211> LENGTH: 31
<212> TYPE: DNA
<213> ORGANISM: Artificial Sequence
<220> FEATURE:
<223> OTHER INFORMATION: Antisense Primer

<400> SEQUENCE: 2

cgctgaagct ttcacgcgac acaagctgcg a                                  31


<210> SEQ ID NO 3
<211> LENGTH: 7478
<212> TYPE: DNA
<213> ORGANISM: Toxoplasma gondii
<220> FEATURE:
<221> NAME/KEY: CDS
<222> LOCATION: (1528)...(3555)
<223> OTHER INFORMATION: pMBP-c2X-ToxoP30 (52-336aa)

<400> SEQUENCE: 3

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5
```

-continued

```
atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg      1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa      1746
Pro Asp Ile Ile Phe Trp Ala His Asp Arg Phe Gly Gly Tyr Ala Gln
         60                  65                  70

tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
     75                  80                  85

ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
```

-continued

```
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc acg gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565

tgt tcc ggg acg acg ctg act ggt tgc aac gag aaa tcg ttc aaa gat      3282
Cys Ser Gly Thr Thr Leu Thr Gly Cys Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga tgc aca ggg gga tcg cct gag aag cat      3426
Ser Lys Ser Val Ile Ile Gly Cys Thr Gly Gly Ser Pro Glu Lys His
        620                 625                 630

cac tgt acc gtg aaa ctg gag ttt gcc ggg gct gca ggg tca gca aaa      3474
```

-continued

```
His Cys Thr Val Lys Leu Glu Phe Ala Gly Ala Ala Gly Ser Ala Lys
    635                 640                 645

tcg gct gcg gga aca gcc agt cac gtt tcc att ttt gcc atg gtg atc     3522
Ser Ala Ala Gly Thr Ala Ser His Val Ser Ile Phe Ala Met Val Ile
650                 655                 660                 665

gga ctt att ggc tct atc gca gct tgt gtc gcg tgaaagcttg gcactggccg   3575
Gly Leu Ile Gly Ser Ile Ala Ala Cys Val Ala
                670                 675

tcgttttaca acgtcgtgac tgggaaaacc ctggcgttac ccaacttaat cgccttgcag   3635

cacatccccc tttcgccagc tggcgtaata gcgaagaggc ccgcaccgat cgcccttccc   3695

aacagttgcg cagcctgaat ggcgaatggc agcttggctg ttttggcgga tgagataaga   3755

ttttcagcct gatacagatt aaatcagaac gcagaagcgg tctgataaaa cagaatttgc   3815

ctggcggcag tagcgcggtg gtcccacctg accccatgcc gaactcagaa gtgaaacgcc   3875

gtagcgccga tggtagtgtg gggtctcccc atgcgagagt agggaactgc caggcatcaa   3935

ataaaacgaa aggctcagtc gaaagactgg gcctttcgtt ttatctgttg tttgtcggtg   3995

aacgctctcc tgagtaggac aaatccgccg ggagcggatt tgaacgttgc gaagcaacgg   4055

cccggagggt ggcgggcagg acgcccgcca taaactgcca ggcatcaaat taagcagaag   4115

gccatcctga cggatggcct ttttgcgttt ctacaaactc tttttgttta tttttctaaa   4175

tacattcaaa tatgtatccg ctcatgagac aataaccctg ataaatgctt caataatatt   4235

gaaaaaggaa gagtatgagt attcaacatt tccgtgtcgc ccttattccc ttttttgcgg   4295

cattttgcct tcctgttttt gctcacccag aaacgctggt gaaagtaaaa gatgctgaag   4355

atcagttggg tgcacgagtg ggttacatcg aactggatct caacagcggt aagatccttg   4415

agagttttcg ccccgaagaa cgttctccaa tgatgagcac ttttaaagtt ctgctatgtg   4475

gcgcggtatt atcccgtgtt gacgccgggc aagagcaact cggtcgccgc atacactatt   4535

ctcagaatga cttggttgag tactcaccag tcacagaaaa gcatcttacg gatggcatga   4595

cagtaagaga attatgcagt gctgccataa ccatgagtga taacactgcg gccaacttac   4655

ttctgacaac gatcggagga ccgaaggagc taaccgcttt tttgcacaac atgggggatc   4715

atgtaactcg ccttgatcgt tgggaaccgg agctgaatga agccatacca aacgacgagc   4775

gtgacaccac gatgcctgta gcaatggcaa caacgttgcg caaactatta actggcgaac   4835

tacttactct agcttcccgg caacaattaa tagactggat ggaggcggat aaagttgcag   4895

gaccacttct gcgctcggcc cttccggctg gctggtttat tgctgataaa tctggagccg   4955

gtgagcgtgg gtctcgcggt atcattgcag cactggggcc agatggtaag ccctcccgta   5015

tcgtagttat ctacacgacg gggagtcagg caactatgga tgaacgaaat agacagatcg   5075

ctgagatagg tgcctcactg attaagcatt ggtaactgtc agaccaagtt tactcatata   5135

tactttagat tgatttaccc cggttgataa tcagaaaagc ccccaaaaaca ggaagattgt  5195

ataagcaaat atttaaattg taaacgttaa tattttgtta aaattcgcgt taaatttttg   5255

ttaaatcagc tcatttttta accaataggc cgaaatcggc aaaatccctt ataaatcaaa   5315

agaatagacc gagatagggt tgagtgttgt tccagtttgg aacaagagtc cactattaaa   5375

gaacgtggac tccaacgtca aagggcgaaa aaccgtctat cagggcgatg gcccactacg   5435

tgaaccatca cccaaatcaa gtttttttggg gtcgaggtgc cgtaaagcac taaatcggaa  5495

ccctaaaggg agcccccgat ttagagcttg acggggaaag ccggcgaacg tggcgagaaa   5555

ggaagggaag aaagcgaaag gagcgggcgc tagggcgctg gcaagtgtag cggtcacgct   5615
```

-continued

```
gcgcgtaacc accacacccg ccgcgcttaa tgcgccgcta cagggcgcgt aaaaggatct   5675

aggtgaagat cctttttgat aatctcatga ccaaaatccc ttaacgtgag ttttcgttcc   5735

actgagcgtc agaccccgta gaaaagatca aaggatcttc ttgagatcct ttttttctgc   5795

gcgtaatctg ctgcttgcaa acaaaaaaac caccgctacc agcggtggtt tgtttgccgg   5855

atcaagagct accaactctt tttccgaagg taactggctt cagcagagcg cagataccaa   5915

atactgtcct tctagtgtag ccgtagttag gccaccactt caagaactct gtagcaccgc   5975

ctacatacct cgctctgcta atcctgttac cagtggctgc tgccagtggc gataagtcgt   6035

gtcttaccgg gttggactca agacgatagt taccggataa ggcgcagcgg tcgggctgaa   6095

cggggggttc gtgcacacag cccagcttgg agcgaacgac ctacaccgaa ctgagatacc   6155

tacagcgtga gctatgagaa agcgccacgc ttcccgaagg gagaaaggcg gacaggtatc   6215

cggtaagcgg cagggtcgga acaggagagc gcacgaggga gcttccaggg ggaaacgcct   6275

ggtatcttta tagtcctgtc gggtttcgcc acctctgact tgagcgtcga tttttgtgat   6335

gctcgtcagg ggggcggagc ctatggaaaa acgccagcaa cgcggccttt ttacggttcc   6395

tggccttttg ctggcctttt gctcacatgt tctttcctgc gttatcccct gattctgtgg   6455

ataaccgtat taccgccttt gagtgagctg ataccgctcg ccgcagccga acgaccgagc   6515

gcagcgagtc agtgagcgag gaagcggaag agcgcctgat gcggtatttt ctccttacgc   6575

atctgtgcgg tatttcacac cgcatatatg gtgcactctc agtacaatct gctctgatgc   6635

cgcatagtta agccagtata cactccgcta tcgctacgtg actgggtcat ggctgcgccc   6695

cgacacccgc caacacccgc tgacgcgccc tgacgggctt gtctgctccc ggcatccgct   6755

tacagacaag ctgtgaccgt ctccgggagc tgcatgtgtc agaggttttc accgtcatca   6815

ccgaaacgcg cgaggcagct gcggtaaagc tcatcagcgt ggtcgtgcag cgattcacag   6875

atgtctgcct gttcatccgc gtccagctcg ttgagtttct ccagaagcgt taatgtctgg   6935

cttctgataa agcgggccat gttaagggcg gttttttcct gtttggtcac tgatgcctcc   6995

gtgtaagggg gatttctgtt catgggggta atgataccga tgaaacgaga gaggatgctc   7055

acgatacggg ttactgatga tgaacatgcc cggttactgg aacgttgtga gggtaaacaa   7115

ctggcggtat ggatgcggcg ggaccagaga aaaatcactc agggtcaatg ccagcgcttc   7175

gttaatacag atgtaggtgt tccacagggt agccagcagc atcctgcgat gcagatccgg   7235

aacataatgg tgcagggcgc tgacttccgc gtttccagac tttacgaaac acggaaaccg   7295

aagaccattc atgttgttgc tcaggtcgca gacgttttgc agcagcagtc gcttcacgtt   7355

cgctcgcgta tcggtgattc attctgctaa ccagtaaggc aaccccgcca gcctagccgg   7415

gtcctcaacg acaggagcac gatcatgcgc acccgtggcc aggacccaac gctgcccgaa   7475

att                                                                 7478
```

<210> SEQ ID NO 4
<211> LENGTH: 676
<212> TYPE: PRT
<213> ORGANISM: Toxoplasma gondii
<220> FEATURE:
<223> OTHER INFORMATION: pMBP-c2X-ToxoP30 (52-336aa)

<400> SEQUENCE: 4

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30
```

-continued

```
Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445
```

-continued

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala Ala Gly Thr Ala Ser
                645                 650                 655

His Val Ser Ile Phe Ala Met Val Ile Gly Leu Ile Gly Ser Ile Ala
            660                 665                 670

Ala Cys Val Ala
        675

<210> SEQ ID NO 5
<211> LENGTH: 855
<212> TYPE: DNA
<213> ORGANISM: Toxoplasma gondii
<220> FEATURE:
<221> NAME/KEY: CDS
<222> LOCATION: (1)...(855)
<223> OTHER INFORMATION: ToxoP30 (52-336aa)

<400> SEQUENCE: 5 ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct       96
Ala Val Ile Leu Thr Pro Thr Glu Asn His Phe Thr Leu Lys Cys Pro
             20                  25                  30 aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta      192
Gln Ile Cys Pro Ala Gly Thr Thr Ser Ser Cys Thr Ser Lys Ala Val
     50                  55                  60 aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc acg gtt cca atc      288
Asp Ser Ala Ser Leu Asp Thr Ala Gly Ile Lys Leu Thr Val Pro Ile -continued

```
                85                  90                  95

gag aag ttc ccc gtg aca acg cag acg ttt gtg gtc ggt tgc atc aag        336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga        384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac        432
Ala Ser Ser Val Val Asn Asn Val Ala Arg Cys Ser Tyr Gly Ala Asp
    130                 135                 140

agc act ctt ggt cct gtc aag ttg tct gcg gaa gga ccc act aca atg        480
Ser Thr Leu Gly Pro Val Lys Leu Ser Ala Glu Gly Pro Thr Thr Met
145                 150                 155                 160

acc ctc gtg tgc ggg aaa gat gga gtc aaa gtt cct caa gac aac aat        528
Thr Leu Val Cys Gly Lys Asp Gly Val Lys Val Pro Gln Asp Asn Asn
                165                 170                 175

cag tac tgt tcc ggg acg acg ctg act ggt tgc aac gag aaa tcg ttc        576
Gln Tyr Cys Ser Gly Thr Thr Leu Thr Gly Cys Asn Glu Lys Ser Phe
            180                 185                 190

aaa gat att ttg cca aaa tta act gag aac ccg tgg cag ggt aac gct        624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca        672
Ser Ser Asp Lys Gly Ala Thr Leu Thr Ile Lys Lys Glu Ala Phe Pro
    210                 215                 220

gcc gag tca aaa agc gtc att att gga tgc aca ggg gga tcg cct gag        720
Ala Glu Ser Lys Ser Val Ile Ile Gly Cys Thr Gly Gly Ser Pro Glu
225                 230                 235                 240

aag cat cac tgt acc gtg aaa ctg gag ttt gcc ggg gct gca ggg tca        768
Lys His His Cys Thr Val Lys Leu Glu Phe Ala Gly Ala Ala Gly Ser
                245                 250                 255

gca aaa tcg gct gcg gga aca gcc agt cac gtt tcc att ttt gcc atg        816
Ala Lys Ser Ala Ala Gly Thr Ala Ser His Val Ser Ile Phe Ala Met
            260                 265                 270

gtg atc gga ctt att ggc tct atc gca gct tgt gtc gcg                    855
Val Ile Gly Leu Ile Gly Ser Ile Ala Ala Cys Val Ala
        275                 280                 285


<210> SEQ ID NO 6
<211> LENGTH: 285
<212> TYPE: PRT
<213> ORGANISM: Toxoplasma gondii
<220> FEATURE:
<223> OTHER INFORMATION: ToxoP30 (52-336aa)

<400> SEQUENCE: 6

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
```

-continued 100 105 110

Gly Asp Asp Ala Gln Ser Cys Met Val Thr Val Thr Val Gln Ala Arg
115 120 125

Ala Ser Ser Val Val Asn Asn Val Ala Arg Cys Ser Tyr Gly Ala Asp
130 135 140

Ser Thr Leu Gly Pro Val Lys Leu Ser Ala Glu Gly Pro Thr Thr Met
145 150 155 160

Thr Leu Val Cys Gly Lys Asp Gly Val Lys Val Pro Gln Asp Asn Asn
165 170 175

Gln Tyr Cys Ser Gly Thr Thr Leu Thr Gly Cys Asn Glu Lys Ser Phe
180 185 190

Lys Asp Ile Leu Pro Lys Leu Thr Glu Asn Pro Trp Gln Gly Asn Ala
195 200 205

Ser Ser Asp Lys Gly Ala Thr Leu Thr Ile Lys Lys Glu Ala Phe Pro
210 215 220

Ala Glu Ser Lys Ser Val Ile Ile Gly Cys Thr Gly Gly Ser Pro Glu
225 230 235 240

Lys His His Cys Thr Val Lys Leu Glu Phe Ala Gly Ala Ala Gly Ser
245 250 255

Ala Lys Ser Ala Ala Gly Thr Ala Ser His Val Ser Ile Phe Ala Met
260 265 270

Val Ile Gly Leu Ile Gly Ser Ile Ala Ala Cys Val Ala
275 280 285

<210> SEQ ID NO 7
<211> LENGTH: 7553
<212> TYPE: DNA
<213> ORGANISM: Toxoplasma gondii
<220> FEATURE:
<221> NAME/KEY: CDS
<222> LOCATION: (1528)...(3630)
<223> OTHER INFORMATION: pMBP-p2X-ToxoP30 (52-336aa)

<400> SEQUENCE: 7
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960

-continued

```
gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa ata aaa aca ggt gca cgc atc   1554
                              Met Lys Ile Lys Thr Gly Ala Arg Ile
                               1               5

ctc gca tta tcc gca tta acg acg atg atg ttt tcc gcc tcg gct ctc     1602
Leu Ala Leu Ser Ala Leu Thr Thr Met Met Phe Ser Ala Ser Ala Leu
 10                  15                  20                  25

gcc aaa atc gaa gaa ggt aaa ctg gta atc tgg att aac ggc gat aaa     1650
Ala Lys Ile Glu Glu Gly Lys Leu Val Ile Trp Ile Asn Gly Asp Lys
                 30                  35                  40

ggc tat aac ggt ctc gct gaa gtc ggt aag aaa ttc gag aaa gat acc     1698
Gly Tyr Asn Gly Leu Ala Glu Val Gly Lys Lys Phe Glu Lys Asp Thr
             45                  50                  55

gga att aaa gtc acc gtt gag cat ccg gat aaa ctg gaa gag aaa ttc     1746
Gly Ile Lys Val Thr Val Glu His Pro Asp Lys Leu Glu Glu Lys Phe
         60                  65                  70

cca cag gtt gcg gca act ggc gat ggc cct gac att atc ttc tgg gca     1794
Pro Gln Val Ala Ala Thr Gly Asp Gly Pro Asp Ile Ile Phe Trp Ala
     75                  80                  85

cac gac cgc ttt ggt ggc tac gct caa tct ggc ctg ttg gct gaa atc     1842
His Asp Arg Phe Gly Gly Tyr Ala Gln Ser Gly Leu Leu Ala Glu Ile
 90                  95                 100                 105

acc ccg gac aaa gcg ttc cag gac aag ctg tat ccg ttt acc tgg gat     1890
Thr Pro Asp Lys Ala Phe Gln Asp Lys Leu Tyr Pro Phe Thr Trp Asp
                110                 115                 120

gcc gta cgt tac aac ggc aag ctg att gct tac ccg atc gct gtt gaa     1938
Ala Val Arg Tyr Asn Gly Lys Leu Ile Ala Tyr Pro Ile Ala Val Glu
            125                 130                 135

gcg tta tcg ctg att tat aac aaa gat ctg ctg ccg aac ccg cca aaa     1986
Ala Leu Ser Leu Ile Tyr Asn Lys Asp Leu Leu Pro Asn Pro Pro Lys
        140                 145                 150

acc tgg gaa gag atc ccg gcg ctg gat aaa gaa ctg aaa gcg aaa ggt     2034
Thr Trp Glu Glu Ile Pro Ala Leu Asp Lys Glu Leu Lys Ala Lys Gly
    155                 160                 165

aag agc gcg ctg atg ttc aac ctg caa gaa ccg tac ttc acc tgg ccg     2082
Lys Ser Ala Leu Met Phe Asn Leu Gln Glu Pro Tyr Phe Thr Trp Pro
170                 175                 180                 185

ctg att gct gct gac ggg ggt tat gcg ttc aag tat gaa aac ggc aag     2130
Leu Ile Ala Ala Asp Gly Gly Tyr Ala Phe Lys Tyr Glu Asn Gly Lys
                190                 195                 200

tac gac att aaa gac gtg ggc gtg gat aac gct ggc gcg aaa gcg ggt     2178
Tyr Asp Ile Lys Asp Val Gly Val Asp Asn Ala Gly Ala Lys Ala Gly
            205                 210                 215

ctg acc ttc ctg gtt gac ctg att aaa aac aaa cac atg aat gca gac     2226
Leu Thr Phe Leu Val Asp Leu Ile Lys Asn Lys His Met Asn Ala Asp
        220                 225                 230

acc gat tac tcc atc gca gaa gct gcc ttt aat aaa ggc gaa aca gcg     2274
```

-continued

```
Thr Asp Tyr Ser Ile Ala Glu Ala Ala Phe Asn Lys Gly Glu Thr Ala
    235                 240                 245

atg acc atc aac ggc ccg tgg gca tgg tcc aac atc gac acc agc aaa      2322
Met Thr Ile Asn Gly Pro Trp Ala Trp Ser Asn Ile Asp Thr Ser Lys
250                 255                 260                 265

gtg aat tat ggt gta acg gta ctg ccg acc ttc aag ggt caa cca tcc      2370
Val Asn Tyr Gly Val Thr Val Leu Pro Thr Phe Lys Gly Gln Pro Ser
                270                 275                 280

aaa ccg ttc gtt ggc gtg ctg agc gca ggt att aac gcc gcc agt ccg      2418
Lys Pro Phe Val Gly Val Leu Ser Ala Gly Ile Asn Ala Ala Ser Pro
            285                 290                 295

aac aaa gag ctg gca aaa gag ttc ctc gaa aac tat ctg ctg act gat      2466
Asn Lys Glu Leu Ala Lys Glu Phe Leu Glu Asn Tyr Leu Leu Thr Asp
        300                 305                 310

gaa ggt ctg gaa gcg gtt aat aaa gac aaa ccg ctg ggt gcc gta gcg      2514
Glu Gly Leu Glu Ala Val Asn Lys Asp Lys Pro Leu Gly Ala Val Ala
    315                 320                 325

ctg aag tct tac gag gaa gag ttg gcg aaa gat cca cgt att gcc gcc      2562
Leu Lys Ser Tyr Glu Glu Glu Leu Ala Lys Asp Pro Arg Ile Ala Ala
330                 335                 340                 345

act atg gaa aac gcc cag aaa ggt gaa atc atg ccg aac atc ccg cag      2610
Thr Met Glu Asn Ala Gln Lys Gly Glu Ile Met Pro Asn Ile Pro Gln
                350                 355                 360

atg tcc gct ttc tgg tat gcc gtg cgt act gcg gtg atc aac gcc gcc      2658
Met Ser Ala Phe Trp Tyr Ala Val Arg Thr Ala Val Ile Asn Ala Ala
            365                 370                 375

agc ggt cgt cag act gtc gat gaa gcc ctg aaa gac gcg cag act aat      2706
Ser Gly Arg Gln Thr Val Asp Glu Ala Leu Lys Asp Ala Gln Thr Asn
        380                 385                 390

tcg agc tcg aac aac aac aac aat aac aat aac aac aac ctc ggg atc      2754
Ser Ser Ser Asn Asn Asn Asn Asn Asn Asn Asn Asn Asn Leu Gly Ile
    395                 400                 405

gag gga agg att tca gaa ttc ctt gtt gcc aat caa gtt gtc acc tgc      2802
Glu Gly Arg Ile Ser Glu Phe Leu Val Ala Asn Gln Val Val Thr Cys
410                 415                 420                 425

cca gat aaa aaa tcg aca gcc gcg gtc att ctc aca ccg acg gag aac      2850
Pro Asp Lys Lys Ser Thr Ala Ala Val Ile Leu Thr Pro Thr Glu Asn
                430                 435                 440

cac ttc act ctc aag tgc cct aaa aca gcg ctc aca gag cct ccc act      2898
His Phe Thr Leu Lys Cys Pro Lys Thr Ala Leu Thr Glu Pro Pro Thr
            445                 450                 455

ctt gcg tac tca ccc aac agg caa atc tgc cca gcg ggt act aca agt      2946
Leu Ala Tyr Ser Pro Asn Arg Gln Ile Cys Pro Ala Gly Thr Thr Ser
        460                 465                 470

agc tgt aca tca aag gct gta aca ttg agc tcc ttg att cct gaa gca      2994
Ser Cys Thr Ser Lys Ala Val Thr Leu Ser Ser Leu Ile Pro Glu Ala
    475                 480                 485

gaa gat agc tgg tgg acg ggg gat tct gct agt ctc gac acg gca ggc      3042
Glu Asp Ser Trp Trp Thr Gly Asp Ser Ala Ser Leu Asp Thr Ala Gly
490                 495                 500                 505

atc aaa ctc aca gtt cca atc gag aag ttc ccc gtg aca acg cag acg      3090
Ile Lys Leu Thr Val Pro Ile Glu Lys Phe Pro Val Thr Thr Gln Thr
                510                 515                 520

ttt gtg gtc ggt tgc atc aag gga gac gac gca cag agt tgt atg gtc      3138
Phe Val Val Gly Cys Ile Lys Gly Asp Asp Ala Gln Ser Cys Met Val
            525                 530                 535

aca gtg aca gta caa gcc aga gcc tca tcg gtc gtc aat aat gtc gca      3186
Thr Val Thr Val Gln Ala Arg Ala Ser Ser Val Val Asn Asn Val Ala
        540                 545                 550
```

-continued

```
agg tgc tcc tac ggt gca gac agc act ctt ggt cct gtc aag ttg tct     3234
Arg Cys Ser Tyr Gly Ala Asp Ser Thr Leu Gly Pro Val Lys Leu Ser
    555                 560                 565

gcg gaa gga ccc act aca atg acc ctc gtg tgc ggg aaa gat gga gtc     3282
Ala Glu Gly Pro Thr Thr Met Thr Leu Val Cys Gly Lys Asp Gly Val
570                 575                 580                 585

aaa gtt cct caa gac aac aat cag tac tgt tcc ggg acg acg ctg act     3330
Lys Val Pro Gln Asp Asn Asn Gln Tyr Cys Ser Gly Thr Thr Leu Thr
                590                 595                 600

ggt tgc aac gag aaa tcg ttc aaa gat att ttg cca aaa tta act gag     3378
Gly Cys Asn Glu Lys Ser Phe Lys Asp Ile Leu Pro Lys Leu Thr Glu
            605                 610                 615

aac ccg tgg cag ggt aac gct tcg agt gat aag ggt gcc acg cta acg     3426
Asn Pro Trp Gln Gly Asn Ala Ser Ser Asp Lys Gly Ala Thr Leu Thr
        620                 625                 630

atc aag aag gaa gca ttt cca gcc gag tca aaa agc gtc att att gga     3474
Ile Lys Lys Glu Ala Phe Pro Ala Glu Ser Lys Ser Val Ile Ile Gly
    635                 640                 645

tgc aca ggg gga tcg cct gag aag cat cac tgt acc gtg aaa ctg gag     3522
Cys Thr Gly Gly Ser Pro Glu Lys His His Cys Thr Val Lys Leu Glu
650                 655                 660                 665

ttt gcc ggg gct gca ggg tca gca aaa tcg gct gcg gga aca gcc agt     3570
Phe Ala Gly Ala Ala Gly Ser Ala Lys Ser Ala Ala Gly Thr Ala Ser
                670                 675                 680

cac gtt tcc att ttt gcc atg gtg atc gga ctt att ggc tct atc gca     3618
His Val Ser Ile Phe Ala Met Val Ile Gly Leu Ile Gly Ser Ile Ala
            685                 690                 695

gct tgt gtc gcg tgaaagcttg gcactggccg tcgttttaca acgtcgtgac         3670
Ala Cys Val Ala
        700

tgggaaaacc ctggcgttac ccaacttaat cgccttgcag cacatccccc tttcgccagc   3730

tggcgtaata gcgaagaggc ccgcaccgat cgcccttccc aacagttgcg cagcctgaat   3790

ggcgaatggc agcttggctg ttttggcgga tgagataaga ttttcagcct gatacagatt   3850

aaatcagaac gcagaagcgg tctgataaaa cagaatttgc ctggcggcag tagcgcggtg   3910

gtcccacctg accccatgcc gaactcagaa gtgaaacgcc gtagcgccga tggtagtgtg   3970

gggtctcccc atgcgagagt agggaactgc caggcatcaa ataaaacgaa aggctcagtc   4030

gaaagactgg gcctttcgtt ttatctgttg tttgtcggtg aacgctctcc tgagtaggac   4090

aaatccgccg ggagcggatt tgaacgttgc gaagcaacgg cccggagggt ggcgggcagg   4150

acgcccgcca taaactgcca ggcatcaaat taagcagaag gccatcctga cggatggcct   4210

ttttgcgttt ctacaaactc tttttgttta tttttctaaa tacattcaaa tatgtatccg   4270

ctcatgagac aataaccctg ataaatgctt caataatatt gaaaaaggaa gagtatgagt   4330

attcaacatt tccgtgtcgc ccttattccc ttttttgcgg cattttgcct tcctgttttt   4390

gctcacccag aaacgctggt gaaagtaaaa gatgctgaag atcagttggg tgcacgagtg   4450

ggttacatcg aactggatct caacagcggt aagatccttg agagttttcg ccccgaagaa   4510

cgttctccaa tgatgagcac ttttaaagtt ctgctatgtg gcgcggtatt atcccgtgtt   4570

gacgccgggc aagagcaact cggtcgccgc atacactatt ctcagaatga cttggttgag   4630

tactcaccag tcacagaaaa gcatcttacg gatggcatga cagtaagaga attatgcagt   4690

gctgccataa ccatgagtga taacactgcg gccaacttac ttctgacaac gatcggagga   4750

ccgaaggagc taaccgcttt tttgcacaac atgggggatc atgtaactcg ccttgatcgt   4810

tgggaaccgg agctgaatga agccatacca aacgacgagc gtgacaccac gatgcctgta   4870
```

-continued

```
gcaatggcaa caacgttgcg caaactatta actggcgaac tacttactct agcttcccgg   4930
caacaattaa tagactggat ggaggcggat aaagttgcag gaccacttct gcgctcggcc   4990
cttccggctg gctggtttat tgctgataaa tctggagccg gtgagcgtgg gtctcgcggt   5050
atcattgcag cactggggcc agatggtaag ccctcccgta tcgtagttat ctacacgacg   5110
gggagtcagg caactatgga tgaacgaaat agacagatcg ctgagatagg tgcctcactg   5170
attaagcatt ggtaactgtc agaccaagtt tactcatata tactttagat tgatttaccc   5230
cggttgataa tcagaaaagc cccaaaaaca ggaagattgt ataagcaaat atttaaattg   5290
taaacgttaa tattttgtta aaattcgcgt taaatttttg ttaaatcagc tcatttttta   5350
accaataggc cgaaatcggc aaaatccctt ataaatcaaa agaatagacc gagatagggt   5410
tgagtgttgt tccagtttgg aacaagagtc cactattaaa gaacgtggac tccaacgtca   5470
aagggcgaaa aaccgtctat cagggcgatg gcccactacg tgaaccatca cccaaatcaa   5530
gttttttggg gtcgaggtgc cgtaaagcac taaatcggaa ccctaaaggg agcccccgat   5590
ttagagcttg acggggaaag ccggcgaacg tggcgagaaa ggaagggaag aaagcgaaag   5650
gagcgggcgc tagggcgctg gcaagtgtag cggtcacgct gcgcgtaacc accacacccg   5710
ccgcgcttaa tgcgccgcta cagggcgcgt aaaaggatct aggtgaagat cctttttgat   5770
aatctcatga ccaaaatccc ttaacgtgag ttttcgttcc actgagcgtc agaccccgta   5830
gaaaagatca aaggatcttc ttgagatcct ttttttctgc gcgtaatctg ctgcttgcaa   5890
acaaaaaaac caccgctacc agcggtggtt tgtttgccgg atcaagagct accaactctt   5950
tttccgaagg taactggctt cagcagagcg cagataccaa atactgtcct tctagtgtag   6010
ccgtagttag gccaccactt caagaactct gtagcaccgc ctacatacct cgctctgcta   6070
atcctgttac cagtggctgc tgccagtggc gataagtcgt gtcttaccgg gttggactca   6130
agacgatagt taccggataa ggcgcagcgg tcgggctgaa cggggggttc gtgcacacag   6190
cccagcttgg agcgaacgac ctacaccgaa ctgagatacc tacagcgtga gctatgagaa   6250
agcgccacgc ttcccgaagg gagaaaggcg gacaggtatc cggtaagcgg cagggtcgga   6310
acaggagagc gcacgaggga gcttccaggg ggaaacgcct ggtatcttta tagtcctgtc   6370
gggtttcgcc acctctgact tgagcgtcga tttttgtgat gctcgtcagg ggggcggagc   6430
ctatggaaaa acgccagcaa cgcggccttt ttacggttcc tggccttttg ctggcctttt   6490
gctcacatgt tctttcctgc gttatcccct gattctgtgg ataaccgtat taccgccttt   6550
gagtgagctg ataccgctcg ccgcagccga acgaccgagc gcagcgagtc agtgagcgag   6610
gaagcggaag agcgcctgat gcggtatttt ctccttacgc atctgtgcgg tatttcacac   6670
cgcatatatg gtgcactctc agtacaatct gctctgatgc cgcatagtta agccagtata   6730
cactccgcta tcgctacgtg actgggtcat ggctgcgccc cgacacccgc caacacccgc   6790
tgacgcgccc tgacgggctt gtctgctccc ggcatccgct tacagacaag ctgtgaccgt   6850
ctccgggagc tgcatgtgtc agaggttttc accgtcatca ccgaaacgcg cgaggcagct   6910
gcggtaaagc tcatcagcgt ggtcgtgcag cgattcacag atgtctgcct gttcatccgc   6970
gtccagctcg ttgagtttct ccagaagcgt taatgtctgg cttctgataa agcgggccat   7030
gttaagggcg gttttttcct gtttggtcac tgatgcctcc gtgtaagggg gatttctgtt   7090
catgggggta atgataccga tgaaacgaga gaggatgctc acgatacggg ttactgatga   7150
tgaacatgcc cggttactgg aacgttgtga gggtaaacaa ctggcggtat ggatgcggcg   7210
```

-continued

```
ggaccagaga aaaatcactc agggtcaatg ccagcgcttc gttaatacag atgtaggtgt   7270

tccacagggt agccagcagc atcctgcgat gcagatccgg aacataatgg tgcagggcgc   7330

tgacttccgc gtttccagac tttacgaaac acggaaaccg aagaccattc atgttgttgc   7390

tcaggtcgca gacgttttgc agcagcagtc gcttcacgtt cgctcgcgta tcggtgattc   7450

attctgctaa ccagtaaggc aaccccgcca gcctagccgg gtcctcaacg acaggagcac   7510

gatcatgcgc acccgtggcc aggacccaac gctgcccgaa att                     7553
```

<210> SEQ ID NO 8
<211> LENGTH: 701
<212> TYPE: PRT
<213> ORGANISM: Toxoplasma gondii
<220> FEATURE:
<223> OTHER INFORMATION: pMBP-p2X-ToxoP30 (52-336aa)

<400> SEQUENCE: 8

```
Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300
```

-continued

```
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Ile Glu Gly Arg Ile Ser Glu Phe
                405                 410                 415

Leu Val Ala Asn Gln Val Val Thr Cys Pro Asp Lys Lys Ser Thr Ala
            420                 425                 430

Ala Val Ile Leu Thr Pro Thr Glu Asn His Phe Thr Leu Lys Cys Pro
        435                 440                 445

Lys Thr Ala Leu Thr Glu Pro Pro Thr Leu Ala Tyr Ser Pro Asn Arg
    450                 455                 460

Gln Ile Cys Pro Ala Gly Thr Thr Ser Ser Cys Thr Ser Lys Ala Val
465                 470                 475                 480

Thr Leu Ser Ser Leu Ile Pro Glu Ala Glu Asp Ser Trp Trp Thr Gly
                485                 490                 495

Asp Ser Ala Ser Leu Asp Thr Ala Gly Ile Lys Leu Thr Val Pro Ile
            500                 505                 510

Glu Lys Phe Pro Val Thr Thr Gln Thr Phe Val Val Gly Cys Ile Lys
        515                 520                 525

Gly Asp Asp Ala Gln Ser Cys Met Val Thr Val Thr Val Gln Ala Arg
    530                 535                 540

Ala Ser Ser Val Val Asn Asn Val Ala Arg Cys Ser Tyr Gly Ala Asp
545                 550                 555                 560

Ser Thr Leu Gly Pro Val Lys Leu Ser Ala Glu Gly Pro Thr Thr Met
                565                 570                 575

Thr Leu Val Cys Gly Lys Asp Gly Val Lys Val Pro Gln Asp Asn Asn
            580                 585                 590

Gln Tyr Cys Ser Gly Thr Thr Leu Thr Gly Cys Asn Glu Lys Ser Phe
        595                 600                 605

Lys Asp Ile Leu Pro Lys Leu Thr Glu Asn Pro Trp Gln Gly Asn Ala
    610                 615                 620

Ser Ser Asp Lys Gly Ala Thr Leu Thr Ile Lys Lys Glu Ala Phe Pro
625                 630                 635                 640

Ala Glu Ser Lys Ser Val Ile Ile Gly Cys Thr Gly Gly Ser Pro Glu
                645                 650                 655

Lys His His Cys Thr Val Lys Leu Glu Phe Ala Gly Ala Ala Gly Ser
            660                 665                 670

Ala Lys Ser Ala Ala Gly Thr Ala Ser His Val Ser Ile Phe Ala Met
        675                 680                 685

Val Ile Gly Leu Ile Gly Ser Ile Ala Ala Cys Val Ala
    690                 695                 700
```

<210> SEQ ID NO 9
<211> LENGTH: 39
<212> TYPE: DNA

-continued

<213> ORGANISM: Artificial Sequence
<220> FEATURE:
<223> OTHER INFORMATION: Antisense Primer

<400> SEQUENCE: 9
caggtcaagc tttcacacca tggcaaaaat ggaaacgtg 39

<210> SEQ ID NO 10
<211> LENGTH: 7442
<212> TYPE: DNA
<213> ORGANISM: Toxoplasma gondii
<220> FEATURE:
<221> NAME/KEY: CDS
<222> LOCATION: (1528)...(3519)
<223> OTHER INFORMATION: pMBP-c2X-ToxoP30del1C (52-324aa)

<400> SEQUENCE: 10

```
ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
```

-continued

```
Lys Lys Phe Glu Lys Asp Thr Gly Ile Lys Val Thr Val Glu His Pro
                30                  35                  40

gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
            45                  50                  55

cct gac att atc ttc tgg gca cac gac cgc ttt ggt ggc tac gct caa      1746
Pro Asp Ile Ile Phe Trp Ala His Asp Arg Phe Gly Gly Tyr Ala Gln
        60                  65                  70

tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
    75                  80                  85

ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345
```

-continued

```
act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565

tgt tcc ggg acg acg ctg act ggt tgc aac gag aaa tcg ttc aaa gat      3282
Cys Ser Gly Thr Thr Leu Thr Gly Cys Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga tgc aca ggg gga tcg cct gag aag cat      3426
Ser Lys Ser Val Ile Ile Gly Cys Thr Gly Gly Ser Pro Glu Lys His
        620                 625                 630

cac tgt acc gtg aaa ctg gag ttt gcc ggg gct gca ggg tca gca aaa      3474
His Cys Thr Val Lys Leu Glu Phe Ala Gly Ala Ala Gly Ser Ala Lys
    635                 640                 645

tcg gct gcg gga aca gcc agt cac gtt tcc att ttt gcc atg gtg          3519
Ser Ala Ala Gly Thr Ala Ser His Val Ser Ile Phe Ala Met Val
650                 655                 660
```

-continued tgaaagcttg gcactggccg tcgttttaca acgtcgtgac tgggaaaacc ctggcgttac 3579 ccaacttaat cgccttgcag cacatccccc tttcgccagc tggcgtaata gcgaagaggc 3639 ccgcaccgat cgcccttccc aacagttgcg cagcctgaat ggcgaatggc agcttggctg 3699 ttttggcgga tgagataaga ttttcagcct gatacagatt aaatcagaac gcagaagcgg 3759 tctgataaaa cagaatttgc ctggcggcag tagcgcggtg gtcccacctg accccatgcc 3819 gaactcagaa gtgaaacgcc gtagcgccga tggtagtgtg gggtctcccc atgcgagagt 3879 agggaactgc caggcatcaa ataaaacgaa aggctcagtc gaaagactgg gcctttcgtt 3939 ttatctgttg tttgtcggtg aacgctctcc tgagtaggac aaatccgccg ggagcggatt 3999 tgaacgttgc gaagcaacgg cccggagggt ggcgggcagg acgcccgcca taaactgcca 4059 ggcatcaaat taagcagaag gccatcctga cggatggcct ttttgcgttt ctacaaactc 4119 tttttgttta tttttctaaa tacattcaaa tatgtatccg ctcatgagac aataaccctg 4179 ataaatgctt caataatatt gaaaaaggaa gagtatgagt attcaacatt tccgtgtcgc 4239 ccttattccc ttttttgcgg cattttgcct tcctgttttt gctcacccag aaacgctggt 4299 gaaagtaaaa gatgctgaag atcagttggg tgcacgagtg ggttacatcg aactggatct 4359 caacagcggt aagatccttg agagttttcg ccccgaagaa cgttctccaa tgatgagcac 4419 ttttaaagtt ctgctatgtg gcgcggtatt atcccgtgtt gacgccgggc aagagcaact 4479 cggtcgccgc atacactatt ctcagaatga cttggttgag tactcaccag tcacagaaaa 4539 gcatcttacg gatggcatga cagtaagaga attatgcagt gctgccataa ccatgagtga 4599 taacactgcg gccaacttac ttctgacaac gatcggagga ccgaaggagc taaccgcttt 4659 tttgcacaac atgggggatc atgtaactcg ccttgatcgt tgggaaccgg agctgaatga 4719 agccatacca aacgacgagc gtgacaccac gatgcctgta gcaatggcaa caacgttgcg 4779 caaactatta actggcgaac tacttactct agcttcccgg caacaattaa tagactggat 4839 ggaggcggat aaagttgcag gaccacttct gcgctcggcc cttccggctg gctggtttat 4899 tgctgataaa tctggagccg gtgagcgtgg gtctcgcggt atcattgcag cactggggcc 4959 agatggtaag ccctcccgta tcgtagttat ctacacgacg gggagtcagg caactatgga 5019 tgaacgaaat agacagatcg ctgagatagg tgcctcactg attaagcatt ggtaactgtc 5079 agaccaagtt tactcatata tactttagat tgatttaccc cggttgataa tcagaaaagc 5139 cccaaaaaca ggaagattgt ataagcaaat atttaaattg taaacgttaa tattttgtta 5199 aaattcgcgt taaatttttg ttaaatcagc tcatttttta accaataggc cgaaatcggc 5259 aaaatccctt ataaatcaaa agaatagacc gagatagggt tgagtgttgt tccagtttgg 5319 aacaagagtc cactattaaa gaacgtggac tccaacgtca aagggcgaaa aaccgtctat 5379 cagggcgatg gcccactacg tgaaccatca cccaaatcaa gttttttggg gtcgaggtgc 5439 cgtaaagcac taaatcggaa ccctaaaggg agcccccgat ttagagcttg acggggaaag 5499 ccggcgaacg tggcgagaaa ggaagggaag aaagcgaaag gagcgggcgc tagggcgctg 5559 gcaagtgtag cggtcacgct gcgcgtaacc accacacccg ccgcgcttaa tgcgccgcta 5619 cagggcgcgt aaaaggatct aggtgaagat cctttttgat aatctcatga ccaaaatccc 5679 ttaacgtgag ttttcgttcc actgagcgtc agaccccgta gaaaagatca aaggatcttc 5739 ttgagatcct ttttttctgc gcgtaatctg ctgcttgcaa acaaaaaaac caccgctacc 5799 agcggtggtt tgtttgccgg atcaagagct accaactctt tttccgaagg taactggctt 5859

-continued cagcagagcg cagataccaa atactgtcct tctagtgtag ccgtagttag gccaccactt 5919 caagaactct gtagcaccgc ctacatacct cgctctgcta atcctgttac cagtggctgc 5979 tgccagtggc gataagtcgt gtcttaccgg gttggactca agacgatagt taccggataa 6039 ggcgcagcgg tcgggctgaa cggggggttc gtgcacacag cccagcttgg agcgaacgac 6099 ctacaccgaa ctgagatacc tacagcgtga gctatgagaa agcgccacgc ttcccgaagg 6159 gagaaaggcg gacaggtatc cggtaagcgg cagggtcgga acaggagagc gcacgaggga 6219 gcttccaggg ggaaacgcct ggtatcttta tagtcctgtc gggtttcgcc acctctgact 6279 tgagcgtcga tttttgtgat gctcgtcagg ggggcggagc ctatggaaaa acgccagcaa 6339 cgcggccttt ttacggttcc tggccttttg ctggcctttt gctcacatgt tctttcctgc 6399 gttatcccct gattctgtgg ataaccgtat taccgccttt gagtgagctg ataccgctcg 6459 ccgcagccga acgaccgagc gcagcgagtc agtgagcgag gaagcggaag agcgcctgat 6519 gcggtatttt ctccttacgc atctgtgcgg tatttcacac cgcatatatg gtgcactctc 6579 agtacaatct gctctgatgc cgcatagtta agccagtata cactccgcta tcgctacgtg 6639 actgggtcat ggctgcgccc cgacacccgc caacacccgc tgacgcgccc tgacgggctt 6699 gtctgctccc ggcatccgct tacagacaag ctgtgaccgt ctccgggagc tgcatgtgtc 6759 agaggttttc accgtcatca ccgaaacgcg cgaggcagct gcggtaaagc tcatcagcgt 6819 ggtcgtgcag cgattcacag atgtctgcct gttcatccgc gtccagctcg ttgagtttct 6879 ccagaagcgt taatgtctgg cttctgataa agcgggccat gttaagggcg gtttttttcct 6939 gtttggtcac tgatgcctcc gtgtaagggg gatttctgtt catgggggta atgataccga 6999 tgaaacgaga gaggatgctc acgatacggg ttactgatga tgaacatgcc cggttactgg 7059 aacgttgtga gggtaaacaa ctggcggtat ggatgcggcg ggaccagaga aaaatcactc 7119 agggtcaatg ccagcgcttc gttaatacag atgtaggtgt tccacagggt agccagcagc 7179 atcctgcgat gcagatccgg aacataatgg tgcagggcgc tgacttccgc gtttccagac 7239 tttacgaaac acggaaaccg aagaccattc atgttgttgc tcaggtcgca gacgttttgc 7299 agcagcagtc gcttcacgtt cgctcgcgta tcggtgattc attctgctaa ccagtaaggc 7359 aaccccgcca gcctagccgg gtcctcaacg acaggagcac gatcatgcgc acccgtggcc 7419 aggacccaac gctgcccgaa att 7442

<210> SEQ ID NO 11
<211> LENGTH: 664
<212> TYPE: PRT
<213> ORGANISM: Toxoplasma gondii
<220> FEATURE:
<223> OTHER INFORMATION: pMBP-c2X-ToxoP30del1C (52-324aa)

<400> SEQUENCE: 11

Met Lys Ile Glu Glu Gly Lys Leu Val Ile Trp Ile Asn Gly Asp Lys
1 5 10 15

Gly Tyr Asn Gly Leu Ala Glu Val Gly Lys Lys Phe Glu Lys Asp Thr
20 25 30

Gly Ile Lys Val Thr Val Glu His Pro Asp Lys Leu Glu Glu Lys Phe
35 40 45

Pro Gln Val Ala Ala Thr Gly Asp Gly Pro Asp Ile Ile Phe Trp Ala
50 55 60

His Asp Arg Phe Gly Gly Tyr Ala Gln Ser Gly Leu Leu Ala Glu Ile
65 70 75 80

-continued

```
Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
```

-continued

```
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala Ala Gly Thr Ala Ser
                645                 650                 655

His Val Ser Ile Phe Ala Met Val
            660


<210> SEQ ID NO 12
<211> LENGTH: 819
<212> TYPE: DNA
<213> ORGANISM: Toxoplasma gondii
<220> FEATURE:
<221> NAME/KEY: CDS
<222> LOCATION: (1)...(819)
<223> OTHER INFORMATION: ToxoP30del1C (52-324aa)

<400> SEQUENCE: 12

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
        35                  40                  45

caa atc tgc cca gcg ggt act aca agt agc tgt aca tca aag gct gta      192
Gln Ile Cys Pro Ala Gly Thr Thr Ser Ser Cys Thr Ser Lys Ala Val
    50                  55                  60

aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
65                  70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
    130                 135                 140
```

-continued

```
agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160

acc ctc gtg tgc ggg aaa gat gga gtc aaa gtt cct caa gac aac aat      528
Thr Leu Val Cys Gly Lys Asp Gly Val Lys Val Pro Gln Asp Asn Asn
                165                 170                 175

cag tac tgt tcc ggg acg acg ctg act ggt tgc aac gag aaa tcg ttc      576
Gln Tyr Cys Ser Gly Thr Thr Leu Thr Gly Cys Asn Glu Lys Ser Phe
            180                 185                 190

aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220

gcc gag tca aaa agc gtc att att gga tgc aca ggg gga tcg cct gag      720
Ala Glu Ser Lys Ser Val Ile Ile Gly Cys Thr Gly Gly Ser Pro Glu
225                 230                 235                 240

aag cat cac tgt acc gtg aaa ctg gag ttt gcc ggg gct gca ggg tca      768
Lys His His Cys Thr Val Lys Leu Glu Phe Ala Gly Ala Ala Gly Ser
                245                 250                 255

gca aaa tcg gct gcg gga aca gcc agt cac gtt tcc att ttt gcc atg      816
Ala Lys Ser Ala Ala Gly Thr Ala Ser His Val Ser Ile Phe Ala Met
            260                 265                 270

gtg                                                                  819
Val


<210> SEQ ID NO 13
<211> LENGTH: 273
<212> TYPE: PRT
<213> ORGANISM: Toxoplasma gondii
<220> FEATURE:
<223> OTHER INFORMATION: ToxoP30del1C (52-324aa)

<400> SEQUENCE: 13

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175
```

-continued

```
Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu Phe Ala Gly Ala Ala Gly Ser
                245                 250                 255

Ala Lys Ser Ala Ala Gly Thr Ala Ser His Val Ser Ile Phe Ala Met
            260                 265                 270

Val


<210> SEQ ID NO 14
<211> LENGTH: 41
<212> TYPE: DNA
<213> ORGANISM: Artificial Sequence
<220> FEATURE:
<223> OTHER INFORMATION: Antisense Primer

<400> SEQUENCE: 14

caggtcaagc tttcaagccg attttgctga ccctgcagcc c                          41


<210> SEQ ID NO 15
<211> LENGTH: 7403
<212> TYPE: DNA
<213> ORGANISM: Toxoplasma gondii
<220> FEATURE:
<221> NAME/KEY: CDS
<222> LOCATION: (1528)...(3480)
<223> OTHER INFORMATION: pMBP-c2X-ToxoP30del2 (52-311aa)

<400> SEQUENCE: 15

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080
```

-continued

```
cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
            45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
        60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
    75                  80                  85

ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa     2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc     2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg     2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg     2274
Ser Asn Ile Asp Thr Ser Lys Val Asn Tyr Gly Val Thr Val Leu Pro
    235                 240                 245
```

-continued

```
acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565
```

-continued

```
tgt tcc ggg acg acg ctg act ggt tgc aac gag aaa tcg ttc aaa gat     3282
Cys Ser Gly Thr Thr Leu Thr Gly Cys Asn Glu Lys Ser Phe Lys Asp
570                 575                 580                 585

att ttg cca aaa tta act gag aac ccg tgg cag ggt aac gct tcg agt     3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag     3378
Asp Lys Gly Ala Thr Leu Thr Ile Lys Lys Glu Ala Phe Pro Ala Glu
            605                 610                 615

tca aaa agc gtc att att gga tgc aca ggg gga tcg cct gag aag cat     3426
Ser Lys Ser Val Ile Ile Gly Cys Thr Gly Gly Ser Pro Glu Lys His
        620                 625                 630

cac tgt acc gtg aaa ctg gag ttt gcc ggg gct gca ggg tca gca aaa     3474
His Cys Thr Val Lys Leu Glu Phe Ala Gly Ala Ala Gly Ser Ala Lys
    635                 640                 645

tcg gct tgaaagcttg gcactggccg tcgttttaca acgtcgtgac tgggaaaacc     3530
Ser Ala
650

ctggcgttac ccaacttaat cgccttgcag cacatccccc tttcgccagc tggcgtaata   3590

gcgaagaggc ccgcaccgat cgcccttccc aacagttgcg cagcctgaat ggcgaatggc   3650

agcttggctg ttttggcgga tgagataaga ttttcagcct gatacagatt aaatcagaac   3710

gcagaagcgg tctgataaaa cagaatttgc ctggcggcag tagcgcggtg gtcccacctg   3770

accccatgcc gaactcagaa gtgaaacgcc gtagcgccga tggtagtgtg gggtctcccc   3830

atgcgagagt agggaactgc caggcatcaa ataaaacgaa aggctcagtc gaaagactgg   3890

gcctttcgtt ttatctgttg tttgtcggtg aacgctctcc tgagtaggac aaatccgccg   3950

ggagcggatt tgaacgttgc gaagcaacgg cccggagggt ggcgggcagg acgcccgcca   4010

taaactgcca ggcatcaaat taagcagaag gccatcctga cggatggcct ttttgcgttt   4070

ctacaaactc tttttgttta tttttctaaa tacattcaaa tatgtatccg ctcatgagac   4130

aataaccctg ataaatgctt caataatatt gaaaaaggaa gagtatgagt attcaacatt   4190

tccgtgtcgc ccttattccc ttttttgcgg cattttgcct tcctgttttt gctcacccag   4250

aaacgctggt gaaagtaaaa gatgctgaag atcagttggg tgcacgagtg ggttacatcg   4310

aactggatct caacagcggt aagatccttg agagttttcg ccccgaagaa cgttctccaa   4370

tgatgagcac ttttaaagtt ctgctatgtg gcgcggtatt atcccgtgtt gacgccgggc   4430

aagagcaact cggtcgccgc atacactatt ctcagaatga cttggttgag tactcaccag   4490

tcacagaaaa gcatcttacg gatggcatga cagtaagaga attatgcagt gctgccataa   4550

ccatgagtga taacactgcg gccaacttac ttctgacaac gatcggagga ccgaaggagc   4610

taaccgcttt tttgcacaac atgggggatc atgtaactcg ccttgatcgt tgggaaccgg   4670

agctgaatga agccatacca aacgacgagc gtgacaccac gatgcctgta gcaatggcaa   4730

caacgttgcg caaactatta actggcgaac tacttactct agcttcccgg caacaattaa   4790

tagactggat ggaggcggat aaagttgcag gaccacttct gcgctcggcc cttccggctg   4850

gctggtttat tgctgataaa tctggagccg gtgagcgtgg gtctcgcggt atcattgcag   4910

cactggggcc agatggtaag ccctcccgta tcgtagttat ctacacgacg gggagtcagg   4970

caactatgga tgaacgaaat agacagatcg ctgagatagg tgcctcactg attaagcatt   5030

ggtaactgtc agaccaagtt tactcatata tactttagat tgatttaccc cggttgataa   5090

tcagaaaagc cccaaaaaca ggaagattgt ataagcaaat atttaaattg taaacgttaa   5150
```

-continued

```
tattttgtta aaattcgcgt taaatttttg ttaaatcagc tcatttttta accaataggc   5210

cgaaatcggc aaaatccctt ataaatcaaa agaatagacc gagatagggt tgagtgttgt   5270

tccagtttgg aacaagagtc cactattaaa gaacgtggac tccaacgtca aagggcgaaa   5330

aaccgtctat cagggcgatg gcccactacg tgaaccatca cccaaatcaa gtttttgggg   5390

gtcgaggtgc cgtaaagcac taaatcggaa ccctaaaggg agcccccgat ttagagcttg   5450

acggggaaag ccggcgaacg tggcgagaaa ggaagggaag aaagcgaaag gagcgggcgc   5510

tagggcgctg gcaagtgtag cggtcacgct gcgcgtaacc accacacccg ccgcgcttaa   5570

tgcgccgcta cagggcgcgt aaaaggatct aggtgaagat cctttttgat aatctcatga   5630

ccaaaatccc ttaacgtgag ttttcgttcc actgagcgtc agaccccgta gaaaagatca   5690

aaggatcttc ttgagatcct ttttttctgc gcgtaatctg ctgcttgcaa acaaaaaaac   5750

caccgctacc agcggtggtt tgtttgccgg atcaagagct accaactctt tttccgaagg   5810

taactggctt cagcagagcg cagataccaa atactgtcct tctagtgtag ccgtagttag   5870

gccaccactt caagaactct gtagcaccgc ctacatacct cgctctgcta atcctgttac   5930

cagtggctgc tgccagtggc gataagtcgt gtcttaccgg gttggactca agacgatagt   5990

taccggataa ggcgcagcgg tcgggctgaa cggggggttc gtgcacacag cccagcttgg   6050

agcgaacgac ctacaccgaa ctgagatacc tacagcgtga gctatgagaa agcgccacgc   6110

ttcccgaagg gagaaaggcg gacaggtatc cggtaagcgg cagggtcgga acaggagagc   6170

gcacgaggga gcttccaggg ggaaacgcct ggtatcttta tagtcctgtc gggtttcgcc   6230

acctctgact tgagcgtcga tttttgtgat gctcgtcagg ggggcggagc ctatggaaaa   6290

acgccagcaa cgcggccttt ttacggttcc tggccttttg ctggcctttt gctcacatgt   6350

tctttcctgc gttatcccct gattctgtgg ataaccgtat taccgccttt gagtgagctg   6410

ataccgctcg ccgcagccga acgaccgagc gcagcgagtc agtgagcgag gaagcggaag   6470

agcgcctgat gcggtatttt ctccttacgc atctgtgcgg tatttcacac cgcatatatg   6530

gtgcactctc agtacaatct gctctgatgc cgcatagtta agccagtata cactccgcta   6590

tcgctacgtg actgggtcat ggctgcgccc cgacacccgc caacacccgc tgacgcgccc   6650

tgacgggctt gtctgctccc ggcatccgct tacagacaag ctgtgaccgt ctccgggagc   6710

tgcatgtgtc agaggttttc accgtcatca ccgaaacgcg cgaggcagct gcggtaaagc   6770

tcatcagcgt ggtcgtgcag cgattcacag atgtctgcct gttcatccgc gtccagctcg   6830

ttgagtttct ccagaagcgt taatgtctgg cttctgataa agcgggccat gttaagggcg   6890

gtttttttcct gtttggtcac tgatgcctcc gtgtaagggg gatttctgtt catgggggta   6950

atgataccga tgaaacgaga gaggatgctc acgatacggg ttactgatga tgaacatgcc   7010

cggttactgg aacgttgtga gggtaaacaa ctggcggtat ggatgcggcg ggaccagaga   7070

aaaatcactc agggtcaatg ccagcgcttc gttaatacag atgtaggtgt tccacagggt   7130

agccagcagc atcctgcgat gcagatccgg aacataatgg tgcagggcgc tgacttccgc   7190

gtttccagac tttacgaaac acggaaaccg aagaccattc atgttgttgc tcaggtcgca   7250

gacgttttgc agcagcagtc gcttcacgtt cgctcgcgta tcggtgattc attctgctaa   7310

ccagtaaggc aaccccgcca gcctagccgg gtcctcaacg acaggagcac gatcatgcgc   7370

acccgtggcc aggacccaac gctgcccgaa att                                7403
```

<210> SEQ ID NO 16
<211> LENGTH: 651

-continued

<212> TYPE: PRT
<213> ORGANISM: Toxoplasma gondii
<220> FEATURE:
<223> OTHER INFORMATION: pMBP-c2X-ToxoP30del2 (52-311aa)

<400> SEQUENCE: 16

Met Lys Ile Glu Glu Gly Lys Leu Val Ile Trp Ile Asn Gly Asp Lys
1 5 10 15

Gly Tyr Asn Gly Leu Ala Glu Val Gly Lys Lys Phe Glu Lys Asp Thr
20 25 30

Gly Ile Lys Val Thr Val Glu His Pro Asp Lys Leu Glu Glu Lys Phe
35 40 45

Pro Gln Val Ala Ala Thr Gly Asp Gly Pro Asp Ile Ile Phe Trp Ala
50 55 60

His Asp Arg Phe Gly Gly Tyr Ala Gln Ser Gly Leu Leu Ala Glu Ile
65 70 75 80

Thr Pro Asp Lys Ala Phe Gln Asp Lys Leu Tyr Pro Phe Thr Trp Asp
85 90 95

Ala Val Arg Tyr Asn Gly Lys Leu Ile Ala Tyr Pro Ile Ala Val Glu
100 105 110

Ala Leu Ser Leu Ile Tyr Asn Lys Asp Leu Leu Pro Asn Pro Pro Lys
115 120 125

Thr Trp Glu Glu Ile Pro Ala Leu Asp Lys Glu Leu Lys Ala Lys Gly
130 135 140

Lys Ser Ala Leu Met Phe Asn Leu Gln Glu Pro Tyr Phe Thr Trp Pro
145 150 155 160

Leu Ile Ala Ala Asp Gly Gly Tyr Ala Phe Lys Tyr Glu Asn Gly Lys
165 170 175

Tyr Asp Ile Lys Asp Val Gly Val Asp Asn Ala Gly Ala Lys Ala Gly
180 185 190

Leu Thr Phe Leu Val Asp Leu Ile Lys Asn Lys His Met Asn Ala Asp
195 200 205

Thr Asp Tyr Ser Ile Ala Glu Ala Ala Phe Asn Lys Gly Glu Thr Ala
210 215 220

Met Thr Ile Asn Gly Pro Trp Ala Trp Ser Asn Ile Asp Thr Ser Lys
225 230 235 240

Val Asn Tyr Gly Val Thr Val Leu Pro Thr Phe Lys Gly Gln Pro Ser
245 250 255

Lys Pro Phe Val Gly Val Leu Ser Ala Gly Ile Asn Ala Ala Ser Pro
260 265 270

Asn Lys Glu Leu Ala Lys Glu Phe Leu Glu Asn Tyr Leu Leu Thr Asp
275 280 285

Glu Gly Leu Glu Ala Val Asn Lys Asp Lys Pro Leu Gly Ala Val Ala
290 295 300

Leu Lys Ser Tyr Glu Glu Glu Leu Ala Lys Asp Pro Arg Ile Ala Ala
305 310 315 320

Thr Met Glu Asn Ala Gln Lys Gly Glu Ile Met Pro Asn Ile Pro Gln
325 330 335

Met Ser Ala Phe Trp Tyr Ala Val Arg Thr Ala Val Ile Asn Ala Ala
340 345 350

Ser Gly Arg Gln Thr Val Asp Glu Ala Leu Lys Asp Ala Gln Thr Asn
355 360 365

Ser Ser Ser Asn Asn Asn Asn Asn Asn Asn Asn Asn Asn Leu Gly Ile
370 375 380

-continued

```
Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala
                645                 650


<210> SEQ ID NO 17
<211> LENGTH: 780
<212> TYPE: DNA
<213> ORGANISM: Toxoplasma gondii
<220> FEATURE:
<221> NAME/KEY: CDS
<222> LOCATION: (1)...(780)
<223> OTHER INFORMATION: ToxoP30del2 (52-311aa)

<400> SEQUENCE: 17

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
        35                  40                  45

caa atc tgc cca gcg ggt act aca agt agc tgt aca tca aag gct gta      192
Gln Ile Cys Pro Ala Gly Thr Thr Ser Ser Cys Thr Ser Lys Ala Val
    50                  55                  60
```

-continued

```
aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                 85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
    130                 135                 140

agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160

acc ctc gtg tgc ggg aaa gat gga gtc aaa gtt cct caa gac aac aat      528
Thr Leu Val Cys Gly Lys Asp Gly Val Lys Val Pro Gln Asp Asn Asn
                165                 170                 175

cag tac tgt tcc ggg acg acg ctg act ggt tgc aac gag aaa tcg ttc      576
Gln Tyr Cys Ser Gly Thr Thr Leu Thr Gly Cys Asn Glu Lys Ser Phe
            180                 185                 190

aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220

gcc gag tca aaa agc gtc att att gga tgc aca ggg gga tcg cct gag      720
Ala Glu Ser Lys Ser Val Ile Ile Gly Cys Thr Gly Gly Ser Pro Glu
225                 230                 235                 240

aag cat cac tgt acc gtg aaa ctg gag ttt gcc ggg gct gca ggg tca      768
Lys His His Cys Thr Val Lys Leu Glu Phe Ala Gly Ala Ala Gly Ser
                245                 250                 255

gca aaa tcg gct                                                      780
Ala Lys Ser Ala
            260


<210> SEQ ID NO 18
<211> LENGTH: 260
<212> TYPE: PRT
<213> ORGANISM: Toxoplasma gondii
<220> FEATURE:
<223> OTHER INFORMATION: ToxoP30del2 (52-311aa)

<400> SEQUENCE: 18

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95
```

-continued

```
Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu Phe Ala Gly Ala Ala Gly Ser
                245                 250                 255

Ala Lys Ser Ala
            260


<210> SEQ ID NO 19
<211> LENGTH: 36
<212> TYPE: DNA
<213> ORGANISM: Artificial Sequence
<220> FEATURE:
<223> OTHER INFORMATION: Antisense Primer

<400> SEQUENCE: 19

caggtcaagc tttcactcca gtttcacggt acagtg                              36


<210> SEQ ID NO 20
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-Toxo30del3C (52-300aa)

<400> SEQUENCE: 20

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660
```

-continued

```
cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
     75                  80                  85

ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa     2130
Asn Ala Gly Ala Lys Ala Gly Leu Thr Phe Leu Val Asp Leu Ile Lys
```

-continued

```
            190                 195                 200

aac aaa cac atg aat gca gac acc gat tac tcc atc gca gaa gct gcc     2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg     2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg     2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca     2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc     2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac     2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg     2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa     2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt     2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc     2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac     2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt     2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc     2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca     2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc     2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg     2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct     2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag     2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac     3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca     3090
```

-continued

```
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act     3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc     3186
Leu Gly Pro Val Lys Leu Ser Ala Glu Gly Pro Thr Thr Met Thr Leu
        540                 545                 550

gtg tgc ggg aaa gat gga gtc aaa gtt cct caa gac aac aat cag tac     3234
Val Cys Gly Lys Asp Gly Val Lys Val Pro Gln Asp Asn Asn Gln Tyr
    555                 560                 565

tgt tcc ggg acg acg ctg act ggt tgc aac gag aaa tcg ttc aaa gat     3282
Cys Ser Gly Thr Thr Leu Thr Gly Cys Asn Glu Lys Ser Phe Lys Asp
570                 575                 580                 585

att ttg cca aaa tta act gag aac ccg tgg cag ggt aac gct tcg agt     3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag     3378
Asp Lys Gly Ala Thr Leu Thr Ile Lys Lys Glu Ala Phe Pro Ala Glu
            605                 610                 615

tca aaa agc gtc att att gga tgc aca ggg gga tcg cct gag aag cat     3426
Ser Lys Ser Val Ile Ile Gly Cys Thr Gly Gly Ser Pro Glu Lys His
        620                 625                 630

cac tgt acc gtg aaa ctg gag tgaaagcttg gcactggccg tcgttttaca        3477
His Cys Thr Val Lys Leu Glu
    635                 640

acgtcgtgac tgggaaaacc ctggcgttac ccaacttaat cgccttgcag cacatccccc   3537

tttcgccagc tggcgtaata gcgaagaggc ccgcaccgat cgcccttccc aacagttgcg   3597

cagcctgaat ggcgaatggc agcttggctg ttttggcgga tgagataaga ttttcagcct   3657

gatacagatt aaatcagaac gcagaagcgg tctgataaaa cagaatttgc ctggcggcag   3717

tagcgcggtg gtcccacctg accccatgcc gaactcagaa gtgaaacgcc gtagcgccga   3777

tggtagtgtg gggtctcccc atgcgagagt agggaactgc caggcatcaa ataaaacgaa   3837

aggctcagtc gaaagactgg gcctttcgtt ttatctgttg tttgtcggtg aacgctctcc   3897

tgagtaggac aaatccgccg ggagcggatt tgaacgttgc gaagcaacgg cccggagggt   3957

ggcgggcagg acgcccgcca taaactgcca ggcatcaaat taagcagaag gccatcctga   4017

cggatggcct ttttgcgttt ctacaaactc tttttgttta tttttctaaa tacattcaaa   4077

tatgtatccg ctcatgagac aataaccctg ataaatgctt caataatatt gaaaaaggaa   4137

gagtatgagt attcaacatt tccgtgtcgc ccttattccc ttttttgcgg cattttgcct   4197

tcctgttttt gctcacccag aaacgctggt gaaagtaaaa gatgctgaag atcagttggg   4257

tgcacgagtg ggttacatcg aactggatct caacagcggt aagatccttg agagttttcg   4317

ccccgaagaa cgttctccaa tgatgagcac ttttaaagtt ctgctatgtg gcgcggtatt   4377

atcccgtgtt gacgccgggc aagagcaact cggtcgccgc atacactatt ctcagaatga   4437

cttggttgag tactcaccag tcacagaaaa gcatcttacg gatggcatga cagtaagaga   4497

attatgcagt gctgccataa ccatgagtga taacactgcg gccaacttac ttctgacaac   4557

gatcggagga ccgaaggagc taaccgcttt tttgcacaac atgggggatc atgtaactcg   4617

ccttgatcgt tgggaaccgg agctgaatga agccatacca aacgacgagc gtgacaccac   4677

gatgcctgta gcaatggcaa caacgttgcg caaactatta actggcgaac tacttactct   4737

agcttcccgg caacaattaa tagactggat ggaggcggat aaagttgcag gaccacttct   4797
```

-continued

```
gcgctcggcc cttccggctg gctggtttat tgctgataaa tctggagccg gtgagcgtgg   4857

gtctcgcggt atcattgcag cactggggcc agatggtaag ccctcccgta tcgtagttat   4917

ctacacgacg gggagtcagg caactatgga tgaacgaaat agacagatcg ctgagatagg   4977

tgcctcactg attaagcatt ggtaactgtc agaccaagtt tactcatata tactttagat   5037

tgatttaccc cggttgataa tcagaaaagc cccaaaaaca ggaagattgt ataagcaaat   5097

atttaaattg taaacgttaa tattttgtta aaattcgcgt taaatttttg ttaaatcagc   5157

tcatttttta accaataggc cgaaatcggc aaaatccctt ataaatcaaa agaatagacc   5217

gagatagggt tgagtgttgt tccagtttgg aacaagagtc cactattaaa gaacgtggac   5277

tccaacgtca aagggcgaaa aaccgtctat cagggcgatg gcccactacg tgaaccatca   5337

cccaaatcaa gttttttggg gtcgaggtgc cgtaaagcac taaatcggaa ccctaaaggg   5397

agcccccgat ttagagcttg acggggaaag ccggcgaacg tggcgagaaa ggaagggaag   5457

aaagcgaaag gagcgggcgc tagggcgctg gcaagtgtag cggtcacgct gcgcgtaacc   5517

accacacccg ccgcgcttaa tgcgccgcta cagggcgcgt aaaaggatct aggtgaagat   5577

cctttttgat aatctcatga ccaaaatccc ttaacgtgag ttttcgttcc actgagcgtc   5637

agaccccgta gaaaagatca aaggatcttc ttgagatcct ttttttctgc gcgtaatctg   5697

ctgcttgcaa acaaaaaaac caccgctacc agcggtggtt tgtttgccgg atcaagagct   5757

accaactctt tttccgaagg taactggctt cagcagagcg cagataccaa atactgtcct   5817

tctagtgtag ccgtagttag gccaccactt caagaactct gtagcaccgc ctacatacct   5877

cgctctgcta atcctgttac cagtggctgc tgccagtggc gataagtcgt gtcttaccgg   5937

gttggactca agacgatagt taccggataa ggcgcagcgg tcgggctgaa cggggggttc   5997

gtgcacacag cccagcttgg agcgaacgac ctacaccgaa ctgagatacc tacagcgtga   6057

gctatgagaa agcgccacgc ttcccgaagg gagaaaggcg gacaggtatc cggtaagcgg   6117

cagggtcgga acaggagagc gcacgaggga gcttccaggg ggaaacgcct ggtatcttta   6177

tagtcctgtc gggtttcgcc acctctgact tgagcgtcga tttttgtgat gctcgtcagg   6237

ggggcggagc ctatggaaaa acgccagcaa cgcggccttt ttacggttcc tggccttttg   6297

ctggcctttt gctcacatgt tctttcctgc gttatcccct gattctgtgg ataaccgtat   6357

taccgccttt gagtgagctg ataccgctcg ccgcagccga acgaccgagc gcagcgagtc   6417

agtgagcgag gaagcggaag agcgcctgat gcggtatttt ctccttacgc atctgtgcgg   6477

tatttcacac cgcatatatg gtgcactctc agtacaatct gctctgatgc cgcatagtta   6537

agccagtata cactccgcta tcgctacgtg actgggtcat ggctgcgccc cgacacccgc   6597

caacacccgc tgacgcgccc tgacgggctt gtctgctccc ggcatccgct tacagacaag   6657

ctgtgaccgt ctccgggagc tgcatgtgtc agaggttttc accgtcatca ccgaaacgcg   6717

cgaggcagct gcggtaaagc tcatcagcgt ggtcgtgcag cgattcacag atgtctgcct   6777

gttcatccgc gtccagctcg ttgagtttct ccagaagcgt taatgtctgg cttctgataa   6837

agcgggccat gttaagggcg gttttttcct gtttggtcac tgatgcctcc gtgtaagggg   6897

gatttctgtt catgggggta atgataccga tgaaacgaga gaggatgctc acgatacggg   6957

ttactgatga tgaacatgcc cggttactgg aacgttgtga gggtaaacaa ctggcggtat   7017

ggatgcggcg ggaccagaga aaaatcactc agggtcaatg ccagcgcttc gttaatacag   7077

atgtaggtgt tccacagggt agccagcagc atcctgcgat gcagatccgg aacataatgg   7137

tgcagggcgc tgacttccgc gtttccagac tttacgaaac acggaaaccg aagaccattc   7197
```

-continued

```
atgttgttgc tcaggtcgca gacgttttgc agcagcagtc gcttcacgtt cgctcgcgta   7257

tcggtgattc attctgctaa ccagtaaggc aaccccgcca gcctagccgg gtcctcaacg   7317

acaggagcac gatcatgcgc acccgtggcc aggacccaac gctgcccgaa att          7370


<210> SEQ ID NO 21
<211> LENGTH: 640
<212> TYPE: PRT
<213> ORGANISM: Toxoplasma gondii
<220> FEATURE:
<223> OTHER INFORMATION: pMBP-c2X-Toxo30del3C (52-300aa)

<400> SEQUENCE: 21

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

-continued

```
Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640
```

<210> SEQ ID NO 22
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: Toxo30del3C (52-300aa)

<400> SEQUENCE: 22

```
ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
```

-continued

```
Lys Thr Ala Leu Thr Glu Pro Pro Thr Leu Ala Tyr Ser Pro Asn Arg
        35                  40                  45

caa atc tgc cca gcg ggt act aca agt agc tgt aca tca aag gct gta       192
Gln Ile Cys Pro Ala Gly Thr Thr Ser Ser Cys Thr Ser Lys Ala Val
    50                  55                  60

aca ttg agc tcc ttg att cct gaa gca gaa gat agc tgg tgg acg ggg       240
Thr Leu Ser Ser Leu Ile Pro Glu Ala Glu Asp Ser Trp Trp Thr Gly
 65                  70                  75                  80

gat tct gct agt ctc gac acg gca ggc atc aaa ctc aca gtt cca atc       288
Asp Ser Ala Ser Leu Asp Thr Ala Gly Ile Lys Leu Thr Val Pro Ile
                 85                  90                  95

gag aag ttc ccc gtg aca acg cag acg ttt gtg gtc ggt tgc atc aag       336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga       384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac       432
Ala Ser Ser Val Val Asn Asn Val Ala Arg Cys Ser Tyr Gly Ala Asp
    130                 135                 140

agc act ctt ggt cct gtc aag ttg tct gcg gaa gga ccc act aca atg       480
Ser Thr Leu Gly Pro Val Lys Leu Ser Ala Glu Gly Pro Thr Thr Met
145                 150                 155                 160

acc ctc gtg tgc ggg aaa gat gga gtc aaa gtt cct caa gac aac aat       528
Thr Leu Val Cys Gly Lys Asp Gly Val Lys Val Pro Gln Asp Asn Asn
                165                 170                 175

cag tac tgt tcc ggg acg acg ctg act ggt tgc aac gag aaa tcg ttc       576
Gln Tyr Cys Ser Gly Thr Thr Leu Thr Gly Cys Asn Glu Lys Ser Phe
            180                 185                 190

aaa gat att ttg cca aaa tta act gag aac ccg tgg cag ggt aac gct       624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca       672
Ser Ser Asp Lys Gly Ala Thr Leu Thr Ile Lys Lys Glu Ala Phe Pro
    210                 215                 220

gcc gag tca aaa agc gtc att att gga tgc aca ggg gga tcg cct gag       720
Ala Glu Ser Lys Ser Val Ile Ile Gly Cys Thr Gly Gly Ser Pro Glu
225                 230                 235                 240

aag cat cac tgt acc gtg aaa ctg gag                                   747
Lys His His Cys Thr Val Lys Leu Glu
                245


<210> SEQ ID NO 23
<211> LENGTH: 249
<212> TYPE: PRT
<213> ORGANISM: Toxoplasma gondii
<220> FEATURE:
<223> OTHER INFORMATION: Toxo30del3C (52-300aa)

<400> SEQUENCE: 23

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80
```

-continued

```
Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu
                245


<210> SEQ ID NO 24
<211> LENGTH: 38
<212> TYPE: DNA
<213> ORGANISM: Artificial Sequence
<220> FEATURE:
<223> OTHER INFORMATION: Antisense Primer

<400> SEQUENCE: 24

caggtcaagc tttcagtgat gcttctcagg cgatcccc                              38


<210> SEQ ID NO 25
<211> LENGTH: 7352
<212> TYPE: DNA
<213> ORGANISM: Toxoplasma gondii
<220> FEATURE:
<221> NAME/KEY: CDS
<222> LOCATION: (1528)...(3429)
<223> OTHER INFORMATION: pMBP-c2X-ToxoP30del4C (52-294aa)

<400> SEQUENCE: 25

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660
```

-continued

```
cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                              1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
     75                  80                  85

ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa     2130
Asn Ala Gly Ala Lys Ala Gly Leu Thr Phe Leu Val Asp Leu Ile Lys
```

-continued

```
                190                 195                 200

aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca      3090
```

-continued

```
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565

tgt tcc ggg acg acg ctg act ggt tgc aac gag aaa tcg ttc aaa gat      3282
Cys Ser Gly Thr Thr Leu Thr Gly Cys Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga tgc aca ggg gga tcg cct gag aag cat      3426
Ser Lys Ser Val Ile Ile Gly Cys Thr Gly Gly Ser Pro Glu Lys His
        620                 625                 630

cac tgaaagcttg gcactggccg tcgttttaca acgtcgtgac tgggaaaacc          3479
His

ctggcgttac ccaacttaat cgccttgcag cacatccccc tttcgccagc tggcgtaata   3539

gcgaagaggc ccgcaccgat cgcccttccc aacagttgcg cagcctgaat ggcgaatggc   3599

agcttggctg ttttggcgga tgagataaga ttttcagcct gatacagatt aaatcagaac   3659

gcagaagcgg tctgataaaa cagaatttgc ctggcggcag tagcgcggtg gtcccacctg   3719

accccatgcc gaactcagaa gtgaaacgcc gtagcgccga tggtagtgtg gggtctcccc   3779

atgcgagagt agggaactgc caggcatcaa ataaaacgaa aggctcagtc gaaagactgg   3839

gcctttcgtt ttatctgttg tttgtcggtg aacgctctcc tgagtaggac aaatccgccg   3899

ggagcggatt tgaacgttgc gaagcaacgg cccggagggt ggcgggcagg acgcccgcca   3959

taaactgcca ggcatcaaat taagcagaag gccatcctga cggatggcct ttttgcgttt   4019

ctacaaactc tttttgttta tttttctaaa tacattcaaa tatgtatccg ctcatgagac   4079

aataaccctg ataaatgctt caataatatt gaaaaaggaa gagtatgagt attcaacatt   4139

tccgtgtcgc ccttattccc ttttttgcgg cattttgcct tcctgttttt gctcacccag   4199

aaacgctggt gaaagtaaaa gatgctgaag atcagttggg tgcacgagtg ggttacatcg   4259

aactggatct caacagcggt aagatccttg agagttttcg ccccgaagaa cgttctccaa   4319

tgatgagcac ttttaaagtt ctgctatgtg gcgcggtatt atcccgtgtt gacgccgggc   4379

aagagcaact cggtcgccgc atacactatt ctcagaatga cttggttgag tactcaccag   4439

tcacagaaaa gcatcttacg gatggcatga cagtaagaga attatgcagt gctgccataa   4499

ccatgagtga taacactgcg gccaacttac ttctgacaac gatcggagga ccgaaggagc   4559

taaccgcttt tttgcacaac atgggggatc atgtaactcg ccttgatcgt tgggaaccgg   4619

agctgaatga agccatacca aacgacgagc gtgacaccac gatgcctgta gcaatggcaa   4679

caacgttgcg caaactatta actggcgaac tacttactct agcttcccgg caacaattaa   4739

tagactggat ggaggcggat aaagttgcag gaccacttct gcgctcggcc cttccggctg   4799

gctggtttat tgctgataaa tctggagccg gtgagcgtgg gtctcgcggt atcattgcag   4859
```

-continued

```
cactggggcc agatggtaag ccctcccgta tcgtagttat ctacacgacg gggagtcagg   4919

caactatgga tgaacgaaat agacagatcg ctgagatagg tgcctcactg attaagcatt   4979

ggtaactgtc agaccaagtt tactcatata tactttagat tgatttaccc cggttgataa   5039

tcagaaaagc cccaaaaaca ggaagattgt ataagcaaat atttaaattg taaacgttaa   5099

tattttgtta aaattcgcgt taaatttttg ttaaatcagc tcatttttta accaataggc   5159

cgaaatcggc aaaatccctt ataaatcaaa agaatagacc gagatagggt tgagtgttgt   5219

tccagtttgg aacaagagtc cactattaaa gaacgtggac tccaacgtca aagggcgaaa   5279

aaccgtctat cagggcgatg gcccactacg tgaaccatca cccaaatcaa gttttttggg   5339

gtcgaggtgc cgtaaagcac taaatcggaa ccctaaaggg agcccccgat ttagagcttg   5399

acggggaaag ccggcgaacg tggcgagaaa ggaagggaag aaagcgaaag gagcgggcgc   5459

tagggcgctg gcaagtgtag cggtcacgct gcgcgtaacc accacacccg ccgcgcttaa   5519

tgcgccgcta cagggcgcgt aaaaggatct aggtgaagat cctttttgat aatctcatga   5579

ccaaaatccc ttaacgtgag ttttcgttcc actgagcgtc agaccccgta gaaaagatca   5639

aaggatcttc ttgagatcct ttttttctgc gcgtaatctg ctgcttgcaa acaaaaaaac   5699

caccgctacc agcggtggtt tgtttgccgg atcaagagct accaactctt tttccgaagg   5759

taactggctt cagcagagcg cagataccaa atactgtcct tctagtgtag ccgtagttag   5819

gccaccactt caagaactct gtagcaccgc ctacatacct cgctctgcta atcctgttac   5879

cagtggctgc tgccagtggc gataagtcgt gtcttaccgg gttggactca agacgatagt   5939

taccggataa ggcgcagcgg tcgggctgaa cggggggttc gtgcacacag cccagcttgg   5999

agcgaacgac ctacaccgaa ctgagatacc tacagcgtga gctatgagaa agcgccacgc   6059

ttcccgaagg gagaaaggcg gacaggtatc cggtaagcgg cagggtcgga acaggagagc   6119

gcacgaggga gcttccaggg ggaaacgcct ggtatcttta tagtcctgtc gggtttcgcc   6179

acctctgact tgagcgtcga tttttgtgat gctcgtcagg ggggcggagc ctatggaaaa   6239

acgccagcaa cgcggccttt ttacggttcc tggccttttg ctggcctttt gctcacatgt   6299

tctttcctgc gttatcccct gattctgtgg ataaccgtat taccgccttt gagtgagctg   6359

ataccgctcg ccgcagccga acgaccgagc gcagcgagtc agtgagcgag gaagcggaag   6419

agcgcctgat gcggtatttt ctccttacgc atctgtgcgg tatttcacac cgcatatatg   6479

gtgcactctc agtacaatct gctctgatgc cgcatagtta agccagtata cactccgcta   6539

tcgctacgtg actgggtcat ggctgcgccc cgacacccgc caacacccgc tgacgcgccc   6599

tgacgggctt gtctgctccc ggcatccgct tacagacaag ctgtgaccgt ctccgggagc   6659

tgcatgtgtc agaggttttc accgtcatca ccgaaacgcg cgaggcagct gcggtaaagc   6719

tcatcagcgt ggtcgtgcag cgattcacag atgtctgcct gttcatccgc gtccagctcg   6779

ttgagtttct ccagaagcgt taatgtctgg cttctgataa agcgggccat gttaagggcg   6839

gtttttttcct gtttggtcac tgatgcctcc gtgtaagggg gatttctgtt catgggggta   6899

atgataccga tgaaacgaga gaggatgctc acgatacggg ttactgatga tgaacatgcc   6959

cggttactgg aacgttgtga gggtaaacaa ctggcggtat ggatgcggcg ggaccagaga   7019

aaaatcactc agggtcaatg ccagcgcttc gttaatacag atgtaggtgt tccacagggt   7079

agccagcagc atcctgcgat gcagatccgg aacataatgg tgcagggcgc tgacttccgc   7139

gtttccagac tttacgaaac acggaaaccg aagaccattc atgttgttgc tcaggtcgca   7199
```

-continued

```
gacgttttgc agcagcagtc gcttcacgtt cgctcgcgta tcggtgattc attctgctaa   7259

ccagtaaggc aaccccgcca gcctagccgg gtcctcaacg acaggagcac gatcatgcgc   7319

acccgtggcc aggacccaac gctgcccgaa att                                 7352


<210> SEQ ID NO 26
<211> LENGTH: 634
<212> TYPE: PRT
<213> ORGANISM: Toxoplasma gondii
<220> FEATURE:
<223> OTHER INFORMATION: pMBP-c2X-ToxoP30del4C (52-294aa)

<400> SEQUENCE: 26

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

-continued

```
Met Ser Ala Phe Trp Tyr Ala Val Arg Thr Ala Val Ile Asn Ala Ala
        340                 345                 350

Ser Gly Arg Gln Thr Val Asp Glu Ala Leu Lys Asp Ala Gln Thr Asn
    355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
        420                 425                 430

Leu Ala Tyr Ser Pro Asn Arg Gln Ile Cys Pro Ala Gly Thr Thr Ser
    435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
        500                 505                 510

Thr Val Thr Val Gln Ala Arg Ala Ser Ser Val Val Asn Asn Val Ala
    515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
        580                 585                 590

Asn Pro Trp Gln Gly Asn Ala Ser Ser Asp Lys Gly Ala Thr Leu Thr
    595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His
625                 630
```

```
<210> SEQ ID NO 27
<211> LENGTH: 729
<212> TYPE: DNA
<213> ORGANISM: Toxoplasma gondii
<220> FEATURE:
<221> NAME/KEY: CDS
<222> LOCATION: (1)...(729)
<223> OTHER INFORMATION: ToxoP30del4C (52-294aa)

<400> SEQUENCE: 27

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
```

-continued

```
        35                  40                  45

caa atc tgc cca gcg ggt act aca agt agc tgt aca tca aag gct gta      192
Gln Ile Cys Pro Ala Gly Thr Thr Ser Ser Cys Thr Ser Lys Ala Val
     50                  55                  60

aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                 85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
    130                 135                 140

agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160

acc ctc gtg tgc ggg aaa gat gga gtc aaa gtt cct caa gac aac aat      528
Thr Leu Val Cys Gly Lys Asp Gly Val Lys Val Pro Gln Asp Asn Asn
                165                 170                 175

cag tac tgt tcc ggg acg acg ctg act ggt tgc aac gag aaa tcg ttc      576
Gln Tyr Cys Ser Gly Thr Thr Leu Thr Gly Cys Asn Glu Lys Ser Phe
            180                 185                 190

aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220

gcc gag tca aaa agc gtc att att gga tgc aca ggg gga tcg cct gag      720
Ala Glu Ser Lys Ser Val Ile Ile Gly Cys Thr Gly Gly Ser Pro Glu
225                 230                 235                 240

aag cat cac                                                          729
Lys His His


<210> SEQ ID NO 28
<211> LENGTH: 243
<212> TYPE: PRT
<213> ORGANISM: Toxoplasma gondii
<220> FEATURE:
<223> OTHER INFORMATION: ToxoP30del4C (52-294aa)

<400> SEQUENCE: 28

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
```

-continued

```
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His


<210> SEQ ID NO 29
<211> LENGTH: 30
<212> TYPE: DNA
<213> ORGANISM: Artificial Sequence
<220> FEATURE:
<223> OTHER INFORMATION: Sense Primer

<400> SEQUENCE: 29

ggcgaattcc ctaaaacagc gctcacagag                                     30


<210> SEQ ID NO 30
<211> LENGTH: 7259
<212> TYPE: DNA
<213> ORGANISM: Toxoplasma gondii
<220> FEATURE:
<221> NAME/KEY: CDS
<222> LOCATION: (1528)...(3336)
<223> OTHER INFORMATION: pMBP-c2X-ToxoP30del4del8 (83-294aa)

<400> SEQUENCE: 30

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720
```

-continued

```
cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                              1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
     75                  80                  85

ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa     2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc     2178
```

-continued

```
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
            270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
            350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc cct aaa      2706
Asn Asn Asn Asn Leu Gly Ile Glu Gly Arg Ile Ser Glu Phe Pro Lys
        380                 385                 390

aca gcg ctc aca gag cct ccc act ctt gcg tac tca ccc aac agg caa      2754
Thr Ala Leu Thr Glu Pro Pro Thr Leu Ala Tyr Ser Pro Asn Arg Gln
    395                 400                 405

atc tgc cca gcg ggt act aca agt agc tgt aca tca aag gct gta aca      2802
Ile Cys Pro Ala Gly Thr Thr Ser Ser Cys Thr Ser Lys Ala Val Thr
410                 415                 420                 425

ttg agc tcc ttg att cct gaa gca gaa gat agc tgg tgg acg ggg gat      2850
Leu Ser Ser Leu Ile Pro Glu Ala Glu Asp Ser Trp Trp Thr Gly Asp
            430                 435                 440

tct gct agt ctc gac acg gca ggc atc aaa ctc aca gtt cca atc gag      2898
Ser Ala Ser Leu Asp Thr Ala Gly Ile Lys Leu Thr Val Pro Ile Glu
            445                 450                 455

aag ttc ccc gtg aca acg cag acg ttt gtg gtc ggt tgc atc aag gga      2946
Lys Phe Pro Val Thr Thr Gln Thr Phe Val Val Gly Cys Ile Lys Gly
        460                 465                 470

gac gac gca cag agt tgt atg gtc aca gtg aca gta caa gcc aga gcc      2994
Asp Asp Ala Gln Ser Cys Met Val Thr Val Thr Val Gln Ala Arg Ala
    475                 480                 485

tca tcg gtc gtc aat aat gtc gca agg tgc tcc tac ggt gca gac agc      3042
Ser Ser Val Val Asn Asn Val Ala Arg Cys Ser Tyr Gly Ala Asp Ser
490                 495                 500                 505

act ctt ggt cct gtc aag ttg tct gcg gaa gga ccc act aca atg acc      3090
Thr Leu Gly Pro Val Lys Leu Ser Ala Glu Gly Pro Thr Thr Met Thr
            510                 515                 520
```

-continued

```
ctc gtg tgc ggg aaa gat gga gtc aaa gtt cct caa gac aac aat cag     3138
Leu Val Cys Gly Lys Asp Gly Val Lys Val Pro Gln Asp Asn Asn Gln
            525                 530                 535

tac tgt tcc ggg acg acg ctg act ggt tgc aac gag aaa tcg ttc aaa     3186
Tyr Cys Ser Gly Thr Thr Leu Thr Gly Cys Asn Glu Lys Ser Phe Lys
        540                 545                 550

gat att ttg cca aaa tta act gag aac ccg tgg cag ggt aac gct tcg     3234
Asp Ile Leu Pro Lys Leu Thr Glu Asn Pro Trp Gln Gly Asn Ala Ser
    555                 560                 565

agt gat aag ggt gcc acg cta acg atc aag aag gaa gca ttt cca gcc     3282
Ser Asp Lys Gly Ala Thr Leu Thr Ile Lys Lys Glu Ala Phe Pro Ala
570                 575                 580                 585

gag tca aaa agc gtc att att gga tgc aca ggg gga tcg cct gag aag     3330
Glu Ser Lys Ser Val Ile Ile Gly Cys Thr Gly Gly Ser Pro Glu Lys
                590                 595                 600

cat cac tgaaagcttg gcactggccg tcgttttaca acgtcgtgac tgggaaaacc     3386
His His

ctggcgttac ccaacttaat cgccttgcag cacatccccc tttcgccagc tggcgtaata   3446

gcgaagaggc ccgcaccgat cgcccttccc aacagttgcg cagcctgaat ggcgaatggc   3506

agcttggctg ttttggcgga tgagataaga ttttcagcct gatacagatt aaatcagaac   3566

gcagaagcgg tctgataaaa cagaatttgc ctggcggcag tagcgcggtg gtcccacctg   3626

accccatgcc gaactcagaa gtgaaacgcc gtagcgccga tggtagtgtg gggtctcccc   3686

atgcgagagt agggaactgc caggcatcaa ataaaacgaa aggctcagtc gaaagactgg   3746

gcctttcgtt ttatctgttg tttgtcggtg aacgctctcc tgagtaggac aaatccgccg   3806

ggagcggatt tgaacgttgc gaagcaacgg cccggagggt ggcgggcagg acgcccgcca   3866

taaactgcca ggcatcaaat taagcagaag gccatcctga cggatggcct ttttgcgttt   3926

ctacaaactc tttttgttta tttttctaaa tacattcaaa tatgtatccg ctcatgagac   3986

aataaccctg ataaatgctt caataatatt gaaaaaggaa gagtatgagt attcaacatt   4046

tccgtgtcgc ccttattccc ttttttgcgg cattttgcct tcctgttttt gctcacccag   4106

aaacgctggt gaaagtaaaa gatgctgaag atcagttggg tgcacgagtg ggttacatcg   4166

aactggatct caacagcggt aagatccttg agagttttcg ccccgaagaa cgttctccaa   4226

tgatgagcac ttttaaagtt ctgctatgtg gcgcggtatt atcccgtgtt gacgccgggc   4286

aagagcaact cggtcgccgc atacactatt ctcagaatga cttggttgag tactcaccag   4346

tcacagaaaa gcatcttacg gatggcatga cagtaagaga attatgcagt gctgccataa   4406

ccatgagtga taacactgcg gccaacttac ttctgacaac gatcggagga ccgaaggagc   4466

taaccgcttt tttgcacaac atgggggatc atgtaactcg ccttgatcgt tgggaaccgg   4526

agctgaatga agccatacca aacgacgagc gtgacaccac gatgcctgta gcaatggcaa   4586

caacgttgcg caaactatta actggcgaac tacttactct agcttcccgg caacaattaa   4646

tagactggat ggaggcggat aaagttgcag gaccacttct gcgctcggcc cttccggctg   4706

gctggtttat tgctgataaa tctggagccg gtgagcgtgg gtctcgcggt atcattgcag   4766

cactggggcc agatggtaag ccctcccgta tcgtagttat ctacacgacg gggagtcagg   4826

caactatgga tgaacgaaat agacagatcg ctgagatagg tgcctcactg attaagcatt   4886

ggtaactgtc agaccaagtt tactcatata tactttagat tgatttaccc cggttgataa   4946

tcagaaaagc cccaaaaaca ggaagattgt ataagcaaat atttaaattg taaacgttaa   5006

tattttgtta aaattcgcgt taaatttttg ttaaatcagc tcatttttta accaataggc   5066
```

-continued

```
cgaaatcggc aaaatccctt ataaatcaaa agaatagacc gagatagggt tgagtgttgt   5126

tccagtttgg aacaagagtc cactattaaa gaacgtggac tccaacgtca aagggcgaaa   5186

aaccgtctat cagggcgatg gcccactacg tgaaccatca cccaaatcaa gtttttttggg   5246

gtcgaggtgc cgtaaagcac taaatcggaa ccctaaaggg agcccccgat ttagagcttg   5306

acggggaaag ccggcgaacg tggcgagaaa ggaagggaag aaagcgaaag gagcgggcgc   5366

tagggcgctg gcaagtgtag cggtcacgct gcgcgtaacc accacacccg ccgcgcttaa   5426

tgcgccgcta cagggcgcgt aaaaggatct aggtgaagat cctttttgat aatctcatga   5486

ccaaaatccc ttaacgtgag ttttcgttcc actgagcgtc agaccccgta gaaaagatca   5546

aaggatcttc ttgagatcct ttttttctgc gcgtaatctg ctgcttgcaa acaaaaaaac   5606

caccgctacc agcggtggtt tgtttgccgg atcaagagct accaactctt tttccgaagg   5666

taactggctt cagcagagcg cagataccaa atactgtcct tctagtgtag ccgtagttag   5726

gccaccactt caagaactct gtagcaccgc ctacatacct cgctctgcta atcctgttac   5786

cagtggctgc tgccagtggc gataagtcgt gtcttaccgg gttggactca agacgatagt   5846

taccggataa ggcgcagcgg tcgggctgaa cggggggttc gtgcacacag cccagcttgg   5906

agcgaacgac ctacaccgaa ctgagatacc tacagcgtga gctatgagaa agcgccacgc   5966

ttcccgaagg gagaaaggcg gacaggtatc cggtaagcgg cagggtcgga acaggagagc   6026

gcacgaggga gcttccaggg ggaaacgcct ggtatcttta tagtcctgtc gggtttcgcc   6086

acctctgact tgagcgtcga tttttgtgat gctcgtcagg ggggcggagc ctatggaaaa   6146

acgccagcaa cgcggccttt ttacggttcc tggccttttg ctggcctttt gctcacatgt   6206

tctttcctgc gttatcccct gattctgtgg ataaccgtat taccgccttt gagtgagctg   6266

ataccgctcg ccgcagccga acgaccgagc gcagcgagtc agtgagcgag gaagcggaag   6326

agcgcctgat gcggtatttt ctccttacgc atctgtgcgg tatttcacac cgcatatatg   6386

gtgcactctc agtacaatct gctctgatgc cgcatagtta agccagtata cactccgcta   6446

tcgctacgtg actgggtcat ggctgcgccc cgacacccgc caacacccgc tgacgcgccc   6506

tgacgggctt gtctgctccc ggcatccgct tacagacaag ctgtgaccgt ctccgggagc   6566

tgcatgtgtc agaggttttc accgtcatca ccgaaacgcg cgaggcagct gcggtaaagc   6626

tcatcagcgt ggtcgtgcag cgattcacag atgtctgcct gttcatccgc gtccagctcg   6686

ttgagtttct ccagaagcgt taatgtctgg cttctgataa agcgggccat gttaagggcg   6746

gtttttttcct gtttggtcac tgatgcctcc gtgtaagggg gatttctgtt catgggggta   6806

atgataccga tgaaacgaga gaggatgctc acgatacggg ttactgatga tgaacatgcc   6866

cggttactgg aacgttgtga gggtaaacaa ctggcggtat ggatgcggcg ggaccagaga   6926

aaaatcactc agggtcaatg ccagcgcttc gttaatacag atgtaggtgt tccacagggt   6986

agccagcagc atcctgcgat gcagatccgg aacataatgg tgcagggcgc tgacttccgc   7046

gtttccagac tttacgaaac acggaaaccg aagaccattc atgttgttgc tcaggtcgca   7106

gacgttttgc agcagcagtc gcttcacgtt cgctcgcgta tcggtgattc attctgctaa   7166

ccagtaaggc aaccccgcca gcctagccgg gtcctcaacg acaggagcac gatcatgcgc   7226

acccgtggcc aggacccaac gctgcccgaa att                                7259
```

<210> SEQ ID NO 31
<211> LENGTH: 603
<212> TYPE: PRT
<213> ORGANISM: Toxoplasma gondii -continued
<220> FEATURE:
<223> OTHER INFORMATION: pMBP-c2X-ToxoP30del4del8 (83-294aa)

<400> SEQUENCE: 31

Met Lys Ile Glu Glu Gly Lys Leu Val Ile Trp Ile Asn Gly Asp Lys
1 5 10 15

Gly Tyr Asn Gly Leu Ala Glu Val Gly Lys Lys Phe Glu Lys Asp Thr
20 25 30

Gly Ile Lys Val Thr Val Glu His Pro Asp Lys Leu Glu Glu Lys Phe
35 40 45

Pro Gln Val Ala Ala Thr Gly Asp Gly Pro Asp Ile Ile Phe Trp Ala
50 55 60

His Asp Arg Phe Gly Gly Tyr Ala Gln Ser Gly Leu Leu Ala Glu Ile
65 70 75 80

Thr Pro Asp Lys Ala Phe Gln Asp Lys Leu Tyr Pro Phe Thr Trp Asp
85 90 95

Ala Val Arg Tyr Asn Gly Lys Leu Ile Ala Tyr Pro Ile Ala Val Glu
100 105 110

Ala Leu Ser Leu Ile Tyr Asn Lys Asp Leu Leu Pro Asn Pro Pro Lys
115 120 125

Thr Trp Glu Glu Ile Pro Ala Leu Asp Lys Glu Leu Lys Ala Lys Gly
130 135 140

Lys Ser Ala Leu Met Phe Asn Leu Gln Glu Pro Tyr Phe Thr Trp Pro
145 150 155 160

Leu Ile Ala Ala Asp Gly Gly Tyr Ala Phe Lys Tyr Glu Asn Gly Lys
165 170 175

Tyr Asp Ile Lys Asp Val Gly Val Asp Asn Ala Gly Ala Lys Ala Gly
180 185 190

Leu Thr Phe Leu Val Asp Leu Ile Lys Asn Lys His Met Asn Ala Asp
195 200 205

Thr Asp Tyr Ser Ile Ala Glu Ala Ala Phe Asn Lys Gly Glu Thr Ala
210 215 220

Met Thr Ile Asn Gly Pro Trp Ala Trp Ser Asn Ile Asp Thr Ser Lys
225 230 235 240

Val Asn Tyr Gly Val Thr Val Leu Pro Thr Phe Lys Gly Gln Pro Ser
245 250 255

Lys Pro Phe Val Gly Val Leu Ser Ala Gly Ile Asn Ala Ala Ser Pro
260 265 270

Asn Lys Glu Leu Ala Lys Glu Phe Leu Glu Asn Tyr Leu Leu Thr Asp
275 280 285

Glu Gly Leu Glu Ala Val Asn Lys Asp Lys Pro Leu Gly Ala Val Ala
290 295 300

Leu Lys Ser Tyr Glu Glu Glu Leu Ala Lys Asp Pro Arg Ile Ala Ala
305 310 315 320

Thr Met Glu Asn Ala Gln Lys Gly Glu Ile Met Pro Asn Ile Pro Gln
325 330 335

Met Ser Ala Phe Trp Tyr Ala Val Arg Thr Ala Val Ile Asn Ala Ala
340 345 350

Ser Gly Arg Gln Thr Val Asp Glu Ala Leu Lys Asp Ala Gln Thr Asn
355 360 365

Ser Ser Ser Asn Asn Asn Asn Asn Asn Asn Asn Asn Asn Leu Gly Ile
370 375 380

Glu Gly Arg Ile Ser Glu Phe Pro Lys Thr Ala Leu Thr Glu Pro Pro
385 390 395 400

-continued

```
Thr Leu Ala Tyr Ser Pro Asn Arg Gln Ile Cys Pro Ala Gly Thr Thr
                405                 410                 415

Ser Ser Cys Thr Ser Lys Ala Val Thr Leu Ser Ser Leu Ile Pro Glu
            420                 425                 430

Ala Glu Asp Ser Trp Trp Thr Gly Asp Ser Ala Ser Leu Asp Thr Ala
        435                 440                 445

Gly Ile Lys Leu Thr Val Pro Ile Glu Lys Phe Pro Val Thr Thr Gln
    450                 455                 460

Thr Phe Val Val Gly Cys Ile Lys Gly Asp Asp Ala Gln Ser Cys Met
465                 470                 475                 480

Val Thr Val Thr Val Gln Ala Arg Ala Ser Ser Val Val Asn Asn Val
                485                 490                 495

Ala Arg Cys Ser Tyr Gly Ala Asp Ser Thr Leu Gly Pro Val Lys Leu
            500                 505                 510

Ser Ala Glu Gly Pro Thr Thr Met Thr Leu Val Cys Gly Lys Asp Gly
        515                 520                 525

Val Lys Val Pro Gln Asp Asn Asn Gln Tyr Cys Ser Gly Thr Thr Leu
    530                 535                 540

Thr Gly Cys Asn Glu Lys Ser Phe Lys Asp Ile Leu Pro Lys Leu Thr
545                 550                 555                 560

Glu Asn Pro Trp Gln Gly Asn Ala Ser Ser Asp Lys Gly Ala Thr Leu
                565                 570                 575

Thr Ile Lys Lys Glu Ala Phe Pro Ala Glu Ser Lys Ser Val Ile Ile
            580                 585                 590

Gly Cys Thr Gly Gly Ser Pro Glu Lys His His
        595                 600


<210> SEQ ID NO 32
<211> LENGTH: 636
<212> TYPE: DNA
<213> ORGANISM: Toxoplasma gondii
<220> FEATURE:
<221> NAME/KEY: CDS
<222> LOCATION: (1)...(636)
<223> OTHER INFORMATION: ToxoP30del4del8 (83-294aa)

<400> SEQUENCE: 32

cct aaa aca gcg ctc aca gag cct ccc act ctt gcg tac tca ccc aac       48
Pro Lys Thr Ala Leu Thr Glu Pro Pro Thr Leu Ala Tyr Ser Pro Asn
 1               5                  10                  15

agg caa atc tgc cca gcg ggt act aca agt agc tgt aca tca aag gct       96
Arg Gln Ile Cys Pro Ala Gly Thr Thr Ser Ser Cys Thr Ser Lys Ala
             20                  25                  30

gta aca ttg agc tcc ttg att cct gaa gca gaa gat agc tgg tgg acg      144
Val Thr Leu Ser Ser Leu Ile Pro Glu Ala Glu Asp Ser Trp Trp Thr
         35                  40                  45

ggg gat tct gct agt ctc gac acg gca ggc atc aaa ctc aca gtt cca      192
Gly Asp Ser Ala Ser Leu Asp Thr Ala Gly Ile Lys Leu Thr Val Pro
     50                  55                  60

atc gag aag ttc ccc gtg aca acg cag acg ttt gtg gtc ggt tgc atc      240
Ile Glu Lys Phe Pro Val Thr Thr Gln Thr Phe Val Val Gly Cys Ile
 65                  70                  75                  80

aag gga gac gac gca cag agt tgt atg gtc aca gtg aca gta caa gcc      288
Lys Gly Asp Asp Ala Gln Ser Cys Met Val Thr Val Thr Val Gln Ala
                 85                  90                  95

aga gcc tca tcg gtc gtc aat aat gtc gca agg tgc tcc tac ggt gca      336
Arg Ala Ser Ser Val Val Asn Asn Val Ala Arg Cys Ser Tyr Gly Ala
            100                 105                 110
```

-continued

```
gac agc act ctt ggt cct gtc aag ttg tct gcg gaa gga ccc act aca      384
Asp Ser Thr Leu Gly Pro Val Lys Leu Ser Ala Glu Gly Pro Thr Thr
        115                 120                 125

atg acc ctc gtg tgc ggg aaa gat gga gtc aaa gtt cct caa gac aac      432
Met Thr Leu Val Cys Gly Lys Asp Gly Val Lys Val Pro Gln Asp Asn
    130                 135                 140

aat cag tac tgt tcc ggg acg acg ctg act ggt tgc aac gag aaa tcg      480
Asn Gln Tyr Cys Ser Gly Thr Thr Leu Thr Gly Cys Asn Glu Lys Ser
145                 150                 155                 160

ttc aaa gat att ttg cca aaa tta act gag aac ccg tgg cag ggt aac      528
Phe Lys Asp Ile Leu Pro Lys Leu Thr Glu Asn Pro Trp Gln Gly Asn
                165                 170                 175

gct tcg agt gat aag ggt gcc acg cta acg atc aag aag gaa gca ttt      576
Ala Ser Ser Asp Lys Gly Ala Thr Leu Thr Ile Lys Lys Glu Ala Phe
            180                 185                 190

cca gcc gag tca aaa agc gtc att att gga tgc aca ggg gga tcg cct      624
Pro Ala Glu Ser Lys Ser Val Ile Ile Gly Cys Thr Gly Gly Ser Pro
        195                 200                 205

gag aag cat cac                                                      636
Glu Lys His His
    210


<210> SEQ ID NO 33
<211> LENGTH: 212
<212> TYPE: PRT
<213> ORGANISM: Toxoplasma gondii
<220> FEATURE:
<223> OTHER INFORMATION: ToxoP30del4del8 (83-294aa)

<400> SEQUENCE: 33

Pro Lys Thr Ala Leu Thr Glu Pro Pro Thr Leu Ala Tyr Ser Pro Asn
 1               5                  10                  15

Arg Gln Ile Cys Pro Ala Gly Thr Thr Ser Ser Cys Thr Ser Lys Ala
            20                  25                  30

Val Thr Leu Ser Ser Leu Ile Pro Glu Ala Glu Asp Ser Trp Trp Thr
        35                  40                  45

Gly Asp Ser Ala Ser Leu Asp Thr Ala Gly Ile Lys Leu Thr Val Pro
    50                  55                  60

Ile Glu Lys Phe Pro Val Thr Thr Gln Thr Phe Val Val Gly Cys Ile
65                  70                  75                  80

Lys Gly Asp Asp Ala Gln Ser Cys Met Val Thr Val Thr Val Gln Ala
                85                  90                  95

Arg Ala Ser Ser Val Val Asn Asn Val Ala Arg Cys Ser Tyr Gly Ala
            100                 105                 110

Asp Ser Thr Leu Gly Pro Val Lys Leu Ser Ala Glu Gly Pro Thr Thr
        115                 120                 125

Met Thr Leu Val Cys Gly Lys Asp Gly Val Lys Val Pro Gln Asp Asn
    130                 135                 140

Asn Gln Tyr Cys Ser Gly Thr Thr Leu Thr Gly Cys Asn Glu Lys Ser
145                 150                 155                 160

Phe Lys Asp Ile Leu Pro Lys Leu Thr Glu Asn Pro Trp Gln Gly Asn
                165                 170                 175

Ala Ser Ser Asp Lys Gly Ala Thr Leu Thr Ile Lys Lys Glu Ala Phe
            180                 185                 190

Pro Ala Glu Ser Lys Ser Val Ile Ile Gly Cys Thr Gly Gly Ser Pro
        195                 200                 205

Glu Lys His His
```

-continued

```
210


<210> SEQ ID NO 34
<211> LENGTH: 39
<212> TYPE: DNA
<213> ORGANISM: Artificial Sequence
<220> FEATURE:
<223> OTHER INFORMATION: Antisense Primer

<400> SEQUENCE: 34

caggtcaagc tttcatccaa taatgacgct ttttgactc                         39


<210> SEQ ID NO 35
<211> LENGTH: 7322
<212> TYPE: DNA
<213> ORGANISM: Toxoplasma gondii
<220> FEATURE:
<221> NAME/KEY: CDS
<222> LOCATION: (1528)...(3399)
<223> OTHER INFORMATION: pMBP-c2X-ToxoP30del10 (52-284aa)

<400> SEQUENCE: 35

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5
```

-continued

```
atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                 15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
            45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
        60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
    75                  80                  85

ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                 95                 100                 105

gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa     2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc     2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg     2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg     2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca     2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc     2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac     2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg     2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa     2514
Lys Asp Pro Arg Ile Ala Ala Thr Met Glu Asn Ala Gln Lys Gly Glu
```

-continued

```
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
                445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gga gga ccc act aca atg acc ctc      3186
Leu Gly Pro Val Lys Leu Ser Ala Gly Gly Pro Thr Thr Met Thr Leu
        540                 545                 550

gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565

tgt tcc ggg acg acg ctg act ggt tgc aac gag aaa tcg ttc aaa gat      3282
Cys Ser Gly Thr Thr Leu Thr Gly Cys Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga tgaaagcttg gcactggccg tcgttttaca         3429
Ser Lys Ser Val Ile Ile Gly
        620

acgtcgtgac tgggaaaacc ctggcgttac ccaacttaat cgccttgcag cacatccccc    3489
```

-continued

```
tttcgccagc tggcgtaata gcgaagaggc ccgcaccgat cgcccttccc aacagttgcg   3549
cagcctgaat ggcgaatggc agcttggctg ttttggcgga tgagataaga ttttcagcct   3609
gatacagatt aaatcagaac gcagaagcgg tctgataaaa cagaatttgc ctggcggcag   3669
tagcgcggtg gtcccacctg accccatgcc gaactcagaa gtgaaacgcc gtagcgccga   3729
tggtagtgtg gggtctcccc atgcgagagt agggaactgc caggcatcaa ataaaacgaa   3789
aggctcagtc gaaagactgg gcctttcgtt ttatctgttg tttgtcggtg aacgctctcc   3849
tgagtaggac aaatccgccg ggagcggatt tgaacgttgc gaagcaacgg cccggagggt   3909
ggcgggcagg acgcccgcca taaactgcca ggcatcaaat taagcagaag gccatcctga   3969
cggatggcct ttttgcgttt ctacaaactc tttttgttta tttttctaaa tacattcaaa   4029
tatgtatccg ctcatgagac aataaccctg ataaatgctt caataatatt gaaaaaggaa   4089
gagtatgagt attcaacatt tccgtgtcgc ccttattccc ttttttgcgg cattttgcct   4149
tcctgttttt gctcacccag aaacgctggt gaaagtaaaa gatgctgaag atcagttggg   4209
tgcacgagtg ggttacatcg aactggatct caacagcggt aagatccttg agagttttcg   4269
ccccgaagaa cgttctccaa tgatgagcac ttttaaagtt ctgctatgtg gcgcggtatt   4329
atcccgtgtt gacgccgggc aagagcaact cggtcgccgc atacactatt ctcagaatga   4389
cttggttgag tactcaccag tcacagaaaa gcatcttacg gatggcatga cagtaagaga   4449
attatgcagt gctgccataa ccatgagtga taacactgcg gccaacttac ttctgacaac   4509
gatcggagga ccgaaggagc taaccgcttt tttgcacaac atgggggatc atgtaactcg   4569
ccttgatcgt tgggaaccgg agctgaatga agccatacca aacgacgagc gtgacaccac   4629
gatgcctgta gcaatggcaa caacgttgcg caaactatta actggcgaac tacttactct   4689
agcttcccgg caacaattaa tagactggat ggaggcggat aaagttgcag gaccacttct   4749
gcgctcggcc cttccggctg gctggtttat tgctgataaa tctggagccg gtgagcgtgg   4809
gtctcgcggt atcattgcag cactggggcc agatggtaag ccctcccgta tcgtagttat   4869
ctacacgacg gggagtcagg caactatgga tgaacgaaat agacagatcg ctgagatagg   4929
tgcctcactg attaagcatt ggtaactgtc agaccaagtt tactcatata tactttagat   4989
tgatttaccc cggttgataa tcagaaaagc cccaaaaaca ggaagattgt ataagcaaat   5049
atttaaattg taaacgttaa tattttgtta aaattcgcgt taaatttttg ttaaatcagc   5109
tcatttttta accaataggc cgaaatcggc aaaatccctt ataaatcaaa agaatagacc   5169
gagatagggt tgagtgttgt tccagtttgg aacaagagtc cactattaaa gaacgtggac   5229
tccaacgtca aagggcgaaa aaccgtctat cagggcgatg gcccactacg tgaaccatca   5289
cccaaatcaa gttttttggg gtcgaggtgc cgtaaagcac taaatcggaa ccctaaaggg   5349
agcccccgat ttagagcttg acggggaaag ccggcgaacg tggcgagaaa ggaagggaag   5409
aaagcgaaag gagcgggcgc tagggcgctg gcaagtgtag cggtcacgct gcgcgtaacc   5469
accacacccg ccgcgcttaa tgcgccgcta cagggcgcgt aaaaggatct aggtgaagat   5529
cctttttgat aatctcatga ccaaaatccc ttaacgtgag ttttcgttcc actgagcgtc   5589
agaccccgta gaaaagatca aaggatcttc ttgagatcct ttttttctgc gcgtaatctg   5649
ctgcttgcaa acaaaaaaac caccgctacc agcggtggtt tgtttgccgg atcaagagct   5709
accaactctt tttccgaagg taactggctt cagcagagcg cagataccaa atactgtcct   5769
tctagtgtag ccgtagttag gccaccactt caagaactct gtagcaccgc ctacatacct   5829
```

-continued

```
cgctctgcta atcctgttac cagtggctgc tgccagtggc gataagtcgt gtcttaccgg   5889

gttggactca agacgatagt taccggataa ggcgcagcgg tcgggctgaa cggggggttc   5949

gtgcacacag cccagcttgg agcgaacgac ctacaccgaa ctgagatacc tacagcgtga   6009

gctatgagaa agcgccacgc ttcccgaagg gagaaaggcg gacaggtatc cggtaagcgg   6069

cagggtcgga acaggagagc gcacgaggga gcttccaggg ggaaacgcct ggtatcttta   6129

tagtcctgtc gggtttcgcc acctctgact tgagcgtcga tttttgtgat gctcgtcagg   6189

ggggcggagc ctatggaaaa acgccagcaa cgcggccttt ttacggttcc tggccttttg   6249

ctggcctttt gctcacatgt tctttcctgc gttatcccct gattctgtgg ataaccgtat   6309

taccgccttt gagtgagctg ataccgctcg ccgcagccga acgaccgagc gcagcgagtc   6369

agtgagcgag gaagcggaag agcgcctgat gcggtatttt ctccttacgc atctgtgcgg   6429

tatttcacac cgcatatatg gtgcactctc agtacaatct gctctgatgc cgcatagtta   6489

agccagtata cactccgcta tcgctacgtg actgggtcat ggctgcgccc cgacacccgc   6549

caacacccgc tgacgcgccc tgacgggctt gtctgctccc ggcatccgct tacagacaag   6609

ctgtgaccgt ctccgggagc tgcatgtgtc agaggttttc accgtcatca ccgaaacgcg   6669

cgaggcagct gcggtaaagc tcatcagcgt ggtcgtgcag cgattcacag atgtctgcct   6729

gttcatccgc gtccagctcg ttgagtttct ccagaagcgt taatgtctgg cttctgataa   6789

agcgggccat gttaagggcg gtttttcct gtttggtcac tgatgcctcc gtgtaagggg   6849

gatttctgtt catgggggta atgataccga tgaaacgaga gaggatgctc acgatacggg   6909

ttactgatga tgaacatgcc cggttactgg aacgttgtga gggtaaacaa ctggcggtat   6969

ggatgcggcg ggaccagaga aaaatcactc agggtcaatg ccagcgcttc gttaatacag   7029

atgtaggtgt tccacagggt agccagcagc atcctgcgat gcagatccgg aacataatgg   7089

tgcagggcgc tgacttccgc gtttccagac tttacgaaac acggaaaccg aagaccattc   7149

atgttgttgc tcaggtcgca gacgttttgc agcagcagtc gcttcacgtt cgctcgcgta   7209

tcggtgattc attctgctaa ccagtaaggc aaccccgcca gcctagccgg gtcctcaacg   7269

acaggagcac gatcatgcgc acccgtggcc aggacccaac gctgcccgaa att          7322
```

```
<210> SEQ ID NO 36
<211> LENGTH: 624
<212> TYPE: PRT
<213> ORGANISM: Toxoplasma gondii
<220> FEATURE:
<223> OTHER INFORMATION: pMBP-c2X-ToxoP30del10 (52-284aa)

<400> SEQUENCE: 36

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
```

-continued

```
        100                 105                 110

Ala Leu Ser Leu Ile Tyr Asn Lys Asp Leu Leu Pro Asn Pro Pro Lys
    115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525
```

-continued

```
Arg Cys Ser Tyr Gly Ala Asp Ser Thr Leu Gly Pro Val Lys Leu Ser
    530                 535                 540

Ala Gly Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620


<210> SEQ ID NO 37
<211> LENGTH: 699
<212> TYPE: DNA
<213> ORGANISM: Toxoplasma gondii
<220> FEATURE:
<221> NAME/KEY: CDS
<222> LOCATION: (1)...(699)
<223> OTHER INFORMATION: ToxoP30del10 (52-284aa)

<400> SEQUENCE: 37

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
        35                  40                  45

caa atc tgc cca gcg ggt act aca agt agc tgt aca tca aag gct gta      192
Gln Ile Cys Pro Ala Gly Thr Thr Ser Ser Cys Thr Ser Lys Ala Val
    50                  55                  60

aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
65                  70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
    130                 135                 140

agc act ctt ggt cct gtc aag ttg tct gcg gga gga ccc act aca atg      480
Ser Thr Leu Gly Pro Val Lys Leu Ser Ala Gly Gly Pro Thr Thr Met
145                 150                 155                 160

acc ctc gtg tgc ggg aaa gat gga gtc aaa gtt cct caa gac aac aat      528
Thr Leu Val Cys Gly Lys Asp Gly Val Lys Val Pro Gln Asp Asn Asn
                165                 170                 175

cag tac tgt tcc ggg acg acg ctg act ggt tgc aac gag aaa tcg ttc      576
Gln Tyr Cys Ser Gly Thr Thr Leu Thr Gly Cys Asn Glu Lys Ser Phe
            180                 185                 190
```

-continued

```
aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220

gcc gag tca aaa agc gtc att att gga                                  699
Ala Glu Ser Lys Ser Val Ile Ile Gly
225                 230


<210> SEQ ID NO 38
<211> LENGTH: 233
<212> TYPE: PRT
<213> ORGANISM: Toxoplasma gondii
<220> FEATURE:
<223> OTHER INFORMATION: ToxoP30del10 (52-284aa)

<400> SEQUENCE: 38

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Gly Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly
225                 230


<210> SEQ ID NO 39
<211> LENGTH: 36
<212> TYPE: DNA
<213> ORGANISM: Artificial Sequence
<220> FEATURE:
<223> OTHER INFORMATION: Antisense Primer

<400> SEQUENCE: 39

caggtcaagc tttcacacga gggtcattgt agtggg                               36
```

-continued

<210> SEQ ID NO 40
<211> LENGTH: 7112
<212> TYPE: DNA
<213> ORGANISM: Toxoplasma gondii
<220> FEATURE:
<221> NAME/KEY: CDS
<222> LOCATION: (1528)...(3189)
<223> OTHER INFORMATION: pMBP-c2X-ToxoP30del11 (52-214aa)

<400> SEQUENCE: 40

```
ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                                1               5

atc tgg att aac ggc gat aaa ggc tat aac ggt ctc gct gaa gtc ggt    1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg    1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc    1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa    1746
```

-continued

```
Pro Asp Ile Ile Phe Trp Ala His Asp Arg Phe Gly Gly Tyr Ala Gln
        60                  65                  70

tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
    75                  80                  85

ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
90                  95                  100                 105

gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375
```

-continued

```
aat aac aac aac ctc ggg atc gag gga agg att tca gaa ttc ctt gtt     2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc     2754
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca     2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc     2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg     2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct     2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag     2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac     3042
Phe Pro Val Thr Thr Gln Thr Phe Val Val Gly Cys Ile Lys Gly Asp
490                 495                 500                 505

gac gca cag agt tgt atg gtc aca gtg aca gta caa gcc aga gcc tca     3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act     3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc     3186
Leu Gly Pro Val Lys Leu Ser Ala Glu Gly Pro Thr Thr Met Thr Leu
        540                 545                 550

gtg tgaaagcttg gcactggccg tcgttttaca acgtcgtgac tgggaaaacc          3239
Val

ctggcgttac ccaacttaat cgccttgcag cacatccccc tttcgccagc tggcgtaata   3299

gcgaagaggc ccgcaccgat cgcccttccc aacagttgcg cagcctgaat ggcgaatggc   3359

agcttggctg ttttggcgga tgagataaga ttttcagcct gatacagatt aaatcagaac   3419

gcagaagcgg tctgataaaa cagaatttgc ctggcggcag tagcgcggtg gtcccacctg   3479

accccatgcc gaactcagaa gtgaaacgcc gtagcgccga tggtagtgtg gggtctcccc   3539

atgcgagagt agggaactgc caggcatcaa ataaaacgaa aggctcagtc gaaagactgg   3599

gcctttcgtt ttatctgttg tttgtcggtg aacgctctcc tgagtaggac aaatccgccg   3659

ggagcggatt tgaacgttgc gaagcaacgg cccggagggt ggcgggcagg acgcccgcca   3719

taaactgcca ggcatcaaat taagcagaag gccatcctga cggatggcct ttttgcgttt   3779

ctacaaactc tttttgttta tttttctaaa tacattcaaa tatgtatccg ctcatgagac   3839

aataaccctg ataaatgctt caataatatt gaaaaaggaa gagtatgagt attcaacatt   3899

tccgtgtcgc ccttattccc ttttttgcgg cattttgcct tcctgttttt gctcacccag   3959

aaacgctggt gaaagtaaaa gatgctgaag atcagttggg tgcacgagtg ggttacatcg   4019

aactggatct caacagcggt aagatccttg agagttttcg ccccgaagaa cgttctccaa   4079

tgatgagcac ttttaaagtt ctgctatgtg gcgcggtatt atcccgtgtt gacgccgggc   4139

aagagcaact cggtcgccgc atacactatt ctcagaatga cttggttgag tactcaccag   4199
```

-continued

```
tcacagaaaa gcatcttacg gatggcatga cagtaagaga attatgcagt gctgccataa   4259
ccatgagtga taacactgcg gccaacttac ttctgacaac gatcggagga ccgaaggagc   4319
taaccgcttt tttgcacaac atgggggatc atgtaactcg ccttgatcgt tgggaaccgg   4379
agctgaatga agccatacca aacgacgagc gtgacaccac gatgcctgta gcaatggcaa   4439
caacgttgcg caaactatta actggcgaac tacttactct agcttcccgg caacaattaa   4499
tagactggat ggaggcggat aaagttgcag gaccacttct gcgctcggcc cttccggctg   4559
gctggtttat tgctgataaa tctggagccg gtgagcgtgg gtctcgcggt atcattgcag   4619
cactggggcc agatggtaag ccctcccgta tcgtagttat ctacacgacg gggagtcagg   4679
caactatgga tgaacgaaat agacagatcg ctgagatagg tgcctcactg attaagcatt   4739
ggtaactgtc agaccaagtt tactcatata tactttagat tgatttaccc cggttgataa   4799
tcagaaaagc cccaaaaaca ggaagattgt ataagcaaat atttaaattg taaacgttaa   4859
tattttgtta aaattcgcgt taaatttttg ttaaatcagc tcatttttta accaataggc   4919
cgaaatcggc aaaatccctt ataaatcaaa agaatagacc gagatagggt tgagtgttgt   4979
tccagtttgg aacaagagtc cactattaaa gaacgtggac tccaacgtca aagggcgaaa   5039
aaccgtctat cagggcgatg gcccactacg tgaaccatca cccaaatcaa gttttttggg   5099
gtcgaggtgc cgtaaagcac taaatcggaa ccctaaaggg agcccccgat ttagagcttg   5159
acggggaaag ccggcgaacg tggcgagaaa ggaagggaag aaagcgaaag gagcgggcgc   5219
tagggcgctg gcaagtgtag cggtcacgct gcgcgtaacc accacacccg ccgcgcttaa   5279
tgcgccgcta cagggcgcgt aaaaggatct aggtgaagat cctttttgat aatctcatga   5339
ccaaaatccc ttaacgtgag ttttcgttcc actgagcgtc agaccccgta gaaaagatca   5399
aaggatcttc ttgagatcct ttttttctgc gcgtaatctg ctgcttgcaa acaaaaaaac   5459
caccgctacc agcggtggtt tgtttgccgg atcaagagct accaactctt tttccgaagg   5519
taactggctt cagcagagcg cagataccaa atactgtcct tctagtgtag ccgtagttag   5579
gccaccactt caagaactct gtagcaccgc ctacatacct cgctctgcta atcctgttac   5639
cagtggctgc tgccagtggc gataagtcgt gtcttaccgg gttggactca agacgatagt   5699
taccggataa ggcgcagcgg tcgggctgaa cggggggttc gtgcacacag cccagcttgg   5759
agcgaacgac ctacaccgaa ctgagatacc tacagcgtga gctatgagaa agcgccacgc   5819
ttcccgaagg gagaaaggcg gacaggtatc cggtaagcgg cagggtcgga acaggagagc   5879
gcacgaggga gcttccaggg ggaaacgcct ggtatcttta tagtcctgtc gggtttcgcc   5939
acctctgact tgagcgtcga tttttgtgat gctcgtcagg ggggcggagc ctatggaaaa   5999
acgccagcaa cgcggccttt ttacggttcc tggccttttg ctggcctttt gctcacatgt   6059
tctttcctgc gttatcccct gattctgtgg ataaccgtat taccgccttt gagtgagctg   6119
ataccgctcg ccgcagccga acgaccgagc gcagcgagtc agtgagcgag gaagcggaag   6179
agcgcctgat gcggtatttt ctccttacgc atctgtgcgg tatttcacac cgcatatatg   6239
gtgcactctc agtacaatct gctctgatgc cgcatagtta agccagtata cactccgcta   6299
tcgctacgtg actgggtcat ggctgcgccc cgacacccgc caacacccgc tgacgcgccc   6359
tgacgggctt gtctgctccc ggcatccgct tacagacaag ctgtgaccgt ctccgggagc   6419
tgcatgtgtc agaggttttc accgtcatca ccgaaacgcg cgaggcagct gcggtaaagc   6479
tcatcagcgt ggtcgtgcag cgattcacag atgtctgcct gttcatccgc gtccagctcg   6539
ttgagtttct ccagaagcgt taatgtctgg cttctgataa agcgggccat gttaagggcg   6599
```

-continued

```
gttttttcct gtttggtcac tgatgcctcc gtgtaagggg gatttctgtt catgggggta   6659

atgataccga tgaaacgaga gaggatgctc acgatacggg ttactgatga tgaacatgcc   6719

cggttactgg aacgttgtga gggtaaacaa ctggcggtat ggatgcggcg ggaccagaga   6779

aaaatcactc agggtcaatg ccagcgcttc gttaatacag atgtaggtgt tccacagggt   6839

agccagcagc atcctgcgat gcagatccgg aacataatgg tgcagggcgc tgacttccgc   6899

gtttccagac tttacgaaac acggaaaccg aagaccattc atgttgttgc tcaggtcgca   6959

gacgttttgc agcagcagtc gcttcacgtt cgctcgcgta tcggtgattc attctgctaa   7019

ccagtaaggc aaccccgcca gcctagccgg gtcctcaacg acaggagcac gatcatgcgc   7079

acccgtggcc aggacccaac gctgcccgaa att                                7112


<210> SEQ ID NO 41
<211> LENGTH: 554
<212> TYPE: PRT
<213> ORGANISM: Toxoplasma gondii
<220> FEATURE:
<223> OTHER INFORMATION: pMBP-c2X-ToxoP30del11 (52-214aa)

<400> SEQUENCE: 41

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270
```

-continued

```
Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val
545                 550


<210> SEQ ID NO 42
<211> LENGTH: 489
<212> TYPE: DNA
<213> ORGANISM: Toxoplasma gondii
<220> FEATURE:
<221> NAME/KEY: CDS
<222> LOCATION: (1)...(489)
<223> OTHER INFORMATION: ToxoP30del11 (52-214aa)

<400> SEQUENCE: 42

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
        35                  40                  45
```

-continued

```
caa atc tgc cca gcg ggt act aca agt agc tgt aca tca aag gct gta      192
Gln Ile Cys Pro Ala Gly Thr Thr Ser Ser Cys Thr Ser Lys Ala Val
     50                  55                  60

aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                 85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc aca gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
    130                 135                 140

agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160

acc ctc gtg                                                          489
Thr Leu Val
```

<210> SEQ ID NO 43
<211> LENGTH: 163
<212> TYPE: PRT
<213> ORGANISM: Toxoplasma gondii
<220> FEATURE:
<223> OTHER INFORMATION: ToxoP30del11 (52-214aa)

<400> SEQUENCE: 43

```
Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val
```

<210> SEQ ID NO 44
<211> LENGTH: 70
<212> TYPE: DNA
<213> ORGANISM: Artificial Sequence
<220> FEATURE:

-continued

<223> OTHER INFORMATION: P30.001 Primer

<400> SEQUENCE: 44
cttgttgcca atcaagttgt cacctgccca gataaaaaat cgacagccgc ggtcattctc 60
acaccgacgg 70

<210> SEQ ID NO 45
<211> LENGTH: 69
<212> TYPE: DNA
<213> ORGANISM: Artificial Sequence
<220> FEATURE:
<223> OTHER INFORMATION: P30.002 Primer

<400> SEQUENCE: 45
gaggctctgt gagcgctgtt ttagggcact tgagagtgaa gtggttctcc gtcggtgtga 60
gaatgaccg 69

<210> SEQ ID NO 46
<211> LENGTH: 67
<212> TYPE: DNA
<213> ORGANISM: Artificial Sequence
<220> FEATURE:
<223> OTHER INFORMATION: P30.003 Primer

<400> SEQUENCE: 46
cctaaaacag cgctcacaga gcctcccact cttgcgtact cacccaacag gcaaatctgc 60
ccagcgg 67

<210> SEQ ID NO 47
<211> LENGTH: 72
<212> TYPE: DNA
<213> ORGANISM: Artificial Sequence
<220> FEATURE:
<223> OTHER INFORMATION: P30.004 Primer

<400> SEQUENCE: 47
ggaatcaagg agctcaatgt tacagccttt gatgtacagc tacttgtagt acccgctggg 60
cagatttgcc tg 72

<210> SEQ ID NO 48
<211> LENGTH: 73
<212> TYPE: DNA
<213> ORGANISM: Artificial Sequence
<220> FEATURE:
<223> OTHER INFORMATION: P30.005 Primer

<400> SEQUENCE: 48
gtaacattga gctccttgat tcctgaagca gaagatagct ggtggacggg ggattctgct 60
agtctcgaca cgg 73

<210> SEQ ID NO 49
<211> LENGTH: 72
<212> TYPE: DNA
<213> ORGANISM: Artificial Sequence
<220> FEATURE:
<223> OTHER INFORMATION: P30.006 Primer

<400> SEQUENCE: 49
ctgcgttgtc acggggaact tctcgattgg aactgtgagt ttgatgcctg ccgtgtcgag 60
actagcagaa tc 72

-continued

<210> SEQ ID NO 50
<211> LENGTH: 70
<212> TYPE: DNA
<213> ORGANISM: Artificial Sequence
<220> FEATURE:
<223> OTHER INFORMATION: P30.007 Primer

<400> SEQUENCE: 50
gaagttcccc gtgacaacgc agacgtttgt ggtcggttgc atcaagggag acgacgcaca 60
gagttgtatg 70

<210> SEQ ID NO 51
<211> LENGTH: 71
<212> TYPE: DNA
<213> ORGANISM: Artificial Sequence
<220> FEATURE:
<223> OTHER INFORMATION: P30.008 Primer

<400> SEQUENCE: 51
gcgacattat tgacgaccga tgaggctctg gcttgtactg tcaccgtgac catacaactc 60
tgtgcgtcgt c 71

<210> SEQ ID NO 52
<211> LENGTH: 70
<212> TYPE: DNA
<213> ORGANISM: Artificial Sequence
<220> FEATURE:
<223> OTHER INFORMATION: P30.009 Primer

<400> SEQUENCE: 52
catcggtcgt caataatgtc gcaaggtgct cctacggtgc agacagcact cttggtcctg 60
tcaagttgtc 70

<210> SEQ ID NO 53
<211> LENGTH: 71
<212> TYPE: DNA
<213> ORGANISM: Artificial Sequence
<220> FEATURE:
<223> OTHER INFORMATION: P30.010Ala8 Primer

<400> SEQUENCE: 53
gactccatct ttcccagcca cgagggtcat tgtagtgggt ccttccgcag acaacttgac 60
aggaccaaga g 71

<210> SEQ ID NO 54
<211> LENGTH: 71
<212> TYPE: DNA
<213> ORGANISM: Artificial Sequence
<220> FEATURE:
<223> OTHER INFORMATION: P30.011Ala8Ala9 Primer

<400> SEQUENCE: 54
gtggctggga aagatggagt caaagttcct caagacaaca atcagtacgc ttccgggacg 60
acgctgactg g 71

<210> SEQ ID NO 55
<211> LENGTH: 71
<212> TYPE: DNA
<213> ORGANISM: Artificial Sequence
<220> FEATURE:
<223> OTHER INFORMATION: P30.012Ala9Ala10 Primer

<400> SEQUENCE: 55

-continued gttctcagtt aattttggca aaatatcttt gaacgatttc tcgttagcac cagtcagcgt 60
cgtcccggaa g 71

<210> SEQ ID NO 56
<211> LENGTH: 71
<212> TYPE: DNA
<213> ORGANISM: Artificial Sequence
<220> FEATURE:
<223> OTHER INFORMATION: P30.013 Primer

<400> SEQUENCE: 56
gatattttgc caaaattaac tgagaacccg tggcagggta acgcttcgag tgataagggt 60
gccacgctaa c 71

<210> SEQ ID NO 57
<211> LENGTH: 70
<212> TYPE: DNA
<213> ORGANISM: Artificial Sequence
<220> FEATURE:
<223> OTHER INFORMATION: P30.014 Primer

<400> SEQUENCE: 57
ccaataatga cgctttttga ctcggctgga aatgcttcct tcttgatcgt tagcgtggca 60
cccttatcac 70

<210> SEQ ID NO 58
<211> LENGTH: 70
<212> TYPE: DNA
<213> ORGANISM: Artificial Sequence
<220> FEATURE:
<223> OTHER INFORMATION: P30.015Ala11Ala12 Primer

<400> SEQUENCE: 58
gtcaaaaagc gtcattattg gagctacagg gggatcgcct gagaagcatc acgctaccgt 60
gaaactggag 70

<210> SEQ ID NO 59
<211> LENGTH: 70
<212> TYPE: DNA
<213> ORGANISM: Artificial Sequence
<220> FEATURE:
<223> OTHER INFORMATION: P30.016Ala12 Primer

<400> SEQUENCE: 59
gactggctgt tcccgcagcc gattttgctg accctgcagc cccggcaaac tccagtttca 60
cggtagcgtg 70

<210> SEQ ID NO 60
<211> LENGTH: 36
<212> TYPE: DNA
<213> ORGANISM: Artificial Sequence
<220> FEATURE:
<223> OTHER INFORMATION: Antisense Primer

<400> SEQUENCE: 60
caggtcaagc tttcactcca gtttcacggt agcgtg 36

<210> SEQ ID NO 61
<211> LENGTH: 7370
<212> TYPE: DNA
<213> ORGANISM: Toxoplasma gondii
<220> FEATURE:
<221> NAME/KEY: CDS -continued
<222> LOCATION: (1528)...(3447)
<223> OTHER INFORMATION: pMBP-c2X-ToxoP30MIX1

<400> SEQUENCE: 61

```
ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
     75                  80                  85
```

-continued

```
ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405
```

-continued

```
att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc acg gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg gct ggg aaa gat gga gtc aaa gtt cct caa gac aat aat cag tac      3234
Val Ala Gly Lys Asp Gly Val Lys Val Pro Gln Asp Asn Asn Gln Tyr
    555                 560                 565

gct tcc ggg acg acg ctg act ggt gct aac gag aaa tcg ttc aaa gat      3282
Ala Ser Gly Thr Thr Leu Thr Gly Ala Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga gct aca ggg gga tcg cct gag aag cat      3426
Ser Lys Ser Val Ile Ile Gly Ala Thr Gly Gly Ser Pro Glu Lys His
        620                 625                 630

cac gct acc gtg aaa ctg gag tgaaagcttg gcactggccg tcgttttaca        3477
His Ala Thr Val Lys Leu Glu
    635                 640

acgtcgtgac tgggaaaacc ctggcgttac ccaacttaat cgccttgcag cacatccccc   3537

tttcgccagc tggcgtaata gcgaagaggc ccgcaccgat cgcccttccc aacagttgcg   3597

cagcctgaat ggcgaatggc agcttggctg ttttggcgga tgagataaga ttttcagcct   3657

gatacagatt aaatcagaac gcagaagcgg tctgataaaa cagaatttgc ctggcggcag   3717

tagcgcggtg gtcccacctg accccatgcc gaactcagaa gtgaaacgcc gtagcgccga   3777

tggtagtgtg gggtctcccc atgcgagagt agggaactgc caggcatcaa ataaaacgaa   3837

aggctcagtc gaaagactgg gcctttcgtt ttatctgttg tttgtcggtg aacgctctcc   3897

tgagtaggac aaatccgccg ggagcggatt tgaacgttgc gaagcaacgg cccggagggt   3957

ggcgggcagg acgcccgcca taaactgcca ggcatcaaat taagcagaag gccatcctga   4017
```

-continued

```
cggatggcct ttttgcgttt ctacaaactc tttttgttta tttttctaaa tacattcaaa   4077
tatgtatccg ctcatgagac aataaccctg ataaatgctt caataatatt gaaaaaggaa   4137
gagtatgagt attcaacatt tccgtgtcgc ccttattccc ttttttgcgg cattttgcct   4197
tcctgttttt gctcacccag aaacgctggt gaaagtaaaa gatgctgaag atcagttggg   4257
tgcacgagtg ggttacatcg aactggatct caacagcggt aagatccttg agagttttcg   4317
ccccgaagaa cgttctccaa tgatgagcac ttttaaagtt ctgctatgtg gcgcggtatt   4377
atcccgtgtt gacgccgggc aagagcaact cggtcgccgc atacactatt ctcagaatga   4437
cttggttgag tactcaccag tcacagaaaa gcatcttacg gatggcatga cagtaagaga   4497
attatgcagt gctgccataa ccatgagtga taacactgcg gccaacttac ttctgacaac   4557
gatcggagga ccgaaggagc taaccgcttt tttgcacaac atgggggatc atgtaactcg   4617
ccttgatcgt tgggaaccgg agctgaatga agccatacca aacgacgagc gtgacaccac   4677
gatgcctgta gcaatggcaa caacgttgcg caaactatta actggcgaac tacttactct   4737
agcttcccgg caacaattaa tagactggat ggaggcggat aaagttgcag gaccacttct   4797
gcgctcggcc cttccggctg gctggtttat tgctgataaa tctggagccg gtgagcgtgg   4857
gtctcgcggt atcattgcag cactggggcc agatggtaag ccctcccgta tcgtagttat   4917
ctacacgacg gggagtcagg caactatgga tgaacgaaat agacagatcg ctgagatagg   4977
tgcctcactg attaagcatt ggtaactgtc agaccaagtt tactcatata tactttagat   5037
tgatttaccc cggttgataa tcagaaaagc cccaaaaaca ggaagattgt ataagcaaat   5097
atttaaattg taaacgttaa tattttgtta aaattcgcgt taaatttttg ttaaatcagc   5157
tcatttttta accaataggc cgaaatcggc aaaatccctt ataaatcaaa agaatagacc   5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta cagggcgcgt aaaaggatct aggtgaagat   5577
cctttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga tttttgtgat gctcgtcagg   6237
ggggcggagc ctatggaaaa acgccagcaa cgcggccttt ttacggttcc tggccttttg   6297
ctggcctttt gctcacatgt tctttcctgc gttatcccct gattctgtgg ataaccgtat   6357
taccgccttt gagtgagctg ataccgctcg ccgcagccga acgaccgagc gcagcgagtc   6417
```

-continued

```
agtgagcgag gaagcggaag agcgcctgat gcggtatttt ctccttacgc atctgtgcgg   6477

tatttcacac cgcatatatg gtgcactctc agtacaatct gctctgatgc cgcatagtta   6537

agccagtata cactccgcta tcgctacgtg actgggtcat ggctgcgccc cgacacccgc   6597

caacacccgc tgacgcgccc tgacgggctt gtctgctccc ggcatccgct tacagacaag   6657

ctgtgaccgt ctccgggagc tgcatgtgtc agaggttttc accgtcatca ccgaaacgcg   6717

cgaggcagct gcggtaaagc tcatcagcgt ggtcgtgcag cgattcacag atgtctgcct   6777

gttcatccgc gtccagctcg ttgagtttct ccagaagcgt taatgtctgg cttctgataa   6837

agcgggccat gttaagggcg gttttttcct gtttggtcac tgatgcctcc gtgtaagggg   6897

gatttctgtt catgggggta atgataccga tgaaacgaga gaggatgctc acgatacggg   6957

ttactgatga tgaacatgcc cggttactgg aacgttgtga gggtaaacaa ctggcggtat   7017

ggatgcggcg ggaccagaga aaaatcactc agggtcaatg ccagcgcttc gttaatacag   7077

atgtaggtgt tccacagggt agccagcagc atcctgcgat gcagatccgg aacataatgg   7137

tgcagggcgc tgacttccgc gtttccagac tttacgaaac acggaaaccg aagaccattc   7197

atgttgttgc tcaggtcgca gacgttttgc agcagcagtc gcttcacgtt cgctcgcgta   7257

tcggtgattc attctgctaa ccagtaaggc aaccccgcca gcctagccgg gtcctcaacg   7317

acaggagcac gatcatgcgc acccgtggcc aggacccaac gctgcccgaa att          7370
```

<210> SEQ ID NO 62
<211> LENGTH: 640
<212> TYPE: PRT
<213> ORGANISM: Toxoplasma gondii
<220> FEATURE:
<223> OTHER INFORMATION: pMBP-c2X-ToxoP30MIX1

<400> SEQUENCE: 62

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190
```

-continued

```
Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
                565                 570                 575

Gly Ala Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
```

-continued

```
    610                 615                 620

Ala Thr Gly Gly Ser Pro Glu Lys His His Ala Thr Val Lys Leu Glu
625                 630                 635                 640


<210> SEQ ID NO 63
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX1

<400> SEQUENCE: 63

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
             20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
         35                  40                  45

caa atc tgc cca gcg ggt act aca agt agc tgt aca tca aag gct gta      192
Gln Ile Cys Pro Ala Gly Thr Thr Ser Ser Cys Thr Ser Lys Ala Val
     50                  55                  60

aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                 85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc acg gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
    130                 135                 140

agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160

acc ctc gtg gct ggg aaa gat gga gtc aaa gtt cct caa gac aat aat      528
Thr Leu Val Ala Gly Lys Asp Gly Val Lys Val Pro Gln Asp Asn Asn
                165                 170                 175

cag tac gct tcc ggg acg acg ctg act ggt gct aac gag aaa tcg ttc      576
Gln Tyr Ala Ser Gly Thr Thr Leu Thr Gly Ala Asn Glu Lys Ser Phe
            180                 185                 190

aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220

gcc gag tca aaa agc gtc att att gga gct aca ggg gga tcg cct gag      720
Ala Glu Ser Lys Ser Val Ile Ile Gly Ala Thr Gly Gly Ser Pro Glu
225                 230                 235                 240

aag cat cac gct acc gtg aaa ctg gag                                  747
Lys His His Ala Thr Val Lys Leu Glu
```

-continued

245

<210> SEQ ID NO 64
<211> LENGTH: 249
<212> TYPE: PRT
<213> ORGANISM: Toxoplasma gondii
<220> FEATURE:
<223> OTHER INFORMATION: ToxoP30MIX1

<400> SEQUENCE: 64

```
Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
                245
```

<210> SEQ ID NO 65
<211> LENGTH: 70
<212> TYPE: DNA
<213> ORGANISM: Artificial Sequence
<220> FEATURE:
<223> OTHER INFORMATION: P30.009Ala7 Primer

<400> SEQUENCE: 65

```
catcggtcgt caataatgtc gcaagggctt cctacggtgc agacagcact cttggtcctg     60

tcaagttgtc                                                            70
```

<210> SEQ ID NO 66
<211> LENGTH: 7370
<212> TYPE: DNA
<213> ORGANISM: Toxoplasma gondii -continued

```
<220> FEATURE:
<221> NAME/KEY: CDS
<222> LOCATION: (1528)...(3447)
<223> OTHER INFORMATION: pMBP-c2X-ToxoP30MIX3

<400> SEQUENCE: 66

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                               1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70

tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
```

-continued

```
     75                  80                  85

ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa     2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc     2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg     2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg     2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca     2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc     2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac     2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg     2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa     2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt     2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc     2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac     2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt     2706
Asn Asn Asn Asn Leu Gly Ile Glu Gly Arg Ile Ser Glu Phe Leu Val
        380                 385                 390

gcc aat caa gtt gtc acc tgc cca gat aaa aaa tcg aca gcc gcg gtc     2754
```

-continued

```
Ala Asn Gln Val Val Thr Cys Pro Asp Lys Lys Ser Thr Ala Ala Val
    395                 400                 405

att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc acg gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg gct tcc tac ggt gca gac agc act      3138
Ser Val Val Asn Asn Val Ala Arg Ala Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg gct ggg aaa gat gga gtc aaa gtt cct caa gac aac aat cag tac      3234
Val Ala Gly Lys Asp Gly Val Lys Val Pro Gln Asp Asn Asn Gln Tyr
    555                 560                 565

gct tcc ggg acg acg ctg act ggt gct aac gag aaa tcg ttc aaa gat      3282
Ala Ser Gly Thr Thr Leu Thr Gly Ala Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga gct aca ggg gga tcg cct gag aag cat      3426
Ser Lys Ser Val Ile Ile Gly Ala Thr Gly Gly Ser Pro Glu Lys His
        620                 625                 630

cac gct acc gtg aaa ctg gag tgaaagcttg gcactggccg tcgttttaca        3477
His Ala Thr Val Lys Leu Glu
    635                 640

acgtcgtgac tgggaaaacc ctggcgttac ccaacttaat cgccttgcag cacatccccc   3537

tttcgccagc tggcgtaata gcgaagaggc ccgcaccgat cgcccttccc aacagttgcg   3597

cagcctgaat ggcgaatggc agcttggctg ttttggcgga tgagataaga ttttcagcct   3657

gatacagatt aaatcagaac gcagaagcgg tctgataaaa cagaatttgc ctggcggcag   3717

tagcgcggtg gtcccacctg accccatgcc gaactcagaa gtgaaacgcc gtagcgccga   3777

tggtagtgtg gggtctcccc atgcgagagt agggaactgc caggcatcaa ataaaacgaa   3837

aggctcagtc gaaagactgg gcctttcgtt ttatctgttg tttgtcggtg aacgctctcc   3897

tgagtaggac aaatccgccg ggagcggatt tgaacgttgc gaagcaacgg cccggagggt   3957
```

-continued

```
ggcgggcagg acgcccgcca taaactgcca ggcatcaaat taagcagaag gccatcctga   4017

cggatggcct tttgcgtttt ctacaaactc tttttgttta tttttctaaa tacattcaaa   4077

tatgtatccg ctcatgagac aataaccctg ataaatgctt caataatatt gaaaaaggaa   4137

gagtatgagt attcaacatt tccgtgtcgc ccttattccc ttttttgcgg cattttgcct   4197

tcctgttttt gctcacccag aaacgctggt gaaagtaaaa gatgctgaag atcagttggg   4257

tgcacgagtg ggttacatcg aactggatct caacagcggt aagatccttg agagttttcg   4317

ccccgaagaa cgttctccaa tgatgagcac ttttaaagtt ctgctatgtg gcgcggtatt   4377

atcccgtgtt gacgccgggc aagagcaact cggtcgccgc atacactatt ctcagaatga   4437

cttggttgag tactcaccag tcacagaaaa gcatcttacg gatggcatga cagtaagaga   4497

attatgcagt gctgccataa ccatgagtga taacactgcg gccaacttac ttctgacaac   4557

gatcggagga ccgaaggagc taaccgcttt tttgcacaac atgggggatc atgtaactcg   4617

ccttgatcgt tgggaaccgg agctgaatga agccatacca aacgacgagc gtgacaccac   4677

gatgcctgta gcaatggcaa caacgttgcg caaactatta actggcgaac tacttactct   4737

agcttcccgg caacaattaa tagactggat ggaggcggat aaagttgcag gaccacttct   4797

gcgctcggcc cttccggctg gctggtttat tgctgataaa tctggagccg gtgagcgtgg   4857

gtctcgcggt atcattgcag cactggggcc agatggtaag ccctcccgta tcgtagttat   4917

ctacacgacg gggagtcagg caactatgga tgaacgaaat agacagatcg ctgagatagg   4977

tgcctcactg attaagcatt ggtaactgtc agaccaagtt tactcatata tactttagat   5037

tgatttaccc cggttgataa tcagaaaagc cccaaaaaca ggaagattgt ataagcaaat   5097

atttaaattg taaacgttaa tattttgtta aaattcgcgt taaatttttg ttaaatcagc   5157

tcatttttta accaataggc cgaaatcggc aaaatccctt ataaatcaaa agaatagacc   5217

gagatagggt tgagtgttgt tccagtttgg aacaagagtc cactattaaa gaacgtggac   5277

tccaacgtca aagggcgaaa aaccgtctat cagggcgatg gcccactacg tgaaccatca   5337

cccaaatcaa gttttttggg gtcgaggtgc cgtaaagcac taaatcggaa ccctaaaggg   5397

agcccccgat ttagagcttg acggggaaag ccggcgaacg tggcgagaaa ggaagggaag   5457

aaagcgaaag gagcgggcgc tagggcgctg gcaagtgtag cggtcacgct gcgcgtaacc   5517

accacacccg ccgcgcttaa tgcgccgcta cagggcgcgt aaaaggatct aggtgaagat   5577

cctttttgat aatctcatga ccaaaatccc ttaacgtgag ttttcgttcc actgagcgtc   5637

agaccccgta gaaaagatca aaggatcttc ttgagatcct ttttttctgc gcgtaatctg   5697

ctgcttgcaa acaaaaaaac caccgctacc agcggtggtt tgtttgccgg atcaagagct   5757

accaactctt tttccgaagg taactggctt cagcagagcg cagataccaa atactgtcct   5817

tctagtgtag ccgtagttag gccaccactt caagaactct gtagcaccgc ctacatacct   5877

cgctctgcta atcctgttac cagtggctgc tgccagtggc gataagtcgt gtcttaccgg   5937

gttggactca agacgatagt taccggataa ggcgcagcgg tcgggctgaa cggggggttc   5997

gtgcacacag cccagcttgg agcgaacgac ctacaccgaa ctgagatacc tacagcgtga   6057

gctatgagaa agcgccacgc ttcccgaagg gagaaaggcg gacaggtatc cggtaagcgg   6117

cagggtcgga acaggagagc gcacgaggga gcttccaggg ggaaacgcct ggtatcttta   6177

tagtcctgtc gggtttcgcc acctctgact tgagcgtcga tttttgtgat gctcgtcagg   6237

ggggcggagc ctatggaaaa acgccagcaa cgcggccttt ttacggttcc tggccttttg   6297

ctggcctttt gctcacatgt tctttcctgc gttatcccct gattctgtgg ataaccgtat   6357
```

-continued

```
taccgccttt gagtgagctg ataccgctcg ccgcagccga acgaccgagc gcagcgagtc   6417

agtgagcgag gaagcggaag agcgcctgat gcggtatttt ctccttacgc atctgtgcgg   6477

tatttcacac cgcatatatg gtgcactctc agtacaatct gctctgatgc cgcatagtta   6537

agccagtata cactccgcta tcgctacgtg actgggtcat ggctgcgccc cgacacccgc   6597

caacacccgc tgacgcgccc tgacgggctt gtctgctccc ggcatccgct tacagacaag   6657

ctgtgaccgt ctccgggagc tgcatgtgtc agaggttttc accgtcatca ccgaaacgcg   6717

cgaggcagct gcggtaaagc tcatcagcgt ggtcgtgcag cgattcacag atgtctgcct   6777

gttcatccgc gtccagctcg ttgagtttct ccagaagcgt taatgtctgg cttctgataa   6837

agcgggccat gttaagggcg gtttttcct gtttggtcac tgatgcctcc gtgtaagggg   6897

gatttctgtt catgggggta atgataccga tgaaacgaga gaggatgctc acgatacggg   6957

ttactgatga tgaacatgcc cggttactgg aacgttgtga gggtaaacaa ctggcggtat   7017

ggatgcggcg ggaccagaga aaaatcactc agggtcaatg ccagcgcttc gttaatacag   7077

atgtaggtgt tccacagggt agccagcagc atcctgcgat gcagatccgg aacataatgg   7137

tgcagggcgc tgacttccgc gtttccagac tttacgaaac acggaaaccg aagaccattc   7197

atgttgttgc tcaggtcgca gacgttttgc agcagcagtc gcttcacgtt cgctcgcgta   7257

tcggtgattc attctgctaa ccagtaaggc aaccccgcca gcctagccgg gtcctcaacg   7317

acaggagcac gatcatgcgc acccgtggcc aggacccaac gctgcccgaa att          7370
```

<210> SEQ ID NO 67
<211> LENGTH: 640
<212> TYPE: PRT
<213> ORGANISM: Toxoplasma gondii
<220> FEATURE:
<223> OTHER INFORMATION: pMBP-c2X-ToxoP30MIX3

<400> SEQUENCE: 67

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
```

-continued

```
        180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Ala Ser Tyr Gly Ala Asp Ser Thr Leu Gly Pro Val Lys Leu Ser
    530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
                565                 570                 575

Gly Ala Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605
```

-continued

```
Ile Lys Lys Glu Ala Phe Pro Ala Glu Ser Lys Ser Val Ile Ile Gly
    610                 615                 620

Ala Thr Gly Gly Ser Pro Glu Lys His His Ala Thr Val Lys Leu Glu
625                 630                 635                 640


<210> SEQ ID NO 68
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX3

<400> SEQUENCE: 68

ctt gtt gcc aat caa gtt gtc acc tgc cca gat aaa aaa tcg aca gcc       48
Leu Val Ala Asn Gln Val Val Thr Cys Pro Asp Lys Lys Ser Thr Ala
 1               5                  10                  15

gcg gtc att ctc aca ccg acg gag aac cac ttc act ctc aag tgc cct       96
Ala Val Ile Leu Thr Pro Thr Glu Asn His Phe Thr Leu Lys Cys Pro
            20                  25                  30

aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
        35                  40                  45

caa atc tgc cca gcg ggt act aca agt agc tgt aca tca aag gct gta      192
Gln Ile Cys Pro Ala Gly Thr Thr Ser Ser Cys Thr Ser Lys Ala Val
    50                  55                  60

aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                 70                  75                  80

gat tct gct agt ctc gac acg gca ggc atc aaa ctc aca gtt cca atc      288
Asp Ser Ala Ser Leu Asp Thr Ala Gly Ile Lys Leu Thr Val Pro Ile
                85                  90                  95

gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110

gga gac gac gca cag agt tgt atg gtc acg gtg aca gta caa gcc aga      384
Gly Asp Asp Ala Gln Ser Cys Met Val Thr Val Thr Val Gln Ala Arg
        115                 120                 125

gcc tca tcg gtc gtc aat aat gtc gca agg gct tcc tac ggt gca gac      432
Ala Ser Ser Val Val Asn Asn Val Ala Arg Ala Ser Tyr Gly Ala Asp
    130                 135                 140

agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160

acc ctc gtg gct ggg aaa gat gga gtc aaa gtt cct caa gac aac aat      528
Thr Leu Val Ala Gly Lys Asp Gly Val Lys Val Pro Gln Asp Asn Asn
                165                 170                 175

cag tac gct tcc ggg acg acg ctg act ggt gct aac gag aaa tcg ttc      576
Gln Tyr Ala Ser Gly Thr Thr Leu Thr Gly Ala Asn Glu Lys Ser Phe
            180                 185                 190

aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205

tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220

gcc gag tca aaa agc gtc att att gga gct aca ggg gga tcg cct gag      720
Ala Glu Ser Lys Ser Val Ile Ile Gly Ala Thr Gly Gly Ser Pro Glu
225                 230                 235                 240
```

-continued

```
aag cat cac gct acc gtg aaa ctg gag                                747
Lys His His Ala Thr Val Lys Leu Glu
                245


<210> SEQ ID NO 69
<211> LENGTH: 249
<212> TYPE: PRT
<213> ORGANISM: Toxoplasma gondii
<220> FEATURE:
<223> OTHER INFORMATION: ToxoP30MIX3

<400> SEQUENCE: 69

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Ala Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
                245


<210> SEQ ID NO 70
<211> LENGTH: 69
<212> TYPE: DNA
<213> ORGANISM: Artificial Sequence
<220> FEATURE:
<223> OTHER INFORMATION: P30.002Ala2 Primer

<400> SEQUENCE: 70

gaggctctgt gagcgctgtt ttaggagcct tgagagtgaa gtggttctcc gtcggtgtga     60

gaatgaccg                                                             69


<210> SEQ ID NO 71
<211> LENGTH: 7370
```

-continued

<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-ToxoP30MIX5

<400> SEQUENCE: 71

```
ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380

ctggcaaata ttctgaaatg agctgttgac aattaatcat cggctcgtat aatgtgtgga   1440

attgtgagcg gataacaatt tcacacagga aacagccagt ccgtttaggt gttttcacga   1500

gcacttcacc aacaaggacc atagcat atg aaa atc gaa gaa ggt aaa ctg gta   1554
                              Met Lys Ile Glu Glu Gly Lys Leu Val
                                1               5

atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25

aag aaa ttc gag aaa gat acc gga att aaa gtc acc gtt gag cat ccg     1650
Lys Lys Phe Glu Lys Asp Thr Gly Ile Lys Val Thr Val Glu His Pro
                 30                  35                  40

gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
             45                  50                  55

cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70
```

-continued

```
tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
     75                  80                  85

ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105

gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120

ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135

aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150

gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165

ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185

aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200

aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215

ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230

tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245

acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265

ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280

gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295

aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310

aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325

atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345

act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360

ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375

aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390
```

-continued

```
gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405

att ctc aca ccg acg gag aac cac ttc act ctc aag gct cct aaa aca      2802
Ile Leu Thr Pro Thr Glu Asn His Phe Thr Leu Lys Ala Pro Lys Thr
410                 415                 420                 425

gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440

tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455

agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470

gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485

ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505

gac gca cag agt tgt atg gtc acg gtg aca gta caa gcc aga gcc tca      3090
Asp Ala Gln Ser Cys Met Val Thr Val Thr Val Gln Ala Arg Ala Ser
                510                 515                 520

tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535

ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550

gtg gct ggg aaa gat gga gtc aaa gtt cct caa gac aac aat cag tac      3234
Val Ala Gly Lys Asp Gly Val Lys Val Pro Gln Asp Asn Asn Gln Tyr
    555                 560                 565

gct tcc ggg acg acg ctg act ggt gct aac gag aaa tcg ttc aaa gat      3282
Ala Ser Gly Thr Thr Leu Thr Gly Ala Asn Glu Lys Ser Phe Lys Asp
570                 575                 580                 585

att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600

gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615

tca aaa agc gtc att att gga gct aca ggg gga tcg cct gag aag cat      3426
Ser Lys Ser Val Ile Ile Gly Ala Thr Gly Gly Ser Pro Glu Lys His
        620                 625                 630

cac gct acc gtg aaa ctg gag tgaaagcttg gcactggccg tcgttttaca         3477
His Ala Thr Val Lys Leu Glu
    635                 640

acgtcgtgac tgggaaaacc ctggcgttac ccaacttaat cgccttgcag cacatccccc   3537

tttcgccagc tggcgtaata gcgaagaggc ccgcaccgat cgcccttccc aacagttgcg   3597

cagcctgaat ggcgaatggc agcttggctg ttttggcgga tgagataaga ttttcagcct   3657

gatacagatt aaatcagaac gcagaagcgg tctgataaaa cagaatttgc ctggcggcag   3717

tagcgcggtg gtcccacctg accccatgcc gaactcagaa gtgaaacgcc gtagcgccga   3777

tggtagtgtg gggtctcccc atgcgagagt agggaactgc caggcatcaa ataaaacgaa   3837

aggctcagtc gaaagactgg gcctttcgtt ttatctgttg tttgtcggtg aacgctctcc   3897
```

-continued

```
tgagtaggac aaatccgccg ggagcggatt tgaacgttgc gaagcaacgg cccggagggt   3957
ggcgggcagg acgcccgcca taaactgcca ggcatcaaat taagcagaag gccatcctga   4017
cggatggcct ttttgcgttt ctacaaactc tttttgttta tttttctaaa tacattcaaa   4077
tatgtatccg ctcatgagac aataaccctg ataaatgctt caataatatt gaaaaaggaa   4137
gagtatgagt attcaacatt tccgtgtcgc ccttattccc ttttttgcgg cattttgcct   4197
tcctgttttt gctcacccag aaacgctggt gaaagtaaaa gatgctgaag atcagttggg   4257
tgcacgagtg ggttacatcg aactggatct caacagcggt aagatccttg agagttttcg   4317
ccccgaagaa cgttctccaa tgatgagcac ttttaaagtt ctgctatgtg gcgcggtatt   4377
atcccgtgtt gacgccgggc aagagcaact cggtcgccgc atacactatt ctcagaatga   4437
cttggttgag tactcaccag tcacagaaaa gcatcttacg gatggcatga cagtaagaga   4497
attatgcagt gctgccataa ccatgagtga taacactgcg gccaacttac ttctgacaac   4557
gatcggagga ccgaaggagc taaccgcttt tttgcacaac atgggggatc atgtaactcg   4617
ccttgatcgt tgggaaccgg agctgaatga agccatacca aacgacgagc gtgacaccac   4677
gatgcctgta gcaatggcaa caacgttgcg caaactatta actggcgaac tacttactct   4737
agcttcccgg caacaattaa tagactggat ggaggcggat aaagttgcag gaccacttct   4797
gcgctcggcc cttccggctg gctggtttat tgctgataaa tctggagccg gtgagcgtgg   4857
gtctcgcggt atcattgcag cactggggcc agatggtaag ccctcccgta tcgtagttat   4917
ctacacgacg gggagtcagg caactatgga tgaacgaaat agacagatcg ctgagatagg   4977
tgcctcactg attaagcatt ggtaactgtc agaccaagtt tactcatata tactttagat   5037
tgatttaccc cggttgataa tcagaaaagc cccaaaaaca ggaagattgt ataagcaaat   5097
atttaaattg taaacgttaa tattttgtta aaattcgcgt taaatttttg ttaaatcagc   5157
tcatttttta accaataggc cgaaatcggc aaaatccctt ataaatcaaa agaatagacc   5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta cagggcgcgt aaaaggatct aggtgaagat   5577
cctttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga tttttgtgat gctcgtcagg   6237
ggggcggagc ctatggaaaa acgccagcaa cgcggccttt ttacggttcc tggccttttg   6297
```

-continued

```
ctggcctttt gctcacatgt tctttcctgc gttatcccct gattctgtgg ataaccgtat   6357

taccgccttt gagtgagctg ataccgctcg ccgcagccga acgaccgagc gcagcgagtc   6417

agtgagcgag gaagcggaag agcgcctgat gcggtatttt ctccttacgc atctgtgcgg   6477

tatttcacac cgcatatatg gtgcactctc agtacaatct gctctgatgc cgcatagtta   6537

agccagtata cactccgcta tcgctacgtg actgggtcat ggctgcgccc cgacacccgc   6597

caacacccgc tgacgcgccc tgacgggctt gtctgctccc ggcatccgct tacagacaag   6657

ctgtgaccgt ctccgggagc tgcatgtgtc agaggttttc accgtcatca ccgaaacgcg   6717

cgaggcagct gcggtaaagc tcatcagcgt ggtcgtgcag cgattcacag atgtctgcct   6777

gttcatccgc gtccagctcg ttgagtttct ccagaagcgt taatgtctgg cttctgataa   6837

agcgggccat gttaagggcg gttttttcct gtttggtcac tgatgcctcc gtgtaagggg   6897

gatttctgtt catgggggta atgataccga tgaaacgaga gaggatgctc acgatacggg   6957

ttactgatga tgaacatgcc cggttactgg aacgttgtga gggtaaacaa ctggcggtat   7017

ggatgcggcg ggaccagaga aaaatcactc agggtcaatg ccagcgcttc gttaatacag   7077

atgtaggtgt tccacagggt agccagcagc atcctgcgat gcagatccgg aacataatgg   7137

tgcagggcgc tgacttccgc gtttccagac tttacgaaac acggaaaccg aagaccattc   7197

atgttgttgc tcaggtcgca gacgttttgc agcagcagtc gcttcacgtt cgctcgcgta   7257

tcggtgattc attctgctaa ccagtaaggc aaccccgcca gcctagccgg gtcctcaacg   7317

acaggagcac gatcatgcgc acccgtggcc aggacccaac gctgcccgaa att          7370
```

<210> SEQ ID NO 72
<211> LENGTH: 640
<212> TYPE: PRT
<213> ORGANISM: Toxoplasma gondii
<220> FEATURE:
<223> OTHER INFORMATION: pMBP-c2X-ToxoP30MIX5

<400> SEQUENCE: 72

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175
```

-continued

```
Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Ala Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
                565                 570                 575

Gly Ala Asn Glu Lys Ser Phe Lys Asp Ile Leu Pro Lys Leu Thr Glu
            580                 585                 590
```

-continued

Asn Pro Trp Gln Gly Asn Ala Ser Ser Asp Lys Gly Ala Thr Leu Thr
595 600 605

Ile Lys Lys Glu Ala Phe Pro Ala Glu Ser Lys Ser Val Ile Ile Gly
610 615 620

Ala Thr Gly Gly Ser Pro Glu Lys His His Ala Thr Val Lys Leu Glu
625 630 635 640

<210> SEQ ID NO 73
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX5

<400> SEQUENCE: 73 ctt gtt gcc aat caa gtt gtc acc tgc cca gat aaa aaa tcg aca gcc 48
Leu Val Ala Asn Gln Val Val Thr Cys Pro Asp Lys Lys Ser Thr Ala
1 5 10 15 gcg gtc att ctc aca ccg acg gag aac cac ttc act ctc aag gct cct 96
Ala Val Ile Leu Thr Pro Thr Glu Asn His Phe Thr Leu Lys Ala Pro
20 25 30 aaa aca gcg ctc aca gag cct ccc act ctt gcg tac tca ccc aac agg 144
Lys Thr Ala Leu Thr Glu Pro Pro Thr Leu Ala Tyr Ser Pro Asn Arg
35 40 45 caa atc tgc cca gcg ggt act aca agt agc tgt aca tca aag gct gta 192
Gln Ile Cys Pro Ala Gly Thr Thr Ser Ser Cys Thr Ser Lys Ala Val
50 55 60 aca ttg agc tcc ttg att cct gaa gca gaa gat agc tgg tgg acg ggg 240
Thr Leu Ser Ser Leu Ile Pro Glu Ala Glu Asp Ser Trp Trp Thr Gly
65 70 75 80 gat tct gct agt ctc gac acg gca ggc atc aaa ctc aca gtt cca atc 288
Asp Ser Ala Ser Leu Asp Thr Ala Gly Ile Lys Leu Thr Val Pro Ile
85 90 95 gag aag ttc ccc gtg aca acg cag acg ttt gtg gtc ggt tgc atc aag 336
Glu Lys Phe Pro Val Thr Thr Gln Thr Phe Val Val Gly Cys Ile Lys
100 105 110 gga gac gac gca cag agt tgt atg gtc acg gtg aca gta caa gcc aga 384
Gly Asp Asp Ala Gln Ser Cys Met Val Thr Val Thr Val Gln Ala Arg
115 120 125 gcc tca tcg gtc gtc aat aat gtc gca agg tgc tcc tac ggt gca gac 432
Ala Ser Ser Val Val Asn Asn Val Ala Arg Cys Ser Tyr Gly Ala Asp
130 135 140 agc act ctt ggt cct gtc aag ttg tct gcg gaa gga ccc act aca atg 480
Ser Thr Leu Gly Pro Val Lys Leu Ser Ala Glu Gly Pro Thr Thr Met
145 150 155 160 acc ctc gtg gct ggg aaa gat gga gtc aaa gtt cct caa gac aac aat 528
Thr Leu Val Ala Gly Lys Asp Gly Val Lys Val Pro Gln Asp Asn Asn
165 170 175 cag tac gct tcc ggg acg acg ctg act ggt gct aac gag aaa tcg ttc 576
Gln Tyr Ala Ser Gly Thr Thr Leu Thr Gly Ala Asn Glu Lys Ser Phe
180 185 190 aaa gat att ttg cca aaa tta act gag aac ccg tgg cag ggt aac gct 624
Lys Asp Ile Leu Pro Lys Leu Thr Glu Asn Pro Trp Gln Gly Asn Ala
195 200 205 tcg agt gat aag ggt gcc acg cta acg atc aag aag gaa gca ttt cca 672
Ser Ser Asp Lys Gly Ala Thr Leu Thr Ile Lys Lys Glu Ala Phe Pro
210 215 220 gcc gag tca aaa agc gtc att att gga gct aca ggg gga tcg cct gag 720
Ala Glu Ser Lys Ser Val Ile Ile Gly Ala Thr Gly Gly Ser Pro Glu -continued

```
225                 230                 235                 240

aag cat cac gct acc gtg aaa ctg gag                                 747
Lys His His Ala Thr Val Lys Leu Glu
                245


<210> SEQ ID NO 74
<211> LENGTH: 249
<212> TYPE: PRT
<213> ORGANISM: Toxoplasma gondii
<220> FEATURE:
<223> OTHER INFORMATION: ToxoP30MIX5

<400> SEQUENCE: 74

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Ala Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
                245
```